US008080376B2

(12) United States Patent
Barber

(10) Patent No.: US 8,080,376 B2
(45) Date of Patent: Dec. 20, 2011

(54) GENE EXPRESSION CONTROL DNA ELEMENT AND ASSOCIATED PROTEIN

(75) Inventor: Elizabeth K. Barber, London (GB)

(73) Assignee: Elizabeth K. Barber, Winfield, IL (US)

( * ) Notice: Subject to any disclaimer, the term of this patent is extended or adjusted under 35 U.S.C. 154(b) by 617 days.

(21) Appl. No.: 11/973,835

(22) Filed: Oct. 9, 2007

(65) Prior Publication Data

US 2008/0076732 A1 Mar. 27, 2008

Related U.S. Application Data

(62) Division of application No. 09/966,264, filed on Sep. 28, 2001, now Pat. No. 7,371,540.

(60) Provisional application No. 60/237,079, filed on Sep. 30, 2000.

(51) Int. Cl.
    C12Q 1/00       (2006.01)
    C12Q 1/68       (2006.01)
    C07H 21/00      (2006.01)
    C07H 21/02      (2006.01)
    C12P 21/06      (2006.01)

(52) U.S. Cl. ............ 435/6.1; 435/4; 435/6.11; 435/6.12; 435/6.14; 435/69.1; 536/23.1; 536/23.5

(58) Field of Classification Search .................... None
    See application file for complete search history.

(56) References Cited

U.S. PATENT DOCUMENTS

| | | | | |
|---|---|---|---|---|
| 5,239,060 | A | 8/1993 | Kunkel et al. ................. | 530/350 |
| 5,430,129 | A | 7/1995 | Campbell et al. ............. | 530/413 |
| 5,858,661 | A | 1/1999 | Shiloh .............................. | 435/6 |
| 5,985,846 | A | 11/1999 | Kochanek et al. ............. | 514/44 |
| 6,011,137 | A | 1/2000 | Pirozzi et al. ................. | 530/324 |
| 6,063,576 | A | 5/2000 | Keating et al. ..................... | 435/6 |
| 6,083,750 | A | 7/2000 | Chamberlain et al. ........ | 435/369 |
| 6,087,108 | A | 7/2000 | Bandman et al. ................. | 435/6 |
| 6,087,111 | A | 7/2000 | Tinsley et al. .................... | 435/6 |

FOREIGN PATENT DOCUMENTS

WO    WO 97/22696    6/1997

OTHER PUBLICATIONS

Ahn, A. H., and Kunkel, L. (1993). The structural and functional diversity of dystrophin. *Nature Genetics*, 3: 283-291.
Alexander, E. L., and Sanders, S. K. (1977). F(ab')2 reagents are not required if goat, rather than rabbit, antibodies are used to detect human surface immunoglobulin. *J Immunol*, 119: 1084-1088.
Anderson, S. J., Chou, H. S., and Loh, D. Y. (1988). A conserved sequence in the T-cell receptor beta-chain promoter region. *Proc. Natl. Acad. Sci. USA*, 85: 3551-3554.
Aruffo, A. and B. Seed (1987). Molecular cloning of a CD28 cDNA by a high-efficiency COS cell expression system. *PNAS (USA)* 84: 8573-8577.
Aruffo, A., Stamenkovic, I., Melnick, M., Underhill, C.B., and Seed, B. (1990). CD44 Is the Principal Cell Surface Receptor for Hyaluronate. *Cell*, 61: 1303-1313.

Atkins, J. F., Weiss, R. B., Thompson, S., and Gesteland, R. F. (1991). Towards a genetic dissection of the basis of triplet decoding, and its natural subversion: programmed reading frame shifts and hops. *Annu. Rev. Genet.*, 25: 201-228.
Ausubel, F. M., Brent, R., Kingston, R.E., Moore, D.D., Seidman, J.G., Smith, J.A., and Stuhl, K. (1993). In Current Protocols in Molecular Biology, (New York: John Wiley & Sons, Inc.).
Baneiji, J., Rusconi, S., and Schaffner, W. (1981). Expression of a β globin gene is enhanced by remote SV40 DNA sequences. *Cell*, 27: 299-308.
Baranger, A. M. et al. (1995). Mechanism of DNA-binding enhancement by the human T-cell leukaemia virus transactivator Tax. *Nature*, 376: 606-608.
Barber, E. K., and Simmons, D.L. (1993). Functional-analysis of the early hematopoietic surface-markers CD33 and CD34. *J. Cell. Biochem.*, 17a: 346.
Barclay, A. N., Birkeland, M.L., Brown, M. L., Beyers, A. D., Davis, S.J., Somoza, C., and Williams, A.F. (1993). The Leucocyte Antigen Facts Book. 424. Academic Press Limited.
Bass, B. L., and Weintraub, H. (1987). A developmentally regulated activity that unwinds RNA duplexes. *Cell*, 48: 607-613.
Baumhueter, S., Singer, M.S., Henzel, W., Hemmerich, S., Renz, M., Rosen, S.D., and Lasky, L.A. (1993). Binding of L-Selectin to the Vascular Sialomucin CD34. *Science*, 262: 436-438.
Bishop, J.M., *Annu. Rev. Biochem.*, 52: 301-354, 1983.
Blackwood, E.M. and R.N. Eisenman, *Science*, 251: 1211-1217, 1991.
Blake, D. J., Tinsley, J.M., and Davies, K.E. (1994). The emerging family of dystrophin-related proteins. *Tr. in Cell Biol.*, 4: 19-23.
Braun, R. E. (1990). Temporal translational regulation of the protamine 1 gene during mouse spermatogenesis. *Enzyme*, 44: 120-128.
Britten, R.J. (1994). Evidence that most human *Alu* sequences were inserted in a process that ceased about 30 million years ago. *Proc. Natl. Acad. Sci.* 91: 6148-6150. Bucher, P. (1990). Weight matrix descriptions of four eukaryotic RNA polymerase II promoter elements derived from 502 unrelated promoter sequences. *J. Mol. Biol.*, 212: 563-578.
Capon, D.J.et al. (1989). Designing CD4 immunoadhesins for AIDS therapy. *Nature* 337: 525-531.
Chelly, J.et al. (1990). Effect of dystrophin gene deletions on mRNA levels and processing in Duchenne and Becker muscular dystrophies. *Cell* 63: 1239-1248.
Chelly, J. et al. (1988). Transcription of the dystrophin gene in human muscle and non-muscle tissue. *Nature*, 333: 858-860.
Chelly, J., Montarras, D., Pinset, C., Berwald, N.Y., Kaplan, J. C., and Kahn, A. (1990). Quantitative estimation of minor mRNAs by cDNA-polymerase chain reaction. Application to dystrophin mRNA in cultured myogenic and brain cells. *Eur. J. Biochem*, 187: 691-698.

(Continued)

*Primary Examiner* — Sumesh Kaushal
(74) *Attorney, Agent, or Firm* — McDonnell Boehnen Hulbert & Berghoff LLP

(57) ABSTRACT

Through screening of an expression library, a cDNA sequence has been identified that encodes a protein that interacts with human CD33, the DNA being highly homologous to a portion of the human dystrophin gene. A region of that cDNA has been identified as an important regulatory element in controlling expression, both transcription and translation, of the DNA with which it is associated. This DNA sequence element may be used as a regulatory cassette in conjunction with any suitable gene, to modify gene expression. The putative controlling DNA sequence element contains a minimum of 137 base pairs (FIG. 1) to 147 base pairs (FIG. 1A) and a maximum of 287 base pairs (FIG. 1B).

2 Claims, 60 Drawing Sheets

OTHER PUBLICATIONS

Chirgwin, J. M., Przybyla, A.E., MacDonald, R.J., and Rutter, W.J. (1979). Isolation of biologically active ribonucleic acid from sources enriched in ribonuclease. *Biochemistry*, 18: 5294-5299.

Church, G.M., and Gilbert, W. (1984). Genomic Sequencing. *Proc. Natl. Acad. Sci. USA*, 81: 1991-1995.

Claros, M. G., and von Heijne, G. (1994). TopPred II: an improved software for membrane protein structure predictions. *CABIOS*, 10: 685-686.

Cole, S. R., Ashman, L. K., and Ey, P. L. (1987). Biotinylation: An Alternative to Radioiodination for the Identification of Cell Surface Antigens in Immunoprecipitates. *Mol. Immunol.*, 24: 699-705.

Croce, C. M., Erikson, J., Ar-rushdi, A., Aden, D. and Nishikura, K. (1984). Translocated c-myc oncogene of Burkitt lymphoma is transcribed in plasma cells and repressed in lymphoblastoid cells. *Proc. Natl. Acad. Sci. USA*, 81: 3170-3174.

Crocker, P.R. et al. (1994). Sialoadhesin, a macrophage sialic acid binding receptor for haemopoietic cells with 17 immunoglobulin-like domains. *The EMBO Journal* 13: 4490-4503.

Darnell, J., Lodish, R, and Baltimore, D. (1986). Molecular Cell Biology. 1192. Scientific American Books.

Davidson, N. O. (1993). Apolipoprotein B mRNA editing: a key controlling element targeting fats to proper tissue. *Ann. Med.*, 25: 539-543.

Dornfeld, K. J., and Livingston, D. M. (1992). Plasmid recombination in a rad52 mutant of *Saccharomyces cerevisiae*. *Genetics*, 131: 261-276.

Drysdale, C. M., Duenas, E., Jackson, B.M., Reusser, U., Braus, G.H., and Hinnebusch, A.G. (1995). The transcriptional activator GCN4 contains multiple activation domains that are critically dependent on hydrophobic amino acids. *Mol. Cell Biol.*, 15: 1220-1233.

Dynan, W. S., and Tjian, R. (1983). The promoter-specific transcription factor Sp1 binds to upstream sequences in the SV40 early promoter. *Cell*, 35: 79-87.

Eliceiri, B., Labella, T., Hagino, Y., Srivastava, A., Schlessinger, D., Pilia, G., Palmieri, G., and D'Urso, M. (1991). Stable integration and expression in mouse cells of yeast artificial chromosomes harboring human genes. *Proc Natl Acad Sci USA*, 88: 2179-2183.

Emerson, S. G., Reilly, P., and Cone, R. E. (1979). Differential radiolabelling of lymphocyte membrane alloantigens and immunoglobulins: variation of H2O2 concentration during lactoperoxidase catalyzed cell surface radio-iodination. *J. Immunogenet*, 6: 87-97.

Fawcett, J., Holness, C.L., and Simmons, D.L. (1994). Molecular Tools for the Analysis of Cell Adhesion. *Cell Adhesion and Communication*, 2: 275-285.

Feinberg, A. P., and Vogelstein, B. (1983). A technique for radiolabeling DNA restriction endonuclease fragments to high specific activity. *Analytical Biochemistry*, 132: 6-13.

Firtel, R. A. (1981). Multigene families encoding actin and tubulin. *Cell*, 24, 6-7. Freeman, S. D., Kelm S., Barber, E.K., and Crocker, P.R. (1995). Characterisation of CD33 as a new member of the sialoadhesin family of cell adhesion molecules. *Blood*, 85: 2005-2012.

Freeman, S.D. et al., *Blood*, 85: 2005-2012, 1995.

Gangopadhyay, S.B., Sherratt, T.G., Heckmatt, J.Z., Dubowitz, V., Miller, G., Shokeir, M., Ray, P.N, Strong, P.N. and Worton, R.G. (1992). Dystrophin in frameshift deletion patients with Becker muscular dystrophy. *Am. J. Hunt Genet*. 51: 562-570.

Garvin, A. M. Pawar, S., Marth, J. D., and Perlmutter, R. M. (1988). Structure of the murine lck gene and its rearrangement in a murine lymphoma cell line. *Mol. Cell Biol.*, 8: 3058-3064.

Gellert, M. (1992). Molecular analysis of V(D)J recombination. *Annu. Rev. Genet.*, 22: 425-446.

Genetics Computer Group, (G. C. G.) (1991). Program Manual for the GCG Package, Version 7. Genetics Computer Group.

Gerondakis, S., Cory, S., and Adams, J.M. (1984). Translocation of the *myc* cellular oncogene to the immunoglobulin heavy chain locus in murine plasmacytomas is an imprecise reciprocal exchange. *Cell*, 36: 973-982.

Gluzman, Y. (1981). SV40-transformed simian cells support the replication of early SV40 mutants. *Cell*, 23: 175-182.

Gorecki, D. C., Monaco, A. P., Deny, J. M, Walker, A. P., Barnard, E. A., and Barnard, P. J. (1992). Expression of four alternative dystrophin transcripts in brain regions regulated by different promoters. *Hum. Mol. Genet*, 1: 505-510.

Guigo, R., Knudsen, S., Drake N., and Smith, T. (1992). Prediction of Gene Structure. *J.Mol.Biol.*, 226: 141-157.

Hamada, H, and Kakunaga, T. (1982). Potential Z-DNA forming sequences are highly dispersed in the human genome. *Nature*, 298: 396-398.

Hames, B. D., and Glover, D.M. (1988). Transcription and Splicing. In Frontiers in Molecular Biology, (Oxford: IRL Press), pp. 212.

Hanke, J.H, Harbor, J.E., and Kavathas, P. (1995). Repetitive *Alu* Elements form a Cruciform Structure that Regulates the Function of the Human CD8 alpha T Cell-specific Enhancer. *J. Mol. Biol.*, 246: 63-73.

Harlow, E., and Lane, D. (1988). Antibodies: a Laboratory Manual. 723. Cold Spring Harbor Laboratory.

Hirt, B. (1967). Selective extraction of polyoma DNA from infected mouse cell cultures. *J. Mol. Biol*, 26: 365-369.

Hnatowich, D. J., Virzi, F., and Rusckowski, M. (1987). Investigations of avidin and biotin for imaging applications. *J. Nucl. Med.*, 28: 1294-1302.

Hollenbaugh, D. et al. (1992). The human T cell antigen gp39, a member of the TNF gene family, is a ligand for the CD40 receptor expression of a soluble form of gp39 with B cell co-stimulatory activity. *EMBO J.*, 11: 4313-4321. 7510.

Honigman, A., Wolf, D., Yaish, S., Falk, H., and Panet, A. (1991). cis Acting RNA sequences control the gag-pol translation readthrough in murine leukemia virus. *Virology*, 183: 313-319.

Hugnot, J. P. at al. (1992). Distal transcript of the dystrophin gene initiated from an alternative first exon and encoding a 75 kDa protein widely distributed in non-muscle tissues. *Proc. Natl. Acad. Sci USA*, 89: 7506-.

Jackson, D. G., Buckley, J., and Bell, J. I. (1992). Multiple Variants of the Human Lymphocyte Homing Receptor CD44 Generated by Insertions at a Single Site in the Extracellular Domain. *J. Biol. Chem.*, 267: 4732-4739.

Jackson, R. J. (1993). Cytoplasmic regulation of mRNA function: the importance of the 3' untranslated region. *Cell*, 74: 9-14.

Jeang, K. T., and Hayward, G. S. (1983). A cytomegalovirus DNA sequence containing tracts of tandemly repeated Ca dinucleotides hybridizes to highly repetitive dispersed elements in mammalian cell genomes. *Mol. Cell. Biol.*, 3: 1389-1402.

Jennings, M. W., Jones, R. W., Wood, W. G., and Weatherall, D. J. (1985). Analysis of an inversion within the human beta globin gene cluster. *Nucleic Acids Res.*, 13: 2897-2906.

Jones, R. W., Old, J. M., Trent, R. J., Clegg, J. B., and Weatherall, D. J. (1981). Major rearrangement in the human beta-globin gene cluster. *Nature*, 291: 39-44.

Kelm, S. et al. (1994). Sialoadhesin, MAG, and CD22 define a new family of sialic acid-dependent adhesion molecules of the immunoglobulin superfamily. *Current Biology*, 4: 965-972.

Kienhuis, C. B., Heuvel, I. J., Ross, R. A., Swinkels, L. M., Foekens, J. A., and Benraad, T. J. (1991). Six methods for direct radioiodination of mouse epidermal growth factor compared: effect of nonequivalence in binding behavior between labeled and unlabeled ligand. *Clin Chem.*, 37: 1749-1755.

Koenig, M., Hoffman, E. P., Bertelson, C. J., Monaco, A. P., Feener, C., and Kunkel, L. M. (1987). Complete cloning of the Duchenne muscular dystrophy (DMD) cDNA and preliminary genomic organization of the DMD gene in normal and affected individuals. *Cell*, 50: 509-517.

Koenig, M., Monaco, A. P., and Kunkel, L. M. (1988). The complete sequence of dystrophin predicts a rod-shaped cytoskeletal protein. *Cell*, 53: 219-228.

Kozak, M. (1987). An analysis of 5'-noncoding sequences from 699 vertebrate messenger RNAs. *Nucleic Acids Res*, 15: 8125-8148.

Kudo, A., and Melchers, F. (1987). A second gene, VpreB in the lambda 5 locus of the mouse, which appears to be selectively expressed in pre-B lymphocytes. *EMBO J*, 6: 2267-2272.

Kudo, A., Pravtcheva, D., Sakaguchi, N., Ruddle, F. H, and Melchers, F. (1987). Localization of the murine lambda 5 gene on chromosome 16. *Genomics*,1: 277-279.

Kunkel, L. M., Lalande, M, Monaco, A. P., Flint, A., Middlesworth, W., and Latt, S. A. (1985). Construction of a human X-chromosome-enriched phage library which facilitates analysis of specific loci. *Gene*, 33: 251-258.

Laemmli, U. K (1970). Cleavage of structural proteins during the assembly of the head of bacteriophage T4. *Nature*, 227: 680-685.

Landau, N. R, St. John, T., Weissman, I. L., Wolf, S. C., Silverstone, A. E., and Baltimore, D. (1984). Cloning of terminal transferase cDNA by antibody screening. *Proc. Natl. Acad. Sci. USA*, 81: 5836-5840.

Larin, Z., Monaco, A. P., and Lehrach, H. (1991). Yeast artificial chromosome libraries containing large inserts from mouse and human DNA. *Proc. Natl. Acad. Sci. USA*, 88: 4123-4127.

Lederfein, D., Levy, Z., Augier, N., Momet, D., Morris, G., Fuchs, O., Yaffe, D., and Nudel U. (1992). A 71-kilodalton protein is a major product of the Duchenne muscular dystrophy gene in brain and other nonmuscle tissues. *Proc. Natl. Acad. Sci. USA*, 89: 5346-5350.

Lejeune, S., Huguet, E.L., Hamby, A., Poulsom, R. and Haris, A. (1995). *Wnt5a* Cloning, Expression, and Up-regulation in Human Primary Breast Cancers. *Clin. Cancer Res.*,1: 215-222.

Lewis, S., Gifford, A., and Baltimore, D. (1985). DNA elements are asymmetrically joined during the site-specific recombination of kappa immunoglobulin genes. *Science*, 228: 677-85.

Lozzio, C. B., and Lozzio, B.B. (1975). Human Chronic Myelogenous Leukemia Cell-Line With Positive Philadelphia Chromosome. *Blood*, 45: 321-334.

Majors, J. E., Swanstrom, R, DeLorbe, W. J., Payne, G. S., Hughes, S. FL, Ortiz, S., Quintrell, N., Bishop, J. M., and Varmus, H. E. (1981). DNA intermediates in the replication of retroviruses are structurally (and perhaps functionally) related to transposable elements. *Cold Spring Harb. Symp. Quant. Biol,*, 2: 731-738.

Matsuoka, M., Nagawa, F., Okazaki, K., Kingsbury, L., Yoshida, K., Muller, U., Larue, D. T., Winer, J. A., and Sakano, H. (1991). Detection of somatic DNA recombination in the transgenic mouse brain. *Science*, 254: 81-86.

McClintock, B. (1956). Controlling elements and the gene. *Cold Spring Harbor Symposium*, 21: 197-216.

McCourt, P. A. G., Ek, B., Forsberg, N., and Gustafson, S. (1994). Intercellular Adhesion Molecule-1 Is a Cell Surface Receptor for Hyaluronan. *J. Biol. Chem.*, 269: 30081-30084.

Miesfeld, R., Krystal, M, and Arnheim, N. (1981). A member of a new repeated sequence family which is conserved throughout eucaryotic evolution is found between the human δ- and β- globin genes. Nucleic Acids Res., 9: 5931-5947.

Monaco, A.P., Bertelson, C.J., Liechti-Gallati, S., Moser, H., Kunkel, L.M. (1988). An explanation for the phenotypic differences between patients bearing partial deletions of the DMD locus. *Genomics*, 2: 90-95.

Monaco, A. P., Walker, A. P., Millwood, I., Larin, Z., and Lehrach, H. (1992). A yeast artificial chromosome contig containing the complete Duchenne muscular dystrophy gene. *Genomics*, 12: 465-473.

Murgola, E. J., Prather, N. E., Mims, B. H., Pagel, F. T., and Hijazi, K. A. (1983). Anticodon shift in tRNA: a novel mechanism in missense and nonsense suppression. *Proc. Natl. Acad. Sci. USA*, 80: 4936-4939.

Murray, M. G. and Thompson, W. F. (1980). Rapid isolation of high molecular weight plant DNA. Nucleic Acids Research, 8: 4321-4325.

Nicholson, L.V., Bushby, K.M., Johnson, M.A., den Dunnen, I.T., Ginjaar, I.B., van Ommen, G.J. (1992). Predicted and observed sizes of dystrophin in some patients with gene deletions that disrupt the open reading frame. *J. Med. Genet*. 29: 892-896.

Oxley, S. M., and Sackstein, R. (1994). Detection of an L-selectin ligand on a hematopoietic progenitor cell line. *Blood*, 84: 3299-3306.

Payne, G. S., Bishop, J. M., and Vannus, H. E. (1982). Multiple arrangements of viral DNA and an activated host oncogene in bursal lymphomas. *Nature*, 295: 209-214.

Pearson, W. R, and Lipman, D. J. (1988). Improved tools for biological sequence comparison. *Proc. Natl. Acad. Sci. USA*, 85: 2444-2448.

Rabbitts, T. H. (1991). Translocations, Master Genes, and Differences between the Origins of Acute and Chronic Leukemias. *Cell*, 67: 641-644.

Rastinejad, F., and Blau, H. M. (1993). Genetic complementation reveals a novel regulatory role for 3' untranslated regions in growth and differentiation. *Cell*, 72: 903-917.

Rastinejad, F., Conboy, M. J., Rando, T. A., and Blau, H. M. (1993). Tumor suppression by RNA from the 3' untranslated region of alpha-tropomyosin. *Cell*, 75: 1107-1117.

Roberts, R. G., Barby, T. F. M., Manners, E., Bobrow, M., and Bentley, D. R. (1991). Direct detection of dystrophin gene rearrangements by analysis of dystrophin mRNA in peripheral blood lymphocytes. *Am. J. Hum. Genet.*, 49: 298-310.

Rosenstein, Y., Park, J. K., Hahn, W. C., Rosen, F. S., Bierer, B. E. and Burakoff, S. J. (1991). CD43, a molecule defective in Wiskott-Aldrich syndrome, binds ICAM-1. *Nature.*, 354: 233-235.

Rowley, J. D. (1995). Chromosome translocations: good genes gone wrong. *Pathol. Biol. Paris*, 43: 197-201.

Sambrook, J., Fritsch, E.F. and Maniatis, T. (1989). Molecular Cloning: A Laboratory Manual. (N. Ford), Cold Spring Harbor Laboratory Press.

Sandri, G. R., Goldrin, A. L., Levine, M., and Glorioso, J. (1983). High-efficiency transfer of DNA into eukaryotic cells by protoplast fusion. *Methods in Enzymology*, 101: 402-411.

Sanger, F., Nicklen, S., and Coulson, A.R. (1977). DNA sequencing with chain-terminating inhibitors. *Proc. Natl. Acad. Sci. USA*, 74: 5463-5467.

Seed, B. (1987). An LFA-3 cDNA encodes a phospholipid-linked membrane protein homologous to its receptor CD2. *Nature.*, 329: 840-842.

Seed, B., and Aruffo, A. (1987). Molecular cloning of the CD2 antigen, the T-cell erythrocyte receptor, by a rapid immunoselection procedure. *Proc. Natl. Acad. Sci. USA.*, 84: 3365-3369.

Sgroi, D., Nocks, A., and Stamenkovic, L (1996). A Single N-linked Glycosylation Site Is Implicated in the Regulation of Ligand Recognition by the I-type Lectins CD22 and CD33. *J. Biol. Chem.*, 271: 18803-18809.

Sheen, J. Y., and Seed, B. (1988). Electrolyte gradient gels for DNA sequencing. *Biotechniques*, 6: 942-944.

Sherratt, T.G., Vulliamy, T., Dubowitz, V., Sewry, C.A., Strong, P.N. (1993). Exon skipping and translation in patients with frameshift deletions in the dystrophin gene. *Am J. Hum. Genet*. 53: 1007-1015.

Simmons, D., and Seed., B. (1988). Isolation of a cDNA encoding CD33, a differentiation antigen of myeloid progenitor cells. *J. Immunol.*, 141: 2797-2800.

Simmons, D. L. (1993). Cloning cell surface molecules by transient expression in mammalian cells. In *Cellular Interactions in Development—A Practical Approach*, (Oxford: IRL Press), pp. 93-128.

Simmons, D. L., Satterthwaite, A.B., Tenen, D.G., and Seed, B. (1992). Molecular Cloning of a cDNA Encoding CD34, a Sialomucin of Human Hematopoietic Stem Cells. *J. Immunol.*,148: 267-271.

Simmons, D. L., and Needham, L., In *Vascular endothelium: Interactions with circulating cells*, (Oxford: Elsevier Science Publishers B.V.), 3-29, 1991).

Smale, S. T., and Baltimore, D. (1989). The "initiator" as a transcription control element *Cell*, 57: 103-113.

Southern, E. M. (1975). Detection of specific sequences among DNA fragments separated by gel electrophoresis. *J. Mol. Biol.*, 98: 503-517.

Staden, R. (1990). Searching for patterns in protein and nucleic acid sequences. *Methods in Enzymology*, 183: 193-211.

Sussman, D. J., and Milman, G. (1984). Short-term, high-efficiency expression of transfected DNA. *Mol. Cell. Biol.*, 4: 1641-1643.

Swanson, R., Hoben, P., Sumner, S. M., Uemura, H, Watson, L., and Soll, D. (1988). Accuracy of in vivo aminoacylation requires proper balance of tRNA and aminoacyl-tRNA synthetase. *Science*, 242: 1548-1551.

Temin, H. (1964). Nature of the provirus of *Rous sarcoma. Natl. Cancer Inst. Monogr.*, 17: 557-570.

Thomas, M., Shackelford, D., Ralph, S., and Trowbridge, I. (1987). Structural studies of T200 glycoprotein and the IL-2 receptor. *J. Recept. Res*, 7: 133-155.

Tuohy, T. M., Thompson, S., Gesteland, R F., and Atkins, J. F. (1992). Seven, eight and nine-membered anticodon loop mutants of tRNA(2Arg) which cause +1 flarneshitting. Tolerance of DHU arm and other secondary mutations. *J. Mol. Biol.*, 228: 1042-1054.

Varmus, H. E. (1984). The molecular genetics of cellular oncogenes. *Annu. Rev. Genet.*, 18: 553-612.

Vitelli, L., and Weinberg, E. S. (1983). An inverted sea urchin histone gene sequence with breakpoints between TATA boxes and mRNA cap sites. *Nucleic Acids Res*, 11: 2135-2153.

Weber, J. L. (1990). Human DNA Polymorphisms Based on Length Variations in Simple-sequence Tandem Repeats. In Genetic and Physical Mapping, (Plainview Cold Spring Harbor Laboratory Press), pp. 159-181.

Weiner, Am, Deininger, P.L., and Efstratiadis, A. (1986). Nonviral retroposons: genes, pseudogenes, and transposable elements generated by the reverse flow of genetic information. *Ann. Rev. Biochem.* 55: 631-661.

Wheater, P. R., Burkitt, H. G., and, and Daniels, V. G. (1987). Functional Histology. 348. Churchill Livingstone.

Woolf, T. M., Chase, J. M., and Stinchcomb, D. T. (1995). Toward the therapeutic editing of mutated RNA sequences. *Proc. Natl. Acad. Sci. USA*, 92: 8298-8302.

Wysocki, L. J., and Sato, V. L. (1978). "Panning" for lymphocytes: a method for cell selection. *Proc. Natl. Acad. Sci. USA*, 75: 2844-2848.

Yanofsky, C. (1981). Attenuation in the control of expression of bacterial operons. *Nature*, 289: 751-758.

Zhou, D. F., Ding, J. F., Picker, L. J., Bargatze, R. F., Butcher, E. C., and Goeddel, D. V. (1989). Molecular cloning and expression of Pgp-1. The mouse homolog of the human H-CAM (Hermes) lymphocyte homing receptor. *J. Immunol.*, 143: 3390-3395.

EMBL Sequence Database Acc. No. AW385154 (Feb. 6, 2000).

EMBL Sequence Database Acc. No. AC006061 (Nov. 27, 1998). Nucleotides 91659-91795, p. 30.

```
       Inversion start site
       |
       ATTATAAAGGAAAAAGAAAATAACGCAATGGACAAGTGGTG
860    +---------+---------+---------+---------+    900
       TAATATTTCCTTTTTCTTTTATTGCGTTACCTGTTCACCAC    (41)
          Y  K  G  K  R  K  *  R  N  G  Q  V  V AAGCTGTGAACTCAGGTGTGCACAATTATCAGGAACACCCCAAAACCAAAGTGAGGTAGA
901    ---------+---------+---------+---------+---------+---------+   960
       TTCGACACTTGAGTCCACACGTGTTAATAGTCCTTGTGGGGTTTTGGTTTCACTCCATCT    (101)
        K  L  *  T  Q  V  C  T  I  I  R  N  T  P  K  P  K  *  G  R AATAGCATGAGAAGCCGTGTTTGATGTTAATTAATT          [SEQ ID NO: 1]
961    ---------+---------+---------+------   996
       TTATCGTACTCTTCGGCACAAACTACAATTAATTAA   (137)  [SEQ ID NO: 65]
        N  S  M  R  S  R  V  *  C  *  L  I           [SEQ ID NO: 66]
```

The inversion sequence of the apo-dystrophin-4 cDNA (SEQ ID NO: 1)

Figure 1

```
                  Inversion start site
                  |
        TAAAGAAAGAATTATAAAGGAAAAAGAAAATAACGCAATGGACAAGTGGTG
    850 +---------+---------+---------+---------+---------+    900
        ATTTCTTTCTTAATATTTCCTTTTTCTTTTATTGCGTTACCTGTTCACCAC     (51)
        *  R  K  N  Y  K  G  K  R  K  *  R  N  G  Q  V  V AAGCTGTGAACTCAGGTGTGCACAATTATCAGGAACACCCCAAAACCAAAGTGAGGTAGA
    901 ---------+---------+---------+---------+---------+---------+    960
        TTCGACACTTGAGTCCACACGTGTTAATAGTCCTTGTGGGGTTTTGGTTTCACTCCATCT    (111)
        K  L  *  T  Q  V  C  T  I  I  R  N  T  P  K  P  K  *  G  R AATAGCATGAGAAGCCGTGTTTGATGTTAATTAATT          [SEQ ID NO: 67]
    961 ---------+---------+---------+------   996
        TTATCGTACTCTTCGGCACAAACTACAATTAATTAA  (147)  [SEQ ID NO: 68]
        N  S  M  R  S  R  V  *  C  *  L  I           [SEQ ID NO: 69]
```

The inversion sequence of the apo-dystrophin-4 cDNA plus a 10 base-pair region 5'
to the start of the inversion sequence [SEQ ID NO: 67]

Figure 1A

```
Start at 710
|
AACAATGGCAG
+--------+    720
TTGTTACCGTC   (11)
  Q  W  Q

GTTTTACACGTCTATGCAATTGTACAAAAAAGTTATAAGAAAACTACATGTAAAATCTTG
721  --------+---------+---------+---------+---------+---------+  780
     CAAAATGTGCAGATACGTTAACATGTTTTTTCAATATTCTTTTGATGTACATTTTAGAAC  (71)
      V  L  H  V  Y  A  I  V  Q  K  S  Y  K  K  T  T  C  K  I  L

ATAGCTAAATAACTTGCCATTTCTTTATATGGAACGCATTTTGGGTTGTTTAAAAATTTA
781  --------+---------+---------+---------+---------+---------+  840
     TATCGATTTATTGAACGGTAAAGAAATATACCTTGCGTAAAACCCAACAAATTTTTAAAT  (131)
      I  A  K  *  L  A  I  S  L  Y  G  T  H  F  G  L  F  K  N  L
                   inversion start site
                          |
     TAACAGTTATAAAGAAAGAATTATAAAGGAAAAAGAAAATAACGCAATGGACAAGTGGTG
841  --------+---------+---------+---------+---------+---------+  900
     ATTGTCAATATTTCTTTCTTAATATTTCCTTTTTCTTTTATTGCGTTACCTGTTCACCAC  (191)
      *  Q  L  *  R  K  N  Y  K  G  K  R  K  *  R  N  G  Q  V  V AAGCTGTGAACTCAGGTGTGCACAATTATCAGGAACACCCCAAAACCAAAGTGAGGTAGA
901  --------+---------+---------+---------+---------+---------+  960
     TTCGACACTTGAGTCCACACGTGTTAATAGTCCTTGTGGGGTTTTGGTTTCACTCCATCT  (251)
      K  L  *  T  Q  V  C  T  I  I  R  N  T  P  K  P  K  *  G  R AATAGCATGAGAAGCCGTGTTTGATGTTAATTAATT       [SEQ ID NO: 70]
961  --------+---------+---------+------  996
     TTATCGTACTCTTCGGCACAAACTACAATTAATTAA  (287) [SEQ ID NO: 71]
      N  S  M  R  S  R  V  *  C  *  L  I        [SEQ ID NO: 72]
```

The inversion sequence of the apo-dystrophin-4 cDNA plus the upstream 150 bp from the start of the inversion at 860 to the Hpa I enzyme site (SEQ ID NO: 70)

Figure 1B

```
     GTGGTTTGATTGATAGTAAAAAAAATGTTCGTTAATACAAGTAGAGAGTAAGTAATCAAT
1    ----------+---------+---------+---------+---------+---------+    60
     CACCAAACTAACTATCATTTTTTTACAAGCAATTATGTTCATCTCTCATTCATTAGTTA
     V  V  *  L  I  V  K  K  M  F  V  N  T  S  R  E  *  V  I  N

CAATCACTCATAGCCAAGGTGGAAAAGATGTATCCCATCATGGAATATTCCTGTTCTGAT
61   ----------+---------+---------+---------+---------+---------+    120
     GTTAGTGAGTATCGGTTCCACCTTTTCTACATAGGGTAGTACCTTATAAGGACAAGACTA
        Q  S  L  I  A  K  V  E  K  M  Y  P  I  M  E  Y  S  C  S  D

AGAAATCTTGTGCTTATCTATGGAATTCTTTTGATATATATTTACATTGGGAACCTGAAT
121  ----------+---------+---------+---------+---------+---------+    180
     TCTTTAGAACACGAATAGATACCTTAAGAAAACTATATATAAATGTAACCCTTGGACTTA
      R  N  L  V  L  I  Y  G  I  L  L  I  Y  I  Y  I  G  N  L  N

GTAGCTTGACATTTTTCCATGTAAACACCAGTAGCCTGATCCAACATTAAGCTGATACTA
181  ----------+---------+---------+---------+---------+---------+    240
     CATCGAACTGTAAAAAGGTACATTTGTGGTCATCGGACTAGGTTGTAATTCGACTATGAT
      V  A  *  H  F  S  M  *  T  P  V  A  *  S  N  I  K  L  I  L

ACAAACAACGTGTAATGGCTTCATTAATAAGGCTTTGCTTCTTCCTGGAAACTGGTGAAA
241  ----------+---------+---------+---------+---------+---------+    300
     TGTTTGTTGCACATTACCGAAGTAATTATTCCGAAACGAAGAAGGACCTTTGACCACTTT
      T  N  N  V  *  W  L  H  *  *  G  F  A  S  S  W  K  L  V  K

AATCAAACCTTGTTGTGTACACCCTCGATGCAGCTTCTGTGTTGTCTTCACCCAGAAATG
301  ----------+---------+---------+---------+---------+---------+    360
     TTAGTTTGGAACAACACATGTGGGAGCTACGTCGAAGACACAACAGAAGTGGGTCTTTAC
      N  Q  T  L  L  C  T  P  S  M  Q  L  L  C  C  L  H  P  E  M
```

The polynucleotide sequence of apo-dystrophin-4 (SEQ ID NO: 2)

Figure 2

```
       GGGAATGATTTCCCAAATGGCAAAGAAACAGAGTGATGCTATCTATCTGCACCTTTTGTA
361    ---------+---------+---------+---------+---------+---------+    420
       CCCTTACTAAAGGGTTTACCGTTTCTTTGTCTCACTACGATAGATAGACGTGGAAAACAT
        G  N  D  F  P  N  G  K  E  T  E  *  C  Y  L  S  A  P  F  V

AAGTCTGTCTTTCTTTCTCTTTGTTTTCCAGGACACAATGTAGGAAGTCTTTTCCACATG
421    ---------+---------+---------+---------+---------+---------+    480
       TTCAGACAGAAAGAAAGAGAAACAAAAGGTCCTGTGTTACATCCTTCAGAAAAGGTGTAC
        K  S  V  F  L  S  L  C  F  P  G  H  N  V  G  S  L  F  H  M

GCAGATGATTTGGGCAGAGCGATGGAGTCCTTAGTATCAGTCATGACAGATGAAGAAGGA
481    ---------+---------+---------+---------+---------+---------+    540
       CGTCTACTAAACCCGTCTCGCTACCTCAGGAATCATAGTCAGTACTGTCTACTTCTTCCT
        A  D  D  L  G  R  A  M  E  S  L  V  S  V  M  T  D  E  E  G

GCAGAATAAATGTTTTACAACTCCTGATTCCCGCATGGTTTTTATAATATTCATACAACA
541    ---------+---------+---------+---------+---------+---------+    600
       CGTCTTATTTACAAAATGTTGAGGACTAAGGGCGTACCAAAAATATTATAAGTATGTTGT
        A  E  *  M  F  Y  N  S  *  F  P  H  G  F  Y  N  I  H  T  T

AAGAGGATTAGACAGTAAGAGTTTACAAGAAATAAATCTATATTTTTGTGAAGGGTAGTG
601    ---------+---------+---------+---------+---------+---------+    660
       TTCTCCTAATCTGTCATTCTCAAATGTTCTTTATTTAGATATAAAAACACTTCCCATCAC
        K  R  I  R  Q  *  E  F  T  R  N  K  S  I  F  L  *  R  V  V

GTATTATACTGTAGATTTCAGTAGTTTCTAAGTCTGTTATTGTTTTGTTAACAATGGCAG
661    ---------+---------+---------+---------+---------+---------+    720
       CATAATATGACATCTAAAGTCATCAAAGATTCAGACAATAACAAAACAATTGTTACCGTC
        V  L  Y  C  R  F  Q  *  F  L  S  L  L  L  F  C  *  Q  W  Q
```

Figure 2 (cont'd)

```
     GTTTTACACGTCTATGCAATTGTACAAAAAAGTTATAAGAAAACTACATGTAAAATCTTG
721  ---------+---------+---------+---------+---------+---------+  780
     CAAAATGTGCAGATACGTTAACATGTTTTTTCAATATTCTTTTGATGTACATTTTAGAAC
     V  L  H  V  Y  A  I  V  Q  K  S  Y  K  K  T  T  C  K  I  L

ATAGCTAAATAACTTGCCATTTCTTTATATGGAACGCATTTTGGGTTGTTTAAAAATTTA
781  ---------+---------+---------+---------+---------+---------+  840
     TATCGATTTATTGAACGGTAAAGAAATATACCTTGCGTAAAACCCAACAAATTTTTAAAT
     I  A  K  *  L  A  I  S  L  Y  G  T  H  F  G  L  F  K  N  L

TAACAGTTATAAAGAAAGAATTATAAAGGAAAAAGAAAATAACGCAATGGACAAGTGGTG
841  ---------+---------+---------+---------+---------+---------+  900
     ATTGTCAATATTTCTTTCTTAATATTTCCTTTTTCTTTTATTGCGTTACCTGTTCACCAC
     *  Q  L  *  R  K  N  Y  K  G  K  R  K  *  R  N  G  Q  V  V

AAGCTGTGAACTCAGGTGTGCACAATTATCAGGAACACCCCAAAACCAAAGTGACGTAGA
901  ---------+---------+---------+---------+---------+---------+  960
     TTCGACACTTGAGTCCACACGTGTTAATAGTCCTTGTGGGGTTTTGGTTTCACTCCATCT
     K  L  *  T  Q  V  C  T  I  I  R  N  T  P  K  P  K  *  G  R

AATAGCATGAGAAGCCGTGTTTGATGTTAATTAATT       [SEQ ID NO: 2]
961  ---------+---------+---------+------  996
     TTATCGTACTCTTCGGCACAAACTACAATTAATTAA       [SEQ ID NO: 73]
     N  S  M  R  S  R  V  *  C  *  L  I        [SEQ ID NO: 74]
```

Figure 2 (cont'd)

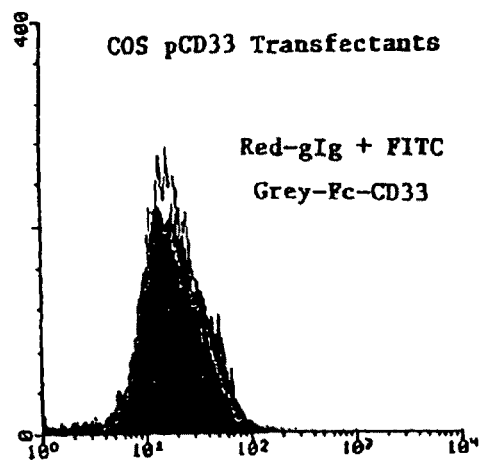 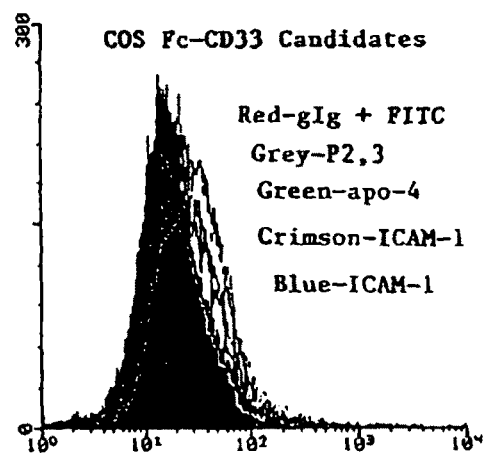
Figure 4A Figure 4B
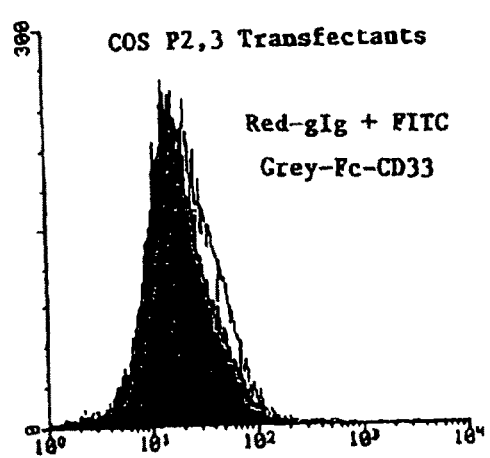 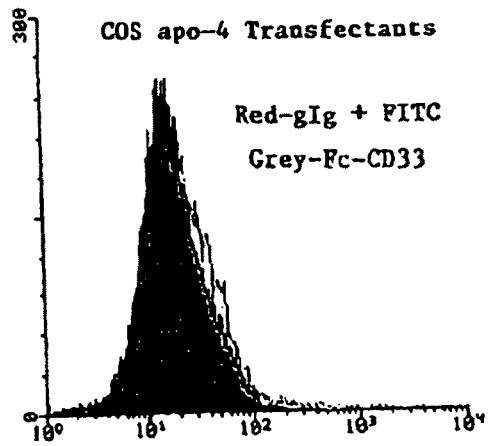
Figure 4C Figur 4D

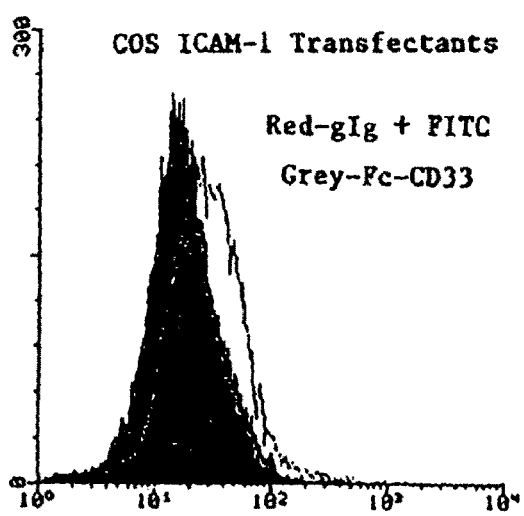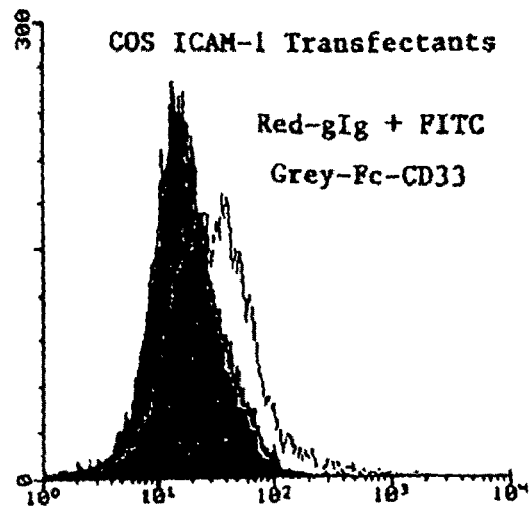
Figure 4E          Figure 4F
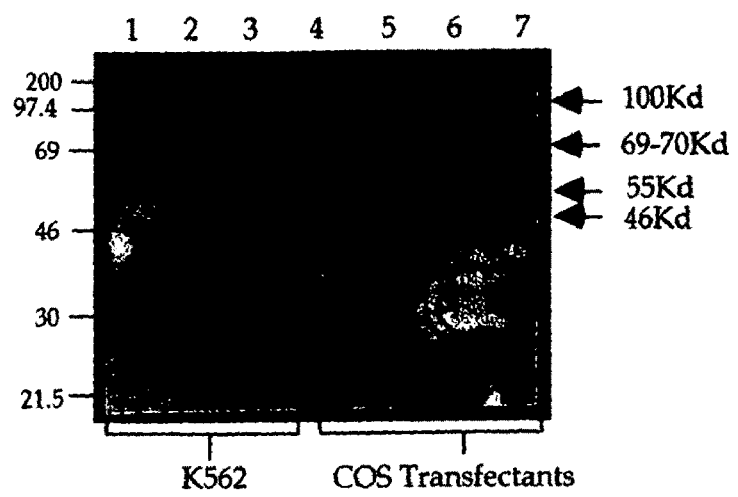
Figure 5

```
        ..TAGTTTCCTATTCAATGTATAGTGCACCAAAGGTCAATTCAAGAGTTTATTATTATT
-239    ---------+---------+---------+---------+---------+---------+    -180
        ...ATCAAAGGATAAGTTACATATCACGTGGTTTCCAGTTAAGTTCTCAAATAATAATAA
         .  *  F  P  I  Q  C  I  V  H  Q  R  S  I  Q  E  F  I  I  I

ATTTTCAACCCAAGTAAAAGCAGAGAGAAAATAGCCACCTCCACCATAGCCTCAGAAGCA
-179    ---------+---------+---------+---------+---------+---------+    -120
        TAAAAGTTGGGTTCATTTTCGTCTCTCTTTTATCGGTGGAGGTGGTATCGGAGTCTTCGT
         I  F  N  P  S  K  S  R  E  K  I  A  T  S  T  I  A  S  E  A

AGCCAACAGCCTGAAACAGCTTTGAAATGAAAAGTTGGTGTGGCGGTGATGGTGGCAGTG
-119    ---------+---------+---------+---------+---------+---------+    -60
        TCGGTTGTCGGACTTTGTCGAAACTTTACTTTTCAACCACACCGCCACTACCACCGTCAC
         S  Q  Q  P  E  T  A  L  K  *  K  V  G  V  A  V  M  V  A  V

ATAATGGTGACCGATGGTTGGGTGCTGGTGATGGTAGTGGTAGTTGTGAAGGTGGTGATG
-59     ---------+---------+---------+---------+---------+---------+    0
        TATTACCACTGGCTACCAACCCACGACCACTACCATCACCATCAACACTTCCACCACTAC
         I  M  V  T  D  G  W  V  L  V  M  V  V  V  V  K  V  V  M

GTGGTTTGATTGATAGTAAAAAAAATGTTCGTTAATACAAGTAGAGAGTAAGTAATCAAT
1       ---------+---------+---------+---------+---------+---------+    60
        CACCAAACTAACTATCATTTTTTTTACAAGCAATTATGTTCATCTCTCATTCATTAGTTA
         V  V  *  L  I  V  K  K  M  F  V  N  T  S  R  E  *  V  I  N

CAATCACTCATAGCCAAGGTGGAAAAGATGTATCCCATCATGGAATATTCCTGTTCTGAT
61      ---------+---------+---------+---------+---------+---------+    120
        GTTAGTGAGTATCGGTTCCACCTTTTCTACATAGGGTAGTACCTTATAAGGACAAGACTA
         Q  S  L  I  A  K  V  E  K  M  Y  P  I  M  E  Y  S  C  S  D

AGAAATCTTGTGCTTATCTATGGAATTCTTTTGATATATATTTACATTGGGAACCTGAAT
121     ---------+---------+---------+---------+---------+---------+    180
        TCTTTAGAACACGAATAGATACCTTAAGAAAACTATATATAAATGTAACCCTTGGACTTA
         R  N  L  V  L  I  Y  G  I  L  L  I  Y  I  Y  I  G  N  L  N

GTAGCTTGACATTTTTCCATGTAAACACCAGTAGCCTGATCCAACATTAAGCTGATACTA
181     ---------+---------+---------+---------+---------+---------+    240
        CATCGAACTGTAAAAAGGTACATTTGTGGTCATCGGACTAGGTTGTAATTCGACTATGAT
         V  A  *  H  F  S  M  *  T  P  V  A  *  S  N  I  K  L  I  L

ACAAACAACGTGTAATGGCTTCATTAATAAGGCTTTGCTTCTTCCTGGAAACTGGTGAAA
241     ---------+---------+---------+---------+---------+---------+    300
        TGTTTGTTGCACATTACCGAAGTAATTATTCCGAAACGAAGAAGGACCTTTGACCACTTT
         T  N  N  V  *  W  L  H  *  *  G  F  A  S  S  W  K  L  V  K

AATCAAACCTTGTTGTGTACACCCTCGATGCAGCTTCTGTGTTGTCTTCACCCAGAAATG
301     ---------+---------+---------+---------+---------+---------+    360
        TTAGTTTGGAACAACACATGTGGGAGCTACGTCGAAGACACAACAGAAGTGGGTCTTTAC
         N  Q  T  L  L  C  T  P  S  M  Q  L  L  C  C  L  H  P  E  M
```

Figure 6

```
       GGGAATGATTTCCCAAATGGCAAAGAAACAGAGTGATGCTATCTATCTGCACCTTTTGTA
361    ---------+---------+---------+---------+---------+---------+    420
       CCCTTACTAAAGGGTTTACCGTTTCTTTGTCTCACTACGATAGATAGACGTGGAAAACAT
       G  N  D  F  P  N  G  K  E  T  E  *  C  Y  L  S  A  P  F  V
                                    begin exon 79
                                              |
       AAGTCTGTCTTTCTTTCTCTTTGTTTTCCAGGACACAATGTAGGAAGTCTTTTCCACATG
421    ---------+---------+---------+---------+---------+---------+    480
       TTCAGACAGAAAGAAAGAGAAACAAAAGGTCCTGTGTTACATCCTTCAGAAAAGGTGTAC
       K  S  V  F  L  S  L  C  F  P  G  H  N  V  G  S  L  F  H  M GCAGATGATTTGGGCAGAGCGATGGAGTCCTTAGTATCAGTCATGACAGATGAAGAAGGA
481    ---------+---------+---------+---------+---------+---------+    540
       CGTCTACTAAACCCGTCTCGCTACCTCAGGAATCATAGTCAGTACTGTCTACTTCTTCCT
       A  D  D  L  G  R  A  M  E  S  L  V  S  V  M  T  D  E  E  G GCAGAATAAATGTTTTACAACTCCTGATTCCCGCATGGTTTTTATAATATTCATACAACA
541    ---------+---------+---------+---------+---------+---------+    600
       CGTCTTATTTACAAAATGTTGAGGACTAAGGGCGTACCAAAAATATTATAAGTATGTTGT
       A  E  *  M  F  Y  N  S  *  F  P  H  G  F  Y  N  I  H  T  T (----N----)
       AAGAGGATTAGACAGTAAGAGTTTACAAGAAATAAATCTATATTTTTGTGAAGGGTAGTG
601    ---------+---------+---------+---------+---------+---------+    660
       TTCTCCTAATCTGTCATTCTCAAATGTTCTTTATTTAGATATAAAAACACTTCCCATCAC
       K  R  I  R  Q  *  E  F  T  R  N  K  S  I  F  L  *  R  V  V GTATTATACTGTAGATTTCAGTAGTTTCTAAGTCTGTTATTGTTTTGTTAACAATGGCAG
661    ---------+---------+---------+---------+---------+---------+    720
       CATAATATGACATCTAAAGTCATCAAAGATTCAGACAATAACAAAACAATTGTTACCGTC
       V  L  Y  C  R  F  Q  *  F  L  S  L  L  L  F  C  *  Q  W  Q GTTTTACACGTCTATGCAATTGTACAAAAAAGTTATAAGAAAACTACATGTAAAATCTTG
721    ---------+---------+---------+---------+---------+---------+    780
       CAAAATGTGCAGATACGTTAACATGTTTTTTCAATATTCTTTTGATGTACATTTTAGAAC
       V  L  H  V  Y  A  I  V  Q  K  S  Y  K  K  T  T  C  K  I  L ATAGCTAAATAACTTGCCATTTCTTTATATGGAACGCATTTTGGGTTGTTTAAAAATTTA
781    ---------+---------+---------+---------+---------+---------+    840
       TATCGATTTATTGAACGGTAAAGAAATATACCTTGCGTAAAACCCAACAAATTTTTAAAT
       I  A  K  *  L  A  I  S  L  Y  G  T  H  F  G  L  F  K  N  L
                       inversion start site
                                  |
       TAACAGTTATAAAGAAAGAATTATAAAGGAAAAAGAAAATAACGCAATGGACAAGTGGTG
841    ---------+---------+---------+---------+---------+---------+    900
       ATTGTCAATATTTCTTTCTTAATATTTCCTTTTTCTTTTATTGCGTTACCTGTTCACCAC
       *  Q  L  *  R  K  N  Y  K  G  K  R  K  *  R  N  G  Q  V  V
```

Figure 6 (cont'd)

```
       AAGCTGTGAACTCAGGTGTGCACAATTATCAGGAACACCCCAAAACCAAAGTGAGGTAGA
901    ---------+---------+---------+---------+---------+---------+   960
       TTCGACACTTGAGTCCACACGTGTTAATAGTCCTTGTGGGGTTTTGGTTTCACTCCATCT
       K   L   *   T   Q   V   C   T   I   I   R   N   T   P   K   P   K   *   G   R

AATAGCATGAGAAGCCGTGTTTGATGTTAATTAATT          [SEQ ID NO: 53]
961    ---------+---------+---------+------   996
       TTATCGTACTCTTCGGCACAAACTACAATTAATTAA          [SEQ ID NO: 76]
       N   S   M   R   S   R   V   *   C   *   L   I          [SEQ ID NO: 54]
```

Figure 6 (cont'd)

•cDNA map is not precisely drawn to scale

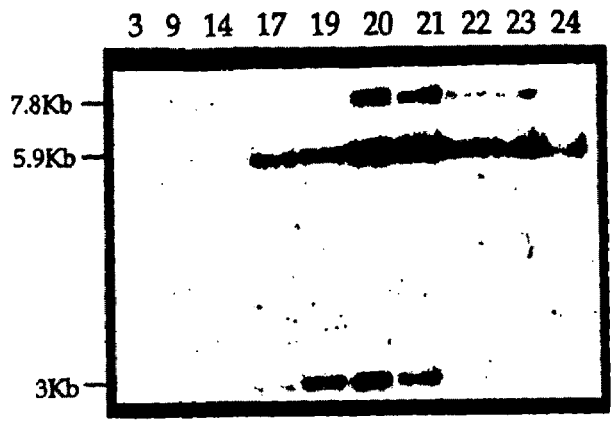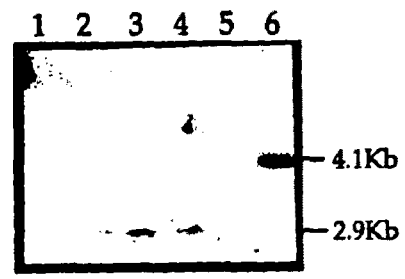
Figure 9A  Figure 9B
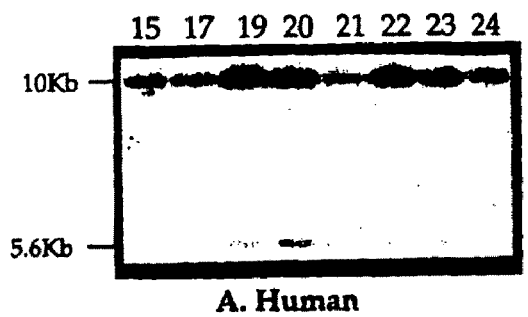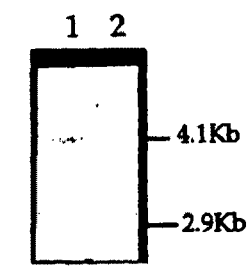
Figure 10A  Figure 10B

```
                1                                                  50
Mgen1073        ..........  ..........  ..........  ..........  ..........
Hapo1234        ctagtttcct  attcaatgta  tagtgcacca  aaggtcaatt  caagagttta
Consensus       ----------  ----------  ----------  ----------  ----------

51                                                 100
Mgen1073        ..........  ..........  ..........  ..........  ..........
Hapo1234        ttattattat  tttcaaccca  agtaaaagca  gagagaaaat  agccacctcc
Consensus       ----------  ----------  ----------  ----------  ----------

101                            begin GRAIL exon @149 150
Mgen1073        ..........  ..........  ttcACAGgCT  tAAgCAGCca  gtAAATGAcA
Hapo1234        accatagcct  cagaagcaag  ccaACAGcCT  gAAaCAGCtt  tgAAATGAaA
Consensus       ----------  ----------  ---ACAG-CT  -AA-CAGC--  --AAATGA-A 151                                                200
Mgen1073        AtT.......  ..........  .........T  AtgtGgtAgt  cAgGtcactG
Hapo1234        AgTtggtgtg  gcggtgatgg  tggcagtgaT  AatgGtgAcc  gAtGgttggG
Consensus       A-T-------  ----------  ---------T  A---G--A--  -A-G-----G 201                                      apo-4 5'end 250
Mgen1073        TGCTGGTaAT  GGTgaTctTA  GcaGgcAgAG  aaGGTGgTaG  TGaTTTGATa
Hapo1234        TGCTGGTgAT  GGTagTggTA  GttGtgA.AG  gtGGTGaTgG  TGgTTTGATt
Consensus       TGCTGGT-AT  GGT--T--TA  G--G--A-AG  --GGTG-T-G  TG-TTTGAT- 251            M1                                  300
Mgen1073        GtaAaagtgt  AgAcTaTaCa  acAgaAtAAa  TACAagtatA  GTAA......
Hapo1234        GatAgtaaaa  AaAaTgTtCg  ttAatAcAAg  TAgAgagtaA  GTAAtcaatc
Consensus       G--A------  A-A-T-T-C-  --A--A-AA-  TA-A-----A  GTAA------

301                    M2              M3         350
Mgen1073        .......atc  caaCAAaGTG  tgAAAGgTGT  gTgCCATtAc  acAtctTTCt
Hapo1234        aatcactcat  agcCAAgGTG  gaAAAGaTGT  aTcCCATcAt  ggAataTTCc
Consensus       ----------  ---CAA-GTG  --AAAG-TGT  -T-CCAT-A-  --A---TTC- 351                                                400
Mgen1073        cG........  GtgATaagag  cCTTgTCTAT  GaAgTTC...  TGAgATgTgT
Hapo1234        tGttctgata  GaaATcttgt  gCTTaTCTAT  GgAaTTCttt  TGAtATaTaT
Consensus       -G--------  G--AT-----  -CTT-TCTAT  G-A-TTC---  TGA-AT-T-T 401                                                450
Mgen1073        TaggAagatG  AAtCatcAat  TtaCaT....  TTcTcCCcat  cAAAtgaCAc
Hapo1234        TtacAttggG  AAcCtgaAtg  TagCtTgaca  TTtTtCCatg  tAAAcacCAg
Consensus       T---A-----G AA-C---A--  T--C-T----  TT-T-CC---  -AAA---CA- 451            begin mouse GRAIL exon               500
Mgen1073        cAtgCTGATC  CAgtATTAAG  CTaATACTAA  C.....ACca  tgcAatGCTT
Hapo1234        tAgcCTGATC  CAacATTAAG  CTgATACTAA  CaaacaACgt  gtaAtgGCTT
Consensus       -A--CTGATC  CA--ATTAAG  CT-ATACTAA  C-----AC--  ---A--GCTT 501                                                550
Mgen1073        CATTAAcAAG  GaTTTGCTTC  TTgCTaGAAA  tgGGT..AAA  AaCggACtgT
Hapo1234        CATTAAtAAG  GcTTTGCTTC  TTcCTgGAAA  ctGGTgaAAA  AtCaaACctT
Consensus       CATTAA-AAG  G-TTTGCTTC  TT-CT-GAAA  --GGT--AAA  A-C--AC--T
```

Figure 11

```
            551                                              600
Mgen1073    GgTcTGTAtA CCtTCaATGC AGCTTaTGTG TTGTCTTttC C..tgAAatG
Hapo1234    GtTgTGTAcA CCcTCgATGC AGCTTcTGTG TTGTCTTcaC CcagaAAtgG
Consensus   G-T-TGTA-A CC-TC-ATGC AGCTT-TGTG TTGTCTT--C C----AA--G 601                                              650
Mgen1073    GtAATGAcTc CCaAtAgtGg cAAccAgggG tacaATaCT. ......TGCA
Hapo1234    GgAATGAtTt CCcAaAtgGc aAAgaAacaG agtgATgCTa tctatcTGCA
Consensus   G-AATGA-T- CC-A-A--G- -AA--A---G ----AT-CT- ------TGCA 651                                     exon79    700
Mgen1073    CacTTTGTAA A....cTCTT TCTTTCTCTT TGTTTTCCAG GACACAATGT
Hapo1234    CctTTTGTAA AgtctgTCTT TCTTTCTCTT TGTTTTCCAG GACACAATGT
Consensus   C--TTTGTAA A-----TCTT TCTTTCTCTT TGTTTTCCAG GACACAATGT 701                                              750
Mgen1073    AGGAAGcCTT TTCCACATGG CAGATGATTT GGGCAGAGCG ATGGAGTCCT
Hapo1234    AGGAAGtCTT TTCCACATGG CAGATGATTT GGGCAGAGCG ATGGAGTCCT
Consensus   AGGAAG-CTT TTCCACATGG CAGATGATTT GGGCAGAGCG ATGGAGTCCT 751                                              800
Mgen1073    TAGTtTCAGT CATGACAGAT GAAGAAGGAG CAGAATAAAT GTTTTACAAC
Hapo1234    TAGTaTCAGT CATGACAGAT GAAGAAGGAG CAGAATAAAT GTTTTACAAC
Consensus   TAGT-TCAGT CATGACAGAT GAAGAAGGAG CAGAATAAAT GTTTTACAAC 801                                              850
Mgen1073    TCCTGATTCC CGCATGGTTT TTATAATATT CgTACAACAA AGAGGATTAG
Hapo1234    TCCTGATTCC CGCATGGTTT TTATAATATT CaTACAACAA AGAGGATTAG
Consensus   TCCTGATTCC CGCATGGTTT TTATAATATT C-TACAACAA AGAGGATTAG 851                                              900
Mgen1073    ACAGTAAGAG TTTACAAGAA ATaAAATCTA TATTTTTGTG AAGGGTAGTG
Hapo1234    ACAGTAAGAG TTTACAAGAA AT.AAATCTA TATTTTTGTG AAGGGTAGTG
Consensus   ACAGTAAGAG TTTACAAGAA AT-AAATCTA TATTTTTGTG AAGGGTAGTG 901                                              950
Mgen1073    GTAcTATACT GTAGATTTCA GTAGTTTCTA AGTCTGTTAT TGTTTTGTTA
Hapo1234    GTAtTATACT GTAGATTTCA GTAGTTTCTA AGTCTGTTAT TGTTTTGTTA
Consensus   GTA-TATACT GTAGATTTCA GTAGTTTCTA AGTCTGTTAT TGTTTTGTTA 951                                              1000
Mgen1073    ACAATGGCAG GTTTTACACG TCTATGCAAT TGTACAAAAA AGTTAaAAGA
Hapo1234    ACAATGGCAG GTTTTACACG TCTATGCAAT TGTACAAAAA AGTTAtAAGA
Consensus   ACAATGGCAG GTTTTACACG TCTATGCAAT TGTACAAAAA AGTTA-AAGA 1001                                             1050
Mgen1073    AA...ACATG TAAAATCTTG ATAGCTAAAT AACTTGCCAT TTCTTTATAT
Hapo1234    AAactACATG TAAAATCTTG ATAGCTAAAT AACTTGCCAT TTCTTTATAT
Consensus   AA---ACATG TAAAATCTTG ATAGCTAAAT AACTTGCCAT TTCTTTATAT
```

Figure 11 (cont'd)

```
                                        begin inversion@1100
             1051                                           1100
 Mgen1073    GGAACGCATT TTGGGTTGTT TAAAAATTTA TAACAGTTAT AAAGAAAGAt
 Hapo1234    GGAACGCATT TTGGGTTGTT TAAAAATTTA TAACAGTTAT AAAGAAAGAa
 Consensus   GGAACGCATT TTGGGTTGTT TAAAAATTTA TAACAGTTAT AAAGAAAGA- 1101                                           1150
 Mgen1073    TgtaAActaA Agtgtgcttt AtAAAAaAAg ttgtTtataA AaaccccctAa
 Hapo1234    TtatAAaggA A.......aa AgAAAAtAAc gcaaTggacA AgtggtgaAg
 Consensus   T---AA---A A--------- A-AAAA-AA- ----T----A A--------A-

1151                                           1200
 Mgen1073    acaaacACaC AcGcacaCAC AcacAcacac AcacaCaCAc AcaCAcAcTG
 Hapo1234    ctgtgaACtC AgGtgtgCAC AattAtcagg AacacCcCAa AacCAaAgTG
 Consensus   ------AC-C A-G----CAC A---A----- A----C-CA- A--CA-A-TG 1201                            1243
 Mgen1073    AGGcAGcAca ttgtTttGcA ttacTtTagc gTGTatcaTA t..   [SEQ ID NO: 57]
 Hapo1234    AGGtAGaAat agcaTgaGaA gccgTgTttg aTGTtaatTA att   [SEQ ID NO: 58]
 Consensus   AGG-AG-A-- ----T--G-A ----T-T--- -TGT----TA ---   [SEQ ID NO: 75]
```

Figure 11 (cont'd)

-70 bp from 5' end of apo-4

Inr   = GCCC TCAT TCTG GAGAC   [SEQ ID NO: 62]
apo-4 = GCGG TGAT GGTG GCAGT   [SEQ ID NO: 63]

- 48% perfect homology with Inr

71% match on type of base (purine vs. pyrimidine)

Figure 12B

A.
```
                    12/23bp spacer
        CACAGTG------------------ACAAAAACC   [SEQ ID NO: 76]
        heptamer                  nonamer
```

```
                                inversion breakpoint₁
          11640      11650      11660   |  11670      11680
            *          *          *     |    *          *
dystrophin  T TTATAACAGT TATAAAGAAA GA^TTGTAAAC TAAAGTGTGC
            A AATATTGTCA ATATTTCTTT CT^AACATTTG ATTTCACACG
                                        a
apo-4 cDNA  840        850           |     870
[ 138 ]     T TTATAACAGT TATAAAGAAA GA^TTaTAAAg gAAAaaGaaa>
            ^ ^^^^^^^^^^ ^^^^^^^^^^ ^^ ^^v^^^^v v^^^vv^vvv
dystrophin  T TTATAACAGT TATAAAGAAA GA^TTGTAAAC TAAAGTGTGC
```

```
          11690      11700      11710      11720      11730
            *          *          *          *          *
dystrophin  TTTATAAAAA AAAGTTGTTT ATAAAAACCC CTAAAAACAA AACAAACACA
            AAATATTTTT TTTCAACAAA TATTTTTGGG GATTTTTGTT TTGTTTGTGT
apo-4 cDNA  880        890        900        910        920        930
[ 138 ]     aTaAaAtggA cAAGTgGTga ATgtgAACtC aggtgtgCAc AAttAtCAgg>
            v^v^v^vvv^ v^^^^v^^vv ^^vvv^^^v^ vvvvvvv^^v ^^vv^v^^vv
dystrophin  TTTATAAAAA AAAGTTGTTT ATAAAAACCC CTAAAAACAA AACAAACACA
```

```
          11740      11750
            *          *
dystrophin  CACACACACA CATACACACA    [SEQ ID NO: 77]
            GTGTGTGTGT GTATGTGTGT    [SEQ ID NO: 78]
apo-4 cDNA  940        950
[ 138 ]     aACAC-CcCA -AaAC-CAaA>   [SEQ ID NO: 79]
            v^^^^ ^v^^ ^v^^ ^^v^
dystrophin  CACACACACA CATACACACA
```

Figure 18B

```
                                                      inversion breakpoint₂
                    13130       13140       13150       13160    |  13170
                      *           *           *           *      |    *
dystrophin    AATTAGCTTT  TGGAGAGTGG GTTTTGTCCA TTATTAATAA   TTAATTAATT
              TTAATCGAAA  ACCTCTCACC CAAAACAGGT AATAATTATT   AATTAATTAA 990
apo-4                                                        _<AATTAATT
                                                              ^^^^^^^^
dystrophin                                                    AATTAATT ------------------------------------------------------------------------
                    13180       13190       13200       13210       13220
                      *           *           *           *           *
dystrophin    AACATCAAAC ACGGCTTCTC ATGCTATTTC TACCTCACTT TGGTTTTGGG
              TTGTAGTTTG TGCCGAAGAG TACGATAAAG ATGGAGTGAA ACCAAAACCC 980        970        960        950        940
apo-4         <AACATCAAAC ACGGCTTCTC ATGCTATTTC TACCTCACTT TGGTTTTGGG
              ^^^^^^^^^^ ^^^^^^^^^^ ^^^^^^^^^^ ^^^^^^^^^^ ^^^^^^^^^^
dystrophin    AACATCAAAC ACGGCTTCTC ATGCTATTTC TACCTCACTT TGGTTTTGGG ------------------------------------------------------------------------
                    13230       13240       13250       13260       13270
                      *           *           *           *           *
dystrophin    GTGTTCCTGA TAATTGTGCA CACCTGAGTT CACAGCTTCA CCACTTGTCC
              CACAAGGACT ATTAACACGT GTGGACTCAA GTGTCGAAGT GGTGAACAGG 930        920        910        900        890
apo-4         <GTGTTCCTGA TAATTGTGCA CACCTGAGTT CACAGCTTCA CCACTTGTCC
              ^^^^^^^^^^ ^^^^^^^^^^ ^^^^^^^^^^ ^^^^^^^^^^ ^^^^^^^^^^
dystrophin    GTGTTCCTGA TAATTGTGCA CACCTGAGTT CACAGCTTCA CCACTTGTCC ------------------------------------------------------------------------
                    13280       13290       13300       13310       13320  SEQ ID
                      *           *           *           *           *     NO:
dystrophin    ATTGCGTTAT TTTCTTTTTC CTTTATAATT CTTTCTTTTT CCTTCATAAT        [80]
              TAACGCAATA AAAGAAAAAG GAAATATTAA GAAAGAAAAA GGAAGTATTA        [81]
                                                 |
                                        inversion breakpoint₃
                 880        870        860        850        840
apo-4         <ATTGCGTTAT TTTCTTTTTC CTTTATAATT CTTTCTTTaT aacTgtTAta       [82]
              ^^^^^^^^^^ ^^^^^^^^^^ ^^^^^^^^^^ ^^^^^^^^v^ vvv^vv^^vv
dystrophin    ATTGCGTTAT TTTCTTTTTC CTTTATAATT CTTTCTTTTT CCTTCATAAT
```

Figure 18C

```
                                                          SEQ ID
                    inversion @ 860                         NO:
    TAACAGTTATAAAGAAAGAATTATAAAGGAAAAAGAAAATAACGCAATGGACAAGTGGTG  [85]
841 ---------+---------+---------+---------+---------+---------+ 900
    ATTGTCAATATTTCTTTCTTAATATTTCCTTTTTCTTTATTGCGTTACCTGTTCACCAC   [86]
```

H2 starting at second methionine - 321 bp, predicted weight = 17.4Kd + 1 N-glycosplation site + 20.4 Kd.

Figure 26A

Splice sites for peptide

MYPIMEYSCSDRNLVLIYGILLIYIYIGNLNMKKEQNKCFTTPDSRMVFIIFI
QQRGLDSKSLQEINLYFCEGFYTSMQLYKKVIRKLHKITQWTRTPQNQSEV
EIA [SEQ ID NO: 64]

Figure 26B

| Start | Exon No. | Exon Position | Exon Length | Intron No. | Intron Position | Intron Length |
|---|---|---|---|---|---|---|
| @88 bp | 78.3 | @74-180 | 106 bp | 79.1 | @181-529 | 349 bp |
| | 79.1 | @530-654 | 125 bp | 79.4 | @655-720 | 66 bp |
| | 79.4 | @721-769 | 49 bp | 79.55 | @770-875 | 105 bp |
| | 79.55 | @876-893 | 18 bp | 79.75 | @894-932 | 39 bp |
| | 79.85 | @933-966 | 33 bp | | | |

Hydrophobicity Scale KD; Candidate membrane-spanning segments:

Certain    1    12- 32   1.8833

Figure 26C

A readthrough apo-4S product using the second available methionine

The Apo-4S peptide sequence

```
P1              Begin TM1 (R)
+30              |                P2
MYPIMEYSCSD RNLVLIYGIL LIYIYIGNLN VARHFSMKTP VARSNIKLIL  80

TNNVKWLHKK GFASSWKLVK NQTLLCTPSM QLLCCLHPEM GNDFPNGKET  130
                                       P3
ERCYLSAPFV KSVFLSLCFP GHNVGSLFHM ADDLGRAMES LVSVMTDEEG  180

AEKMFYNSRP PHGFYNIHTT KRIRQKEFTR NKSIFLRRVV VLYCRFQKFL  230

SLLLFCKQWQ VLHVYAIVQK SYKKTTCKIL IAKKLAISLY GTHFGLFKNL  280

KQLKRKNYKG KRKKRNGQVV KLRTQVCTII RNTPKPKRGR NSMRSRVRCK  330

LI 332 (302aa in predicted polypeptide)  [SEQ ID NO: 59]
```

Figure 27A

Candidate membrane-spanning segments:
| | | | |
|---|---|---|---|
| Certain | 1 | 41-61 | 1.9073 |
| Putative | 2 | 101-121 | 0.8052 |
| Certain | 3 | 132-152 | 1.2552 |
| Putative | 4 | 217-237 | 1.1833 |
| Putative | 5 | 254-274 | 0.9240 |

Transmembrane segments included in structure No. 8: 1 2 3 4 5

Loop lengths: 11 39 10 64 16 58; K+R profile: 1   2   5 (9 >22)

K+R difference: -23: -> Orientation: N-out

Charge-difference over N-terminal Membr. segs. (±15 residues): -4
-> Orientation: N-out CYT-EXT profile (neg. values indicate cytoplasmic preference): <   -0.13   <

CYT-EXT difference: 0.13: -> Orientation: N-out

Figure 27B

Additional Oligonucleotide primers used for apo-dystrophin-4
southern blotting and sequencing

FORWARD

| | | |
|---|---|---|
| GTT CGT TAA TAC AAG TAG | F2.3(@28) | (SEQ ID NO 15) |
| GCC AAG GTG GAA AAG ATG | F2.2(@73) | (SEQ ID NO 16) |
| CCA GTA GCC TGA TCC AAC | F3.2(@208) | (SEQ ID NO 17) |
| GGC TTC ATT AAT AAG | F3.1(@257) | (SEQ ID NO 18) |
| GGC AAA GAA ACA GAG TG | F4.2(@379) | (SEQ ID NO 19) |
| CAG GAC ACA ATG TAG GA | F4.1(@449) | (SEQ ID NO 20) |
| GTT ATA AAG AAA GAA TTA TAA AG | FJm(@846) | (SEQ ID NO 21) |
| GAA AAT AAC GCA ATG GAC | F5.1(@875) | (SEQ ID NO 22) |

REVERSE

| | | |
|---|---|---|
| GAT GGG ATA CAT CTT TTC C | R6.1(@99) | (SEQ ID NO 23) |
| CAA GCT ACA TTC AGG TTC CC | F2.2R(@188) | (SEQ ID NO 24) |
| GGA CTC CAT CGC TCT GCC | R4.1(@510) | (SEQ ID NO 25) |
| GAC TTA GAA ACT ACT G | R3.4(@694) | (SEQ ID NO 26) |
| ATA GAC GTG TAA AAC CTG C | R2.1(@735) | (SEQ ID NO 27) |
| AAC TGT TAT AAA TTT TTA | RSP2(@848) | (SEQ ID NO 28) |
| CTT TTT CCT TTA TAA TTC TTT C | R2.3o(@875) | (SEQ ID NO 29) |

Figure 34

An Additional Splice Product Predicted From The Apo-4 Gene

A second potential theoretical splice product which retains exon 78.3 is shown below.

H2 p1-124 spliced product =351 bp, 117 amino acids + 10 from vector + 1 N-glycosylation site; predicted weight = 21.9 Kd

Figure 35A

Peptide Generated

MFVNTTKVEKMYPIMEYSCSDRNLVLIYGILLIYIYIGNLNMKKEQNKCFTTPDSRMVFII
FIQQRGLDSKSLQEINLYFCEGFYTSMQLYKKVIRKLHKITQWTRTPQNQSEVEIA (117
amino acids) (SEQ ID NO 30)

Figure 35B

| Start | Exon No. | Exon Position | Exon Length | Intron No. | Intron Position | Intron Length |
|---|---|---|---|---|---|---|
| @26 bp | 78.1 | @16-41 | 26 bp | 78.3 | @42-74 | 33 bp |
|  | 78.3 | @75-181 | 106 bp | 79.1 | @182-530 | 349 bp |
|  | 79.1 | @531-655 | 125 bp | 79.4 | @656-721 | 66 bp |
|  | 79.4 | @722-770 | 49 bp | 79.55 | @771-876 | 105 bp |
|  | 79.55 | @877-894 | 18 bp | 79.75 | @895-933 | 39 bp |
|  | 79.85 | @934-967 | 33 bp |  |  |  |

Hydrophobicity Scale KD; Candidate membrane-spanning segments:

Certain    1    22- 42   1.8833

Figure 35C

Nucleic Acid Subsequence Sites Identified In Apo-4

| Motif | Position | Significance |
|---|---|---|
| CpG | -7, (+28, +106) | DNA methylation site |
| CAAT | -132, (+127, +131) | Binding of CAAT factors |
| TATAAT (5/6) | -120, -114, (+10) | TFIID Binding site |
| TATA | -154 | Binds RNA polymerase II and TFIID |
| CCATTCA | -162, -131 | Cap Site I |
| TATCAGT | +12, (+25) | Cap Site II |
| TGGCTGCAAGCCCAA (10/14) [SEQ ID NO: 87] | -57, (+41) | Binds CTF/NF-I protein |
| GTGATGG | -140, -4, +11, +32 | Eucaryotic Transcription Initiation Site |

Figure 36

Top Pred predicts 4-5 transmembrane domains for a full-length
apo-4F product in which all the stop codons are suppressed.

Protein sequence and position of predicted TM domains

```
                                            Begin TM1(R)
                        P1                  |         P2
MFVNTSREKV INQSLIAKVE KMYPIMEYSCSD RNLVLIYGIL LIYIYIGNLN VARHFSMK60

TPVARSNIKL ILTNNVKWLH KKGFASSWKL VKNQTLLCTP SMQLLCCLHP EMGNDFPNGK 120
                                            P3
ETERCYLSAP FVKSVFLSLC FPGHNVGSLF HMADDLGRAM ESLVSVMTDE EGAEKMFYNS180

RFPHGFYNIH TTKRIRQKEF TRNKSIFLRR VVVLYCRFQK FLSLLLFCKQ WQVLHVYAIV 240

QKSYKKTTCK ILIAKKLAIS LYGTHFGLFK NLKQLKRKNY KGKRKKRNGQ VVKLRTQVCT 300

IIRNTPKPKR GRNSMRSRVR CKLI (324 amino acids) (SEQ ID NO 31)
```

Hydrophobicity Scale KD

Figure 37A

Apo-4F : Candidate membrane-spanning segments:

| | | | |
|---|---|---|---|
| Certain  | 1 | 33- 53   | 1.9073 |
| Putative | 2 | 93- 113  | 0.8052 |
| Certain  | 3 | 124- 144 | 1.2552 |
| Putative | 4 | 209- 229 | 1.1833 |
| Putative | 5 | 246- 266 | 0.9240 |

---

I. Transmembrane segments included in structure 8: 1 2 3 4 5; Loop lengths: 32 39 10 64 16 58

Figure 37B

K+R difference: -19; -> Orientation: N-out; Charge-difference over N-terminal Membr. segs.

(±15 residues): -3; -> Orientation: N-out

CYT-EXT profile (neg. values indicate cytoplasmic preference): <    <    <    <   -0.13    <

CYT-EXT difference: 0.13
-> Orientation: N-out

II. Transmembrane segments included in structure 7: 1 3 4 5; Loop lengths: 32 70 64 16 58

K+R profile: 5   >   22   >   5; K+R difference: 22 -> Orientation: N-in

Charge-difference over N-terminal Membr. segs. (±15 residues): -3; -> Orientation: N-out

CYT-EXT profile (neg. values indicate cytoplasmic preference): <   -0.13   <   -0.26   <

CYT-EXT difference: 0.13; -> Orientation: N-out

Figure 37B (cont'd)

RNA transcript is promoted from cell sequences but enhanced and terminated by inversion sequences which may also activate suppressor tRNAs or reverse transcriptase activity to prevent the recognition of stop codons. Inverted repeats (IR) are present at both ends of the inversion, as they are in retroviruses and transposable elements.

US 8,080,376 B2

GENE EXPRESSION CONTROL DNA ELEMENT AND ASSOCIATED PROTEIN

This application is divisional of U.S. application Ser. No. 09/966,264 filed Sep. 28, 2001, now U.S. Pat. No. 7,371,540 and claims the benefit of U.S. Provisional Patent Application Ser. No. 60/237,079, filed Sep. 30, 2000, both of which are incorporated herein in their entireties.

BACKGROUND OF THE INVENTION

The present invention relates to proteins and polypeptides that are capable of interaction with the human CD33 protein, and nucleic acids encoding the same. CD33 is a cell surface marker used to differentiate between acute lymphocytic and acute myelocytic leukemias. The regulation of CD33, including those elements to which it binds in vivo, is not fully understood, and there is still a need for investigation of this biological system. The present invention sets out to address this need.

SUMMARY OF THE INVENTION

Through screening of an expression library we have identified a cDNA sequence that encodes a protein capable of interaction with human CD33, the DNA being highly homologous to a portion of the human dystrophin gene. A region of that cDNA has been identified as an important regulatory element in controlling expression, both transcription and translation, of the DNA with which it is associated.

The region that comprises the regulatory element is minimally that which comprises an inversion sequence that is inverted with respect to the orientation of the DNA in the coding strand of the 3' portion of the human dystrophin gene. The inversion sequence is SEQ ID NO: 1.

In one embodiment, the invention relates to a polynucleotide comprising the DNA sequence of SEQ ID NO: 1 and 10 to 150 additional consecutive nucleotides immediately upstream from SEQ ID NO: 1, or a substantial functional equivalent of the polynucleotide, wherein the polynucleotide is contained in SEQ ID NO: 2.

In another embodiment, the invention relates to a regulatory DNA element comprising the polynucleotide described above, that comprises the DNA sequence of SEQ ID NO: 1 and the additional consecutive nucleotides or, alternatively, the regulatory DNA element is SEQ ID NO: 1 alone.

Other embodiments of the invention relate to proteins or polypeptides encoded by the polynucleotide comprising SEQ ID NO: 1 or, alternatively SEQ ID NO: 1 and the additional 10 to 150 consecutive nucleotides immediately upstream from SEQ ID NO: 1; to antibodies specific for the proteins or polypeptides; to vectors comprising a transcription promotor operably linked to the polynucleotide; to a cell comprising the vector; and to a cell comprising the polynucleotide.

In another embodiment, the invention relates to a polynucleotide comprising the DNA sequence of SEQ ID NO: 2, wherein SEQ ID NO: 2 contains SEQ ID NO: 1. In particular, the DNA sequence of SEQ ID NO: 2 codes for a polypeptide that cannot be produced in a coupled in vitro transcription-translation system in the absence of SEQ ID NO: 1. Further embodiments of the invention relate to proteins and polypeptides encoded by the polynucleotide comprising SEQ ID NO: 2, and to antibodies specific for the proteins and polypeptides.

The invention further relates to a pharmaceutical composition comprising the polynucleotides of the invention; a method of gene therapy; and a method of treating an individual affected by a disorder in which protein truncation plays a part.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1: The inversion sequence of the apo-dystrophin-4 cDNA (SEQ ID NO: 1). A cryptic polyadenylation site is underlined at +989. The complementary sequence SEQ ID NO: 1 is shown as SEQ ID NO: 65. Sequence of the polypeptide encoded by SEQ ID NO: 1 is shown as SEQ ID NO: 66.

FIG. 1A: The inversion sequence of the apo-dystrophin-4 cDNA plus a 10 base-pair region 5' to the start of the inversion sequence (SEQ ID NO: 67). The complementary sequence to SEQ ID NO: 67 is shown as SEQ ID NO: 68. Sequence of the polypeptide encoded by SEQ ID NO: 67 is shown as SEQ ID NO: 69.

FIG. 1B: The inversion sequence of the apo-dystrophin-4 cDNA plus the upstream 150 by from the start of the inversion sequence at base pair 860 to the cleaved Hpa I enzyme site at base pair 710 (SEQ ID NO: 70). The complementary sequence to SEQ ID NO: 70 is shown as SEQ ID NO: 71. Sequence of the polypeptide encoded by SEQ ID NO: 70 is shown as SEQ ID NO: 72.

FIG. 2: The polynucleotide sequence of apo-dystrophin-4 (SEQ ID NO: 2). The inversion sequence shown in FIG. 1 (SEQ ID NO: 1) begins at base pair 860 and ends at base pair 996. The complementary sequence to SEQ ID NO: 2 is shown as SEQ ID NO: 73. Sequence of the polypeptide encoded by SEQ ID NO: 2 is shown as SEQ ID NO: 74.

FIG. 3A. Inserts obtained from a placental cDNA library probed with Fc-CD33 on the 2nd round of panning and digested with Hind III/Pst I; FIG. 3B. Nineteen candidate cDNAs panned with Fc-CD33 and one panned with Fc-CD34, which were subjected to staining for Fc-CD33 binding. Most clones are near 1 Kb in length. The top four Fc-CD33 staining candidates are: b-P2,3; f-apo-4; l-ICAM-1; and n-ICAM-1.

FIGS. 4A, 4B, 4C, 4D, 4E and 4F: FACS Analysis of CD33 candidates shows low avidity binding in COS transfectants (TF). In all the figures, the shaded peak is binding of goat anti-human Ig FITC alone; FIG. 4A. grey peak Fc-CD33 binding to CD33TF; FIG. 4B. Fc-CD33 staining of four candidate ligand transfectants, compared in descending order; individual candidate TF binding to Fc-CD33 is shown in FIG. 4C. to P2, 3TF, 2.2% positive; FIG. 4D. to apo-4, 2.4% positive; FIG. 4E. to ICAM-1, 3.3% positive and FIG. 4F. to ICAM-1, 6.4% positive.

FIG. 5: Fc-CD33 precipitates similar proteins from K562 and transfectants. K562 (Lanes 1-3), and apo-4 (Lanes 4-6) and ICAM-1 (Lane 7) transfectants were iodinated and immunoprecipitated with mouse Ig (Lanes 1 and 4) and Fc-CD33Rg (Lanes 2, 5 and 7) and Fc-CD33pIg1 (Lanes 3 and 6). Fc-CD33 precipitates bands at 46 Kd, 55 Kd, 69-70 Kd and 100 Kd in K562 (Lanes 2-3), a 95-100 Kd doublet ICAM-1 transfectants (Lane 7), and a fainter 100 Kd band from apo-4 (Lanes 5-6) as well as signals at 50 and 66 Kd (Lane 5) more faintly precipitated with Fc-CD33pIg1. Proteins from cell lines are often slightly larger than those from transfectants due to glycosylation differences.

FIG. 6: The full-length apo-dystrophin-4 cDNA and upstream genomic sequence translated (SEQ ID NO: 53). The complementary 76. Sequence of the polypeptide encoded by SEQ ID NO: 53 is shown as SEQ ID NO: 54. Genomic sequence upstream of the apo-dystrophin-4 cDNA is shown from −233 to −1, the start of the apo-4 sequence. The sequence was subjected to a MacVector alignment and was homologous with the 3' end of the dystrophin cDNA, up until the inversion at 860. A search of the 3' 137 bp of apo-4 alone showed that it was precisely homologous to 3' dystrophin sequence 1.62 Kb downstream in the 3' UTR in the reverse orientation and was thus an inversion of the 3' UTR and genomic sequence. Three potential starting methionines are highlighted at +25, +88, and +100 and a potential CAAT box is underlined at +57. These M's are in phase I of apo-4 alone, but appear in phase II here due to the presence of upstream sequence. The longest open reading frame that should be obtainable from this sequence begins with the M at +88 (33aa). The beginning of exon 79 at 453 is also underlined. For a predicted protein in frame 2, a putative transmembrane domain is underlined and putative N-glycosylation sites that follow the Asn-Xxx-Ser/Thr motif are shown (in parentheses when utilized if nonsense suppression occurs). A cryptic polyadenylation site is underlined at +990. The upstream exon identified by GRAIL appears from −90 to −5.

FIGS. 9A and 9B. Human Yeast Artificial Chromosome (YAC) Clone Hybridization verifies the position of the full-length apo-dystrophin-4 cDNA on genomic DNA. FIG. 9A. human and FIG. 9B. mouse YAC clone fragments were probed with the full length 1 Kb human apo-dystrophin-4 cDNA. The apo-4 probe was excised from CDM8 using Hind III and Pst I. FIG. 9A. Human YACs from the 3' end of a genomic dystrophin YAC contig (Monaco et al. 1992) include clones upstream of exons 78 and 79 (3, 7, and 14) as controls and clones 17-24 that include a 3.0 Kb (exon 78), 5.9 Kb and 7.8 Kb (both exon 79) Hind III fragments. The apo-dystrophin-4 cDNA overlaps the human 5.9 and 7.8 Kb fragments. FIG. 9B. The mouse YACs cover the 3' half of the genomic dystrophin DNA (Y. Ishikawa-Brush and A. P. Monaco unpublished). FIG. 9A. Lanes 3, 9 and 14—No hybridization is shown to YAC fragments upstream of exon 79; Lanes 17-24—hybridization is shown to both the 5.9 Kb (5' end of apo-dystrophin-4 cDNA) and 7.8 Kb (3' end of apo-dystrophin-4 cDNA) YAC fragments that contain exon 79. Hybridization to the 3 Kb fragment (Lanes 17-21) may represent cross-hybridization from the probe with the ori and amp regions of the pYAC4 vector (Larin, Z. et al., *Proc. Natl. Acad. Sci. USA*, 88: 4123-4127, 1991) or hybridization to repetitive regions of DNA in intron 78, as apo-4 is not homologous to exon 78, but may be homologous to its intron. FIG. 9B. Lane 6—the full-length probe hybridizes to the 4.1 Kb murine YAC fragment containing the complete region of the apo-dystrophin-4 cDNA. Lanes 1 and 5—no hybridization is shown to a fragment upstream of exon 79. Lanes 3-5—Some intron hybridization is shown to the 2.9 Kb fragment by the probe, which may also represent hybridization to the inverted region of the apo-dystrophin-4 clone. These results show that both the 3' and the 5' ends of the cDNA hybridize genomic mouse DNA in the region of exon 79. There are no Hind III sites in the genomic mouse DNA that overlap the apo-dystrophin-4 cDNA, so all hybridization is in the 4.1 Kb fragment. The 3' region hybridizes to both mouse and human YACs confirming that at least part of this region is well-conserved and provides evidence that the 5' region of the cDNA hybridizes to the expected region in genomic DNA.

FIGS. 10A and 10B: The 5' 451 bp of the apo-dystrophin-4 cDNA hybridizes to both mouse and human YAC clones demonstrating its conservation between species. FIG. 10A. Human and FIG. 10B. Mouse YACs were probed with a 451 bp fragment from the 5' end of the apo-dystrophin-4 cDNA. The probe was excised from the CDM8 vector using Hind III/Pst I and the 451 bp fragment isolated with Xmn I. The human YACs represent 5.6 (3') and 10 Kb (5') fragments cut with Hind III and Sal I that include exon 79 of the complete dystrophin genomic DNA. FIG. 10A. Hybridization is shown to the human "retrofitted" (Eliceiri, B. et al., *Proc Natl Acad Sci USA*, 88: 2179-2183, 1991) 5' 10 Kb genomic fragment containing the 451 5' bp of the apodystrophin cDNA upstream of exon 79. The band at 5.6 Kb could represent hybridization of the probe to intron upstream of exon 79 that acts as an exon in apo-4. FIG. 10B. Lane 1—the mouse 4.1 Kb fragment also hybridizes indicating that some conservation between species exists in the 5' 451 bp region of the apo-dystrophin-4 cDNA. Lane 2—no hybridization is shown to the murine 2.9 Kb fragment that represents the region downstream of exon 79. This analysis verifies that the apo-dystrophin cDNA clone can hybridize in the expected regions of genomic DNA in both mouse and human YACs. The hybridization of the 5' region of the cDNA lends weight to the possibility that this region could contain an intron that could be expressed as an exon and is conserved between species. The figures represent one filter hybridised with the same probe, washed under normal stringency and exposed overnight at −80° C.

FIG. 11. The alignment of Human cDNA and Mouse genomic DNA in the region of Apo-dystrophin-4 (Hapo) sequence. Hapo1234 is the 996 bp of the human apo-4 cDNA, beginning at +239 plus 233 bp of upstream genomic sequence (SEQ ID NO: 58). Mgen1073 represents the genomic mouse DNA sequenced in the apo-4 5' region with some upstream sequence (SEQ ID NO: 57). Apo-4 aligns with genomic DNA apart from the inversion at 1100, where mouse DNA is 35.6% homologous (SEQ ID NO: 75). 96.4% homology is shown at the beginning of the splice acceptor site for exon 79 at 667, to the inversion at 1100. The proposed exon 78.3 ranges from 318-425 and shows 48.5% homology to mouse DNA from the same region. The potential exon identified by GRAIL from 318-425 near the start of the apo-4 cDNA shows 37.9% homology to mouse. The first three starting methionines in apo-4 are underlined between 251 and 350 and designated M1. M2 and M3.

FIG. 12B: An initiation motif found in apo-4 (SEQ ID NO: 62) may act as an Inr promoter (SEQ ID NO: 63) in place of a TATA box. The above sequence begins at −70 in the apo-4 5' UTR and shares nearly 50% homology with the "initiation response element" (Inr) shown to act in place of a promoter.

FIGS. 18A and 18B. Recombination signal sequences are contained around the upstream inversion breakpoint in genomic DNA. FIG. 18A. The nonamer/heptamer motif (SEQ ID NO: 76) found in immunoglobulin sequences surrounding rearrangement breakpoints. Underlining shows regions of 87-100% conservation. FIG. 18B. Sequence begins at 11662 in the 3' UTR of exon 79 of dystrophin cDNA (Koenig et al. 1987) (SEQ ID NO: 77); the complementary sequence to SEQ ID NO: 77 is shown as SEQ ID NO: 78) or 859 on apo-4 (SEQ ID NO: 79). The "a" at 860 in apo-4 was ejected from the alignment by the computer because it decreased the homology. This A appears to be an "orphan" nucleotide" which was inserted to allow a downstream direct repeat to integrate itself into the sequence at the underlining (11,654) similar to the orphan sequence found immediately 5' of the inverted region in the γ globin gene, a causative factor in globin rearrangement (Jones, R. W., et al., Nature, 291: 39-44,1981). Unrearranged genomic DNA contains two sets of recombination signal sequences immediately downstream of the inversion breakpoint in genomic DNA. RSS's are in boldface type and spacers underlined. The second RSS is in a CA repeat, commonly seen in Alu repeats, starting at 11727.

FIG. 18C: Recombination Signal Sequences and direct repeats are found on either side of the uninverted 137 bp sequence in genomic DNA. Sequence of dystrophin fragment is defined as SEQ ID NO: 80; the complementary sequence to SEQ ID NO: 80 is defined as SEQ ID NO: 81; and sequence of apo-4 fragment is defined as SEQ ID NO: 82. RSS's exist on the forward and reverse strands at the upstream junction at 13,163 bp and one with poor homology which overlaps the downstream junction of the inversion breakpoint at 13,299 bp (inclusive) in dystrophin by 1 bp. Potential nonamers/heptamers are in boldface type. A perfect 10 bp overlap is highlighted between apo-4 and dystrophin at 13300-13309, containing a direct repeat and forms a perfect palindrome with its 8 bp inverted repeat 5' at 11,654. In bold area perfect 12 bp inverted repeat upstream of inversion breakpoint$_2$ and a 6 bp inverted repeat upstream of breakpoint$_3$ relative to the lower strands.

FIG. 20A. Reduced gel (left to right). Rabbit Reticulocyte Lysate (RRL) (Lanes 1-4)—Hpa I shows no bands; Pst I shows strong signals at 40 Kd (2 Kd smaller than on a non-reduced gel) and 50 Kd (1 Kd) smaller than on a Nr gel) and 25 Kd; the positive control, Bovine Mosaic Virus (BMV)+RRL does not show bands produced in Pst I (RRL) in a less exposed version shown in (FIG. 20B). Wheat Germ Extracts (WGE) (Lanes 5-8)—only Pst I shows faint broad bands at 34 Kb and 44 Kb, 6 Kb smaller than those in RRL which may reflect differences in glycosylation or an incomplete translation reaction. BMV+WGE shows no band at 33 and a very broad band from 39-46 Kd which is distinct from those in the Pst I lane when compared with the shorter exposure of BMV+WGE in (FIG. 20B). BMV–WGE shows no bands in the same position as Pst I. Reduced samples had 5% β-ME added before SDS-PAGE. The 10% gel was incubated in Amplify for 30 minutes and exposed at –80° C. for 18 hrs and then for five days at –80° C.

FIGS. 26A, 26B, 26C and 26D: Potential apo-4 splice product H2. FIG. 26A. A model of potential splicing of apo-4 using available splice sites. FIG. 26B. Peptide structure with TM underlined (SEQ ID NO: 64); FIG. 26C. potential "new" exons identified; and FIG. 26D. TM domain structure predicted with TopPred showing a cytoplasmic N-terminus. Total spliced length, 321 bp, 107 amino acids=16 Kd+1 N-glycosylation site=3 Kd; proposed weight=19 Kd.

FIGS. 27A, 27B and 27C. Five transmembrane domains are predicted for the full-length apo-4S readthrough product. FIG. 27A. The amino acid sequence (SEQ ID NO: 59) shows the predicted TM sequence as underlined and the regions against which P1 (SEQ ID NO: 3), P2 (SEQ ID NO: 4) and P3 (SEQ ID NO: 5) peptide antisera were designed in bold and underlined beginning with R at +64. Amino acids in which T was changed to A are in bold alone. Structure begins at the "weak" M (+30) included in the P1 peptide antisera followed by the "strong" M at +34. FIG. 27B. A description of the predicted TM domains with those described as "certain" and "putative"; the position of the N-terminus as "outside" is relative to a prediction including all five TM domains, although most predicted TMs which could be utilized predict an "outside" N-terminus. FIG. 27C. The TopPred model of the readthrough apo-4S product which would utilize the second available methionine at +30 aa. The model shows a cytoplasmic N-terminus, although it is calculated to be on the outside of the cell below the model. FIGS. 37A and 37B show the structure predicted beginning at the first M at +8 which would allow for two N-glycosylation sites on an extracellular N-terminus.

FIG. 34: Additional oligonucleotide primers used for apo-dystrophin-4 southern blotting and sequencing, in the forward (SEQ ID NOs 15-22) and reverse (SEQ ID NOs 23-29) directions.

FIGS. 35A, 35B, 35C and 35D: Potential apo-4 splice product of p1-124. FIG. 35A. A model of potential splicing of apo-4 using available splice sites; FIG. 35B. Peptide structure with TM underlined (SEQ ID NO: 30); FIG. 35C. Potential "new" exons identified; FIG. 35D. Tm domain structure predicted with TopPred showing a cytoplasmic N-terminus. Total spliced length, 468 bp, 156 amino acids+10 amino acids in vector, +1 N-glycosylation site; proposed weight=29.5 Kd.

FIG. 36: Nucleic acid subsequence sites identified in Apo-4 (including SEQ ID NO: 87).

FIGS. 37A, 37B and 37C: Five transmembrane domains are predicted for the full-length Apo-4F readthrough product. FIG. 37A. The amino acid sequence (SEQ ID NO: 31) begins at the first available M at 9 aa, underlining the predicted TM domains and the regions against which anti-apo-4 P1 (SEQ ID NO: 3), P2 (SEQ ID NO: 4) and P3 (SE{ } ID NO: 5) peptide antisera were designed in boldface type and underlined beginning with R at +64. Amino acids in which T was changed to A are in boldface alone. FIG. 37B. A description of the predicted TM domains with those described as 'certain" and "putative"; I. the N-terminus is predicted as "outside' relative to a prediction including all five TM domains; II. most predicted combinations of TMs which could be utilized predict an "outside" N-terminus, although the structure to which the program defaulted predicted a cytoplasmic N-terminus, as shown in FIG. 37C. The model shows a cytoplasmic N-terminus although the algorithm predicts an external one.

FIG. 38A. The 5' and 3' terminal inverted repeats characterize retroviruses and transposable elements as well as direct repeats at one end and at the point of insertion. FIG. 38B. The apo-4 pre-inverted sequence has the basic structure of a retrovirus with the exception of a single direct repeat at the 3' end, which probably accounts for the upstream deletion in apo-4 rather than a complete transposition, and a short 118 bp sequence LTR-like sequence containing some repeats. "FIG. 38A" is adapted from a published figure (Temin, H. *Natl. Cancer Inst. Monogr.*, 17: 557-570, 1964) and shows the common elements found in retroviruses and transposable elements (Majors et al., *Cold Spring Harb. Symp. Quant. Biol*, 2: 731-738, 1981).

DETAILED DESCRIPTION OF THE INVENTION

Figure 3A:
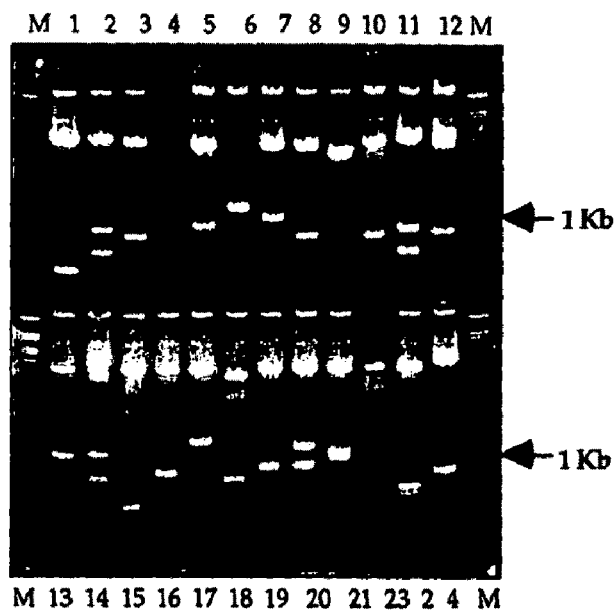
FIGS. 3A and 3B: Representative minipreps from Fc-CD33 Panning.

Unexpectedly, during a process to identify ligands for the CD33 protein, a cDNA was isolated which shares homology to human dystrophin DNA. The putative low-affinity ligand for CD33 was termed apo-dystrophin-4. The apo-dystrophin-4 gene contains an inversion at its 3' end which appears necessary for the production of its two major protein products. Without being bound by theory, it appears that the presence of the inverted sequence in the gene has the basic hallmarks of the insertion of a retrovirus or transposable element into a specific target site in the dystrophin gene prior to splicing and possibly during gene rearrangement.

The naturally occurring 14 Kb dystrophin gene is necessary for normal muscle function. The absence or severe mutation of dystrophin gives rise to Duchenne Muscular Dystrophy (DMD), a progressive, X-linked disease with an incidence of about 1 in 3000. The more benign form of the disease, Becker muscular dystrophy (BMD), is characterized by the presence of an altered dystrophin protein. In normal muscle, dystrophin comprises about 5% of the membrane cytoskeleton. Research focused on how the protein interacts with the plasma membrane, the cytoskeleton and the extracellular matrix (ECM) has found that dystrophin interacts with cell-surface glycoproteins in a dystrophin-associated glycoprotein complex and is thought to function similarly to the integrins with a role in transducing signals from the ECM to the interior of the cell.

The base sequence of the full length cDNA indicates that the normal 427 Kd dystrophin protein encoded by 79 exons has four contiguous domains including: 1) an N-terminal region of 200-240 residues similar to the conserved, actin binding domain, recently shown to bind actin; 2) a large domain comprising 24 helical sequences which resemble spectrin repeats, may be elastic and associated in a coiled-coil structure in the cytoskeleton; 3) a cysteine-rich region between residues 3080 and 3360 which shows homology to C-terminal domain of α-actinin in Dictyostelium and may contain two calcium binding sites, and; 4) 420 unique C terminal residues, apart from their relation to Dystrophin Related Protein, which have been suggested to mediate attachment to at least six lectin-binding membrane glycoproteins. C-terminal deletions or alterations are thought to cause the most severe form of DMD, illustrating the importance of the attachment of dystrophin to cell surface glycoproteins. The members of these glycoproteins, known as Dystrophin Associated Glycoproteins (DAG) and Dystrophin Associated Proteins (DAP) form a tight association with dystrophin and provide evidence that dystrophin could interact via these proteins with the ECM, in an integrin-like manner.

It is known that expression of dystrophin in the brain is distinct from that in muscle and important because approximately one-third of DMD patients suffer from mental retardation. The "brain" form of dystrophin is transcribed from a promoter located at least 90 Kb upstream from the muscle promoter. The brain and muscle forms of dystrophin consequently differ only in the first few N-terminal amino acids. The expression of dystrophin in brain is confined to the postsynaptic regions of cortical neurons and cerebellar Purkinje cells. Dystrophin in Purkinje cells differs from brain dystrophin in that it is transcribed from a third promoter located between the muscle promoter and the second dystrophin exon. "Purkinje cell" dystrophin differs from brain dystrophin by a few amino acids in the N-terminus and accounts for nearly all cerebellar dystrophin.

A series of distal transcripts, termed the apo-dystrophins, also expressed in the brain, have been identified (reviewed in Ahn and Kunkel, *Nature Genetics*, 3: 283-291, 1993; Blake, D. J. et al., *Tr. in Cell Biol.*, 4: 19-23, 1994). Apo-dystrophin-1 or Dp71 is transcribed from a promoter located between exons 62 and 63, splices on the final exon of dystrophin in a new frame which replaces the three usual amino acids with a 31 amino acid (aa) hydrophobic region (Hugnot., J. P. et al., *Proc. Natl. Acad. Sci. USA,* 89: 7506-7510, 1992; Lederfein, D., et al., *Proc. Natl. Acad. Sci. USA,* 89: 5346-5350, 1992). Dp71 is predominantly expressed in brain glial cells, liver, and the stomach and precedes dystrophin expression in embryonic stem cells. Dp116 (apo-dystrophin-2) is transcribed from a promoter between exons 55 and 56 and encodes the last 946 amino acids of dystrophin. It is expressed exclusively in peripheral nerve and some glial cell lines. Another protein of about 40 Kd, apo-dystrophin-3, shares an identical expression pattern with Dp71 and contains the DAG binding site.

The apo-dystrophins arise earlier in development than dystrophin from the 3' end of the dystrophin gene and often produce alternatively spliced products relative to the dystrophin gene. Apo-dystrophin-3, demonstrating conservation with dystrophin at position 9306-10,432 and alternative splice products of apo-1 in exon 78 are positioned nearest to dystrophin homologue described in this study.

The apo-dystrophin cDNA described here, apo-dystrophin-4, demonstrates precise homology to dystrophin from 11,253 to 11,661 and, reversed in an inverted sequence, precise homology at 13,213 to 13,308. Apo-dystrophin-4 also demonstrates a second, weaker homology with dystrophin in an upstream proximal region from position 5070 to 6090, contained within repeats 14-17, and appears to contain the same hydrophobic stretch of 31 aa found in Dp71 in addition to a unique N-terminus. In one embodiment, the present invention relates to a polynucleotide comprising a DNA sequence depicted in FIG. 1 and identified as SEQ ID NO: 1, plus 10 to 150 additional consecutive nucleotides immediately upstream from SEQ ID NO: 1, wherein the polynucleotide is contained in a larger polynucleotide, SEQ ID NO: 2, illustrated in FIG. 2. The polynucleotide of the invention comprising SEQ ID NO: 1 and the additional nucleotides are illustrated in FIG. 1A and/or FIG. 1B and are identified as SEQ ID NO: 67 and/or SEQ ID NO: 70.

It is to be understood that the polynucleotides of the invention include all mutants or variants that differ by base pair additions, deletions, substitutions or inversions, or other mutations, but which retain at least one of the functions of the polynucleotides/DNA sequences and, therefore, are substantial functional equivalents of the polynucleotides, as is known to those of ordinary skill in the art.

In another embodiment, the invention relates to a polynucleotide consisting of the DNA sequence of SEQ ID NO: 1 and 10 to 150 additional consecutive nucleotides immediately upstream from SEQ ID NO: 1, wherein the polynucleotide is contained in SEQ ID NO: 2.

In another embodiment, the invention relates to a regulatory DNA element comprising a polynucleotide having the sequence shown in FIG. 1 and/or FIG. 1A and/or FIG. 1B. That is, the regulatory element comprises SEQ ID NO: 1 and the 10 to 150 additional consecutive nucleotides immediately upstream from SEQ ID NO: 1, as described above, or, alternatively, is SEQ ID NO: 1 alone.

Through screening of an expression library we have identified a cDNA sequence that encodes a protein capable of interaction with human CD33, the DNA being highly homologous to a portion of the human dystrophin gene. A region of that cDNA has been identified as an important regulatory element in controlling expression, both transcription and translation, of the DNA with which it is associated.

The region that comprises the regulatory element is minimally that which comprises an inversion sequence, SEQ ID NO: 1, that is inverted with respect to the orientation of the DNA in the coding strand of the 3' portion of the human dystrophin gene. The polynucleotide that comprises the regulatory element is alternatively that shown in FIG. 1A (SEQ ID NO: 67) or, alternatively, the polynucleotide shown in FIG. 1B (SEQ ID NO: 70), or any portion thereof that includes at least the polynucleotide that consists of SEQ ID NO: 1. It should be appreciated that, from the SEQ ID NO: 70, a group of unique polynucleotides can be formed and that each consists of the base pairs 860 through 996 plus 10 to 150 additional base pairs upstream from the inversion point at 860. By way of example, the group could be described as containing polynucleotides, each represented by one of the following sequences, numbering 144 sequences in total.

base pairs 850-996; base pairs 849-996; base pairs 848-996; bases pairs 847-996; and continuing likewise through base pairs 782-996; base pairs 782-996; base pairs 781-996; base pairs 780-996; and continuing likewise through base pairs 714-996; base pairs 713-996; base pairs 712-996; base pairs 711-996; and base pairs 710-996.

This regulatory DNA element may be used as a regulatory cassette in conjunction with any suitable gene, to modify gene expression.

Accordingly, the regulatory DNA element of the present invention generally serves to control the expression of a gene or other expressed sequence to which it is linked, suitably through controlling the start point of transcription or level of transcription, or the translation of the gene, particularly at the level of translational stop. Preferably the regulatory element acts to control expression at an upstream site, 5' to the regulatory region.

DNA sequences that are substantially functionally equivalent to the DNA sequences of SEQ ID NO: 1 and/or SEQ ID NO: 67 and/or SEQ ID NO: 70 and/or SEQ ID NO: 2 suitably include mutants and variants of such DNA that differ by base pair additions, deletions, substitutions or inversions, or other mutations, but which retain at least one of the functions of SEQ ID NO: 1 in controlling transcription or translation, or other biological functions of this DNA as exemplified herein. DNA sequences that are substantially functionally equivalent to the DNA of SEQ ID NO: 1 may include, by way of example, SEQ ID NO: 67 and, alternatively, SEQ ID NO: 70 and, preferably, one of the group of 144 polynucleotides described above. Of the sequences in the group of polynucleotides, SEQ ID NO: 70 represents the sequence with the maximum number of base pairs that could be required to ensure the presence of the regulatory element of the invention.

Suitably the polynucleotides SEQ ID NO: 1 and/or SEQ ID NO: 67 and/or SEQ ID NO: 70 and/or SEQ ID NO: 2 (which contains the foregoing sequences) are homologous to or identical in sequence to a portion of the human dystrophin gene, preferably at least 70% at the DNA level, preferably 80%, 85%, 86% or even higher, as measured over the length of the polynucleotide. It is to be understood that, although SEQ ID NO: 1 is at least homologous to a portion of the human dystrophin gene, this sequence is inverted with respect to the same sequence in human dystrophin DNA, as described below. Suitable methods for determining such homology are described herein. Preferably the homology is determined in relation to exon 79 of the genomic human dystrophin sequence, or exon 79 and any intronic sequences flanking this exon. Homology to human dystrophin is generally to either strand of the DNA encoding human dystrophin, and suitably as assessed in relation to the human dystrophin sequence that is inverted in orientation with respect to its usual 5'-3' orientation.

Suitably, the polynucleotides SEQ ID NO: 67 and/or SEQ ID NO: 70 and/or SEQ ID NO: 2 comprise a regulatory region of DNA as described herein as SEQ ID NO: 1 that is homologous to human dystrophin, preferably being identical, but is inverted in orientation when compared to the same sequence of the human dystrophin gene. The orientation of the regulatory region is generally the sequence of the DNA from the 5' to 3' direction of the coding strand of the DNA. Preferably the regulatory region is inverted with respect to the orientation of the DNA in the coding strand of the 3' portion of the human dystrophin gene, more preferably in the region of exon 79.

The invention relates further to a polynucleotide comprising the DNA sequence of SEQ ID NO: 2, which contains SEQ ID NO: 1, SEQ ID NO: 67 and SEQ ID NO: 70. It has been unexpectedly discovered that SEQ ID NO: 2 codes for a polypeptide that cannot be produced in a coupled in vitro transcription-translation system in the absence of the DNA sequence of SEQ ID NO: 1 and/or SEQ ID NO: 67 and/or SEQ ID NO: 70. Preferably the invention relates to a polynucleotide wherein a transcriptional start site within the polynucleotide sequence is regulated by the DNA sequence of SEQ ID NO: 1 and/or SEQ ID NO: 67 and/or SEQ ID NO: 70.

Preferably translation of mRNA transcribed from the DNA sequence of SEQ ID NO: 2 is also regulated by the DNA sequence of SEQ ID NO: 1 and/or SEQ ID NO: 67 and/or SEQ ID NO: SEQ ID NO: 70, for example by allowing translational read through of stop codons. DNA having such a property may be ligated or otherwise cloned into any desired gene or regulatory region for a gene, to allow modulation of the expression of that gene.

Accordingly, the invention relates to a polynucleotide wherein the regulatory element that regulates the expression of a region of the polynucleotide. Preferably regulation is at the level of transcription or translation, or both.

Preferably the polynucleotide comprises a regulatory region flanked by a repeat sequence at least one end of the regulatory region, more preferably the sequence AAA-GAAAG 5'-3'. Preferably the repeat sequences are recombination repeat sequences, as defined herein.

Preferably, a polynucleotide of the present invention comprises the sequence shown in FIG. 2 and in the sequence listing as SEQ ID NO: 2, or is a mutant or variant thereof, having substantially the same biological activity. Given the homology of SEQ ID NO: 2 to dystrophin, sequence ID NO: 2 is termed apo-dystrophin-4 herein.

Preferably the polynucleotides of the present invention encode a protein capable of binding to CD33, suitably as assessed by panning technology as described herein. Other suitable methods to identify protein-protein interactions, such as two hybrid screens or immunoprecipitation, are well known in the art.

Preferably a polynucleotide of the present invention encodes a protein or polypeptide that is expressed on the cell surface. Cell surface expression may be of all or part of the protein or polypeptide, and may be assessed by any suitable technology, such as antibody cross reactivity or fluorescence labelling.

Preferably the polynucleotide of the present invention codes for a plurality of translational stop codons. Preferably one or more of the stop codons are rendered non-functional by the presence of the DNA sequence of SEQ ID NO: 1 or a DNA sequence comprising any of the polynucleotides encompassed by SEQ ID NO: 67 and/or SEQ ID NO: 70. Suitably, this regulatory DNA allows the stop codons in the polynucleotide to be ignored, allowing unwanted protein truncation to be avoided, for example.

The present invention also extends to use of a polynucleotide according to the present invention in medicine. The DNA sequence of SEQ ID NO: 1 and/or a DNA sequence comprising any of the polynucleotides encompassed SEQ ID NO: 67 and/or SEQ ID NO: 70 allow read-through of translational stop codons in upstream DNA, and could be used with any suitable gene in this way to, for example, prevent premature translational termination and prevent disease associated with truncated proteins. As such, the invention relates to a method of gene therapy comprising treating an affected individual with an effective amount of a polynucleotide comprising the DNA sequence of SEQ ID NO: 1, or, alternatively a DNA sequence comprising any of the polynucleotides encompassed by SEQ ID NO: 67 and/or SEQ ID NO: 70. Preferably the treatment is targeted to disorders in which the disease results from protein truncation. Such disorders are well known in the art, and include muscular dystrophy, for example.

The treatment of the present invention may be used in combination with other therapies, as appropriate.

The invention also relates to a polynucleotide of the invention in combination with a pharmaceutically acceptable carrier.

We have also determined that the inversion of SEQ ID NO: 1, as found in the context of the polynucleotide of SEQ ID NO: 2, is found in leukemic cells.

Accordingly, the present invention relates to a method of screening for leukemic cells and associated disease states such as leukemia, comprising analyzing DNA for the presence of the inversion sequence of SEQ ID NO: 1 and/or any of the polynucleotides encompassed by SEQ ID NO: 67 and/or SEQ ID NO: 70. Suitable means to analyze DNA for the presence of the inverted sequence are well known in the art, including but not limited to such techniques as PCR followed by sequencing, RFLP analysis or SSCP analysis.

The present invention also extends to a polynucleotide, such as DNA or RNA, which is capable of hybridizing to either strand of the polynucleotide of the present invention under standard conditions of 60° C. and 6×SSC (see, for example, Sambrook, J. et al., Molecular Cloning: A Laboratory Manual. N. Ford, Cold Spring Harbor Laboratory Press, 1989). Suitable polynucleotides include antisense RNA, for example, which may be used therapeutically, where appropriate, to inactivate the expression of apo-dystrophin-4.

Given the association of this gene with leukemia, the invention provides a means to inactivate expression of a gene correlated with a disease phenotype. In addition, antisense technology may be used in conjunction with other therapy, such as gene therapy or drug treatments.

The present invention also extends to vectors comprising DNA sequences of the present invention, such as expression vectors wherein the DNA is in operable linkage with suitable transcription promoter or other regulatory elements. The invention also extends to cells comprising the DNA sequences or vectors of the invention. Suitable vectors into which the polynucleotide of the present invention may be inserted, and suitable cell lines for expression are well known in the art.

The invention also extends to methods of purification of proteins derived from such expression vectors. Suitable purification methods are well known and standard in the art.

In a further aspect the invention relates to any protein or polypeptide encoded by the DNA of SEQ ID NO: 2. Studies using in vitro transcription and translation of SEQ ID NO: 2 have identified 3 protein products capable of being produced from the DNA, depending upon the start codon that is utilized. In particular the invention relates to proteins having molecular weight of ~50, 40 and 25 Kd, obtainable by expression of the DNA of SEQ ID NO: 2, as described herein. Also preferred are multimers of such proteins. Most preferred is the ~50 Kd protein obtainable by expression of the DNA of SEQ ID NO: 2.

The invention also relates to a polypeptide that is a part of one of the proteins of the invention, preferably being polypeptides selected from P1, P2 and P3, as described herein, having the sequences (N terminal to C terminal):

| P1 | MYPIMEYSCSDRN | (SEQ ID NO: 3) |
| P2 | YIYIGNLNVADTM | (SEQ ID NO: 4) |
| P3 | DDLGRAMESLVSVMTDEE | (SEQ ID NO: 5) |

The present invention also relates to antibodies that cross-react with the proteins and polypeptides of the present invention, including both polyclonal and monoclonal antibodies, with antibodies to P1, P2 and P3 especially preferred. Antibodies of the invention may be crude, partially or fully purified, for example.

In a further aspect, antibodies of the present invention may be used in a method of therapy, where appropriate, to interact with the apo-dystrophin-4 proteins of the invention, such that the activity of these proteins is inhibited or reduced. Given the correlation with a disease phenotype, that of leukemia, inhibition of the expression of the apo-dystrophin-4 proteins may be desirable under certain circumstances. Optionally the antibodies of the invention may be used in combination with other therapies, where appropriate.

Antibodies may also be suitably used in a method of screening for a disease state, such as leukemia and leukemic cells. By way of example, cells may be treated with antibodies specific to the proteins or polypeptides of the invention, to check for the presence of such proteins or polypeptides in the cell.

The invention also extends to proteins or polypeptides obtainable (e.g., which may be precipitated) using antisera against the proteins of the present invention, suitably using the antisera identified in the present application.

Also preferred are proteins or polypeptides encoded by a polynucleotide of the invention, wherein at least a portion of the protein or polypeptide is exposed on the extracellular region of a cell in which the protein or polypeptide is expressed. Preferred are the p50 and p40 proteins, as defined herein. Preferably, the protein of the invention is capable of forming a cell surface heterodimer.

The invention further relates to a dystrophin-like protein that is expressed on the cell surface in vivo. A dystrophin-like protein is a protein having homology to dystrophin or portion thereof, at the DNA or protein level. Such a protein is particularly accessible to drugs, such as drugs that do not cross the cell membrane, and may be targeted therapeutically.

Preferably the proteins of the present invention are expressed in one or more of leucocytes, brain, muscle and placental tissues.

Preferably the proteins or polypeptides of the present invention co-precipitate with CD33, as assessed by immunoprecipitation or other suitable techniques standard in the art or as described herein.

Suitably the proteins or polypeptides produced by the polynucleotide of SEQ ID NO: 2 may be markers for disease, or targets for drugs to treat disease. Antibodies to such proteins or polypeptide fragments of such proteins may be used therapeutically, to reduce or eliminate any undesirable effects of the proteins identified in this study.

The present invention is now described with respect to the following figures and examples, which are illustrative of but not binding upon the present invention.

EXAMPLES

CD33 Characteristics

CD33 is a differentiation antigen mainly restricted to cells of the monocytic/myeloid lineage. In clinical diagnosis, CD33 antibodies are used to differentiate between Acute Lymphocytic (ALL) and Acute Myelocytic Leukemias (AML). CD33 transcripts have been reported as 1.8 Kb and 1.4 Kb in a panel of myeloid leukemic cell lines, including U937 (promonocytic lymphoma) from which a cDNA library was constructed. The CD33 cDNA clone was isolated from this library after three rounds of transient expression in COS cells and clonal enrichment through panning with the anti-CD33 Mabs MY9, L1G2 and L4F3. The CD33 insert from transfected COS cells was shown to be 1.5 Kb, possessing a mass slightly smaller than the mass of CD33 expressed on myeloid cells (Simmons, D., and Seed, B. *J. Immunol.*, 141: 2797-2800, 1988). The CD33 cDNA sequence predicts a 40 Kd polypeptide glycosylated to 67 Kd (Simmons 1988). The cDNA sequence of CD33 codes for two immunoglobulin superfamily (IgSF) domains which share the greatest sequence homology (in the V domain) with myelin-associated glycoprotein CD22 (Simmons 1988) and sialoadhesin (Crocker, P. R., et al. *EMBO J*, 13: 4490-4503, 1994) and it has been recently included in a newly defined family of sialic acid binding proteins, the sialoadhesins (Kelm, S., et al., *Current Biology*, 4: 965-972 1994).

CD33 as an Immunoadhesin

The immunoglobulin-like domains found in CD33 suggest that it would be a suitable candidate upon which to develop a CD33 ECD-Fc probe, such as those used previously to construct fusion proteins for HIV therapeutic studies (Capon, E. J., et al., *Nature*, 337: 525-531, 1989), to attempt to probe for CD33 ligand(s) directly using a transient transfection and panning method. This study represents one of the first attempts to employ an ECD-Fc construct like an antibody to identify an unknown ligand, and is believed to be the first attempt with Fc-CD33. Importantly, all previously isolated ligands from the panning technique had used high affinity antibodies as the probe for ligand.

Transient Expression Cloning Systems

The CDM8 vector is known to employ several useful features for the expression of cDNAs in transient expression cloning systems. The CDM8 vector was developed in 1987 by Brian Seed (Seed, B. *Nature.*, 329: 840-842, 1987a) and used in conjunction with the COS cell expression system to achieve high expression of the desired glycoprotein on the cell surface to facilitate the "rescue" of its cDNA by antibody "panning" (Aruffo, A., and Seed, B. *Proc. Nat'l. Acad. Sci. USA.*, 84: 8573-8577, 1987; Seed 1987a; Seed, B., and Aruffo, A., *Proc. Natl. Acad. Sci. USA.*, 84: 3365-3369, 1987b). COS cells were first developed from African green monkey kidney fibroblasts which had been transformed by the SV40 genome and named COS-1 and COS-7 (Gluzman, Y., *Cell*, 23: 175-182, 1981). COS-7 cells were used in the present study. The SV40 genome in the CDM8 vector and in the COS cell, work in conjunction to enable maximal protein expression. The CDM8 based transient expression system has recently been described in detail (Simmons, D. L., *In Cellular Interactions in Development—A Practical Approach*, (Oxford: IRL Press), 93-128.1993; Simmons, D. L., and Needham, L., In *Vascular endothelium: Interactions with circulating cells*, (Oxford: Elsevier Science Publishers B.V.), 3-29, 1991).

Briefly, in the panning method, COS cells are transfected with a cDNA library of interest using the DEAE-Dextran transient expression vector technology. The cells are allowed to express the cDNAs as protein for 36-72 hours post-transfection. The transfected cells are then lifted from the dishes using an EDTA solution, washed and incubated in panning wash with the Fc-adhesin used as a ligand probe in place of antibody. The Fc-adhesin bound cells are then incubated at room temperature on tissue culture dishes pre-coated with Fc-compatible IgG. After 1-2 hours, the dishes are carefully washed 2-3 times and placed under a microscope to observe any binding. Bound cells represent potential ligands expressed on the cell surface binding to the Fc-adhesin. The use of the transfection/transient expression/panning and rescue system and the isolation of apo-dystrophin-4 are described below in detail.

Materials and Methods

A) Monoclonal Antibodies Antisera and Cells

Antibodies included in this work included goat anti-mouse, rabbit anti-mouse and goat anti-human IgG Fc immunoglobulin (Sigma). Anti-CD22 crude and purified polyclonal rabbit anti-mouse CD22 antisera were a gift from Paul Crocker (ICRF Labs, IMM) and were raised against murine Fc-CD22 as previously described (Kelm, S. et al., *Current Biology*, 4: 965-972, 1994). The anti-peptide antisera raised against the apo-dystrophin-4 gene include anti-apo-4 P1, P2 and P3 and were all produced by peptide injection into rabbits in collaboration with Dell Watling at the ICRF antibody production facility at Clare Hall, Hertfordshire, UK. The cell lines were grown in RPMI media supplemented with 10% (wt/vol) fetal calf serum in an atmosphere containing 5% $CO_2$. The cell lines K562 (Lozzio, C. B. and B. B. Lozzio, *Blood*, 45: 321-334, 1975) and COS-7 (COS) (Gluzman, Y., *Cell*, 23: 175-182, 1981) green monkey kidney cells were obtained from the ICRF Cell Production Unit at Clare Hall. The cell lines were grown in RPMI media supplemented with 10% (wt/vol) fetal calf serum. DMEM and RPMI-1640, PBSA, B ($MgCl_2$), and C ($CaCl_2$) and trypsin/EDTA were supplied by ICRF, Clare Hall, Potters Bar, Herts. K562 is an erythroleukemic cell line isolated from a Chronic Myelogenous Leukemia (CML) patient considered to represent an early differentiation stage of the granulocyte lineage and containing a Philadelphia Chromosome 9;22 translocation (Lozzio, 1975).

B) YACS and Related Reagents

Murine λ22 genomic YAC clones were provided by Dr. Jerry Kaplan (Utah School of Medicine, Salt Lake City, Utah, USA). Markers were φX174 RF DNA digested with Hinf I (Gibco BRL). All YAC filters and 3' dystrophin genomic phage clones were supplied by Anthony Monaco and Jamel Chelly (Laboratory of Human Genetics, ICRF Labs, IMM, John Radcliffe Hospital, Headington, Oxford, UK). The dystrophin-negative Blondolet muscle cell line was supplied by the ICRF Cell Culture Unit (Clare Hall, Potters Bar, Herts., U.K).

C) Plasmid Vectors pCDM8 (InVitrogen) and pBluescript (Stratagene) were purchased commercially. Permission to use the Rg vector was granted from Brian Seed, (Department of Molecular Biology, Massachusetts General Hospital, Harvard Medical School, Boston, Mass., USA). David Simmons and John Fawcett (Cell Adhesion Lab, IMM) constructed the pIG1 vector to produce most of the soluble recombinant proteins used in this study (Simmons, D. L., In *Cellular Interactions in Development—A Practical Approach*, (Oxford: IRL Press), 93-128, 1993; Fawcett, J., *Cell Adhesion and Communication*, 2: 275-285, 1994). Murine CD22 in pcDNA I (InVitrogen) was provided by Paul Crocker (Molecular Hemopoiesis Lab, ICRF, IMM, UK) and was constructed as previously described (Kelm, 1994).

D) Molecular Biology Methods

Some basic techniques such as restriction endonuclease digestions are not described here. These methods are well standardized and like other basic molecular biology procedures, were performed using the methods described in the Molecular Cloning Laboratory Manual (Sambrook, 1989), Current Protocols in Molecular Biology (Ausubel, F. M. et al., in Current Protocols in Molecular Biology, John Wiley & Sons, Inc., New York, 1993), or the manual describing antibody use and production (Harlow, E. and D. Lane, Antibodies: a Laboratory Manual, 511-546. Cold Spring Harbor Laboratory, 1988). The same sources were consulted for other essential information such as the safe handling and disposal of ethidium bromide solutions. Standard reagents and solutions are listed at the end of the section except where it is necessary to include them in the body of a given protocol.

(i) Plasmid Preparation (a) Large Scale DNA Preparation ("Maxiprep")

An initial mini culture of bacteria transformed with a particular plasmid were grown in a large volume culture of 800 mls to saturation by overnight incubation in a 37° C. shaking incubator (250 rpm). The following day, the cells were pelleted by centrifugation in a Beckman J6 centrifuge at 4,200 rpm for 20 minutes and the supernatant discarded. The plasmids were extracted by alkaline lysis via the sequential addition of Solution I (40 mls 10 mM EDTA)—followed by vigorous thumping of the bottle to resuspend the pellet; Solution II (80 mls of 0.2 M NaOH—0.1% SDS solution)—followed by swirling the mixture until it became highly viscous indicating complete lysis; and Solution III (40 mls of 3 M KOAc solution)—were added and the bottle gently shaken until flocculated lumps were reduced in size to 2-3 mm indicating that neutralization and genomic DNA and protein precipitation were complete.

The mixture was centrifuged again at 4,200 rpm for 5 minutes and the supernatant poured through a double thickness gauze square into a clean 250 ml centrifuge bottle. The DNA was precipitated from the supernatant by filling the bottle with IsoPropanol, inverting twice and centrifuging again at 4,200 rpm for 10 minutes. The pelleted plasmid DNA was resuspended in 3 mls of high T:E with vigorous agitation or pipeting as necessary. Ideally, the pellet would dissolve immediately.

The final purification of the plasmid DNA was accomplished by Equilibrium Density Gradient Centrifugation ("plasmid banding"). Ethidium bromide solution, 100 µl of a 10 mg/ml solution, was added to plasmid DNA resuspended in 3 ml high T:E in a universal container. Five grams of optical grade cesium chloride (Sigma) was added to each tube, the tops screwed on and the container shaken vigorously until the cesium was taken up into solution, shearing contaminating genomic DNA to facilitate its subsequent separation from plasmid DNA. The mixture was transferred to a 5 ml polyethylene ultracentrifuge tube via a syringe with a 16 gauge needle. The tube would then be filled to the mark with a syringe filled with high T:E, thus avoiding the problem with balancing ultracentrifuge tubes because the entire 5 g of cesium chloride always went into the tube. The balance tubes were sealed on the heat sealing device supplied by the manufacturers before centrifugation in the upright VTi 80 rotor in the Beckman ultracentrifuge T70-M at either 80,000 rpm for 2.5 hours or at 70,000 rpm overnight (>12 hours). The centrifuge was run down without braking to prevent the banded DNA from remixing.

The top of the tube was vented by the insertion of a needle and punctured with a second needle at the position of the nicked plasmids, the upper band of DNA about ⅓ of the way down the tube with the tip being placed 1 mm below the supercoiled plasmid band and then the purified plasmids slowly aspirated with a 1 ml syringe. The aspirate was transferred to a 10 ml polypropylene tube filled with 1 M NaCl saturated Butan-1-ol. The tube was vigorously shaken to extract the ethidium bromide from the lower aqueous phase and the upper organic phase was removed with a pasteur pipette connected to a suction line after 5 minutes. The extraction was repeated if the aqueous phase retained any ethidium bromide as this would inhibit DNA purification. The plasmid DNA was then precipitated by the addition of an equal volume, about 1 ml, of 1 M Ammonium Acetate and the tube filled with ethanol. The plasmid DNA precipitate could usually be immediately visualized as white coiled strands and was recovered by centrifugation in a Beckman GPR benchtop centrifuge at 3,000 rpm for 5 minutes at room temperature. The pelleted DNA was washed with 70% ethanol and resuspended in T:E, usually 1 ml, and the absorbance at A260 measured and usually yielded 1 mg/ml for pCDM8 based plasmid and 3-5 mg from a pUC19 based plasmid, such as pBluescript™ (Stratagene Corporation, La Jolla, Calif., USA).

(b) Small Scale Plasmid DNA Preparation ("Miniprep")

Small-scale preparation of plasmid DNA was done using the alkaline lysis procedure to examine whether colonies from transformed cells contained clones of interest (Murray M. G. and W. F. Thompson, *Nucleic Acids Res.*, 8: 4321-4325, 1980). Colonies were grown from 6-8 hours in universal tubes until saturating growth was achieved. 1 ml of each culture was harvested into Eppendorf tubes and centrifuged in a benchtop microfuge with a 24 position rotor, the limiting factor in the number of minipreps that could be done. An Eppendorf repeating pipette was used to add reagents to tubes. The cells were pelleted by brief (approximately 20 seconds) centrifugation. The supernatants were discarded and 100 µl of Solution I was added to each tube followed by vortexing for 10 seconds until the pellet was resuspended. 200 µl of Solution II was added followed by 100 µl of Solution III to each tube. The tubes were closed and inverted 3 or 4 times by placing an Eppendorf rack on the tubes followed by centrifugation for 5 minutes. Supernatants were transferred to fresh tubes and an equal volume, 500 µl, of the phenol:chloroform mixture (50:50 v/v) added to all tubes. The tubes were closed and vigorously shaken for 1 minute in an Eppendorf rack "sandwich", centrifuged for 1 minute and the upper aqueous phase transferred to new tubes. The tubes were filled with Propan-1-ol from a squeeze bottle, sealed and inverted twice followed by centrifugation for 5 minutes to pellet the DNA. Plasmid pellets were washed twice by filling the tubes with 70% ethanol and inverted by placing a ruler on the Eppendorf lids. Pellets were resuspended in 50 µl T:E containing pre-boiled RNAase A at a final concentration of 10 mg/ml. To aid resuspension and destroy any residual endonucleases the tubes were incubated for 5 minutes at 70° C. The DNA was then ready for restriction digest or with well purified pBluescript plasmids, DNA sequencing.

(ii) Oligonucleotide Synthesis

Oligonucleotides for PCR, probes, and DNA sequencing were synthesized within the laboratory on an Applied BioSystems synthesizer using standard phosphoramidite chemistry with reagents supplied by the manufacturer. Some standard primers such as the universal vector-based primers used for DNA fragments cloned into pCDM8 and pBluescript SK$^+$ were obtained from the Oligonucleotide Synthesis Service Laboratory at ICRF Central Services, Clare Hall, Potters Bar, South Mimms, Herts., U.K. These were supplied as DNA precipitates which were resuspended at 100 ng/ml for use.

(iii) Construction of Fc-Adhesins

The primers listed below were used to amplify the CD33 fragment via PCR for insertion into the pIG1 vector as previously described (Barber, E. K. and D. L. Simmons, *J. Cell. Biochem.*, 17a: 346, 1993; Simmons, 1993; Freeman, S. D. et al., *Blood*, 85: 2005-2012, 1995). In the Forward Amplification Primer (FAMP), a Hind III restriction site was included preceded by the appropriate overhang to allow for restriction enzyme digestion immediately following PCR. The Reverse Amplification Primer (RAMP) includes a Bgl II site followed by a splice donor motif (5' ACTTACCTGT 3') (SEQ ID NO: 6) which will splice directly into the splice acceptor site engineered into the intron 3' of the hinge to create an in-frame splice junction for protein processing. Following PCR of the CD33 insert from the Rg vector, PCR products were resuspended in 11.5 µl T:E and digested in Hind III/Bgl II and 1.5 µl restriction buffer for 3-4 hours prior to ligation into the PIg1 vector.

(iv) Polymerase Chain Reaction (PCR)

The polymerase chain reaction was used to amplify specific fragments of DNA from cDNA libraries or plasmids using a forward and a reverse primer. PCR was always done in a reaction volume of 100 µl. The buffering conditions generally used were those recommended by the manufacturer (Perkin-Elmer) according to the standard protocol for a given reaction which included: 10 µl 10×PCR buffer, 1 µl of each PCR primer (used at a concentration of 1 mg/ml), 1 µl of a dNTP solution (containing all 4 nucleotides at a concentration of 25 mM—supplied by Pharmacia—ultrapure dNTP set), 10 µl of template DNA, 0.5 µl Taq polymerase (2.5 Units, various manufacturers), and distilled water to a final volume of 100 µl.

The reaction mixtures were overlayed with 100 µl of light mineral oil (Sigma Chemical Co., St. Louis, Mo., USA). The DNA templates used included: 1) 10 ng of pure plasmid DNA, either cDNA clones (for constructing soluble forms of cell adhesion molecules or using a captured cDNA as a control), or cDNA libraries; 2) 1st strand cDNA—when reverse transcriptions were performed from 10 µg total RNA, 10 µl of a 100 µl reaction was used immediately following transcription as described under RT-PCR, and; 3) 200 ng of genomic DNA. The PCR program was generally set into 30 cycles consisting of denaturation at 94° C., primer hybridization at 37-50° C., depending on the manipulation, and extension at 72° C. The length of each incubation step and annealing temperature varied according to the target sequence being amplified and conditions used for individual reactions are described under each type of experiment. Following the run, the reactions were kept at 4° C. until 10 µl of each reaction was analyzed by electrophoresis on a 1% agarose gel to check for product amplification. Products could be "blunt" cloned into a vector, usually pBluescript, for DNA sequencing and it was necessary to "end-fill" the amplified product to accomplish this. End filling was accomplished by the direct addition under the oil of 1 µl of 25 mM dNTPs and 10 U of Klenow DNA polymerase followed by incubation for 15 minutes at 37° C., the addition of 10 units of polynucleotide kinase and a final incubation for 30 minutes. The remaining Taq buffer was sufficient to ensure the appropriate buffer concentration. The product DNA was then purified from the mineral oil and Taq polymerase by DNA extraction with an equal volume of a phenol/chloroform mix and precipitation by the addition of an equal volume of 1 M Ammonium Acetate ($NH_4Ac$) solution, 10 µl of 10 mg/ml of a linear polyacrylamide (LPA) carrier and 3 volumes or greater of Propan-1-ol. The mix was placed on dry ice for 10-15 minutes. The DNA was pelleted by centrifugation at 14,000 g in a microfuge for 5 minutes and the pellet was washed twice in 70% ethanol, inverting the tube to discard the supernatant. 100 µl of T:E was added to resuspend the pellet for further manipulations. The $Mg^{++}$ optimum and suitable annealing temperature was established with each set of primers but standard conditions were usually suitable for all primers used. Primer combinations were checked when possible for potential dimerisation using the "Amplify" program. Cycling parameters depend on the primer combination and the product size, if known. A program using 30 cycles was known to give a clear ethidiuim band on an agarose gel. To get this working well on a regular basis without contamination with cDNA, separate stock solutions were made, separate pipetmen were used, and in some cases, experiments were done in a separate laboratory to prevent plasmid cDNA contamination. It was not usually necessary to use a laminar flow hood, with the extra precautions taken, however.

(v) Purification of DNA Fragments Using Geneclean™

For the rapid ligation of PCR products into vector, the Geneclean system (BioRad) was often used to increase the efficiency of DNA purification. To use this system, PCR products were first run out on a 1% low melting point gel. Band was excised from gel and the gel was digested by the addition of 3 volumes of NaI stock solution. Agarose was dissolved by incubation at 5 minutes at 45° to 55° C. Glassmilk suspension was added and incubated for 5 minutes. Glassmilk/DNA complex was pelleted by microfuging the pellet for 5 seconds and removing the supernatant. Pellet was washed 3 times with New Wash and DNA was eluted by the addition T:E into the appropriate volume, usually 100 µl for further manipulations.

(vi) End Filling of DNA for Blunt End Ligation

Following PCR, uneven or "sticky" ends would be left on the PCR products which needed to be filled in prior to blunt end ligation into pBluescript via an enzymatic reaction. The following reaction was set up for each fragment:

5 µl fragment (1 µg or half of the preparation)
2 µl 10× Klenow Kinase buffer
1 µl Klenow (1 U)

1 µl T4 polynucleotide kinase (10 U)
1 µl dNTP's (N=G, T, A, C)
10 µl dH$_2$O
20 µl Total Reactions were incubated at 37° C. for 30 minutes. An insert could be transferred from CDM8 to Bluescript directly by virtue of their compatible EcoRV sites. The insert could then be cut out and end-filled with Klenow and dNTP's using the above method. A 50 µl end filling reaction was allowed to proceed for 15 minutes at 37° C. The DNA was then precipitated to purify it and resuspended in 10 µl (~2 µg) using 5 µl (1 µg) for ligation with 100 ng of vector using the ligation mix described below (4 µl Low Salt Buffer, 4 µl Ligation Additions, 5 µl Ligase, 1 µl vector, 5 µl insert, brought to 40 µl with dH$_2$O. If the DNA was purified using the Geneclean II™ kit, each fragment to be ligated was brought to a final volume of 11.5 µl in dH$_2$O. In preparation for blunt ended ligation, pBluescript SK$^+$ was digested with either canine or shrimp intestinal phosphatase at 37° C. according to standard procedure (Sambrook, 1989), precipitated and the purified product diluted to 100 ng/µl ie. 10 µl (1 mg/ml) DNA in 20 µl H$_2$O. 100 ng vector was used per ligation. Blunt cloning was always done into pBluescript at the EcoRV site which allowed blue/white selection of recombinants by lacZ induction with IPTG in the presence of X-Gal as an indicator substance. Reactions were incubated at 12°-15° C. overnight, transfected into competent TG-1 cells and spread on "high-amp" plates as described below with IPTG/X-Gal and following overnight incubation at 37° C., blue colonies were picked and grown up for small scale DNA preparation.

For "sticky" end ligation to clone the uneven DNA fragments directly, the digested DNA or PCR product was purified by electrophoresis through low melting point agarose on a slide gel as described in "DNA electrophoresis". The insert bands were excised just around the visible portion during brief visualization with long wave ultraviolet light and the fragments were transferred to Eppendorf tubes. The volume of bands excised from slide gels was estimated to be 12.5 µl and 12.5 µl of T:E was added to prevent the gel from congealing during subsequent manipulations. The gel fragments were melted by heating to 70° C. for 15 minutes and quickly transferred to 37° C. at which temperature all subsequent manipulations and incubations were done. To the melted gel slice of approximately 25 µl 4 µl 10× Ligation Additions, 4 µl Low Salt Buffer (10×), 1 µl 100 ng DNA vector or 11 µl of a melted diluted gel slice containing 100 ng vector and 5 µl ligase were added for a final volume of 40 µl. During this time a vector control was prepared by assembling a separate tube with all of the above components but making the volume up to 40 µl by adding water or T:E in place of the insert volume. The reactions were mixed well and allowed to proceed for 30 minutes.

During this time, a vial of transformation competent bacterial cells was taken from the freezer and allowed to thaw on ice for 15-30 minutes. TG1 cells were used with pBluescript ligations and MC1061/p3 cells were used with CDM8 ligations. The preparation of these cells is described in the section below. Agar plates were then either dried or poured, including the appropriate antibiotics to express the drug resistance genes in either CDM8 or pBS. To prepare the plates, a bottle of LB agar was melted for 5-10 minutes on medium power and cooled to 55° C. To prepare "amp/tet" plates for CDM8 plasmids, 75 µl of tet and 100 µl of amp were thawed from freezer stocks for a final concentration of 7.5 mg/ml tetracycline and 12.5 mg/ml ampicillin. For pBluescript, "high amp" plates were prepared with a final concentration of 100 mg/ml ampicillin in LB agar. 10 mls of well mixed LB was poured into 10 cm dishes and 15 mls was poured into 15 cm dishes (for Hirt transformations covered in the panning section) and plates were allowed to set for 10-15 minutes. The thawed competent cells were flicked to mix. 5-10 µl (1/10 volume) of ligation mix was mixed with gentle flicking in a 50-100 µl aliquot of thawed competent cells. The mix was allowed to sit on ice for 10-15 minutes followed by a "heat shock" for five minutes at 37° C. The cells were then kept at room temperature until spreading on the agar plate with a flame-sterilized spreader.

A system was developed by David Simmons to allow MC1061/p3 to recover from heat shock and to begin to express antibiotic resistance genes prior to contacting the antibiotics in the plate. 5-10 minutes before plating, 5 mls of drug-free agar was poured on the amp/tet plates and allowed to set during the incubation on ice and the heat shock period. The cells were then carefully spread on the agar to prevent breaking the surface. It was unnecessary to use top agar with the TG1 cells which contained only conventional ampicillin resistance genes. With these cells, 50 µl of a mix of 20 mg/ml X-Gal and 20 mg/ml of IPTG in Dimethyl Formamide was spread during heat shock when blue-white colour selection was required. The following day, if colonies were evident, 24-48 were picked and grown for small scale DNA preparation.

(vii) DNA Probe Preparation (a) Random Primed Synthesis of DNA Probes

This was always done using commercially available kits (Boehringer Corporation, Mannheim, Germany), which follow the method developed by A. P. Feinberg and B. Vogelstein (*Analytical Biochemistry*, 132: 6-13, 1983). As a template for labelling plasmid inserts were excised by restriction digest and purified by electrophoresis through a thin low melting point agarose gel. To probe yeast artificial chromosome (YAC) clones, a 5' 546 bp cDNA probe was made by digesting the apo-4 cDNA in CDM8 with Hind III and Hinf I. A 3' 280 bp apo-4 probe was made by digesting the apo-4 gene in CDM8 with HindIII, Pst I and Hpa I which cut at 709 bp. For RNAse protection, a 3' probe was made by ligating the cut fragment into pBluescript. The DNA representing the insert to be used as a probe was visualized under long wave, low-intensity ultraviolet light and excised. The excised band was then reloaded on a fresh gel and repurified. An equal volume (12.5 µl) of water was added to the gel slice containing the probe DNA and the gel was melted and the DNA denatured at 100° C. for 5 minutes. The probe was labelled in a reaction according to the manufacturers instructions at 37° C. to prevent the gel from congealing. The reaction components included:

Insert DNA (25-100 ng)~12.5 µl gel mixture
3 µl of dNTPs (bases G, A and T only)
2 µl of 10× reaction buffer supplied
5 µl of $\alpha^{32}$P-dCTP (specific activity 3000 Ci/mmol)
water to bring volume to 19 µl
1 µl of supplied DNA polymerase (Klenow fragment)
20 µl final volume The reaction tube was closed after mixing the contents with a pipetman. Reactions were incubated for 1 hour. 100 µl of "high" S:T:E buffer was added to the reaction and the unincorporated nucleotides were separated from the labelled probe DNA by gel filtration through Sephadex G-50 columns pre-equilibrated with S:T:E, by spinning at 1000 rpm for 5 minutes. The activity not retained through the column was the probe DNA and specific activity was then measured by measuring Cerenkov counting, expecting a specific activity of at least 5×10$^5$ cpm per µl of DNA. Before use all probes were denatured by heating to 100° C. for 5 minutes.

(b) End Labelling of Oligonucleotides

For southern blotting, oligonucleotides were end labelled by a 5' phosphorylation reaction catalyzed by T4 polynucleotide kinase. Labelling reactions consisted of:

15 µl sterile distilled $H_2O$
1 µl oligo 15-21 mer 20 pm/ml (~1 mg/ml)
2 µl 10× kinase buffer
1 µl T4 polynucleotide kinase (Pharmacia, Uppsala, Sweden)
1 µl $\gamma^{32}$p-ATP (3000 Ci/mmol, Amersham, UK)

After 30 minutes to an hour incubation at 37° C., labelled oligonucleotide was purified from excess radioactivity by the use of Sephadex G-25 spin columns or ethanol precipitation as described above. Each probe mix was enough for two filters.

(viii) DNA Analysis (a) DNA Agarose Gel Electrophoresis

All DNA gel electrophoresis was done through agarose gels cast in T:A:E buffer containing 10 mg/ml of ethidium bromide solution. For many purposes e.g. to check for the presence of amplified products indicating successful PCR reactions, electrophoresis through pre-cast mini-gels on 3×2 inch glass slides was used. These gels were stored for up to 2 weeks in an airtight container stacked on paper soaked in 70% ethanol. Since they are very thin gels these have the advantages that small quantities of DNA can be analyzed and, for applications such as probe preparation and purification of PCR products for sub-cloning, DNA fragments can be cut from gels in a minimum quantity of agarose. The estimated volume of excised gel fragments was 12.5 µl. If the gels are stored too long, the gel can separate from the slide and sample can be lost.

For more than five samples (e.g. miniprep analysis) or prior to transfer to nylon membranes gels of 1 to 1½ cm thickness were cast immediately before use by melting 100 ml of T:A:E/agarose solution for 3-5 minutes in a microwave oven and cooling under tap water to 50° C. before pouring. The standard running buffer was also T:A:E containing 10 mg/ml ethidium bromide. Before loading gels, ⅒th volume of Ficoll-containing 10×DNA loading buffer was mixed with each sample. The voltage applied to gels was: 100V for mini gels and 150V for large gels, running the gel until the orange G dye front reached the anodal or lower end of the gel. 1% agarose Mini-gels were run quickly in about 15 minutes and 1% low melting point agarose in 30 minutes at 60-70V to prevent melting and loss of resolution. For all gels DNA size markers were included, usually λBst XI (4 Kb) DNA restricted with BstE II or φX 174 (1 Kb) DNA restricted with Hae III for the sizing of small fragments. DNA fragments were viewed under ultraviolet light with protective goggles and photographed by Polaroid photography. Fragments viewed for the purposes of excising bands for cloning were examined under long wave ultraviolet light to minimize DNA damage.

(b) Southern Blot Hybridization

DNA samples from RT-PCR were first resolved according to size by electrophoresis as described above. 10 µl of a 100 µl PCR reaction was loaded on to the gel to be transferred for Southern blotting (Southern, E. M., *J. Mol. Biol.*, 98: 503-517, 1975). To prepare the gel for transfer, after photographing the gel, the DNA was denatured in a 1 litre solution of 1.5 M NaOH/0.5 M NaCl for 1 hour. A piece of Hybond N+ nylon transfer membrane was cut to the exact size of the gel and several pieces of Whatman 3 paper slightly smaller than the gel as described (Ausubel, 1993). The gel was transferred to the membrane and paper, the bubbles were removed, and the apparatus assembled to effect capillary transfer to the membrane using denaturing solution to wick the solution up onto the membrane. Transfer was continued overnight, although several hours was usually adequate. Alkaline transfer was carried out in the same solution as denaturation. Lanes of the membrane were marked with pencil, noting the DNA side. Membrane was neutralized with 2×SSC for 1 minute and dried under light between two sheets of Whatman paper. Blot can be baked at 80° C. for 2 hours although this is not strictly necessary. DNA was immobilized to the blot with crosslinking under U.V. light at 1000 J for 1 minute (Stratalinker, Stratagene Corporation, La Jolla, Calif., USA). The filter was briefly rinsed again in 0.15 M NaCl and could be stored wrapped at room temperature or damp in the −20° C. freezer in plastic wrap. Because of the small size of PCR products, transfer could be done in 1 hour, in high salt solutions, although it was usually done overnight using conventional conditions to insure complete transfer and to prevent possible damage to the DNA from rapid transfer or if rapid transfer was not convenient.

Membrane prehybridization used the same solution for YAC and RT-PCR filters. Oligonucleotide hybridizations were done with the Church and Gilbert buffer system (Church, G. M. and W. Gilbert, *Proc. Natl. Acad. Sci. USA*, 81: 1991-1995, 1984). Prior to the addition of probe, the blot was prehybridized at 42° C. for one hour to block potential nonspecific background signals with the prehybridization solution. For 500 ml final volume the following mixture was prepared in a 200 ml flask according to the procedure previously described (Monaco, A. P. et al., *Genomics*, 12: 465-473, 1992) (courtesy of the Human Genetics lab, IMM):

| | |
|---|---|
| 250 ml | 50% formamide |
| 100 ml | 4× SSC |
| 25 ml | 50 mM NaPi |
| 1 ml | 1 mM EDTA |
| 50 g | 10% Dextran sulfate |
| 50 ml | 10% SDS |
| 5 ml | 10X Denhardts Solution |
| 1.25 ml | Yeast tRNA |

All components were mixed except Denhardt's and Dextran Sulfate warming to 40-50° C. Dextran was added slowly and heated while stirring at position 3-4 on the hotplate. When dextran was dissolved, the remaining components were added and stirring continued at 45° C. until the solution became clear. The bags were then cut open at one corner and the denatured probe was added to minimize bubble formation to a final concentration of $10^6$ cpm/ml. The bags were resealed and hybridization was carried out overnight, at the optimum Tm based on the purine and pyrimidine content for a DNA probe as calculated blow. *Tm is calculated to determine hybridization temperature.

G/C=4° C.
A/T=2° C.
GCCCAA 20°=$T_m$
Wash T°=$T_m$ −5° C.

For oligonucleotide probes, hybridization was always carried out at 42° C. Hybridization was carried out for 3 hours or overnight at 42° C. for oligo probes. For Washes 2×SSC+ 0.1% SDS was used unless more or less stringent conditions were required depending on the activity registered on the blot after the first wash. The buffer was changed immediately after first wash and the activity on the blot monitored. The second wash for 10 minutes at room temperature with shaking was followed by a wash for 1.5 minutes at the appropriate Tm* (the same as the hybridization temperature) if high activity was detected or a wash 10 minutes at room temperature with shaking for low activity. Surplus buffer was blotted on 3 mm paper. Damp filters were mounted on 3 mm Whatman paper and wrapped in plastic wrap for autoradiography with fluorescent markers and intensifying screens at −80° C. overnight.

(c) Denaturing Sequencing Gel Electrophoresis

To determine the DNA sequence of cDNA library clones obtained from panning and PCR, the Sanger dideoxy sequencing method was used (Sanger, F. et al., *Proc. Natl. Acad. Sci. USA*, 74: 5463-5467, 1977). The standard BioRad glass plate apparatus was used with seals held by virtue of accompanying rubber brackets. Polyacrylamide sequencing gels consisted of 1× T:B:E/5% acrylamide containing 5 M urea. For sequencing, 200 mls of gel mix was made up by mixing 20 mls of 10×T:B:E, 25 mls of 40% acrylamide solution (39 linear:1 bis), 100 g urea and making up to 200 mls with $dH_2O$. The solution was stirred on a stir plate and heated to allow the urea to go into solution. To form a plug at the bottom of the sequencing plates, 1 ml of 10% Ammonium persulfate solution (APS) and 100 µl of TEMED were added to 50 mls of the solution. The mix was then quickly poured into a casting tray in which the assembled sequencing apparatus was stood and the screws were tightened at the bottom to allow the apparatus to stand. After 10-15 minutes, following polymerization, the rest of the gel mix was polymerized with 1 ml of APS and 100 µl of TEMED and poured slowly between the glass plates as the apparatus was held or rested on a support at its top end. Before the gel set, a comb was inserted with the flat side toward the gel, between the plates, at the top, to create a slot into which shark's teeth combs would be inserted. Following polymerization after about 1 hour or overnight, the top combs were removed and the apparatus was placed in a running tank to which 400 mls of 1×T:B:E were added. The top tank, behind the back sequencing plate, was also filled with 1×T:B:E to cover the gel, the electrodes connected and the gel warmed by running it at 100 W for about 15 minutes until the temperature indicator on the front plate read 50° C. The top well was then flushed out with a large syringe full of 1×T:B:E to remove accumulated urea from the gel and the shark's teeth comb carefully inserted so that the depth of the teeth in the gel was about 1-2 mm. Denatured DNA sequencing reactions could then be loaded (2 µl if narrow width combs were used, otherwise up to 4 µl) and the gel run at 100 W constant power. As soon as the samples had run into the gel, 200 mls of 3 M Sodium Acetate solution were added to the bottom tank to create an electrochemical gradient from the bottom to the top of the gel and to retard the progress of the DNA samples in the gel with the maximum retardation occurring towards the bottom of the gel (Sheen, J. Y. and B. Seed, *Biotechniques*, 6: 942-944, 1988). This allows the gel to be run longer to get improved resolution of the larger sized DNA fragments while preventing the smaller, faster fragments from moving off the gel into the bottom tank. This has the effect of increasing the amount of readable sequence and therefore the alternative practice of loading short and long runs was not necessary. A gel run would be terminated as soon as the bromophenol blue dye front had reached the bottom of the gel. Routinely a single reaction would give up to 300 bp of readable sequence.

After the gel was run the plates were separated and the gel lifted off by carefully adhering a sheet of Whatman No. 3 blotting paper to it covering it with Saran™ wrap (Dow Corporation, USA) followed by transfer to a vacuum gel drier, after trimming if necessary. The gel was dried over two sheets of Whatman paper to prevent urea leeching into the drier under vacuum for approximately 30 minutes to an hour at 80° C. until dry to the touch and the Saran wrap could be fairly easily removed. The gel was cut to the size of a cassette and exposed to X-ray film without the use of intensifying screens at room temperature for 8-12 hours or longer if necessary.

(ix) RNA Analysis (a) RNA Isolation

To determine whether cDNAs isolated from the panning process were expressed in other tissues, ribonucleic acid (RNA) was extracted from cell lines and selected tissues with guanadinium isothiocyante (GuSCN) and separated from other cell components using the cesium chloride step gradient system according to the method originally established (Chirgwin, J. et al., *Biochemistry*, 18: 5294-5299, 1979) and summarized for various tissues (Ausubel, 1993). The procedure takes advantage of the property that RNA is the densest cell component and can thus be relatively easily purified. The initial extraction is performed under completely denaturing conditions. With all further manipulations, however, the standard precautions to avoid RNA degradation by RNAses on the hands and on glassware were insured by using gloves, disposable plasticware and using solutions, apart from EtOH, treated with diethyl pyrocarbonate (DEPC). To further prevent contamination, all RNA for the northern blot of the apo-4 gene and some RT-PCR reactions was prepared in a separate lab in a laminar flow hood (courtesy of Professor Andrew McMichael, Molecular Immunology Lab, IMM, Oxford).

Solid tissue samples were immediately frozen in liquid nitrogen and ground with a mortar and pestle prior to RNA extraction to prevent possible RNA degradation during extraction. Solid tissue samples included 1) a skeletal muscle specimen was collected from theatre during a surgical manipulation (courtesy of Miss Hands, surgeon, John Radcliffe Hospital, Oxford) and; 2) a sample of placenta was immediately isolated following newborn delivery (courtesy of the Maternity Unit midwives, John Radcliffe Hospital, Oxford). For suspension cultures $10^8$ cells in log phase were pelleted by centrifuging at 1000 g for 5 minutes followed by one wash in media and complete removal of the supernatant. For the adherent Blondolet cell line, 1-2 flasks were used depending on confluence, about $10^8$ cells. 5 mls of GuSCN/NaOAc was added to each preparation and pipetted or swirled prior to shearing the DNA. The crude extractions could be stored at −20° C. before RNA extraction, although they were usually used immediately. 5.7 M CsCl solutions were prepared carefully measured into tubes of the appropriate size. Normally 4 mls were used, but 12 mls were used for solid tissue samples. Prepared tubes were set aside and covered while the DNA was sheared.

Genomic DNA from the crude preparations was mechanically sheared using a Polytron™ homogenizer set on the maximum setting for 30 seconds. It was important to wear ear protection and preferably to do the manipulation in a separate room to prevent noise pollution. For solid tissue, the Polytron was applied for one minute. Any remaining large tissue was removed by a quick spin at 1000 g prior to layering over CsCl. The sheared solution was carefully layered with a plastic pipet over the CsCl solution to 3 mm from the top, using extra GnSCN solution to make up shortfalls in volume. Normally a swing-out SW55 rotor was used, but the SW41 was used for large RNA requirements. The volumes used, amount of CsCl, speed and the time required for each run are listed below.

| | CsCl solution | GuSCN solution | Speed (rpm × 10$^{-3}$) | Time (hrs) |
|---|---|---|---|---|
| SW41 | 4 mls | 8 mls | 32 | 12 |
| SW28 | 12 mls | 26 mls | 25 | 20 |

All centrifugations were done at 22° C. and the brake was left off to prevent gradient mixing. Following centrifugation, the upper phase was aspirated to just below the GuSCN/CsCl interface and scored just below it to prevent contamination from the upper phase. The tube was cut at the scored line, and the lower half flicked out and immediately inverted onto a paper towel to wick the remaining liquid away. The pellet was resuspended in 400 µl of DEPC treated water, transferred to a clean Eppendorf and separately phenol and then chloroform extracted as described in small scale DNA preparation. The RNA was precipitated by the addition of ¹/₁₀th volume (40 µl) 3 M NaOAc and 2 volumes 100% EtOH and placed on dry ice for 10 minutes.

The RNA was pelleted by spinning at 14,000 g in a microfuge for 5 minutes at 25° C. The pellet was washed once in 70% EtOH and respun. All traces of EtOH were removed and the pellet was resuspended in 400 µl of DEPC treated water. 5 µl of the preparation was analyzed on a 1% agarose gel prepared with DEPC treated water to confirm the quality of the preparation. Absorbance was analyzed at 260 nm (A260) and the quantity of RNA based on an absorbance of 1=40 mg/ml.

(b) PolyA$^+$ mRNA Isolation Using Dynabeads®

The Dynabead system (Dynal) was used to separate polyadenylated RNA transcripts from total RNA by exploiting the ability of beads precoated with a polyT region to hybridize to the polyA tail in the transcripts. The manufacturers suggested protocol uses 75 µg total RNA as starting material. Of this, approximately 1 to 5% will be mRNA. The approximate capacity of the beads is 2 µg per mg, thus 1 mg beads will separate sufficient mRNA for any further application. In terms of starting quantity and yield, this procedure is very flexible and can be adapted to suit the experimental design. The kit includes the following solutions:

2× Binding Buffer
20 mM Tris-HC$_{1-2}$
2 mM EDTA 1.0 M LiCl
1×Washing Buffer
10 mM Tris-HCl (pH 7.5)
1 mM EDTA, 0.15 M LiCl
1× Elution Buffer
Magnetic particle concentrator—Dynal MPC®-E-1

The volume of 75 µg RNA was adjusted to 100 µl with distilled DEPC treated water, or with elution buffer. If the total RNA was more dilute than 75 µg/100 µl an equal volume of 2× binding buffer was added. The sample was heated to 65° C. for 2 minutes to disrupt any secondary structure, providing optimal conditions for hybridization. 1 mg Dynabeads® Oligo (dT)$_{25}$ was removed from the resuspended stock tube to an Eppendorf tube and placed in the magnetic rack provided. The beads immediately clung to one side and the supernatant was removed. The tube was transferred to another rack and 100 µl of 2× binding buffer was added. If the total RNA had already been diluted in binding buffer, this step was omitted. The total RNA was added to the bead suspension, mixed gently and left to hybridize for 3-5 minutes. The beads were again separated using the Dynabead magnet and the supernatant removed. The beads were washed twice using 200 µl washing buffer each time. All of the supernatant was removed after the last wash, particularly important when working in small volumes. The desired amount of elution buffer was added. The sample was heated to 65° C. for 2 minutes to disrupt secondary structure and immediately separated using the Dynabeads. The supernatant was transferred to an Eppendorf tube. The eluted mRNA was used immediately or stored frozen at −70° C. RNase inhibitors were routinely added to the preparation.

(c) RNA Electrophoresis

For the purposes of checking the quality of RNA samples to detect the presence of undegraded ribosomal bands and the presence of a high molecular weight smear, running small samples could be easily done on routine non-denaturing agarose minigels. These gels were run sufficiently quickly to allow resolution of RNA specimens and for degradation not to be caused by any RNAses in the gel or running buffer.

When RNA samples were resolved prior to transfer to nylon membranes, the denaturing formaldehyde agarose gels were cast, taking the usual precautions to avoid RNAase contamination of solutions and equipment. To remove RNAses, the apparatus could be easily treated by soaking in methanol before use and gloves were routinely worn when working with RNA. The buffer used for these gels was based on the ampholytic compound MOPS and is referred to as 10×MOPS buffer. It also contained 5 mM Iodoacetamide added just prior to use from a separate 1 M stock solution. Typically, a 400 ml agarose gel would be made and just as the mixture was cooling after melting the agarose ¹/₆₀th volume formaldehyde was added and the gel cast.

The gel was transferred to the running tank, which was filled with buffer such that the wells remained dry. The RNA samples diluted to the volume of the well in MOPS buffer (1× final) containing ⅛th volume of formaldehyde and heated at 70° C. for 15 minutes to ensure denaturation before loading in the dry wells. If total RNA was used samples contained 10-25 mg of RNA but if polyA+ selected RNA was separated only 1-2 mg was used. The unused wells were filled with 1×MOPS running buffer containing a small amount of Orange G to indicate the progress of the separation when the gel was run. The gel was then run at 10V/cm for about 4 hours until the dye front had moved close to the anodal end of the gel. Without photographing, the gel was soaked in 1 litre of 50 mM NaOH (to nick the RNA molecules and improve the efficiency of transfer) for 45 minutes, which was then neutralized by the addition of acetic acid to a final concentration of 75 mM. Transfer was achieved using the same solution with a standard arrangement of towels beneath the gel and another stack on top of the nylon membrane that was placed on the surface of the gel. After overnight transfer, the transferred RNA was cross-linked to the membrane by placing the membrane, RNA side up, on a piece of heavy filter paper soaked in 10×SSC in a commercial crosslinking device.

After crosslinking the efficiency of the transfer was checked by methylene blue staining. The filter was immersed in a solution of 0.5 M sodium Acetate (pH 5.5) containing 0.005 M methylene blue for 10 minutes. The filter was then rinsed in water until the stain had washed out of the filter except where it was bound to RNA. The stained filters could be photocopied to keep a permanent record of the position of the ribosomal RNA bands for sizing purposes.

(d) Northern Hybridization

Hybridization of probes to RNA transferred on to nylon membranes was done using random-primed DNA probes according to the same technique employed for southern blotting of DNA.

(x) Reverse Transcriptase-Polymerase Chain Reaction

The reverse transcriptase-polymerase chain reaction (RT-PCR) method used was based on that previously described to detect low levels of dystrophin transcripts in various tissues (Chelly, J. et al., Nature, 333: 858-860, 1988). To synthesize the first strand of cDNA, 2 µg of total RNA, stored on dry ice, was coprecipitated, as with RNA extraction, with 2 µl primer to prime the RNA and start extension (0.2 µg/ml random hexanucleotides (Pharmacia) or 5 µg/µl of oligo-dT (Pharmacia, oligo-dT$_{12-17}$, 5' phosphorylated at 5 mg/ml for anchor PCR), 2 µl dNTPs (25 mM) and 37 µl DEPC-treated dH$_2$O. The mix was heated for 5-10 minutes at 65° C., spun for 2 minutes at 14,000 g and cooled on ice. To this reaction was added 2 µl reverse transcriptase, and 1 µl RNasine™ (destroyed at 65° C.). The RNA was then hydrolysed with NaOH and the reverse transcriptase heat inactivated by incubation at 70° C. for 10 minutes. The reaction was incubated for 30-45 minutes at 42° C. in a water bath, spun down at 14,000 g for 2 minutes and either used immediately or stored at −20° C.

10 µl of the newly synthesized cDNA was then added directly to each reaction using the standard conditions below.

| |
|---|
| 500 ng of each primer. (.5 µl) |
| 4 µl Buffer |
| 0.5 µl amplitaq enzyme (2.5 U.) |
| dH$_2$0 to 50 µl in a PCR tube |
| PCR extension run at 72° C. |

| Temperature | Time |
|---|---|
| Annealing - 40-45° C. | 30 sec. |
| Extension - 72° C. | 1.0 min. |
| Denaturing - 94° C. | 30 sec. |
| Program Run for 30 cycles | |

Following PCR, 10 µl of each sample was analyzed on a 1% ethidium bromide agarose gel and the products visualized by ultraviolet light. If products were visible, the gel was usually subjected to southern blotting with end-labelled oligonucleotides and the products visualized by autoradiography.

(xi) Primer Extension

The protocol is paraphrased from the published version (Ausubel, 1993). The method allows the identification of putative transcription start sites by incubating a complementary oligonucleotide about 80 bp downstream of the 5' end of a given gene with reverse transcriptase in an attempt to produce transcripts that produce a band of RNA at a putative initiation site that is normally found 100-150 bp upstream of the initiating methionine. By running this reaction along known genomic DNA sequence upstream of the 5' end of the gene, a putative position of transcription initiation can be identified. This procedure was used to identify a putative 5' transcription initiation site upstream of the apo-4 gene by annealing a 40 base antisense oligonucleotide probe approximately 80 bp downstream of the 5' end of the apo-4 cDNA.

The oligonucleotide probe was first end labelled with polynucleotide kinase as described above followed by treatment with RNasine for 10 minutes at 37° C. and precipitation with DEPC treated solutions. To anneal the test RNA to the probe, 10 mg of total placental RNA, freshly isolated, was incubated with 1 µl of the 1 mg/ml target oligo, 40 µl of NaAc and two volumes of EtOH, vortexed and placed on dry ice for 15 minutes. The mix was pelleted and washed twice in 70% EtOH with the remaining supernatant removed with a pipetman tip. The RNA was then denatured for 10 minutes at 65° C. The following reverse transcriptase (RT) mix was prepared fresh on ice (per reaction):

3.5 µl 4 mM dNTPs
2.5 µl 10×RT buffer
1.25 µl RNAsin
18 µl H$_2$O

25 µl RT mix was added to each sample and resuspend thoroughly. Resuspension of the RNA and oligo in the RT mix can be read by monitoring the radioactivity. 2 µl (40 U) AMV RT was added to each reaction and incubated for 90 minutes at 42° C. The reaction was stopped by adding 1 µl of 0.5 M EDTA to each reaction, and 1 µl of 1 mg/ml pancreatic ribonuclease A with incubation for 30 minutes at 37° C. 100 µl of 2.5 M ammonium acetate was added followed by extraction with 200 µl phenol/chloroform, isoamyl alcohol. The aqueous phase was transferred to a fresh tube and 300 µl ethanol added to precipitate the RNA. The pellet was washed with 500 µl of 70% ethanol/30% water (vol/vol) spun for 5 minutes and the excess liquid removed with a p200 pipet tip. The pellet was resuspended in 3 µl DEPC treated water followed by 4 µl formamide loading buffer and well mixed. The tubes were boiled for 3 minutes and placed on ice. 3 to 4 µl were analyzed alongside cDNA and phage clone DNA reactions prepared according to the sequencing method described above on a 4-5% sequencing gel. The gel was dried as in the sequencing procedure and subjected to autoradiography overnight at −80° C.

(xii) In Vitro Transcription and Translation of cDNA

The method enclosed in the in vitro transcription and translation kit was followed (Promega, UK) and integrated with the published method (Ausubel, 1993). This method allows the determination of whether a cDNA can produce a protein by first isolating it from all but the T3 or T7 promoter in its carrier vector, producing a transcript by incubation with reverse transcriptase and then incubating the transcribed product with rabbit reticulocyte lysates and/or wheat germ extracts that contain all of the elements necessary for translation. The materials used included:

pBluescript DNA containing a T7 promoter and the cDNA of interest
Appropriate restriction endonucleases to linearize the template
T:E buffer
5× ribonucleoside triphosphate mix
10×T7 RNA polymerase buffer
Pancreatic ribonuclease inhibitor (e.g., RNAsin™ from Promega Biotec)
T7 RNA polymerase
Buffered phenol
Isobutanol
10 M ammonium acetate
100% ethanol
In vitro translation kit (Promega)
$^{35}$S-labeled methionine (1400 Ci/mmol)
0.1 M NaOH
10% trichloroacetic acid (TCA)
Amplify™ (DuPont)

The DNA template was prepared by subcloning the apo-4 cDNA into pBluescript that contains the T7 RNA polymerase upstream of the 5' end. The insert was linearized with Pst I or, to generate a second template that truncated the 3' 270 bp and the inversion, Hpa I. The templates were run out on an agarose minigel and purified using the Geneclean system as described above. The DNA was purified by phenol extraction and ethanol precipitation and resuspended in 50 µl of DEPC treated T:E buffer. The following 25 µl reaction mixture was set up on ice for each template:

8 µl H$_2$O
5 µl DNA (total 1 µg)
5 µl 5× ribonucleoside triphosphate mix
5 µl 10×T7 RNA polymerase buffer
1 µl RNAsin (30 to 60 U)
1 µl T7 RNA polymerase (5 to 20 U)

The reaction tubes were incubated for 60 minutes at 40° C., spiked with an additional µl of T7 polymerase and incubated for another hour. A 1:10 dilution of DNAse was then added, incubated for 15 minutes at 37° C. and the mixture was brought to 100 µl with dH$_2$O. 25 µl of buffered phenol was vortexed and extracted immediately. The aqueous phase was transferred to a new microcentrifuge tube, extracted twice with isobutanol, and 6 µl of 10 M ammonium acetate followed by 70 µl 100% ethanol was added. The RNA was ethanol precipitated on dry ice and washed once with 70% ethanol. The RNA was resuspended in 24 µl DEPC treated dH$_2$O. 6 µl of 10 M NH$_4$Ac and 70 µl ethanol were added, the RNA was reprecipitated and washed once with ethanol. The RNA was resuspended again in 10 µl RNAse-free T:E buffer and samples were run out on a gel to show relative production of product and sizes.

10 µl RNA from each template was then added to the recommended mix in the in vitro translation kit (Promega) of Wheat Germ Extracts and Rabbit Reticulocyte Lysates, which were stored at −80° C. All kit components were quick-thawed and placed on ice prior to use. Bovine Mosaic Virus was included as a positive control for each set of two templates by adding the following mix:

(a) Wheat Germ Extracts (WGE)
25 µl WGE
4 µl 1 mM Amino Acid Mix (minus methionine)
2 µl RNA substrate in H$_2$O
130 mM KAc
1 µl RNasin™ Ribonuclease Inhibitor (40 U/µl)
4 µl [$^{35}$S] methionine (1,200 Ci/mmol) at 10 mCi/ml
Nuclease-free (DEPC treated) water to a final volume of 50 µl (b) Rabbit Reticulocyte Lysates (RRL)
35 µl RRL
7 µl Nuclease-free water
1 µl RNasin™ RNase Inhibitor (at 40 U/µl)
1 µl 1 mM Amino Acid Mixture (minus methionine)
4 µl [$^{35}$S] methionine (1,200 Ci/mmol) at 10 mCi/ml
2 µl RNA substrate in H$_2$O
50 µl final volume Reactions were allowed to proceed at room temperature for 60 minutes. 5 µl of each sample was removed and added to 10 µl of 2×SDS protein loading buffer and tapped to mix. The tubes were heated at 100° C. for 2 minutes and spun down. 5 µl of each sample was loaded immediately onto a 10% SDS-PAGE gel and run out alongside molecular weight standards. The remainder of each reaction was stored at −20° C. Following protein gel fixing in stain and destain for 30 minutes each, as described below, [$^{35}$S] proteins were visualized by fluorography with Amplify followed by autoradiography at −80° C.

(xiii) Protein Expression and Adhesion Work
(a) Small-Scale Production of Recombinant Fc-Adhesins Plasmids containing clones coding for recombinant soluble cell adhesion molecules were transfected into COS cells by the DEAE-Dextran method (Seed, B. and A. Aruffo, *Proc. Natl. Acad. Sci. USA.*, 84: 3365-3369, 1987) as for large scale production below but using 5-10 10 cm tissue culture dishes.

(b) Large Scale Production of Fc-Adhesins

Plasmids containing clones coding for recombinant soluble cell adhesion molecules were transfected into COS cells by the DEAE-Dextran method (Seed and Aruffo 1987). For a large scale transfection 20×15 cm dishes of 80% confluent COS cells were transfected using the protocol described in the section on expression cloning. On the day after the transfection the medium in the cultures was changed for DMEM/1% FCS and the cultures allowed to grow for another 3 days (72 hours). The medium was then collected and the dishes recharged with the same media for a further 48 hours of incubation before being discarded.

Cellular debris was pelleted from the Fc-adhesin-containing medium by centrifugation at 4,200 rpm in the J6 centrifuge. The supernatants were then decanted into clean dry bottles. To capture the Fc proteins, the bottles were placed on a mixer with a magnetic flea and 500 µl of Protein A—Sepharose beads were added to mix overnight at 4° C. The following day, the contents of the bottles were transferred to a disposable polyethylene column to allow the Protein A Sepharose beads to be recovered. The beads were washed with two bed volumes of PBSA or until the beads were white, supplemented with a further 150 mM Sodium chloride. Bound Fc protein was then eluted in fractions by the addition of 1 bed volume (500 µl) of pH 3.5 100 mM acetate buffer 10 times and elution of the unbound protein. The eluted recombinant Fc proteins were checked for quality by SDS-PAGE analysis and an estimation of total protein concentration was taken by a measurement of absorbance at A260. For storage and use in experiments the proteins were then concentrated, using the Amicon centrifugation system. They were then dialyzed against PBSA overnight with stirring at 4° C. To dialyze small volumes of protein without losses Fc proteins were incubated in inverted Eppendorf tubes with the lids cut out and a piece of dialysis membrane placed under them. The tube was secured with parafilm and held in a styrofoam rack on PBSA.

(c) Immunoselection and Episomal Rescue

The principles of the method of cDNA isolation with Fc-chimeric probes by transient expression and immunoselection are discussed in the introduction. The practical details of this procedure are based on previously described methods for antibodies (Seed, B., *Nature,* 329: 840-842, 1987), which have been modified and employed for Fc-probes (Simmons, 1993) as described in the section below.

(d) DEAE-Dextran Transfection of COS Cells

For the first round of panning or for other procedures requiring transfected cells the following method was used to achieve a high transfection efficiency using the DEAE dextran method (Sussman, D. J. and G. Milman, *Mol. Cell. Biol.,* 4: 1641-1643, 1984). cDNA libraries constructed in pCDM8 were transfected directly into COS cells that had been prepared the afternoon before transfection to achieve 80% confluence the following day by splitting at 1×10$^7$ cells/15 cm dish. Two dishes 15 cm in diameter were used for each transfection. A transfection mix was prepared in a 50 ml (Falcon™) tube consisting of 40 µg of CsCl purified DNA diluted in 1 ml of T:E and swirled to mix. To make the DNA adhere to the COS cells, in a laminar flow hood, 800 µl of DEAE-dextran (10 mg/ml) was added to the transfection mix, swirled, and allowed to stand for five minutes at room temperature to allow the DNA to adhere to the Dextran. Any precipitate visible after the incubation meant that the DNA had precipitated in solution and the procedure would have to be repeated with a higher quantity of T:E. 1 ml was in excess, however, and no precipitate was ever seen. 20 mls of DMEM containing 100 mM chloroquine diphosphate (Sigma) was then added and mixed by inverting the capped tube. Chloroquine acts as a lysosomal acidifying agent to increase the stability of the transfected DNA as it is taken up into the primary lysosomal compartment, although it also increases the toxicity of the transfection to the cells, limiting incubation time after the transfection mix is added.

The dishes for transfection were then removed from the incubator and the medium was aspirated and replaced with 10 mls of transfection mix. 10% dialyzed FCS or Nuserum™ was added to the original transfections but it was found that minimal amounts of protein remained in the culture dish making it unnecessary to add this to later transfections. The dishes were replaced in the incubator and observed for vacuole formation during the next 2-4 hours. Transfection normally took place after 3 hours, although 2 hours was sufficient for single-clone transfection. DNA uptake by the cells was considered sufficient when vacuoles were evident in the majority of them. If the cells had become spindly or had started to detach, transfection had proceeded further than the optimal limit. At optimal vacuolization, transfection was stopped by aspirating the transfection mix and adding 10 mls of a PBSA/10% DMSO mixture and leaving it for exactly one minute. The mix was aspirated and 20 mls of 10% FCS/DMSO was added to allow the cells to recover overnight. The following day, the cells were lifted with 2 mls of a 1/5 mixture of trypsin/PBSA and incubated at 37° C. for five to ten minutes. This also allowed residual DMSO to be removed, which would prevent cell lifting with divalent cations prior to the panning process. The cells were removed by tapping the dish and separated from each other by gently pipetting with a 5 ml pipet. The cells were replated in 20 mls of the same medium to dilute the trypsin and inactivate it with the endogenous protein. Dishes were prepared for immunoselection the night before or earlier if the plates were frozen as described below. The following day, 36-72 hours post-transfection, the cells were ready for immunoselection.

(e) Preparation of Immunoselection Antibody Plates

Polystyrene dishes were prepared to allow the Fc portion of a probe adhering to a transfected cell, to be captured by adhering to a secondary antibody on the dish in an attempt to isolate ligand populations. Untreated 10 cm bacteriological plates (Falcon, Oxnard, Calif., USA) were coated with affinity isolated goat anti-human IgFc antibodies (Sigma, UK) by adding 5 mls of a 10 mg/ml solution of antibody in 50 mM Tris-HCl (pH 9.5) and swirling or shaking the dish on the benchtop until the surface was uniformly wet. The dishes were left to stand at 25° C. for two hours. The antibody solution was then aspirated and stored at 4° C. The solution could be used a further two times to coat dishes. The dishes were carefully washed twice with PBSA and the remaining protein binding sites were blocked by the addition of PBSA containing 2 mg/ml of BSA incubated overnight at 4° C. The following day, the solution was aspirated. The dishes were washed once with PBSA and used immediately or aspirated without washing and stored in their original bags at −20° C.

(f) Panning Procedure

The method described is based on the method originally developed for panning with antibodies (Wysocki, L. J. and V. L. Sato, *Proc. Natl. Acad. Sci. USA*, 75: 2844-2848, 1978). COS cells 36-72 hours post-transfection were washed once in PBSA and lifted using PBSA/2 mM EDTA incubated at 37° C. for 15 minutes. Cells were transferred to 50 ml Falcon tubes and washed once in ice-cold panning wash consisting of PBSA/5% FCS/4 mM EDTA/0.02% sodium Azide and pelleted at 1000 g for five minutes. The pellet was resuspended in 400 µls of panning wash on ice and 10-30 µg of Fc-adhesin probe was added and mixed with a 1 ml pipet tip. Cells transfected with libraries containing Fc-receptors were pre-incubated with 20 µg of IgG from an irrelevant species (usually goat or mouse) for 20 minutes and washed once in panning wash followed the addition of Fc probe as above. The cells were incubated with the Fc probe on ice for 30 minutes. As a modification of the procedure, cells were incubated on a rotary mixer in the cold room and media was substituted for PBSA in the panning wash. The tubes were then filled with 50 mls of panning wash and the cells pelleted at 1000 g. The cells were resuspended in 5 mls of panning wash, pipetting to achieve maximum cell separation and gently and evenly plated onto panning dishes that had been thawed and/or rinsed once with panning wash and refilled with five mls. The panning plates were then left undisturbed at room temperature for two hours when cells bound to the Fc probe would bind to the dish via the secondary antibody.

Following the two-hour incubation, unbound cells were removed from the dish with three gentle washes followed by gently aspirating the wash with a pipette. On the third wash, the dish was inspected under a microscope to check for bound cells and the total number of bound cells was counted by carefully moving the dish to see if the cells moved. Bound cells stayed stationary. The maximum number of bound cells that was observed was between 5-10/dish after the second or third rounds of panning. A slightly higher number was sometimes observed after the first round. The dish was then carefully removed and either washed again until most of the unbound cells were removed or tipped up to remove the last traces of panning wash. Excess wash was carefully removed with a p1000 pipetman.

(g) Episomal Rescue of Potential Ligands

To rescue episomes from the bound COS cells, 400 µl of Hirt solution (1% SDS/10 mM EDTA) (Hirt, B., *J. Mol. Biol*, 26: 365-369, 1967) was immediately added to the drained panning plates and swirled to cover the whole dish. A viscous solution became immediately obvious and cells were propped up on their sides at a 45° angle to allow the solution to drain into the corner of the dish for 15-30 minutes. The Hirt solution was then carefully transferred to Eppendorf tubes with a p1000 pipetman to avoid shearing genomic DNA. The genomic DNA was precipitated by the addition of 100 µl of saturated NaCl solution and left overnight in slushy ice. The following day, the genomic DNA and SDS were pelleted at 14,000 g for five minutes at room temperature and the episome or plasmid containing supernatant extracted with 500 µl phenol and then chloroform extraction. 10 µl of LPA carrier solution was added and shaken for 30 seconds. The tube was filled with 95% EtOH, placed on dry ice for 15 minutes and spun at 14,000 g for four minutes. The residual supernatant was removed with a p200 tip and the pellet was allowed to air dry for 1-2 minutes. The DNA was then resuspended in 50 µl T:E. 15 µl of this mixture was added to 100 µl of MC1061/p3 competent cells pre-thawed on ice for 15 minutes. The cells were gently flicked to mix and left on ice to allow the DNA to adhere to the cells for 15 minutes. The cells were heat-shocked to allow DNA entry for five minutes at 37° C. while 10 mls of top-agar was poured onto 15 cm amp/tet LB agar plates and allowed to set. The plates had been prepared by pouring 15 mls of molten LB agar with amp/tet added into it as described in the ligation section above, allowing them to set and then drying them in a drying oven for 30 minutes. The transformed into *E. Coli.* was plated out onto the agar plates with a flame-disinfected glass spreader cooled on the agar plate and incubated overnight at 37° C. The next day colonies were counted and at least 1-2×10³ colonies were necessary to continue to the spheroplast fusion step. If growth was not at this level, the Hirt mixture could be retransformed to assess whether the transformation step was at fault.

(h) Transfection by Spheroplast Fusion

In preparation for rounds two and three of panning, the colonies were amplified to their maximal level in preparation for their conversion to spheroplasts that could be fused with COS cells by polyethylene glycol (PEG) treatment based on the previously described method (Sandri, G. R. et al., *Methods in Enzymology*, 101: 402-411, 1983). After counting the colonies obtained from the transformed Hirt solutions, the plates were allowed to achieve maximum growth throughout the day. To achieve maximal amplification of episomes/bacterium spectinomycin was added to the amp/tet agar prior to pouring the agar dishes. Spectinomycin is a bacteriostatic agent that acts to amplify plasmid number because it cannot prevent the replication of colEl based plasmids. The colonies were then transferred to amp/tet/spectinomycin (100 µl/100 ml of a 100 mg/ml stock) "ATS" LB agar plates by pressing a 0.45 µm nylon (preferably) or nitrocellulose filter cut to fit inside the 15 cm plate over the colonies until complete adherence was achieved. The filter was lifted and placed, colony side up, on the ATS plate at 37° C. until the following morning. This was done in place of the usual procedure with colony amplification in flasks as phage lysis was eliminating colony formation during incubation at 37° C. One 15 cm dish of COS cells at 1×10⁷ density was then split into six 6 cm dishes in preparation for protoplast fusion the next day to allow for 100% confluence necessary to withstand the spheroplast fusions.

The colonies were removed the following morning from the ATS plates by applying 20 ml of LB supplemented with 12.5 µg/ml amp and 7.5 µg/ml tet to the filter of each plate. Plates were placed on a shaker for 30 minutes, removed and gently mixed with a spreader to remove all bacteria. The mix was then pipetted into 250 ml bottles and spun for five minutes at 5000 g in a JA-14 rotor in the J221 centrifuge. The supernatant was then decanted and the excess liquid aspirated. The pellets were resuspended with a pipet in 10 mls of a mixture of ice-cold 20% sucrose/50 mM Tris-HCl, pH 8 and left for five minutes on ice. During this time a stock of chicken egg lysozyme (Sigma) was made up fresh in 250 mM Tris, pH 7.5 with a final concentration of 10 mg/ml. Two mls of this stock was then added to the sucrose/Tris slurry, swirled to mix, and incubated for five minutes on ice to make the bacterial walls permeable. Percent conversion to spheroplasts was then checked by microscopy. Two mls of 250 mM EDTA, pH 8.0 was added and incubated a further 5 minutes on ice followed by the addition of two mls of 50 mM Tris-HCl, pH 8.0 incubated for five minutes at 37° C. In a laminar flow hood, 20 ml of cold DMEM/10% sucrose/10 mM MgCl₂ was then added dropwise with swirling at about 2 drops/second and the slurry replaced on ice. It was most convenient to prepare a maximum of two libraries at a time and stagger the timing of the spheroplast preparation if any more were prepared.

In preparation for fusion with polyethylene glycol (PEG) 1450, the COS cells were then removed from the incubator and the medium aspirated from each set of six dishes. A maximum of 12 dishes were used for each fusion. 5.5 mls of spheroplast suspension was added to each dish, the lids were replaced and stacks of three dishes each were made from each fusion to allow two libraries to be spun at once. The dishes were carefully placed on the inside edge of a Beckman™ centrifuge rotor and spun at 2000 rpm for 10 minutes, run down with the brake off to avoid disturbing the spheroplast layer. The dishes were carefully removed and inspected to insure that a smooth "skin" had attached to the COS cells. The dishes were then placed in two rows of six dishes each in the laminar flow hood with each lid placed behind its dish and the supernatants were carefully aspirated. With a 25 ml pipet, 1.5-2.0 mls 50% PEG 1450/50% DME (no serum) (w/w) was added to each dish by gentle dropping into the center of the dish or swept around the dish to ensure that the PEG was evenly distributed and the timer was started to allow a maximum of two minutes contact with the PEG solution. After adding PEG to the last dish, the dishes were propped up on their lids and the remaining PEG aspirated. After two minutes, with a 25 ml pipet, 1.5 mls of DMEM alone was added to the center of each dish and allowed to spread radially to wash off residual PEG. The dishes were propped up on their lids and the media gently aspirated. The wash was repeated, the media aspirated and the dishes replated with 10% FCS/DMEM containing 15 µg/ml gentamycin sulfate to inhibit contamination while the cells were recovering. The cells were left for 4-6 hours at 37° C. After this time the "skins" had visibly loosened and were removed by aspirating the media washing once in 3 mls of DMEM, aspirating again and replating in 3 mls of 10% FCS/DMEM/gentamycin. The medium was changed again the following day and on the second day the cells were lifted with PBSA/2 mM EDTA as before and subjected to a round of panning.

(i) Analysis of cDNA Clones from Episomal Rescue

With Fc-probes, it became necessary to analyze the cDNA population rescued after the second round of panning, although with antibody panning it had been usual to wait until the third round. It was found that the integrity of the plasmid would sometimes not be retained in the third round and that sometimes the panning efficiency was decreased relative to the second round. To analyze the homogeneity of the cDNA clones selected with Fc-probes, 24-48 random colonies were picked from the transformed Hirt solutions and the rescued plasmids analyzed by DNA minipreps. Ideally, increasing numbers of adherent cells would be followed by a common pattern of cDNA inserts emerging from Hind III/Pst I digestion of miniprep DNA from the final round transformation analyzed as described above. One-half of the mini-prep DNA was run out and for inserts that appeared in duplicate lanes, the residual other half of the miniprep DNA was transfected by the DEAE-Dextran method into COS cells seeded out into 6 well dishes using scaled down volumes as given in the DEAE-Dextran method above. 36-72 hours post-transfection these transfectants were then either stained in situ by fluorescent microscopy or subjected to FACS analysis as described below to confirm binding to the Fc probe. No trypsinization was required for in situ staining but it was necessary for FACS analysis to achieve an even distribution of the cells.

(j) Immunoprecipitation—Stringent Wash Method

The high salt-low salt washing method was contributed by Dr. Paul Crocker, ICRF Labs, IMM, Oxford. Cells were labelled to as high a specific activity as possible. Solutions are listed at the end of this section. All steps were carried out at 4° C. or on ice. Adherent cells were rinsed twice with PBS and 1-2 ml of lysis buffer was added. Cells in suspension were pelleted and resuspended in 1-2 ml lysis buffer for 30 minutes on ice. Nuclei were removed by centrifugation for 10 minutes in a microfuge. The supernatant was ultracentrifuged at 50,000 g at 4° C. for 30 minutes. To pre-clear the lysate the tubes were microfuged for two minutes and the supernatant was transferred to a fresh tube. The addition of protein A was repeated. The lysate was divided into 200-300 µl portions with both a positive and a negative control, if possible. Either 5 µgs of the affinity purified mAb of interest, 100 µl of tissue culture supernatant or 5 µl of antisera were added to each tube. The tubes were inverted and incubated at 4° C. for one hour. 50 µls of protein A/G-agarose suspension was added and mixed on a rotary mixer at 4° C. for ½ hour. The pellet was washed once with 1 ml buffer A, twice with 1 ml buffer B and once with 1 ml buffer C. The lysate was removed with a Hamilton syringe and the pellet was resuspended in 20 µls 1× Laemmli sample buffer containing 1 mM EDTA and 5 mM iodoacetamide. The samples were boiled for 2 minutes, microfuged for 2 minutes, and the supernatant was removed. 10 µls of the sample was loaded on a 10% Laemmli SDS-PAGE gel and run at 150 mV for 1 hour. Samples were analyzed reduced and non-reduced if possible. If cells were metabolically labelled, immediately after SDS-PAGE, Amplify was used to intensify the signals.

(k) Immunoprecipitation with Peptide Blocking

To examine whether specific antigens could be blocked with peptide, the aliquot of either purified or crude antisera (≈1 mg/ml) was incubated for an hour at 4° C. in a 1:2 dilution of 10 mg/ml peptide dissolved in 0.1 M NaHCO$_3$, pH 8.3/0.5 M NaCl. Blocked antibodies were then added to lysates at an equal concentration to the test antibody and immunoprecipitated as described above.

(xiv) Cell Surface Labelling (a) Cell Surface Iodination

For immunoprecipitation analysis of cell surface molecules intact living cells were usually first surface iodinated based on the original method (Emerson, S. G. et al., *J. Immunogenet.*, 6: 87-97, 1979). Successful iodination depended on the presence of tyrosines in the ECD of the molecule of interest. Iodination was done enzymatically with lactoperoxidase and glucose oxidase, supplied commercially as Enzymobeads™ (BioRad Corp., USA), determined to be the superior method to iodinate cells as there is no observed destruction of the labelled protein binding site (Kienhuis, C. B. et al., *Clin. Chem.*, 37: 1749-1755, 1991). β-deoxyglucose was present in labelling reactions as an oxidizing substrate. Enzymobead reagent was rehydrated with 0.5 ml distilled water at least 1 hour before use. 1% Beta-D-Glucose was prepared in aqueous solution. (2% Alpha-D-Glucose can be used; however, it must be allowed to mutarotate overnight to the Beta configuration.) For the iodination reaction, in a tube were mixed:

| | |
|---|---|
| 0.2 M phosphate buffer pH 7.2 | 50 µl |
| Protein sample | 10-25 µl (50-500 ng or 10$^6$ cells) |
| Enzymobead Reagent | 50 µl |
| 1.0 mCi Na $^{125}$I | 2 µl |
| 1% β-D-Glucose | 25 µl |

Iodination was allowed to proceed at room temperature for 15-25 minutes with occasional mixing by gently tapping the tube. The reaction was terminated by the addition of 10 mls of PBSA at 4° C. to eliminate excess iodine. Cells were washed twice in cold PBSA and centrifuged for 5 minutes at 1500 K. The PBSA was decanted and the tube inverted and blotted. Cells were lysed at 10$^7$ cells/ml in 1% NP-40 lysis buffer (20 mM Tris-base, 150 mM NaCl, 0.5 mM ethylenediaminetetraacetic acid (EDTA), 1 mM phenylmethylsulfonylfluoride (PMSF)) for 30 minutes. Following lysis, lysates were microfuged at 20,000 K at 4° C. for 15 minutes to pellet the nuclei and the enzymobeads. The supernatant was precleared overnight at 4° C. with 100 µl of a 50% solution of agarose beads and 40 µg/ml of goat anti-mouse IgG antibodies, which reduced the number of Fc receptors as well as non-specifically labelled proteins. Beads were spun down and lysate removed the next day. 20 µg/ml of mouse immunoglobulin as a negative control or 60 µg/ml of Fc-adhesin was added to 500 µl of lysate containing 5×10$^6$ cells and incubated for 1 hour at 4° C. An excess of Fc-adhesin was sometimes added due to the established low-avidity binding of Fc-chimeras relative to antibodies (Simmons, 1993). Protein A sepharose was then added to precipitate the antibodies for 30 minutes. The beads were washed two to three times in 1 ml of 1% NP-40 lysis buffer by vortexing for 20 seconds, brief microcentrifugation at 4° C., and removal of the lysis buffer. The final traces of lysis buffer were removed with a Hamilton syringe. The beads were resuspended in 20 µl of 1× sample buffer and boiled for 5 minutes at 100° C. to release proteins bound to the beads. Samples were run under reducing conditions by adding 10% β-mercaptoethanol and loaded onto 10% denaturing polyacrylamide gels. SDS-PAGE was carried out for 1 hour at 120 mV. Gels were stained and destained in 10% methanol fixative solution, dried for 1 hour and subjected to autoradiography at −80° C.

(b) Whole Cell Biotinylation

An alternative method to label cell surface molecules was recently developed that allows labelling of the protein with biotin and detection using a biotin-streptavidin antibody detected with the enhanced chemiluminescence system (Cole, S. R. et al., *Mol. Immunol.*, 24: 699-705, 1987). The NHS-LC-biotin was stored frozen at −20° C. To label suspension cells, 10$^7$ cells washed in PBSA were resuspended in 1 ml of a freshly prepared biotinylation solution (20 mM NaHCO$_3$, 150 mM NaCl, 0.1 mg sulfosuccinimidyl-6-biotinamidohexanoate (NHS-LC-biotin; Pierce, Warner, UK) (pH 8.0), vortexed, and allowed to mix for 30 minutes at RT and then for 90 minutes at 4° C. To label transfected COS cells in situ, 4 mls biotin solution/10 cm dish was added either on ice for 30 minutes to 1 hour with shaking or at 25° C. for 20 minutes followed by incubation on ice with shaking for 30 minutes to an hour. Residual biotin was removed by washing twice in 10 mls PBSA and either spinning suspension cells at 1200 g for 5 minutes or aspirating the supernatant from adherent cells. Biotinylated cells were lysed to a final concentration of 25×10$^6$ cells/ml in 1% NP-40 lysis buffer and used directly in immunoprecipitation using normal or stringent washing conditions. The lysates were precleared with 100 µl of beads for 1 hour at 4° C., prior to incubation with the polyclonal antibody, and left to incubate for 1 hour at 4° C. For polyclonal antibodies and Fc-adhesins, the beads were washed three or four times with 1% NP-40 lysis buffer or high and low salt washes by vortexing and centrifugation at 15,000 g for 10 seconds, resuspended in 30 µl of sample buffer, and boiled for 10 minutes. Minigel and immunoblotting were performed according to the western blotting procedure. Blots were washed, blocked, probed with streptavidin horseradish peroxidase (1/2000 dilution), and ECL detected using the ECL kit (Amersham), with film exposures from 5 seconds to 15 minutes.

(c) Metabolic Labelling of Fc-Chimeras or Cell Lines

Recombinant Fc-adhesins were labelled metabolically by labelling the COS cell transfectants. 24 hours post-transfection, the medium in 10 cm diameter dishes of transfected COS cells was replaced with 3 mls of methionine and cysteine-free DMEM/1% FCS and a mixture of $^{35}$S Methionine and Cysteine "Translabel" (New England Nuclear products, U.K.) added to a final concentration of 50 mCi/ml. Following 6-18 hours (overnight) incubation the supernatants were separated from cellular debris and the protein was purified on a protein A sepharose column and run out on SDS-PAGE, as above.

(xv) SDS-PAGE Analysis of Proteins

10%, 12% or 5-20% (gradient) polyacrylamide gels were prepared as previously described (Laemmli, U.K., Nature, 227: 680-685, 1970). Sodium dodecyl sulfate-polyacrylamide gel electrophoreses (SDS-PAGE) was performed rapidly at a constant voltage of 120 mV on the Hoefer minigel apparatus or a large BioRad (UK), Hoeffer (Germany) or ATTO (Japan) apparatus. The Biorad minigel could be run at 200 mV for 1 hour. For the stacking gel 4% gels were used. The gels were made up and run in the SDS-containing buffer described in the section on buffers and solutions below. If the gel was being run to check the quality of a batch of recombinant protein the gel was next transferred into Coomassie Blue stain for 2 hours after which the gel was destained in fixative. For immunoprecipitations of $^{32}P$ or $^{125}I$ labelled cells the gels were fixed for 10 minutes, dried down at 80° C. under vacuum for 30 minutes and autoradiographs made at room temperature overnight or −80° C. for shorter periods. To facilitate the detection of $^{35}S$-labelled proteins after fixing the gel could be treated with a fluorescence intensifying agent (Amplify™, Amersham, UK), for 10 minutes prior to drying down, to increase signal intensity. Protein molecular weight standards included: myosin-200 Kd; E. coli. β-galactosidase-116 Kd; Rabbit muscle phosphorylase b-97.5 Kd; Bovine serum albumin (BSA)-66 Kd; Hen egg white ovalbumin-43 Kd; Bovine carbonic anhydrase-31 Kd; Soybean trypsin inhibitor-21 Kd; and Hen egg white lysozyme-14 Kd (Bio-Rad). To check the quality and estimate the quantity of a batch of recombinant protein the gel was placed in Coomassie Blue/methanol stain with shaking for 1 hour and destained in fixative destain for 1-2 hours. Autoradiography was performed at −80° C. for $^{32}P$ labelling and room temperature for $^{35}S$-labelling.

(xvi) Western Blotting

Western blotting allowed biotinylated proteins to be detected following electrophoretic transfer to a membrane such as PVDF. The procedure for the Western Blot test is paraphrased from the standard method (Ausubel, 1993). 1 liter of 1× transfer buffer was prepared that included: 6 g Tris, 28.8 g Glycine, 40% MeOH, diluted to 1 liter with stirring in $H_2O$ and cooled to 4° C. An Immobilon or PVDF filter (Millipore) cut slightly larger than the gel was pre-set with MeOH and soaked in transfer buffer for 15 minutes. Following electrophoresis using colored protein markers (Bio-Rad), the gel was soaked in transfer buffer for two minutes. The filter pads were also soaked in transfer buffer. Two pieces of Whatman 3 mm paper were briefly dipped in transfer buffer and the blot apparatus was assembled into a sandwich in the order listed below using a BioRad apparatus for minigels or large gels:

Plastic black gridded blot casing
Scotchbrite pad
3 mM filter paper
Polyacrylamide Gel
Immobilon membrane (0.45 um) 3 mM filter paper
Scotchbrite pad
White grid All the air bubbles were rolled out from the gel/membrane sandwich using a pipet. The blotting sandwich was placed in the tank with the membrane toward the anodal side and the gel toward the cathode side, consistent with the direction of transfer of protein from gel to membrane. The tank was filled with transfer buffer and transfer was initiated at 4° C. overnight at 15-18 mV. Transfer could be done in one hour at 60-70 mV with an ice block inserted in the tank. Following transfer, the sandwich was disassembled and cut on a corner cut to show orientation. To visualize transfer, the blot was incubated in PBSA/0.01% Ponceau S™ (Sigma) for one minute and rinsed in water until the protein bands appeared. The filter was then blocked in blocking buffer for 60 minutes at room temperature on a shaker in 20 mls PBSA, 0.05% Tween 20™ and 1% Marvel. Depending on the labelling procedure, antisera was added at a 1:100 in Blocking Buffer, ie. 20 μl antisera in 2 ml blocking buffer. The blot was placed on a shaker at room temperature for 1 hour or overnight at 4° C. and washed 2× for 15 minutes or according to the enhanced chemiluminescence (ECL™) (Amersham) instructions. ECL reagents and equipment were assembled and taken into the darkroom. Solution A was added to solution B, mixed and, with forceps, the protein side of the blot was immediately placed over 1-5 mls of solution and left for 1 minute. Excess solution was wicked from the blot by touching a corner to a paper towel. The blot was then wrapped in plastic wrap, the creases were smoothed out so that no excess moisture was left on the outside of the wrap. The blot was then exposed for a brief period to film using a stopwatch and developed immediately.

(xvii) Immunofluorescent Cell Staining

Immunofluorescence analysis was often performed in situ on COS cell transfectants in 6 well dishes to determine whether cDNA isolation by panning had been successful or whether polyclonal antisera stained candidate transfectants. It was also done as a check on the ability of Fc-adhesins to bind ligand on both EDTA-lifted candidate transfectants from panning and cell lines. The medium was aspirated and the cells washed briefly with staining wash, PBSA.B.C./5% FCS/ 0.02% Sodium Azide. Primary antibody was added, diluted 1:4 in staining wash in the case of monoclonal antibody supernatants, or 1:1000 for mabs as ascites or purified antibodies at 1 mg/ml. Cells in suspension were suspended at a final concentration of $1 \times 10^6$ cells/ml and analyzed on a Becton Dickinson™ FACScan. The medium was aspirated and the cells washed in E4 medium/5% FCS. Cells were incubated briefly with 200 μg/ml goat Ig to block Fc receptors (Alexander, E. A. and S. K. Sanders, J Immunol, 119: 1084-1088, 1977). Primary antibody was added, diluted 1:2 in staining wash in the case of monoclonal antibody (Mab) supernatants, or 2-500 μg/ml Fc-chimera/sample and incubated on ice for 30 minutes with occasional vortexing. Cells were washed twice and supernatant was aspirated. FITC-conjugated goat anti-mouse IgG (for example), diluted 1/500 in staining wash was added to the Mab samples, and goat anti-human Ig-Fc-FITC was added to the Fc-probe samples. After a further 30 minute incubation on ice with occasional vortexing, cells were washed three times in staining wash followed by resuspension in 1 ml of PBSA. Cells were analyzed in the flow-cytometer immediately, without fixing in 2% formaldehyde, as the fixative has been shown to reduce immunofluorescence, particularly for weak ligand-receptor interactions. A specific reaction of antibody to an efficiently expressing COS cell transfectant resulted in intense fluorescence of approximately 30-50% of COS cells, demonstrating the efficiency of the DEAE-Dextran transfection method.

Fluorescence is reported either as percent (%) positive fluorescence, which reflects the total ligands bound in a given population (ligands/sample) or median fluorescence intensity, which reflects the mean number of ligands per cell, with the background values subtracted for each set of data. Percent positive fluorescence can give a more accurate representation of the data as it does not bias the results in favor of larger cells that may have more ligands. Both values are reported where appropriate.

(xviii) Affinity Purification of Polyclonal Antibodies

To test the antibody reactivity of purified polyclonal antibodies, three affinity columns were coated with the peptides against which the antisera were raised and the purified antisera were then eluted. Columns were prepared with the standard procedure using Cyanogen Bromide (CnBr) activated protein A (Pharmacia LKB Biotechnology). CNBr-activated Sepharose 4B is supplied freeze-dried in the presence of additives that must be washed away at low pH (pH 2-3) before coupling the desired ligand. Low pH (pH 2-3) preserves the activity of the reactive groups, which otherwise hydrolyze at high pH. The peptides to be coupled were dissolved in coupling buffer, 0.1 M NaHCO$_3$, pH 8.3 containing 0.5 M NaCl. 5 ml of coupling solution was used per gram of freeze dried CnBr beads. About 5-10 mg protein per ml swollen gel is recommended. Depending on the size of peptide, the formula estimates peptide as 100× smaller than antibody. Each peptide was coupled to beads at 50 mg/ml. Antibody weight molecular density is 10 mg/ml (i.e. for 2 ml of beads—use 20 mg antibody). With peptide the molecular weight (MW) was used. The MW of antibody is 160,000 d.

To prepare the column, 1.5 g of CnBr beads were weighed out and placed in a 50 ml polypropylene (Falcon) tube. The beads were resuspended in 5 ml of 1 mM HCl, pH 2-3. (1:5000 dilution of stock 11.7 M HCl). 1 gram of beads gives about 3.5 ml swollen gel. The gel swells immediately and the additives were immediately washed away by transferring the suspension to a sintered glass filter and washing for 15 minutes with 1 mM HCl (approximately 400 mls or 200 ml/g of freeze-dried powder). The peptide ligand (up to 20 amino acids) was dissolved in 50 mls of coupling buffer (NaHCO$_3$, (0.1 M), pH 8.3/NaCl (0.5 M), 5 ml per gram powder) and mixed with the gel in a 50 ml Falcon tube with rotating end-over-end for 2 hours at room temperature or overnight at 4° C. A 100 μl aliquot (pre-coupling) was removed to measure the OD$_{280}$. A magnetic stirring bar should not be used as it could dislodge the activated coupling groups. The following day 100 μl of the post-coupling eluate was removed to check the OD$_{280}$. The OD of Post vs Pre should be >95%, otherwise the experiment should be repeated. If the OD was sufficiently different, the beads were transferred to a 50 ml Falcon tube, the supernatant was carefully aspirated and excess ligand was washed away by filling the tube with at least five gel volumes of coupling buffer. Any remaining active groups were blocked by incubation with Tris-HCl buffer (0.1 M, pH 8) or ethanolamine (1 M, pH 9) for 2 hours at room temperature or 16 hours at 4° C. The product with three cycles of alternating pH in a 50 ml Falcon tube, pelleted each time in a Beckman benchtop centrifuge at 1000 g with no brake for two minutes. Each cycle should consist of a wash with Sodium Acetate buffer 1 M, pH 4/NaCl, 0.5 M followed by a wash with Tris buffer, 0.1 M, pH 8/NaCl, 0.5 M. The beads were then loaded onto columns and/or stored sealed at 4° C. until ready for use. The beads were never allowed to dry out after ligand coupling.

To couple the antisera to the column, the peptide-coupled beads were resuspended in approximately 20 mls of 0.1 M Tris-HCl, pH 8.0/5 M NaCl. Each set of beads with bound synthetic peptide was transferred to a column (BioRad™), loading a maximum of two mls and keeping the beads hydrated. The column was washed with 10 mls of 0.1 M glycine, pH 2.5 and neutralized with 10 mls or more of PBSA. The column pH was checked to insure it was 8.0. Antiserum was diluted 1:5 in PBSA, thus 20 ml aliquots of serum were diluted to 100 mls in PBSA. The diluted serum was filtered through a 0.22 μm bottle-top filter to remove debris. The antisera was placed in a bottle above the column with a tube inside leading to the lid of the column below, which had been primed by gently allowing a few drops of serum to run down the side of the tube. The flow rate was adjusted by moving the height of the bottle to about 1 drop/second and the eluate was retained. The serum was clear as expected and the elution took 2-3 hours. The column was washed with 40-50 mls of PBSA by the same flow procedure and the eluate again retained. Bound antibodies were eluted by adding 10 mls of 0.1 m glycine pH 2.5 down the side of the column above the beads. The eluate was collected in 1.0 ml fractions containing 100 μl of 0.1 M Tris-HCl, pH 8.0. The column was neutralized with 0.1 M Tris-HCl, pH 8.0 followed by 10 mls of PBSA and the pH was monitored to return to 8.0. The column was capped and stored in PBSA containing 5 mM sodium azide at 4° C. The OD of each fraction of the eluate was checked at 1=280 nm to be >0.7. If it was less than this, something had gone wrong in the procedure or the antibodies had not coupled to the column. The fractions of greatest optical density were pooled, usually about 3 fractions starting at around the third fraction, and placed in dialyzing tube hydrated in PBSA. The dialysis tubing was secured and placed in PBSA overnight in the cold room. The following day, the antibodies were concentrated, loading two mls at a time, using Centricon 100™ columns (Amicon). The columns were spun at 4500 rpm for 20 minutes or until the desired volume of ~300 μl was achieved. The OD$_{280}$ was checked by the antibodies 1/10 to 50 μl. The OD had to be >0.14 or preferably 0.2-0.5 to use the antibodies in further experiments. An OD of 1.4=1 mg/ml protein. The antibodies were stored at 4° C. if used within a few days or −20° C. or −80° C. if the antibodies would not be used for at least two weeks.

(xix) Immunohistochemistry

Frozen histological sections embedded in paraffin were stained using the biotin-avidin horseradish peroxidase Kit™ (DAKO, UK), with the staining performed by Margaret Jones and Helen Turley, Department of Cellular Science, John Radcliffe Hospital, Oxford, UK). The method allows detection of binding via the biotin-avidin complex (Hnatowich, D. J. et al., *J. Nucl. Med.*, 28: 1294-1302, 1987). Cold tissue sections were incubated 30 minutes with 10 μg/ml of biotinylated Fc-chimera or an antisera and washed once in a Tris/Borate/Saline bath. 100 μl of a streptavidin-biotinylated horseradish peroxidase solution was added to sections that were then incubated 30 minutes at room temperature. Binding was detected with the addition of 100 μl DAB solution/section to detect positive binding shown by brown staining.

(xx) Standard Reagents and Solutions (a) Media and Standard Buffers

Trypsin-EDTA was supplied as a 5× stock (0.5%/10 mM) and diluted in PBSA for use. SDS-PAGE solutions included Running Buffer, 15 g Tris base (5× stock) per litre of solution, 72 g Glycine and 5 g SDS. The resolving gel preparation for a 10 ml 10% gel contained: 3 ml of 30% Acrylamide/bis(29:1) 2.5 ml 1.5 M Tris pH 8.8, 100 μl 10% SDS, 4.4 ml H$_2$O, 100 μl of 10% ammonium persulphate (APS), 10 μl of TEMED. A 4% stacking gel required mixing to 5 mls: 1.3 mls of acrylamide stock, 2.5 ml of 0.5 M Tris pH 6.8, 100 μl 10% SDS, 2.1 ml H$_2$O, 50 μl of 10% APS, and 5 μl TEMED.

5× Transcription buffer contained 200 mM Tris-HCl, pH 8.0; 40 mM MgCl$_2$; 10 mM spermidine; and 250 mM NaCl. This buffer can be used for T3 and T7 RNA polymerase driven transcription reactions, but not SP6 driven reactions.

5× Hybridization buffer contained 200 mM PIPES pH 6.4; 2 M NaCl; and 5 mM EDTA. The working solution was 1 part 5× hybridization buffer to 4 parts deionized formamide.

Primer extension reagents used were Diethylpyrocarbonate (DEPC); [γ-$^{32}$P] ATP (10 m Ci/ml, 6000 Ci/mmol); 100 ng/ml oligonucleotide; 10× polynucleotide kinase buffer; T4 polynucleotide kinase (Boehringer Mannheim, Germany); 4 M ammonium acetate; Ethanol; 0.3 M sodium acetate; 1× aqueous hybridization solution; S1 hybridization solution; 75% ethanol/–25% 0.1 M sodium acetate, pH 5.2; 4 mM 4dNTP mix (Pharmacia); 10× reverse transcriptase (RT) buffer; Placental ribonuclease inhibitor (e.g., RNAsin™ from Promega Biotec); AMV reverse transcriptase; 0.5 M EDTA; 1 mg/ml pancreatic ribonuclease A; 2.5 M ammonium acetate; 25:24:1 phenol/chloroform/isoamyl alcohol; 70% ethanol/30% DEPC-treated $H_2O$; T:E buffer; and Formamide loading buffer.

(b) Immunoprecipitation—Stringent Wash Method

The lysis buffer contained 1-3% non-ionic detergent (eg 1% NP-40); 20 mM Tris pH 7.5 or 8.0; 150 mM NaCl; 5 mM EDTA; 2.5 mM iodoacetamide; 200 µg/ml soybean trypsin inhibitor; 1 µg/ml pepstatin; 0.5 µg/ml leupeptin; 0.2 µg/ml aprotinin; and 1.5 mM PMSF Buffer A contained 10 mM Tris pH 8.0, 500 mM NaCl, 0.5% NP40, and 0.5% SDS.

Buffer B contained 10 mM Tris pH 8.0, 150 mM NaCl, 0.5% NP40, 0.5% DOC; and 0.05% SDS.

Buffer C contained 10 mM Tris pH 8.0 and 0.05% SDS.

Depending on primary antibody species and class, a 20% solution (vol/vol) of protein A agarose or protein G-agarose in PBS was prepared.

(c) Standard immunoprecipitation buffer contained 1% Detergent (NP-40, TX-100, etc.); 20 mM Tris (pH 8-8.3) (Tris-Base); 150 mM NaCl; and 5 mM EDTA.

(d) Cell Culture

PBSA was supplied from the ICRF Central Services Facility according to the following formulation: 137 mM NaCl; 2.7 mM KCl; 8.1 mM $Na_2HP$; 1.5 mM KH2PO4 (titrated to pH 7).

Trypsin-EDTA was supplied as a 5× stock (0.5%/10 mM) and diluted in PBSA for use.

(e) Bacterial Culture Solutions

TYM broth (per Litre of solution) contained 20 g Bacto-Tryptone; 5 g Yeast extract; 100 mls 1 M NaCl; and 10 mls 1 M $MgSO_4$. The mixture was autoclaved before use. It can be kept indefinitely at room temperature.

(f) Antibiotic Stocks

Ampicillin and Spectinomycin made up as 100 mg/ml in water and stored at −20° C. Tetracycline made up as a stock solution of 30 mg/ml in 50% ethanol and stored at −20° C.

(xxi) Molecular Biology Solutions and Standard Buffers (a) Tris-Equilibrated Phenol Distilled, water free phenol was tris-equilibrated before use by adding several cycles of 200 mls of 1 M Tris pH 8.0 to 1 litre of Phenol, shaking vigorously, allowing to settle and aspirating the aqueous phase. The cycles were repeated until the aspirated aqueous phase was pH 8.0. A small amount of aqueous phase must be left behind on the surface of the equilibrated phenol storage in a sealed container at 4° C. Before storing, 0.4 g of 2-hydroxy quinoline was added to 1 litre of equilibrated Phenol as an anti-oxidant.

(b) Standard Buffers

Stock solutions of filtered 1 M Tris-HCl (pH 7.0, 7.5, 8.0, 9.0), 0.5 M NaEDTA (pH 8.0), 1 M NaCl, 1 M KCl, 1 M $MgSO_4$, 5 M NaOH, 3 M NaOAc, 1 M Dithiothreitol (DTT), 100 mM ATP, 1 M Spermidine and 1 M $NH_4OAc$ were maintained. BSA at 10 mg/ml was purchased as a molecular biology grade reagent from Boehringer and stored at −20° C.

(c) T:E Buffer

| Standard | High | S:T:E |
| --- | --- | --- |
| 10 mM Tris (pH 8.0) | 20 mM Tris (pH 8.0) | 10 mM Tris (pH 8.0) |
| 1 mM EDTA | 10 mM EDTA | 1 mM EDTA/100 mM NaCl |

(d) 10×T:B:E: Per litre of solution contained 108 g Tris base; 55 g Sodium Borate; 9.3 g Na EDTA (do not pH solution). The working solution was 0.089 M Tris-borate, 0.025 M EDTA (pH 8.3).

(e) 50×T:A:E: Per litre of solution contained 242 g Tris base; 57.1 ml glacial acetic acid; 100 ml 0.5M EDTA (pH 8.0). The working solution was Tris-acetate 0.04 M, 0.001 M EDTA and Ethidium Bromide stock solution (10 mg/ml) added to a final concentration of 20 mg/ml.

(f) 5×MOPS: Per litre of solution contained 41.8 g Sodium MOPS; 16 mls 3 M Sodium Acetate; and 10 mls EDTA. This solution is used for running RNA denaturing formaldehyde gels. MOPS cannot however be DEPC treated (risk of explosion) and therefore must be made up with DEPC-treated water from a clean RNAase free stock. The working solution was 0.04 ml MOPS, pH 7.0; 0.01 M acetate, 0.001 M EDTA. ⅙₀th volume of 37% formaldehyde was added to the gel just before pouring.

(g) DNA sample buffer contained per 50 mls of solution 20% Ficoll; and 0.1 g of Orange G dye; in 1×T:A:E/10 mg/ml ethidium bromide.

(h) RNA sample buffer contained 5 µl of RNA sample; 2 µl of 5×MOPS buffer; 10 µl deionized formamide; and 3.5 µl of 37% formaldehyde (stock). The buffer was heated to 70° C. for 5 minutes.

(i) RNA extraction solution contained 4 M Guanidinium Thiocyanate buffer. For one litre of solution, bring to 7 mls with 3 M Sodium Acetate (0.45 µm filtered and stored at 4° C.).

(j) Cesium Chloride solution: For a 5.7 M solution per 100 mls, 126 g of optical grade CsCl solution and 2 mls 0.5M EDTA was brought to 100 mls with deionized water. The solution was DEPC treated and stored in 20 ml aliquots at room temperature.

(k) Church and Gilbert buffer: For one litre of solution, add the following to a small amount of $dH_2O$ with a stirring bar and bring to one litre with $dH_2O$: 27 g Sodium diHydrogen Phosphate solution; 83 g diSodium Hydrogen Phosphate; and 10 mls 0.5 M EDTA (pH 8.0). The working solution is 2 parts of the above phosphate buffer to 1 part of 10% SDS, mixed immediately before use (0.77M sodium Phosphate, 5 mM EDTA, pH 8.0).

(l) Plasmid Extraction Solutions
Solution I contained per litre of solution, 20 mls of 0.5 mM EDTA (pH 8.0); Solution II contained per litre of solution, 40 mls of 5 M NaOH and 50 mls of 20% SDS. The working solution is 0.2 M NaOH, 1% SDS. Solution III contained per litre of solution, 200 g Potassium Acetate; and 80 mls Glacial Acetic Acid. The working solution is 5 M Potassium Acetate (pH 4.7).

(m) cDNA synthesis and ligation buffers: RT1 buffer (5×) contained 0.25 M Tris pH 8.2 (pH 8.8 at 42° C.); 0.25 M KCl; and 30 mM $MgCl_2$. RT2 buffer contained 0.1 M Tris pH 7.5; 25 mM $MgCl_2$; 0.5 M KCl; 0.25 mg/ml BSA; and 50 mM DTT. 10× Low Salt Buffer contained 60 mM Tris pH 7.5; 60 mM $MgCl_2$; 50 mM NaCl; 70 mM β-mercaptoethanol; and 2.5 mg/ml BSA. The Ligation additions (10×) buffer contained 1 mM ATP; 20 mM DTT; 10 mM Spermidine; 1 mg/ml BSA.

(n) 10× Kinase Buffer for labelling probes contained 0.5 m Tris pH 7.5; 10 mM ATP; 20 mM DTT; 10 mM Spermidine; 100 mM $MgCl_2$; and 1 mg/ml BSA.

(o) Linear Polyacrylamide (LPA) Carrier solution: A 5% solution of polyacrylamide was made in water and 0.5 mls of 10% Ammonium Persulphate and 50 μl TEMED were added and left for 1 hour at room temperature. The solution was diluted 1:25 (to 2 mg/ml) for a working solution and aliquoted and store at −20° C.

(p) 10×PCR buffer contained 100 mM Tris pH 8.3 (at 20° C.); 500 mM KCl; 2 mM $MgCl_2$ and 0.01% gelatin.

(q) DNA sequencing solutions: 5× Annealing Buffer contained 200 mM Tris pH 7.5; 100 mM $MgCl_2$; and 250 mM NaCl. Labelling Mix contained 2 parts of 1.5 mM each of dGTP, dCTP and dTTP; 2 parts of T:E; 1 part of 0.1 M DTT; 0.5 μl of $^{35}$S-dATP (Amersham, UK); 1 μl of 0.5% NP-40 per 50 μl labelling cocktail; and 1 μl of T7 DNA polymerase (Sequenase, US Biochemicals) added per 50 μl of labelling mix.

(r) Termination nucleotide mixtures: One was prepared for each dideoxy-nucleotide containing 80 mM of each dNTP (dATP, dGTP, dCTP and dTTP) and 50 mM NaCl and one containing 8 mM dideoxy-ATP, one containing 80 mM dideoxy-GTP and so on.

(s) Stop solution (Loading Buffer) contained 95% Formamide; 20 mM EDTA; 0.05% each of bromophenol blue and Xylene Cyanol.

(t) Transfection Solutions: DEAE-Dextran solution: 10 mg/ml of DEAE-Dextran (Sigma) was filtered through a 0.45 μm filter and stored at 4° C.

(u) Chloroquine Solution (1000×): A 100 mM stock was made in distilled water and 1 ml aliquots were stored at −20° C. Chloroquine deteriorates after thawing.

(v) PBSA-10% DMSO: To 500 ml PBSA was added 10% (v/v) DMSO and the solution stored at room temperature for up to one week.

(w) PEG solution: PEG-1000 was melted in the microwave for 30 seconds on high power to prevent superheating and aliquoted into 50 ml tubes, which were then frozen. To make PEG solution a 50 ml aliquot was melted by microwaving and added to an equal volume of DMEM. The pH can be titrated back to neutrality with a few drops of 5 M NaOH and judged by the color of the phenol red indicator or with a piece of pH paper. The solution was then filtered through a 0.45 μm filter and stored at 4° C.

(x) Tris and EDTA solutions: For transfection these were either made fresh or by diluting stocks, and filtering through a 0.45 μm filter followed by storage at 4° C.

(y) Protein Electrophoresis Buffer: Running Buffer: 15 g Tris base (5× stock) per litre of solution; 72 g Glycine; and 5 g SDS.

Fc-CD33 as a Probe with the Panning Method

The CDM8 and pIG1Fc expression vectors were used to isolate candidate ligands of interest from cDNA libraries transfected into COS cells, EDTA lifted and probed with Fc-CD33, and then incubated on "panning" plates previously coated with goat anti-human Fc (Simmons 1993). Each round of panning was designed to allow for the enrichment of the population of candidates that were expected to bind to the Fc chimera used as a ligand probe.

Figure 3B:
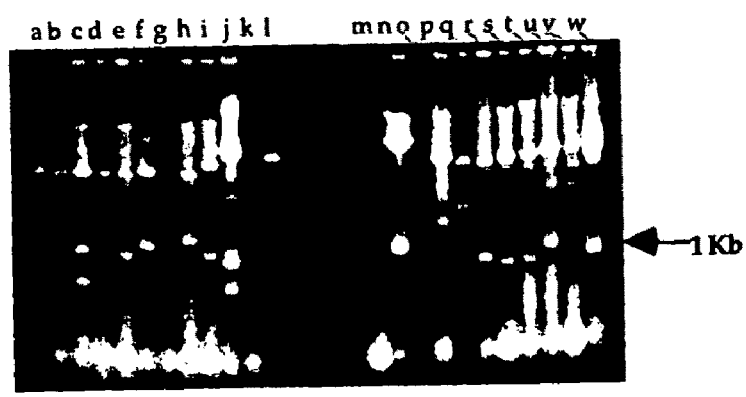

Panning was attempted with Fc-CD33 using transfected U937, HL-60, K562, KG-1, KG-1a, KG-1b and placental cDNA libraries. Libraries from the K562 cell line, derived from early myeloid and erythroid blast cells (erythromyeloblasts), and placenta gave the most promising panning results with Fc-CD33, showing at least five COS cells panning by the second round. In retrospect, this may be due to the high level of potentially CD33-binding sialic acid on K562 cells, which was likely present on COS cells transfected with its cDNA. Panning efforts were pursued several times with little success beyond the second round. This was likely a result of amplification of transfected E. Coli. on amp/tet plates to prevent lysis by bacteriophage, thought to be lysing the cultures normally amplified in flasks in some panning attempts. Following several attempts at panning, 20 novel cDNAs from K562 and placental cDNA libraries were selected as candidates based on their high representation, performing 24-48 minipreps after each round. The 'panel' of candidates is shown below as cut miniprep cDNA (FIGS. 3A and 3B). Most of the candidates had a size of about 1 Kb, a well-represented size in cDNA libraries (Simmons, D. L. et al., *J. Immunol.*, 148: 267-271, 1992).

FACS Staining of "Candidate" cDNAs with Fc-CD33

Following transfection of each of the twenty cDNAs, these candidates were then subjected to a 'blind' screen using the Fluorescence Activated Cell Sorter (FACS) analysis to assess binding with Fc-CD33. Several candidates appeared to be positives with the highest level of staining at 38%. Most candidates were isolated from the 2nd or 3rd rounds of panning using the placental cDNA library. Previous staining showed that several candidates produced levels of staining that differed by only 5-10% making true positives difficult to distinguish. By contrast, FACS analysis of myeloid leukemic cell lines using Fc-CD33 was much higher (up to 97%, data not included). Low levels of staining with the transfectants was attributed to possible low transfection efficiency of the cDNA and the low affinity binding of the ECD-Fc constructs (other labs have reported binding of several ECD-Fc proteins to be far lower than antibodies or other ECD-Fc's) (Hollenbaugh, D. et al., *EMBO J*, 11: 4313-4321, 1992). The existence of several ligands for each molecule, as suggested by iodination experiments with Fc-CD33, would require the transfection of all of the putative ligand chains to achieve full ligand binding efficiency.

Fc-CD33 binding was assessed in a FACS analysis to transfectants with the four major candidates isolated using the panning process as well as to CD33 itself (FIG. 4). All candidates were isolated from the placental library, a good source of diverse genes, on the second or third round of panning. The staining is shown for all candidates together and for each candidate individually. Two of these candidates proved to be ICAM-1 and 250 bp of sequence for the other did not match known sequence. In one transfection out of at least five attempts, 36% binding was achieved to ICAM-1, and 9.6% to apo-4 with Fc-CD33Rg. The highest percentage of staining that one can expect with antibodies to transfected molecules is usually about 10-30%; ECD-Fc proteins bind with lower affinity and thus 2-10% staining was considered positive (personal communication, David Simmons).

Based on the staining data, several candidates were sequenced. Two of these were revealed to be ICAM-1 cDNA and a cDNA clone homologous to the 3' end of the dystrophin gene that was subsequently characterized as apo-dystrophin-4 (apo-4). ICAM-1 was viewed skeptically because several labs had isolated it using Fc-chimeras and it was thus thought to bind non-specifically (D. Simmons, personal communication), although thus far it has been shown to bind to LFA-1 (Simmons, D. et al., *Nature.*, 331: 624-627, 1988), hyaluronan (McCourt, P. S. G. et al., *J. Biol. Chem.*, 269: 30081-30084, 1994), and CD43 (Rosenstein, Y. et al., *Nature*, 354: 233-235, 1991). To directly test the ability of Fc-CD33 to precipitate surface labelled proteins, K562 and COS transfected with the apo-4 cDNA and ICAM-1 were surface iodinated and precipitated with Fc-CD33 (FIG. 5).

Native ICAM-1 precipitates at about 85-110 Kd (Simmons 1988). Fc-CD33Rg precipitated a heavily labelled doublet at 95-100 Kd from the ICAM-1 transfectant (Lane 7). In this assay, ICAM-1 was being used for comparison to the apo-dystrophin-4 cDNA, however, insufficient sample was available for a negative control. Fc-CD33Rg (Lane 5) and Fc-CD33pIg1 (Lane 6) precipitated a band at about 100 Kd from the apo-dystrophin-4 cDNA and fainter bands at average weights of 45, 50 and 66 Kd not seen in the control lane (Lane 4), suggesting that apo-4 could be a low-affinity ligand for CD33. The 66 Kd band is a bit more heavily labelled in Lane 5, suggesting that Fc-CD33 Rg is more efficient at precipitating apo-4. Under stringent washing conditions, Fc-CD33Rg (Lane 2) and Fc-CD33pIg (Lane 3) precipitated a unique band from K562 at 46 Kd and others, although they appear to be similar to those in the control lane. The bands from Fc-CD33pIG are identical to those precipitated with Fc-CD33Rg except that the 70 Kd band is more heavily labelled, which likely accounts for its slightly higher position on the gel (Lane 3).

While Fc-CD33 was not shown to bind ICAM-1 in a further metabolic labelling experiment, the FACS staining and iodination were suggestive that it could be a ligand given the right conditions. CD33 is sialylated and ICAM-1 has been shown to bind sialylated proteins such as CD43 (Rosenstein 1991). CD33 COS transfectants will only bind if they are desialylated and it is probable that neighboring sialic acids on the COS cell will inhibit CD33 binding (Freeman 1995). In vitro, however, it is possible that Fc-CD33 is capable of binding the sialic acids on a transfected ICAM-1 molecule. During the panning process, no one candidate ever emerged as a strong positive for any Fc-adhesin tested (CD31, CD33, CD34, CD68, MUC-18) and, ultimately, Fc molecules, which approximate cell-cell interactions rather than antibody-ligand interactions, were deemed to have an affinity too low to use the panning method to search for ligands. Based on the iodination data shown here, several candidate ligands probably exist for CD33, as is the case for CD34 (Baumhueter, S. et al., *Science*, 262: 436-438, 1993; Oxley, S. M. and R. Sackstein, *Blood*, 84: 3299-3306, 1994) and hyaluronan (Aruffo, A. et al., *Cell*, 61: 1303-1313, 1990; McCourt 1994). Other literature suggests that molecules that bind with low affinity via a protein-carbohydrate interaction (eg. the selectins) are good candidates for having multiple ligands (Baumhueter 1993). As the panning system provided constraints for proving any ligand definitively, the apo-dystrophin-4 clone was thus further characterized as a potential low-affinity ligand for CD33 and a potentially interesting clone that could play a role in both muscle cells and hematopoietic cells as has recently been shown for Dp71 (apo-dystrophin-1) also originating from the 3' end of the dystrophin gene but utilizing a different frame from dystrophin in the final exon (Hugnot, J. P. et al., *Proc. Natl. Acad. Sci. USA*, 89: 7506-7510, 1992; Lederfein, D. et al., *Proc. Natl. Acad. Sci. USA*, 89: 5346-5350, 1992).

An Fc-CD33 Candidate Ligand is Termed Apo-Dystrophin-4

To compare the apo-dystrophin-4 cDNA to known dystrophin and related cDNAs, the entire cDNA was sequenced in both forward and reverse directions and translated into all three frames (the second one of which is shown in FIG. 6) and the oligonucleotides used to sequence it and to perform PCR appear in the appendix. The cDNA sequence begins at position 1, with additional upstream genomic sequence at −233 to −1 obtained with genomic clones from the 3' intronic region of exon 78, later found to match the region of apo-4. The structure of the 3' approximately 546 bp was compared with the sequencing of genomic phage clone DNA from the 3' region of dystrophin (Kunkel, L. M. et al., *Gene*, 33: 251-258, 1985) to confirm the precise point of a 137 bp inversion discovered at the 3' end of apo-4. The second reading frame includes both the putative N-terminus of apo-4, an upstream exon identified with GRAIL and the hydrophobic frame of exon 79 spliced onto the 31 3' terminal amino acids of Dp71 (Lederfein 1992) which appear in unspliced apo-4 from 454 bp to 546 bp (FIG. 2).

The 23 stop codons in the apo-4 sequence prompted a search for additional nucleic acid subsequence sites that could provide a clue as to how apo-4 was translated. The sites identified follow: 1) Splice sites—Potential donor and acceptor sites were found near the start of the cDNA suggesting that the gene is unspliced; 2) Cap sites—Several Cap sites I and II were identified. A Cap site I at −3 bp upstream from a CAAT box at 57 may indicate a transcription start site; 3) CAAT boxes—a CAAT box was found at +57, −31 bp upstream from a potential initiating methionine at +88 bp and −39 bp upstream from the "strong" initiating methionine at +100 bp, based on Kozak sequences (Kozak, M., *Nucleic Acids Res*, 15: 8129-8133, 1987)—a CTF-NF1 transcription factor binding site overlaps with this CAAT box to reinforce the proposal that this could be a potential promoter region. No TATA box is present at −40, but one is found on the genomic DNA at −219 bp. If it is a true TATA box, it could act on sequence upstream of apo-4; 4) Poly A sites—two AATAAA Poly A sites have been observed in the cDNA at +545 and +631 as well as a cryptic AATTAA site at 990, which could potentially be used; 5) Poly T regions—Poly T regions have been found downstream of both Poly A sites, providing evidence that these sites could be used for cleavage following recognition of the Poly A signal; 6) Inverted Repeats (Palindromes)- Seven palindromes, which have been shown to occur near inversions, ranging from 8-10 bps were found in the cDNA and seven more in the upstream genomic sequence; 7) Direct Repeats—signal insertion sites for transposable elements were searched in relation to the inversion. 13 direct repeats have been found in the sequence with a minimum stringency of eight bp (maximum 11 bp). Notably, a direct repeat of 8 bp exists at 861, 1 bp downstream of the inversion and appears as TTATAAAGAAAGA^ATTATAAAG (SEQ ID NO: 7). An 8 bp direct repeat exists at −1 base 5' to the inversion and forms a palindrome with genomic sequence. A detailed list of the subsequence sites found appears in FIG. 36. Nucleic acid subsequence sites not found in apo-4 include AP2, GCN4, Homeo, MaIT box, Octamer, Pu box, and Sp1 sites. Sp1 sites are most often identified with housekeeping genes.

Apo-4 Shares a Similar Inversion with Globin Gγ(γβ)°

Figure 7:
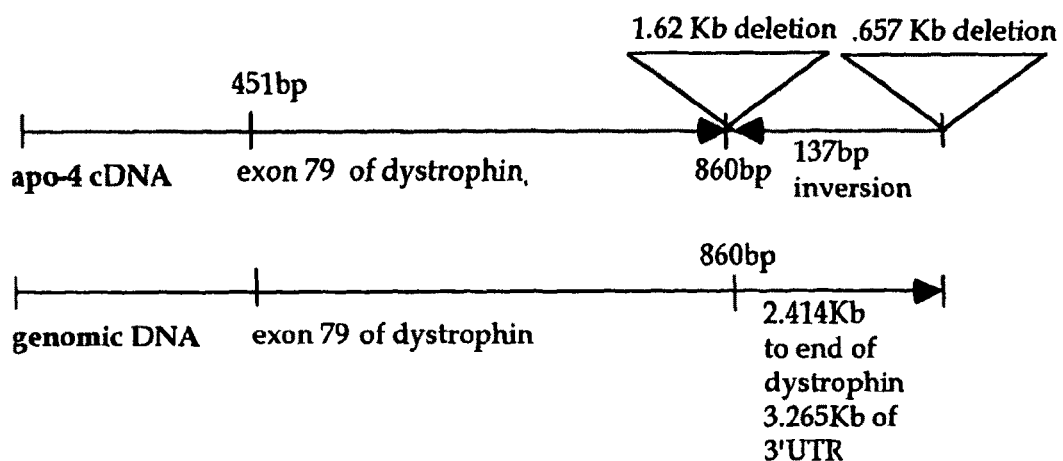
FIG. 7: Gene Structure of apo-4 cDNA compared with the dystrophin 3' UTR. The figure shows a basic comparison of the differences between the apo-4 cDNA and genomic sequence, homologous with the dystrophin 3' UTR, diagramming the deletion and inversion at the apo-4 3' end.

The globin Gγ(γβ)° gene was one of the first disease causing genes identified that contains two deletions and an internal inversion in Indian Aγδβ Thalassaemia (Jones, R. W. et al., Nature, 291: 39-44, 1981). The apo-dystrophin-4 cDNA described here contains a 1.62 Kb and a 657 bp deletion and an insertion of a 137 bp inversion at the 3' end (with an 8-11 bp overlap at the 5' end of the inversion when compared with genomic and known cDNA sequence) (FIG. 7). In genomic DNA, the 137 bp sequence occurs as the reverse and complement of the inversion, 1.623 Kb downstream.

Yeast Artificial Chromosome (YAC) Hybridization

Figure 8:
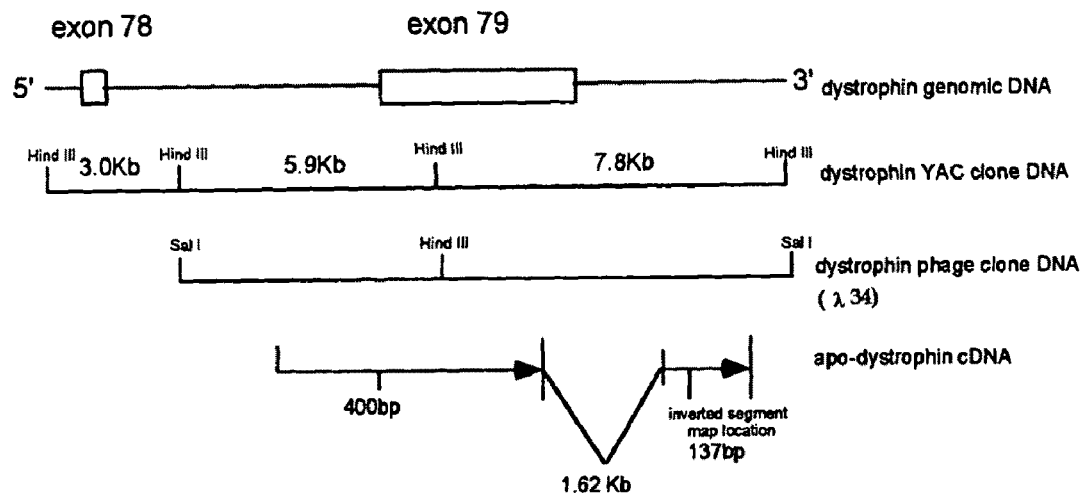
FIG. 8: Comparison of YAC and phage genomic dystrophin DNA and apo-dystrophin-4 cDNA clone. The map indicates the relative sizes and positions of YAC clones in the region found homologous to the apo-dystrophin-4 cDNA. The fragment sizes indicated represent one Hind III YAC fragment each. Full length and partial DNA probes from the apo-dystrophin-4 clone were constructed to confirm that the clone was represented in the region identified in a homology search. A 5' 451 bp probe hybridised to the 5.9 Kb Hind III fragment and the 7.8 Kb Hind III fragment while the 3' 546 bp localised to only the 7.8 Kb Hind III fragment, as expected (data not shown). The intron between exons 78 and 79 is 4.8 Kb. The λ34 phage clones were used in PCR experiments to check whether the inverted region could be reproduced in genomic DNA. Exon 79 of dystrophin occurs 451 bp downstream of the apo-dystrophin-4 cDNA. The 451 bp region was hybridized to human and murine genomic YAC clones to confirm its location on genomic DNA in the region of exon 79 of dystrophin.

Due to the unusual structure of apo-4, work was carried out in collaboration with Dr. Jamel Chelly in Dr. Anthony Monaco's laboratory (ICRF Labs, IMM, Oxford) to map the full length apo-4 gene (FIG. 10) and the 5' 451 bp upstream of exon 79 and 3' 546 bp fragments to genomic YACs (FIG. 9) (Monaco et al. 1992). The YACs probed covered the region from exon 78 and its 3' intron, to exon 79 in genomic dystrophin DNA, with the appropriate fragment sizes (FIG. 8). Restriction sites are indicated. Both the known 3' 546 bp and previously uncharacterized 5' 451 bp fragments hybridised, confirming that this was a novel cDNA, homologous with the 5' region of exon 79, the final carboxy terminal exon of the dystrophin gene. In addition, 451 base pairs of intronic DNA exist 5' to exon 79 in apo-4.

Notably, both the 5' 451 bp and the 3' 546 bp apo-dystrophin-4 cDNA fragments hybridised to mouse YAC clones, indicating that both fragments shared some homology to mouse in the region of exon 79 and the region previously considered intronic upstream of exon 79 (FIG. 10).

Homologous Regions in cDNA, Genomic and Mouse DNA

To assess the level of species conservation of any proposed new exons, mouse and human genomic DNA were aligned with the apo-4 cDNA using GCG Pileup (Genetics Computer Group, Program Manual for the GCG Package, Version 7, 1991). It was found that the 5' 1-451 bps are in the 5' intronic region of exon 79 DNA relative to the full-length dystrophin mRNA (Koenig, M. et al., Cell, 53: 219-226, 1988) and nucleotides 451-859 include the three translated amino acids of frame one of exon 79 in dystrophin (31 aa in the second reading frame used in Dp71 and proposed in apo-4) and its remaining untranslated region (UTR) (FIG. 11). Nucleotides 860-996 are in the inverted region and also normally occur in the reverse orientation at 13,163-13,309 bp in the 3' UTR of the dystrophin cDNA, 1.623 Kb downstream of the inversion beginning at 860. In other words, apart from the inverted region of 137 bp at the 3' end, the apo-dystrophin-4 cDNA is completely homologous to genomic dystrophin DNA from the same region. Thus, only the alignment of the human and mouse genomic clones are shown (FIG. 11) and include 233 bp of genomic sequence upstream of the start of the apo-4 cDNA. It shows 96% homology to the full-length human cDNA beginning 43 bp upstream of exon 79 to 859 (1100 in FIG. 11) and approximately 57.2% overall homology to the expressed 5' apo-4 region 451 bp upstream of exon 79 and 48.5% homology to the proposed exon, termed here as 78.3. The exon identified by GRAIL in the apo-4 cDNA is from 149-243 and shares a 37.9% homology with the mouse DNA shown. Another 75 bp of mouse genomic DNA should be sequenced however, to have a quantitatively identical number of nucleotides in this region and thus determine a more precise alignment. The potential mouse exon identified by GRAIL at 465 shares 64% homology with the human sequence over the next 78 nucleotides to the first available splice site, lending weight to the idea that this region contains additional exons that could be spliced into a functional mRNA.

The 45.5% homology shown for exon 78.3 is markedly less than the homology in the region of exon 79, yet it is not inconsistent with the approximately 40% homology in the N-terminus between human and mouse for other cell surface molecules, including a proximal extracellular domain of phagocytic glycoprotein-1 (Pgp-1, 42%) (Zhou, D. F. et al., *J. Immunol.*, 143: 3390-3395 1989) and the N-terminus of the leukocyte common antigen (LCA, 50%) (Thomas, M. et al., *J. Recept. Res*, 7: 133-155, 1987).

GRAIL Identifies an Exon Upstream of Apo-Dystrophin-4

Because the apo-4 sequence contained stop codons and was from a region that normally acts as an intron, we attempted to identify potential new exons by submitting the apo-4 sequence to a GRAIL search to localize intron/exon borders based on known probabilities. Both the full length mouse sequence (1044 bp) and human sequence (1234 bp), which included the 230 bp of sequence upstream of the apo-dystrophin-4 cDNA were submitted to a GRAIL database search for the potential identification of new exons. While no new exons were found in apo-4, the mouse sequence identified a potential exon at position 291 (465 in FIG. 11) with a score of 0.141 and the human sequence identified a potential exon at position −91 (149 in FIG. 11) with a high score of 0.936 in the same frame as that predicted for apo-4. These studies suggested that the apo-4 gene was unspliced.

A Possible Upstream Transcription Start Site is Found

Figure 12A:
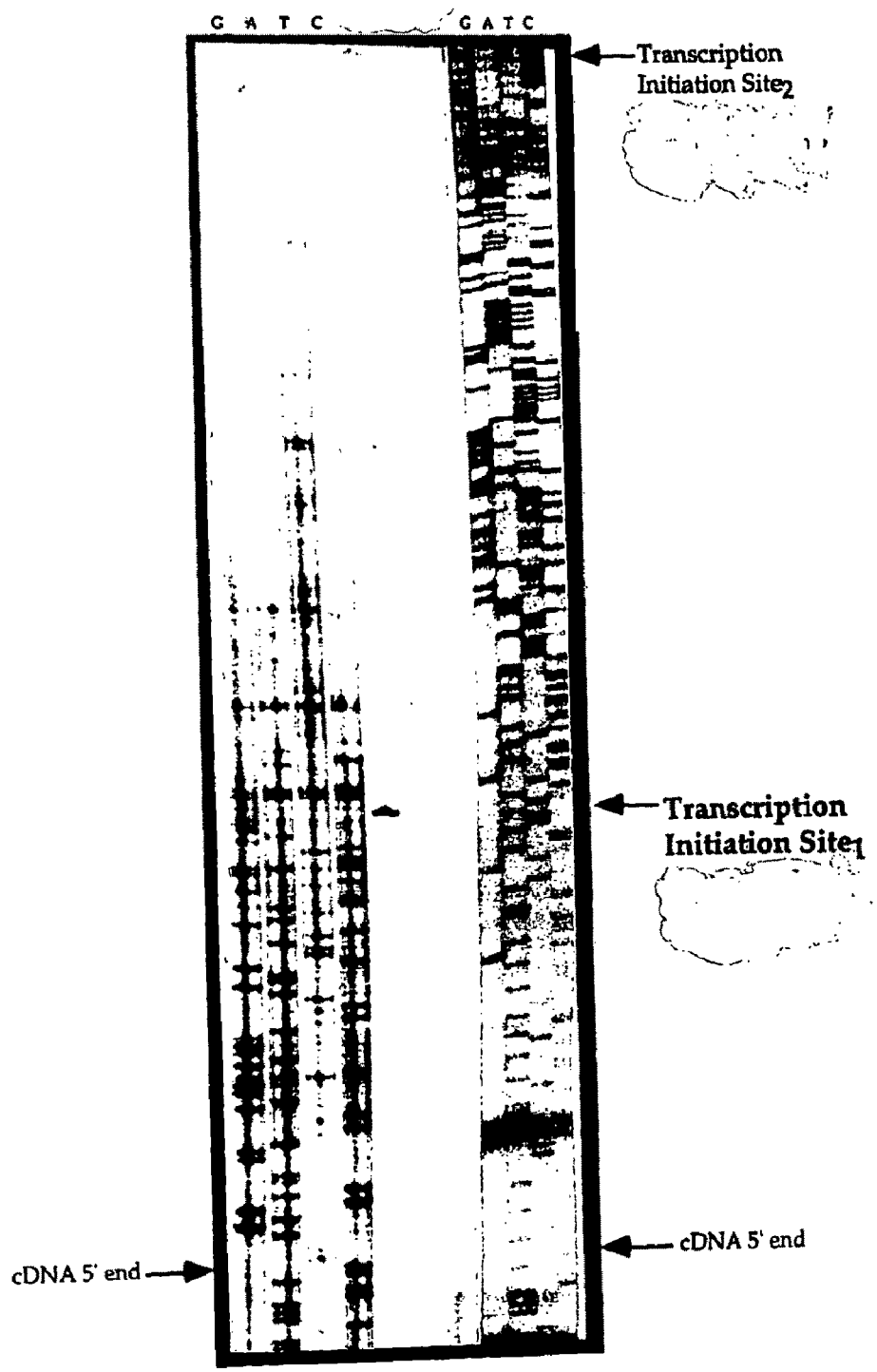
FIG. 12A: Primer Extension shows a putative transcriptional start site for the apo-dystrophin-4 cDNA. Lanes from left to right are GATC for apo-4 cDNA in pBluescript SK; Placental RNA; Blondolet RNA (-dystrophin); tRNA; and GATC for λ34 phage dystrophin DNA. One putative transcription initiation site is shown in genomic DNA at −70 bp from the 5' end of the apo-dystrophin-4 cDNA, −86 from M1 and absent in the Blondolet muscle cell line which lacks dystrophin. A second potential transcription start site appears at approximately −326 bp, present in minor amounts in the cell line. Neither site appears in the control tRNA lane. Exposure time was 12 hrs. at −80° C.

Primer Extension was performed to attempt to identify the 5' end of the mRNA transcript transcribed from apo-4 and a potential upstream transcription start site to determine whether the 5' end of apo-4 contained a truncated open reading frame (FIG. 12A). For the primer extension reaction, an antisense 36 oligonucleotide primer was designed to anneal 80 bp downstream of the 5' end of the apo-dystrophin-4 cDNA with the structure:

(SEQ ID NO: 8)
(5'CCTTGGCTATGAGTGATTGATTGATTACTTACTCTCTACTTG3').

The same primer was used to sequence apo-4 cDNA in pBluescript and γ34 genomic phage clones to precisely map the distance of a transcription initiation site from the 5' end of the apo-4 cDNA. Transcription start sites vary in distance from the initiating methionine, but most are from 50-150 bp upstream (D. Hochhauser, personal communication). The genomic clones had not previously been sequenced in this region, which covered part of the intron between exons 78 and 79 in the full-length dystrophin cDNA. In a comparison with genomic DNA alongside the cDNA, the appearance of a band indicated the end of the RNA transcript and a (proximal) start site for transcription at 70 bp upstream of the 5' end of the cDNA, −70 in the given sequence, near the end of the putative upstream exon identified with the GRAIL search (FIG. 12A) and within range to act on any of the first three methionines in apo-4. Another band, which may correspond to an additional (distal) start site, occurs roughly 250 bp upstream of the proximal start site. This putative promoter may act upon a potential exon upstream of apo-4. A TATA box was not found in what should be the promoter site, although a CAAT box was identified as well as a GC rich region. When the apo-dystrophin-4 upstream sequence was submitted to the Eukaryotic Promoter Database (Bucher, P., *J. Mol. Biol.*, 212: 563-78, 1990), region −139 to −177, 69-108 bp upstream of the putative initiation of transcription, aligned with 70% identity to the Hs arginase liver promoter. Thus far, five promoters, not all with TATA boxes, have been isolated along the length of the dystrophin gene, from tissue including brain (Gorecki, D. C. et al., *Hum. Mol. Genet*, 1: 505-510, 1992), muscle, cerebellum, sciatic nerve, and general non-muscle (reviewed in Ahn, A. H. and L. Kunkel, 1993).

The Start Site Contains a Potential Pol II Binding Region

Promoters for RNA polymerase II genes that do not contain obvious TATA boxes fall into two classes (Smale, S. T. and D. Baltimore, *Cell*, 57: 103-113, 1989). The first is the GC-rich promoter, found primarily in housekeeping genes that usually contain several transcription start sites spread over a large region and several potential binding sites for the Sp1 transcription factor (Dynan, W. S, and R. Tjian, *Cell*, 35: 79-87, 1983). The second class includes the remaining promoters, many of which are not constitutively active but are regulated during differentiation or development and initiate transcription at only one or a few tightly clustered start sites. *Drosophila* homeotic genes are in this class as are genes that are regulated during mammalian immunodifferentiation, such as the terminal deoxynucleotidyltransferase gene (TdT) (Landau, N. R. et al., *Proc. Natl. Acad. Sci. USA*, 81: 5836-5840, 1984); the TcR β-chain genes (Anderson, S. J. et al. *J Immunol*, 119: 1084-1088, 1988); the lck gene (Garvin, A. M. et al., *Mol. Cell. Biol.*, 8: 3058-3064, 1988), the $\gamma_5$ gene (Kudo, A. et al., *Genomics*, 1: 277-279, 1987); and the $V_{pre-\beta}$ gene (Kudo, A. and F. Melchers, *EMBO J.* 6: 2267-2272, 1987). The transcription start site and surrounding sequences characterized in the apo-4 5' UTR suggest that the promoter element is in the second class. This class of promoter is characterized by at least 40-50% homology to a 17 bp "Inr" sequence that flanks the transcription initiation site found in TdT (Smale and Baltimore, 1989) (FIG. 12B).

Northern Blotting Shows a Major Apo-4 Transcript of 1.62 Kb

Figure 13:
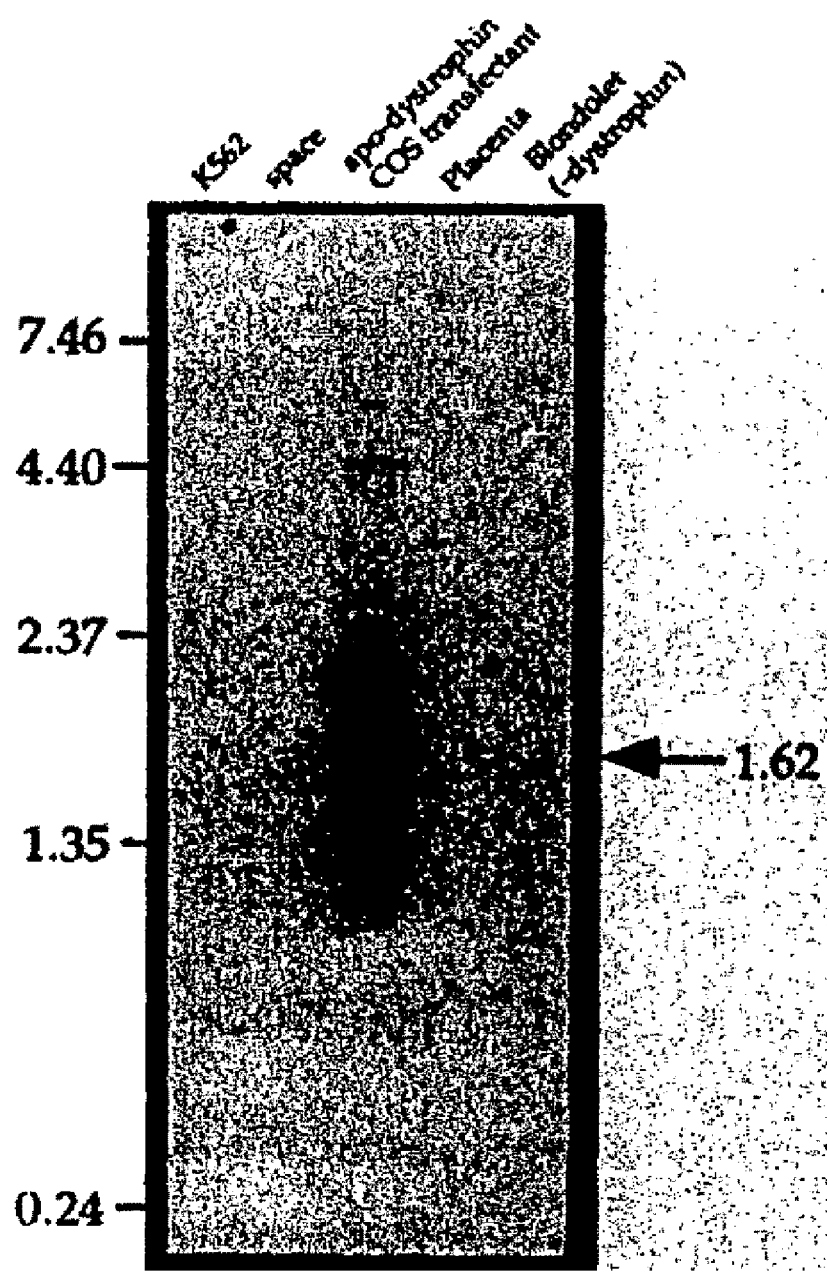
FIG. 13: The apo-dystrophin-4 cDNA hybridizes to RNA from apo-4 transfectants. 10 μg of Poly A selected RNA was probed using a full-length apo-dystrophin-4 DNA probe. Lanes from left to right are K562; space; apo-dystrophin COS transfectant; Placenta; and Blondolet (-dystrophin). CDM8 has an endogenous Poly A site 625 bp from the Pst I site at the 3' end of the insert. Transcripts range in size from 1.2-1.62 Kb with a predominant transcript at 1.62 Kb. The apo-4 cDNA contains endogenous Poly A sites at 546 and 632 and the slightly altered sites TATAAA at 849 and 863 bp and AATTAA at 990 bp which may account for the smaller signals. The K562 cell line, Placenta and dystrophin-deleted Blondolet cell-line did not hybridize to the probe. The placental RNA was total, as insufficient quantities were available for Poly A selection. The blot was washed twice in 2×SSC, once in 1×SSC and exposed for five hours at −80° C.

To test whether the apo-4 gene could be expressed at high levels in selected tissues and cell-lines, a poly(A) selected blot was prepared with 5-10 μg RNA per lane from placenta and leukemic cell lines using oligo dT cellulose columns. The RNA was purified in a separate laboratory to reduce the risk of contamination (courtesy of Professor Andrew McMichael, IMM, Oxford). The blot was probed with a full length apo-dystrophin-4 ssDNA and compared with previously isolated RNA made using oligo dT Dynabeads. Successful hybridization was shown on RNA from apo-4 COS cell transfectants from Dynabead RNA but not to K562 or the dystrophin-negative cell line Blondolet (FIG. 13), although the K562 and Blondolet had slightly less RNA and had been previously thawed a few times. No hybridization was demonstrated against 10 μg of oligo dT column Poly A selected RNA from panel of T, B and myeloid cell lines and only very little against the positive control COS transfectant poly A+ RNA, indicating that the RNA, although it mostly appeared of high quality on coomassie blue staining of the blot, was not hybridising well (data not shown). This shows that the full length transcript is produced in apo-4 transfected COS cells at high levels, as expected.

A 5' 451 bp apo-4 probe also did not hybridize to a commercially available blot with 10 μg Poly A selected RNA from heart, lung, muscle, kidney, liver and placenta (data not shown). Thus, apo-dystrophin-4 transcripts are likely to be restricted and not expressed at a high level.

RNAse Protection Reveals No Protected Transcript

Figure 14:
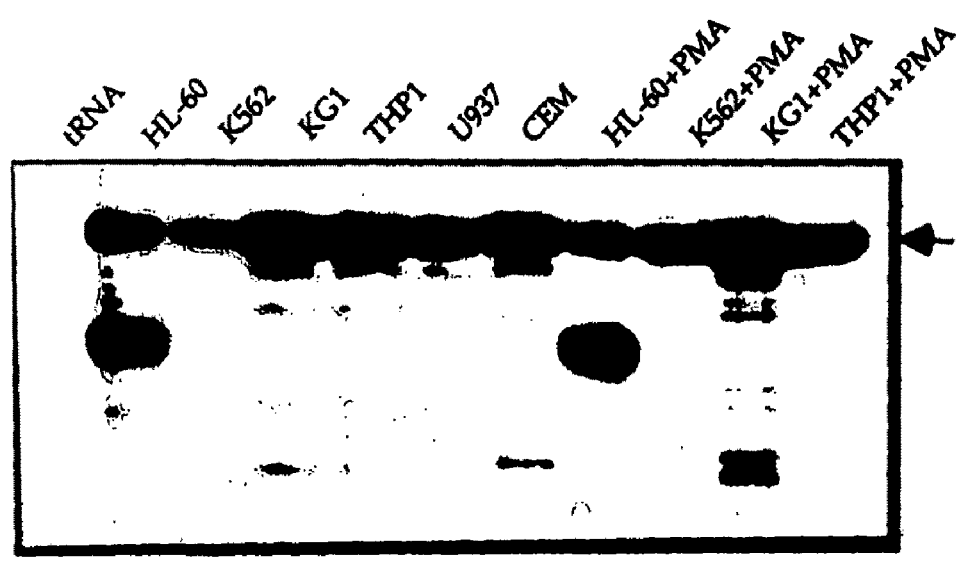
FIG. 14: RNAse protection on 10 μg of total RNA shows hybridization to a GAPDH probe but not to a 3' apo-4 probe. The arrow points to a strongly hybridised GAPDH fragment at 120 bp and demonstrates undegraded RNA, but the expected 287 bp signal was not detected for the 3' apo-4 probe (lanes not shown). Probes were labelled with $^{32}P$ and gel was exposed for 24 hrs. at −80° C.

To determine whether the inversion from apo-4 cDNA could be detected in 10 μg of total RNA, a 287 bp cDNA probe designed from apo-4 cDNA was cloned into pBluescript SK+. The insert was then digested with Hind III and Hpa I to excise the 5' 700 bp from the apo-4 insert and the remaining 287 bp were religated. After scaling up the DNA, the new insert in pBS was digested with Xho I to obtain a probe containing a 287 bp insert and 130 bp of vector sequence, for a 417 bp probe. Following RNAse protection with this probe, no unique signal was seen in the expected region above the 180 bp GAPDH probe, which protected the expected fragment of 120 bp (FIG. 14). Unique signals of about 80 bp were seen on the gel, but they were considered too small to be significant.

To examine whether the 5' 468 bp of apo-4 could be detected in RNAse protection, a probe was prepared by digesting with Pst I and Xmn I to leave the 5' 468 bp, but the protection assay revealed no hybridised product. This confirmed the hypothesis that apo-4 was a very rare transcript that could only be detected via RT-PCR, as was the case for the apo-dystrophin transcript Dp71 (Hugnot 1992) and many of the splice variants of CD44 (Jackson, D. G. et al., *J. Biol. Chem.*, 267: 4732-4739, 1992).

RT-PCR Analysis Produces Evidence for Apo-4

Figure 15:
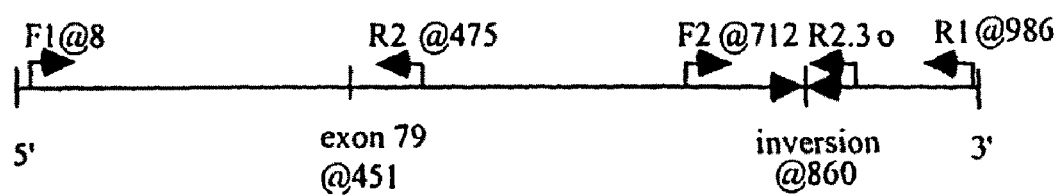
FIG. 15: Position of RT-PCR primers to analyze potential splice products and to attempt to reproduce the inverted region. Three sets of PCR primers were designed to reproduce the 5' unique 451 bp (F1+R2), the 3' 284 bp including the inversion (F2+R1) and 978 bp of the full-length apo-4 cDNA (F1+R1) or smaller, potentially spliced products.
Figure 16:
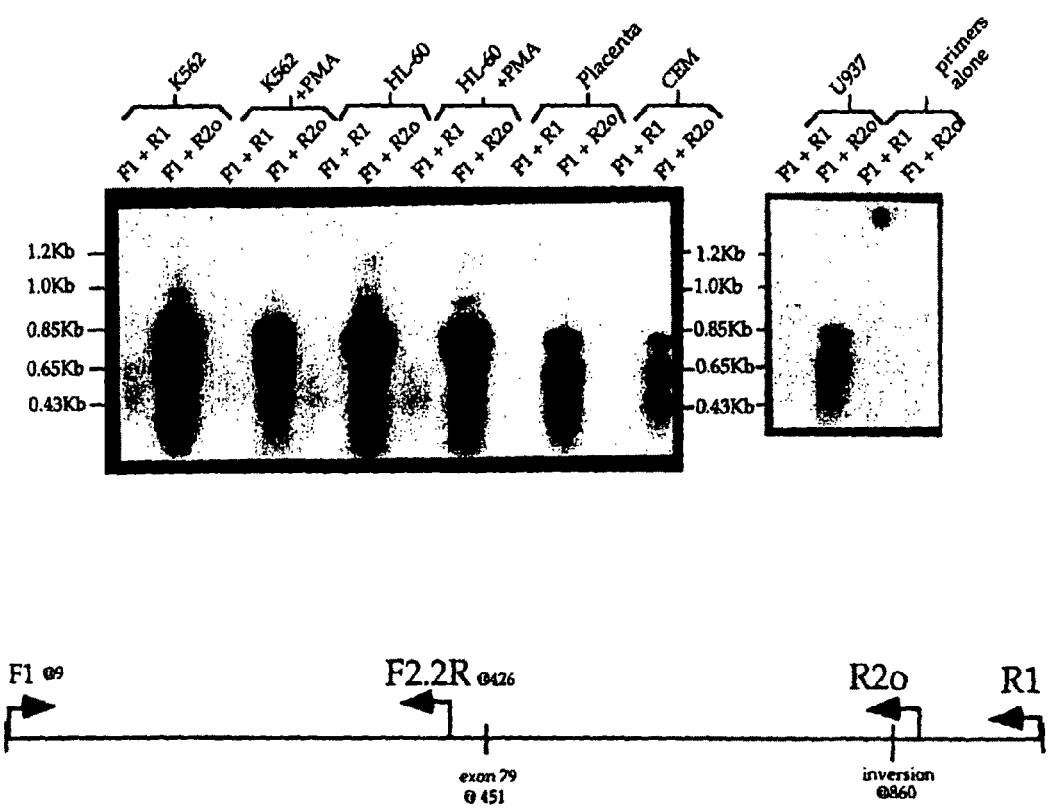
FIG. 16: The 5' 859 base pairs of apo-4 are reproduced in several cell lines with RT-PCR using a probe internal to the primers. Upper Panels: K562 and K562+PMA (F1+R2o) show three main signals at 0.85, 0.65 and 0.29 Kb which are generally reflected in all the samples. These smaller bands may reflect splice product from the original gene. All templates are cDNA made from RNA to test for the presence or absence of the inverted region. No hybridization is shown for primers alone. Blot was exposed 5 days at −80° C. RT-PCR primers and Southern Blotting probe are indicated. F2.2R was used to probe the blot.
Figure 17A:
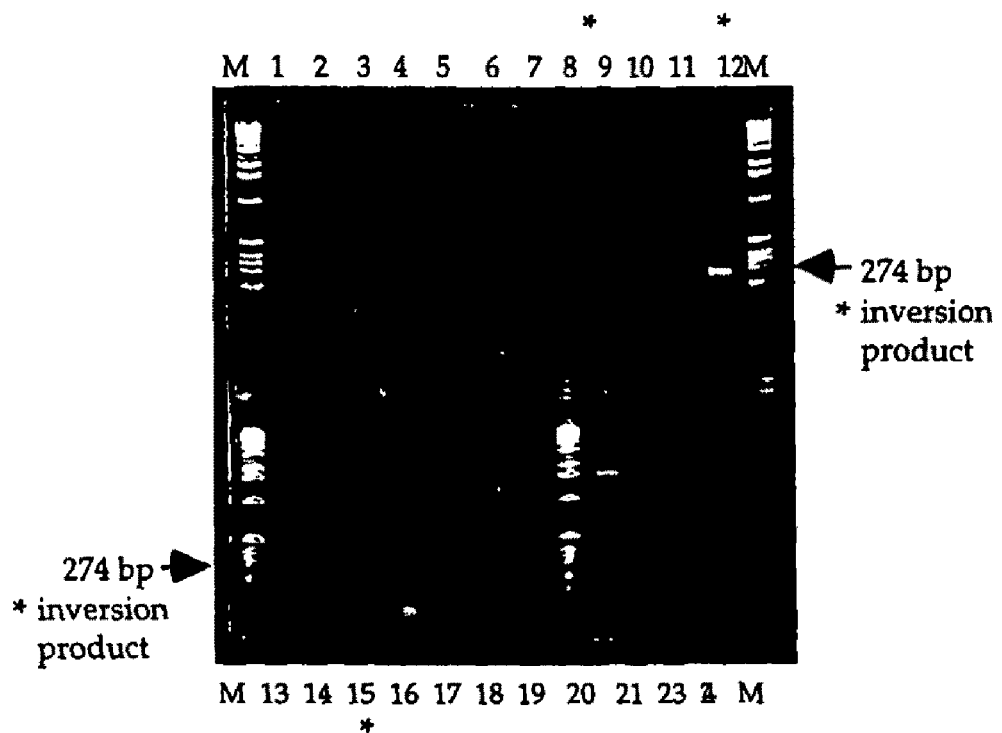
FIG. 17A: RT-PCR performed in the absence of apo-4 shows a reproduced inversion and no primer products. A. RT-PCR on 1st round cDNA with 30 min. rather than 30 sec. annealing shows inversion products. 1. Lymphoblastoma dystrophin (D) negative (−) patient LB (F1+R1)2. LB (F1+R2)3. LB (F2+R1)4. D-patient NJ (F1+R1)5. NJ (F1+R2)6. NJ (F2+R1)7. Adult brain (B) (F1+R1)8. B (F1+R2)9. B (F2+R1) 10. THP1 (F1+R1) 11. THP1 (F1+R2) 12. THP1 (F2+R1) 13. KG-1 (F1+R1) 14. KG-1 (F1+R2) 15. KG-1 (F2+R1) 16. primers alone (PA) (F1+R1) 17. PA (F1+R2) 18. PA (F2+R1) 19. space 20. markers 21. Placental cDNA library (F1+R1) obtained from previous PCR reaction is shown for a size control.
Figure 17B:
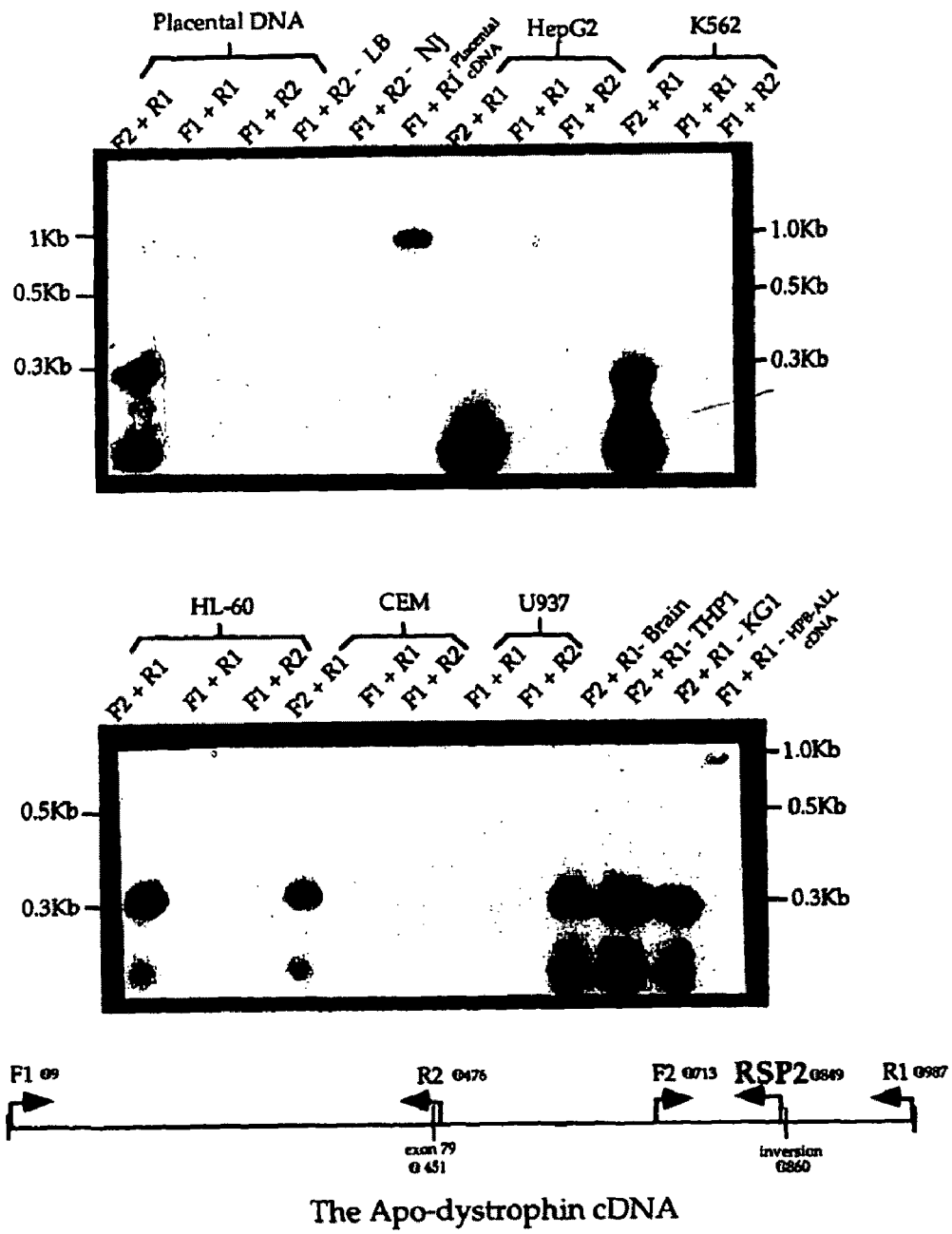
FIG. 17B: A probe just upstream of the inversion strongly hybridizes to all PCR products potentially containing the inversion and the full-length product from HPB-ALL cDNA. Top Panel: A 0.3 Kb fragment is shown for F2+R1 for (left to right) placental DNA and K562. A faint signal is shown for HepG2. A very small product of about 100 bp also hybridizes in placental DNA, HepG2 and K562, which may be primer dimers. Bottom Panel: A 0.3 Kb fragment in the F2+R1 samples hybridizes in HL-60, CEM, Brain, THP1 and KG-1 (final three from a previous run). The F1+R1 fragment from HPB-ALL cDNA also hybridizes at 1.0 Kb showing that it carries the region just upstream of the inversion. Blot was exposed 3 hrs at −80° C. RT-PCR primers and Southern Blotting probe (RSP2) are indicated by the arrows.

To attempt to reproduce a full-length apo-4 gene, isolate potential splice products and/or to reproduce the inversion, oligonucleotide primers were designed around the regions of the novel cDNA known to diverge with published dystrophin cDNAs (FIG. 15). Initial experiments were done in collaboration with Jamel Chelly in the Human Genetics Lab, IMM, who first demonstrated that there is a low level of transcription of tissue specific genes in every cell type by identifying rare "ectopic" or "illegitimate" dystrophin transcripts in lymphoid tissue that could not be detected by Northern blotting or RNAse protection but could by using RT-PCR (Chelly et al. 1988). Dr. Chelly also developed the quantitative PCR technique used in this study (Chelly, J. et al., *Eur. J. Biochem*, 187: 691-698, 1990). The primers were then incubated with 1st-round cDNA made from freshly isolated RNA (hereafter referred to as "RNA" to distinguish it from genomic DNA or a cDNA library) from various tissues in Reverse Transcriptase polymerase chain reactions (RT-PCR), with the apo-4 cDNA used as a control in only one of the three experiments shown. Splice products that would include the inversion were sought by designing a primer that was just downstream of and overlapped the inversion (R2o) and this was used in combination with F1 and R1 (FIG. 16). The initial RT-PCR using dystrophin-negative patient samples and placental genomic DNA was performed in Dr. Monaco's laboratory without the apo-4 cDNA with newly synthesized primers and pipetmen that had not been used with apo-4 cDNA to prevent potential apo-4 contamination in negative controls. Genomic DNA was used to test whether the transcript could be detected in normal DNA and provided an additional control of DNA without reverse transcriptase added. The initial experiment demonstrated a reproduced inversion in RNA from adult brain, KG-1 and THP 1 cell lines and no product in dystrophin-negative patient cell lines or with primers alone, despite an extended annealing time of 30 minutes (FIG. 17A). A further experiment was then performed with similar samples with the addition of commercially available placental DNA, more cell lines and the apo-4 cDNA control. Positive products from the second experiment were Southern blotted alone (FIG. 17C) and with the products from the first experiment (FIG. 17B). Southern blots were probed with an 18-21 bp oligonucleotide, usually internal to those used to produce the product. All combinations of primers were checked with the "Amplify™" program and none were potential dimer formers. The RT-PCR primers included: F1 (@80) GATTGATAGTAAAAAAAATG; (SEQ ID NO: 9)
F2 (@712) CAATGGCAGGTTTTACACGTC; (SEQ ID NO: 10)
R2 (@475) GGAAAAGACTTCCACATTGT; (SEQ ID NO: 11)
R2.3o (@875) CTTTTTCCTTTATAATTCTTTC (SEQ ID NO: 12) and;
R1 (@986) CATCAAACACGGCTTCTCATGC (SEQ ID NO: 13) as pictured in FIG. 15.

Evidence for Splicing and a Reproduced Inversion

Four regions of the apo-dystrophin-4 cDNA were explored using Reverse Transcriptase PCR followed by Southern blotting. The first blot looks only at potential splice products and an attempt to reproduce the full-length apo-4 while the next three examine splice products, whether the inversion could be reproduced and whether an unspliced 5' end of apo-4 could be reproduced:

1) F1+R2o were used to reproduce the apo-4 5' end to the inversion and to probe for splice products containing the inversion. For these reactions, newly isolated cDNA made from freshly isolated RNA was used in the absence of the apo-4 plasmid (FIG. 16). F1+R2o (R2o is 3' of the inversion except for the last 5/22 bp) products provided suggestive evidence that apo-4 could be spliced in addition to full-length reproduced products. In a second experiment, however, only the full-length products were reproduced. As expected, the lane with primers alone yielded no products. However, a full length product was not reproduced despite having reproduced a region immediately over the inversion. Products from F1+R2o that blotted with the F2.2R probe were obtained from K562 (0.85. 0.65, 0.4, 0.2 Kb), K562+PMA (0.85. 0.65, 0.4, 0.2 Kb), HL-60 (1.0, 0.85. 0.65, 0.4, 0.2 Kb), HL-60+PMA (1.0, 0.85. 0.65, 0.4, 0.2 Kb), CEM (0.85. 0.65, 0.4 Kb), placental RNA (0.85. 0.65, 0.4 Kb), U937 (0.85. 0.65, 0.4 Kb) (FIG. 16). In subsequent assays, only the 0.85 Kb product was reproduced indicating that it is more highly represented in the RNA than the potential splice products. Shorter F1+R2 fragments were detected in separate blots.

Figure 17C:
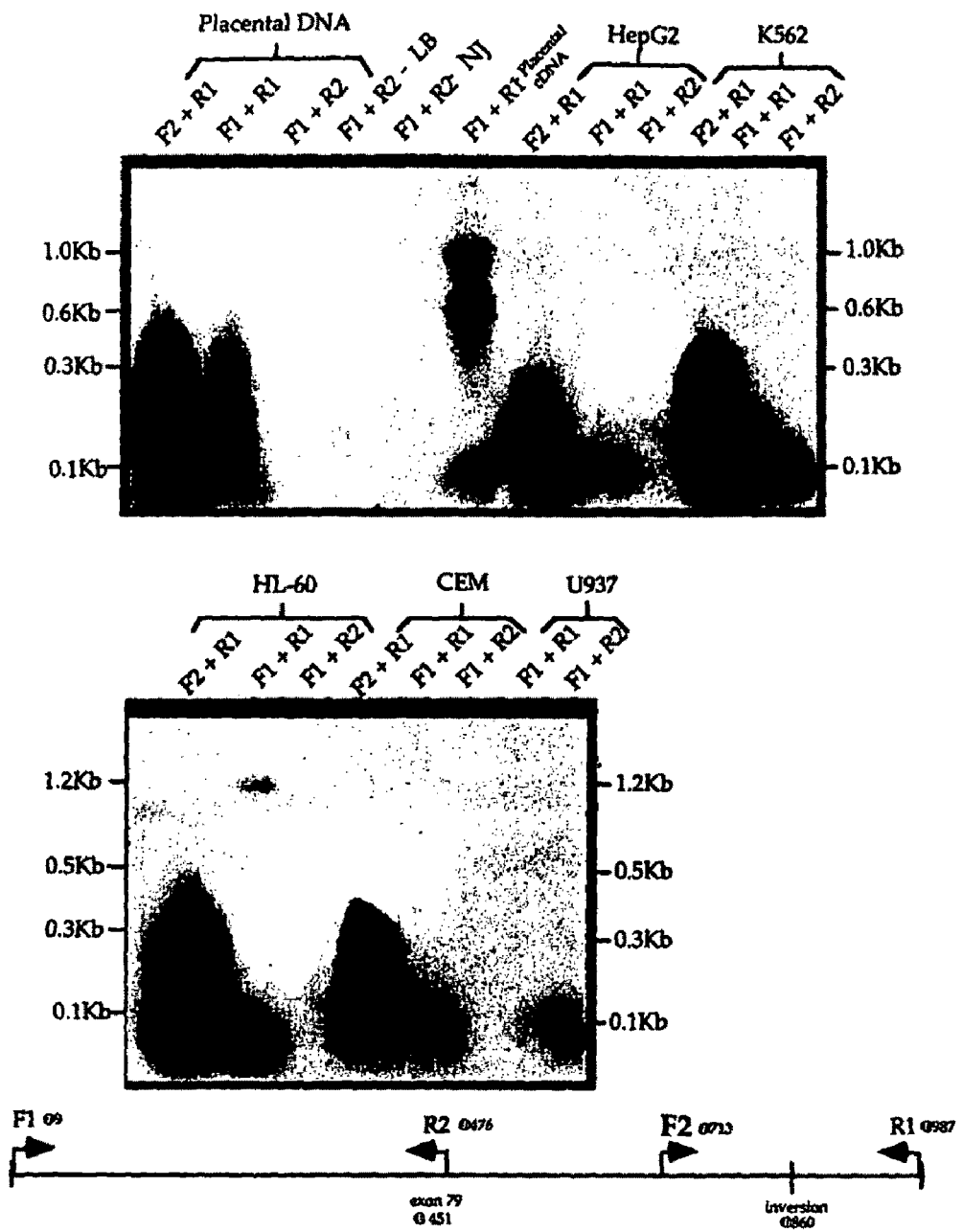
FIG. 17C: The F2 probe hybridizes to a 1.2 Kb PCR product in HL-60 and Placental cDNA which approximates the size of the apodystrophin cDNA. Upper Panel: Placental DNA shows a broad signal from 0.1-0.5 Kb rather than the expected 0.3 Kb for F2+R1 and 1 Kb for F1+R1. As expected, no signal is shown to patient DNA (NJ and LB). Placental cDNA shows a potential splice product at 0.6 Kb and the expected product at 1 Kb and weakly at 1.2 Kb in F1+R1. HepG2 strongly hybridizes at 0.1 Kb and to a faint band at 0.3 Kb in F2+R1. K562 shows a strong signal from 0.1-0.3 Kb for F2+R1 and a strong signal at 0.1 Kb for F1+R1. Lower Panel: HL-60 and CEM show a broad band from 0.1-0.5 Kb for F2+R1. HL-60 shows a signal at 1.2 Kb and a signal at 0.1 Kb which is also in CEM and U937 F1+R1. The blot was exposed for 2 hrs at −80° C. RT-PCR primers are indicated with the arrows. F2 was used as the Southern Blotting probe.

2) F1+R1 were used to attempt to reproduce the complete 1 Kb apo-4 cDNA. From this set of primers, only one product of about 1.2 Kb from HL-60 RNA was produced that successfully hybridised to other primers from regions internal to the product in a Southern blot (FIG. 17C), although an apparent apo-4 product was reproduced from the HPB-ALL cDNA library (FIG. 16) and other cDNA libraries using standard PCR (data not shown). A summary of the PCR products obtained with and without Southern blotting is provided in Table 1. The only potentially spliced RNA products obtained with these primers were 0.29 and 0.43 Kb from K562 and HL-60 RNA (FIG. 16) and one 0.6 Kb one that did not appear to contain the inversion from placental cDNA (FIG. 17C). Other F1+R1 potential splice products from RNA that hybridised to the F2 oligo included those from HepG2 (0.1 Kb), K562 (0.2 and 0.1 Kb), and HL-60, CEM and U937 (0.1 Kb) all (FIG. 17C).

3) F2+R1 were used to reproduce the inversion. These primers predicted an approximately 300 bp product and were used to test whether the inversion could be reproduced in cell lines. In two separate experiments, the inversion was reproduced first in brain, THP1, KG-1 and second in K562, HL-60 and placental DNA and a very faint amount in HepG2 (FIG. 17A). In the first RT-PCR reaction with dystrophin-negative patient samples, the 0.3 Kb full-length inversion product alone was visibly reproduced in Human brain, THPI and KG-1 RNA with F2+R1 but did not appear in the negative control samples with primers alone, patient NJ or LB RNA (FIG. 17B). Significantly, the inversion was reproduced in genomic DNA. The lack of a full-length reproduced apo-4 product and no primer signal in the original gel indicates that the products are not due to apo-4 plasmid contamination. The inversion was consistently reproduced in genomic DNA and 1st round cDNA in a number of future RT-PCR experiments.

Of the candidates sequenced following cloning into Bluescript SK+ (Stratagene), brain cDNA shows highly conserved homology at the peptide level to the inverted sequence (Table 2). This product was from the group of three in the initial RT-PCR that successfully hybridised to probes internal to the PCR product and showed no products in the control lanes or with primers alone (FIG. 17A).

These findings suggest that the 5' 876 bp of apo-4, previously considered "intronic" can be obtained from RNA, and that the overlapping inversion sequence can be reproduced. The overlapping clones suggest that the full-length clone could be obtained with the right combination of primers or nested PCR. All of the techniques with RNA depend on high quality RNA and high abundance as well as the correct PCR strategy or hybridization conditions, all of which can be highly variable. It was thus important to consider the expression of apo-4 in vitro and through in vivo expression and staining studies.

Subcloning Reveals Close Homology with Apo-4

From the initial RT-PCR, several products were successfully subcloned into the pBluescript SK+ (pBS) vector (Table 2). Based on these cloning results, three important features emerge. First, it is apparently possible to duplicate the inverted region beginning at 860 bp in brain cDNA, which suggests that the inversion found in placenta may also be present in brain tissue and a number of cell lines. Second, none of the above subclones shows evidence of splicing as they match the expected size. Third, although the full-length transcript was apparently reproduced from the HPB-ALL cDNA library, upon sequencing it demonstrated a very low nucleotide homology to apo-dystrophin-4 and thus is not a fully reproduced transcript, although some homology was shown at the peptide level. Finally, the 5' 875 bp of apo-4, including approximately 15 bp of the inversion appears to be completely reproduced from freshly isolated RNA in placenta, K562, the version of HL-60, CEM and U937.

Inversion Breakpoints are Identified on Genomic DNA

Figures 18D, 19:
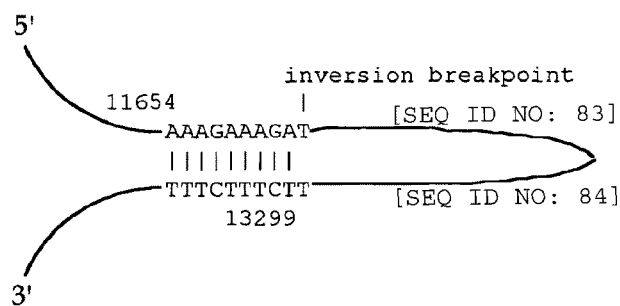
FIG. 18D: A proposed mechanism of inversion formation due to direct repeats. The above structure proposes that during recombination, the dystrophin gene could loop out and rearrange "illegitimately" upstream at direct repeats (SEQ ID NO: 83; the complementary sequence to SEQ ID NO: 83 is defined as SEQ ID NO: 84) found to flank the inversion in apo-4. To accommodate the mismatched T at 13,300 bp, an A appears to be inserted into the upstream sequence upon matching of the direct repeats, potentially contributing to the formation of the inversion breakpoint.
FIG. 19: Signal Sequences and Promoter elements could trigger an inversion (SEQ ID NO: 85; the complementary sequence to SEQ ID NO: 85 is defined as SEQ ID NO: 86). "TATAA" and "CAAT" boxes have been found immediately upstream of the inversion which have also been found in a rearrangement of histone genes.
Figure 20:
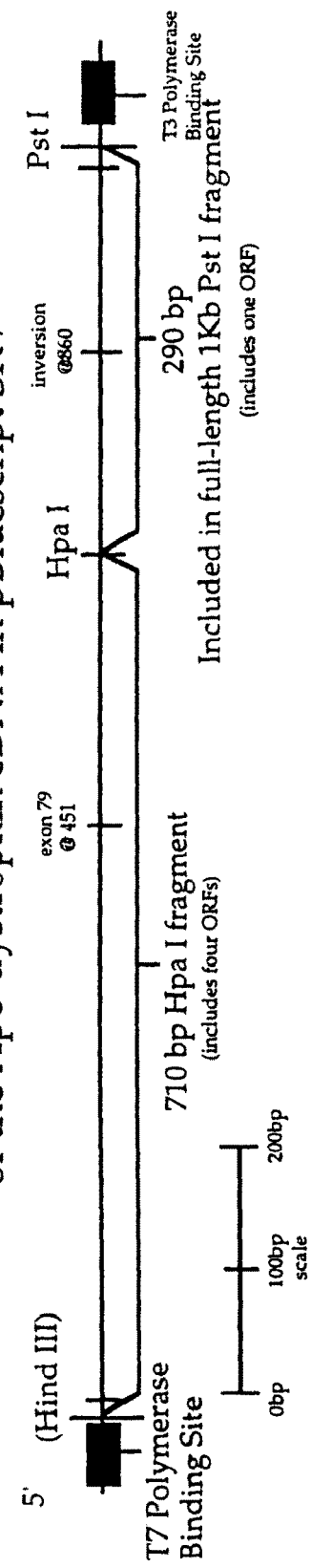
FIGS. 20, 20A and 20B: In Vitro Transcription and Translation (IVT&T) demonstrates that the full-length apo-dystrophin transcript produces proteins of 40 Kd and 50 Kd under reducing conditions.
Figures 20A, 20B:
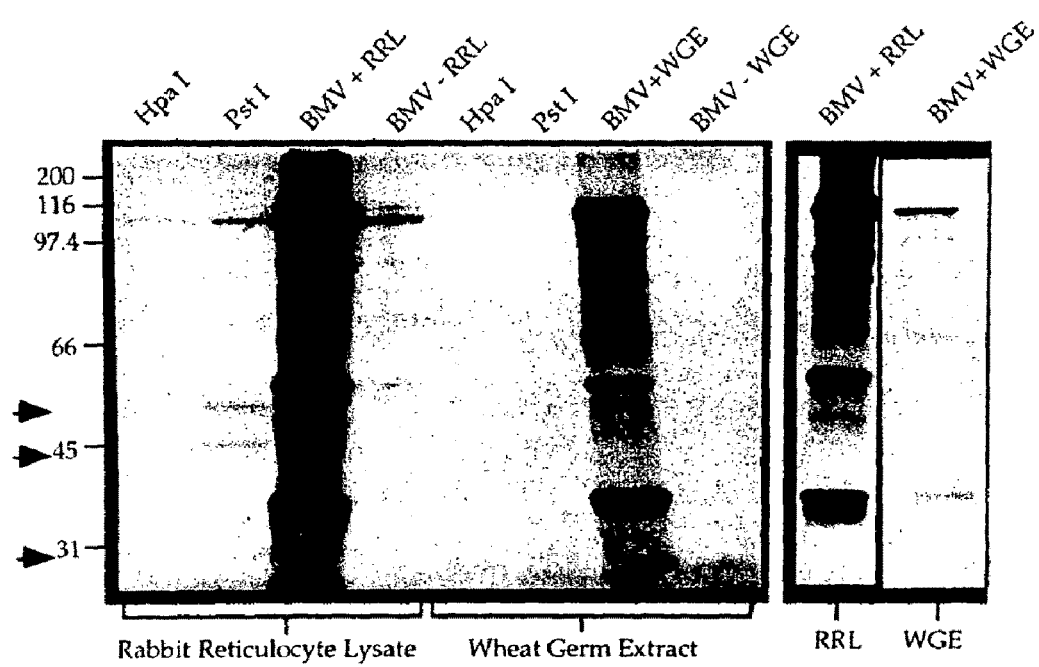

The apo-dystrophin-4 cDNA appears to be a piece of genomic DNA that has undergone rearrangement but not RNA cleavage, polyadenylation or splicing. The rearrangement could be due to signal sequences surrounding the 137 bp region in genomic DNA to trigger it, possibly as a transposable element, to insert itself at the AT-rich stretch that becomes position 860 bp in apo-4. As will be shown, in vitro, the absence of the inverted region eliminates the production of apo-4 proteins, suggesting that it may function as a downstream enhancer or post-transcriptional modifier to activate a normally dormant exon (FIG. 20A-20B). In other words, DNA that was previously considered to be intronic could act as an exon in the presence of this rearrangement. Such is the case with some inverted sequences in V-D-J joining in immunoglobulin rearrangement, where an inversion occurs proximally to an enhancer that then activates transcription. In that case, the enhancer is active only in B lymphocytes as suggested in a model for transcription (Lewis, S. et al., Science, 228: 677-85, 1985). A precedent has also been shown for inversions in DNA rearrangement to occur via recombination signal sequences (RSS'S) in transgenic neonatal brain development with a distribution and affinity for older neural centers (Matsuoka, M. et al., Science, 254: 81-86, 1991). A proposed site of apo-4 recombination to produce the inversion is imprecise relative to V-D-J joining, as with brain rearrangement. Imprecise joining of Ig elements to the oncogene c-myc in Burkitt's lymphoma has also been demonstrated (Gerondakis, S. et al., Cell, 36: 973-982, 1984). A comparison of apo-4 cDNA and genomic DNA with known regions of conservation of the recombination signal sequences (FIG. 18A) reveals that similar sequences are present in the 3' UTR of dystrophin suggesting a role for them in rearrangement at these sequences (FIG. 18C). Significantly, at the upstream inversion, the A at 860 that is found in apo-4 was not included in the alignment with the dystrophin 3' UTR to preserve the homology for 15 bp 3' to the inversion breakpoint (FIG. 18B). If the A were included the homology would be significantly lower in this region. This A appears to be an "orphan" nucleotide that was randomly inserted upon the formation of the inversion. However, if the inversion resulted from the insertion of an 8 bp direct repeat as suggested (FIG. 18D) the A was inserted to accommodate the final T in the direct repeat that is not in the unrearranged sequence but is in the inverted sequence. The insertion of the A could have contributed to the inversion breakpoint and cemented the decision to include the inverted sequence in the gene rather than the usual genomic sequence.

While not all bases in the RSS's are conserved in the dystrophin genomic DNA, those with high conservation are, and the spacing is accurate (FIG. 18C). Near the point of the apo-4 inversion (5'-3') two sets of RSS's are found with the second contained in a CA repeat on unrearranged genomic DNA beginning at 11,727. It is of interest that the inversion point occurs 66 bp upstream of the start of an "imperfect" $(CA)_7(TA)(CA)_7$ repeat in the genomic sequence. The CA microsatellite, often part of the Alu repeat, represents one of the most abundant families of interspersed repetitive DNA in eukaryotic genomes (Hamada, H. and T. Kakunage, Nature, 298: 396-398 1982; Jeang, K. T. and G. S. Hayward, Mol. Cell. Biol., 3: 1389-1402, 1983; Miesfeld, R. et al., Nucleic Acids Res., 9: 5931-5947, 1981) and has characteristically been used as an often polymorphic marker for genomic mapping between patients and/or species (Weber, J. L., In Genetic and Physical Mapping, Plainview: Cold Spring Harbor Laboratory Press, 159-181, 1990). This study shows that a CA repeat could contain signal sequences used in recombination, although its distance from the inversion breakpoint implies that it plays a secondary role in producing the inversion. Repetitive DNA is known to contribute to hairpin loop formation, however, which may have contributed to the formation of the inversion.

Downstream RSS's Flank an Inversion Breakpoint

The 137 bp of the inversion was located in unrearranged Genomic DNA. RSS's were found in the forward and reverse strands of DNA at the upstream breakpoint of the inversion as well as one in the reverse strand near the downstream breakpoint, both of which could have been utilized during rearrangement (FIG. 18C).

Potential Mechanisms to Produce the Inversion

Immediately 5' to the point of inversion in the 3' end of apo-4 is an 8 bp direct repeat, AAAGAAAG 5'-3' at 851-858 bp that forms a palindrome with its reverse and complement CTTTCTTT in dystrophin cDNA at 13000-13307 bp at the second inversion breakpoint in the 3' UTR of dystrophin (FIG. 18C). It would be a 16 bp palindrome if the upstream point of inversion were ligated to the original sequence 1.62 Kb downstream. Direct repeats have been identified as signal points to produce inversions in transposable elements (Temin, H., Natl. Cancer Inst. Monogr., 17: 557-570, 1964) and histones (Vitelli, L. and E. S. Weinberg, Nucleic Acids Res, 11: 2135-2153, 1983) and result in increased crossing-over (Dornfeld, K. J. and D. M. Livingston, Genetics, 131: 261-276, 1992) while palindromes are recognized points for protein recognition in DNA. The inversion could also have resulted from the formation of a hairpin loop structure or triggered insertion by pairing of the inverted repeats and the formation of a palindrome at the point of inversion during an overlap of the arms of genomic DNA in recombination (FIG. 18C).

A stem loop would form between the 3' end of the top strand and the 5' end of the lower strand to form the inversion seen in apo-4. Recognition of the repeats could then influence upstream factors following rearrangement. In histone genes, a relationship between breakpoints and gene coding regions has been found in which normal repeat structures invert to appear in apposition to each other, specifically TATAA and CAAT motifs (Vitelli and Weinberg, 1983). Examples of these sequences have also been identified around the apo-4 inversion (FIG. 19).

These observations also suggest that nucleotide sequence homology may permit alignment of the genes and the subsequent rearrangement having the unusual outcome of producing an inversion, and that the interaction of the sequences may depend upon signaling motifs within regions with transcription potential (Jennings, M. W. et al., Nucleic Acids Res., 13: 2897-2906, 1985). RSS's, direct repeats and histone motifs could all contribute to the production of an inverted sequence, although direct repeats form the most precise alignments at the point of inversion. The 3' UTR may play a role in upstream functions (reviewed in Jackson, R. J., Cell, 74: 9-14, 1993) and we thus attempted to determine whether the inversion could influence the production of a transcript from apo-4 by studying its protein expression.

The Inversion is Necessary to Produce Proteins In Vitro

To test whether apo-4 cDNA could synthesize a protein in vitro apo-4 cDNA in pBS SK+ was linearized with Hind III and Pst I to produce a full-length template and Hind III and Hpa I to produce a truncated 709 bp template lacking the 287 bp containing the inversion. In vitro transcription products were produced by incubating each template with T7 polymerase that bound to the endogenous T7 promoter present in pBS SK+. To produce translated products from these transcripts, both Wheat Germ Extracts (WGE) and Rabbit Reticulocyte Lysates (RRL) were incubated with the transcripts. The full-length apo-4 transcripts in RRL yielded $^{35}$S labelled translation products at 40 Kd and 50 Kd with a more weakly labelled species at 30 Kd and a faint band at 40 Kd from WGE, while no proteins were produced from truncated apo-4 templates (FIG. 20).

These translation products established several important points. First, apo-4 was not a pseudogene, as these are defined by an inability to produce a transcript or a protein as shown in with the repetitive genes in actin and tubulin (Firtel, R. A., Cell, 24, 6-7, 1981). Second, the suppression of the stop codons in the apo-4 gene was most likely due to readthrough rather than splicing, as this was unlikely to happen in a cell-free system, although it could not be completely ruled out (personal communication, Promega). Third, stop-codon translational readthrough was aided by the presence of the inversion as a downstream enhancing element and/or secondary structure that allowed the nonsense codons to be bypassed and amino acids made in their place, possibly by uncharacterized mammalian suppressor tRNAs. The third base of any codon is the least important in determining the amino acid produced according to the "wobble hypothesis" and suppressor tRNAs are often caused by changes in the modification of bases in the anticodon. Thus, the amino acid sequence produced cannot be entirely predicted from the relevant triplet sequences but may be influenced by other features of the molecule (Murgola, E. J. et al., Proc. Natl. Acad. Sci. USA, 80: 4936-4939, 1983; Swanson, R. et al., Science, 242: 1548-1551, 1988). According to the "wobble hypothesis" an A at the end of a codon cannot have a unique meaning because U must also recognize G. Of the 23 stop codons in the apo-4 reading frame presented, 22 end in an A, which could give rise to cysteine or tryptophan and one ends in a G, which with a modified or "wobbly" tRNA, could produce a tyrosine rather than a nonsense codon.

The presence of the inversion may have facilitated translation by functioning as a cis-acting sequence to suppress the stop codons found in the apo-4 sequence. Such a phenomenon has been shown in the pol gene of the Moloney murine leukemia virus (M-MuLV) in which translational readthrough is mediated by an RNA sequence of at least 50 base pairs located 3' to the gag UAG termination codon, containing a short purine-rich sequence adjacent to an amber suppression codon, highly conserved among different retroviruses (Honigman, A. et al., Virology, 183: 313-319, 1991). To test the ability of translation products to be specifically recognized in vivo, peptide antisera were designed against a putative N-terminus and two other regions of apo-4 to analyze the expression of the gene in COS transfectants and K562.

Peptide Antisera Designed Against Putative Antigenic Regions

Three peptides were designed from the apo-4 sequence for the production of polyclonal rabbit antisera to analyze apo-4 cell-surface expression. Based on the full apo-4 sequence these were: P1: (aa 30-42)—MYPIMEYSCSDRN (SEQ ID NO: 3), a putative apo-4 N-terminus; P2: (aa 53-62 in frame 1 predicted to splice onto exon 79 (DTM in dystrophin) at aa 151-153 in frame 2)—YIYIGNLNVADTM) (SEQ ID NO: 4); P3: (aa 133-150 DDLGRAMESLVSVMTDEE (SEQ ID NO: 5)—at the beginning of exon 79 but in the apo-4 frame, which also appears in Dp71 (Lederfein 1992). P1 was of primary importance in analysing the N-terminus of the predicted protein. P1 and P2 were primarily used in these studies, as they were able to precipitate specific polypeptides. All antibodies were affinity purified, although the crude antisera retained specific activity longer than the purified version. P1 displayed a superior antigenic profile based on its greater number of peptide turns and hydrophilicity in a MacVector comparison of the three antisera. P3 displayed one turn in its C-terminal 5 aa, but low specificity in ELISAs. P2 was only hydrophilic in the region of exon 79 in a proposed splice. No significant homologies were revealed in a FASTA homology search against the P1 peptide, showing only 46% complete homology with the cytomegalovirus hypothetical protein and the large tegument protein of the herpes simplex virus. 30-38% homology was shown for the IL-1β convertase precursor and the homeobox protein HOX-C4 (Pearson, W. R. and D. J. Lipman, Proc. Natl. Acad. Sci. USA, 85: 2444-2448, 1988).

Antisera Precipitate Specific Protein Products

Figure 21:
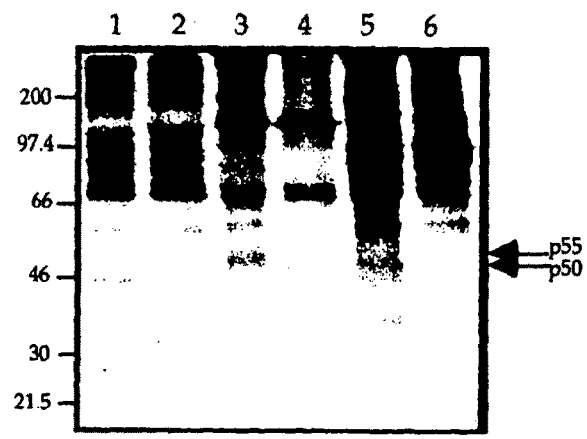
FIG. 21: Anti-apo-4 antisera precipitates unique proteins in metabolically labelled apo-4 transfectants which may be immunoprecipitated from Fc-CD33. Fc-CD33 precipitates faint bands at 50-55 Kd (Lane 1-2). Rabbit-anti-P2c antisera (Lane 3) precipitates a band at 55 Kd not shown in the anti-P2c pre-bleed (Lane 4). A band at 50 Kd is shown by rabbit-anti-P1c antisera (Lane 5) not found in the P1c pre-bleed (Lane 6). This assay demonstrates that anti-apo-4 antisera are capable of precipitating at least two proteins from transfected apo-4.

To test the unpurified (crude) peptide antisera raised against two regions of the ORF at +88 on the cDNA, COS cells transfected with the full length cDNA were pulsed on day two post transfection in −Met media with $^{35}$S and lysed in 1% NP-40. Immunoprecipitation revealed heavily labelled bands at about 50 Kd for anti-P1c and about 53 Kd for anti-P2c that were distinct from the respective prebleed sera. Weaker bands were appeared at 30 and 97 Kd for both P1 and P2. A faint band was immunoprecipitated with Fc-CD33 at 50 Kd in addition to a 28 Kd band common to P1, P2 and Fc-CD33 (FIG. 21).

Surface Labelling Demonstrates at Least Four Species

Figure 22:
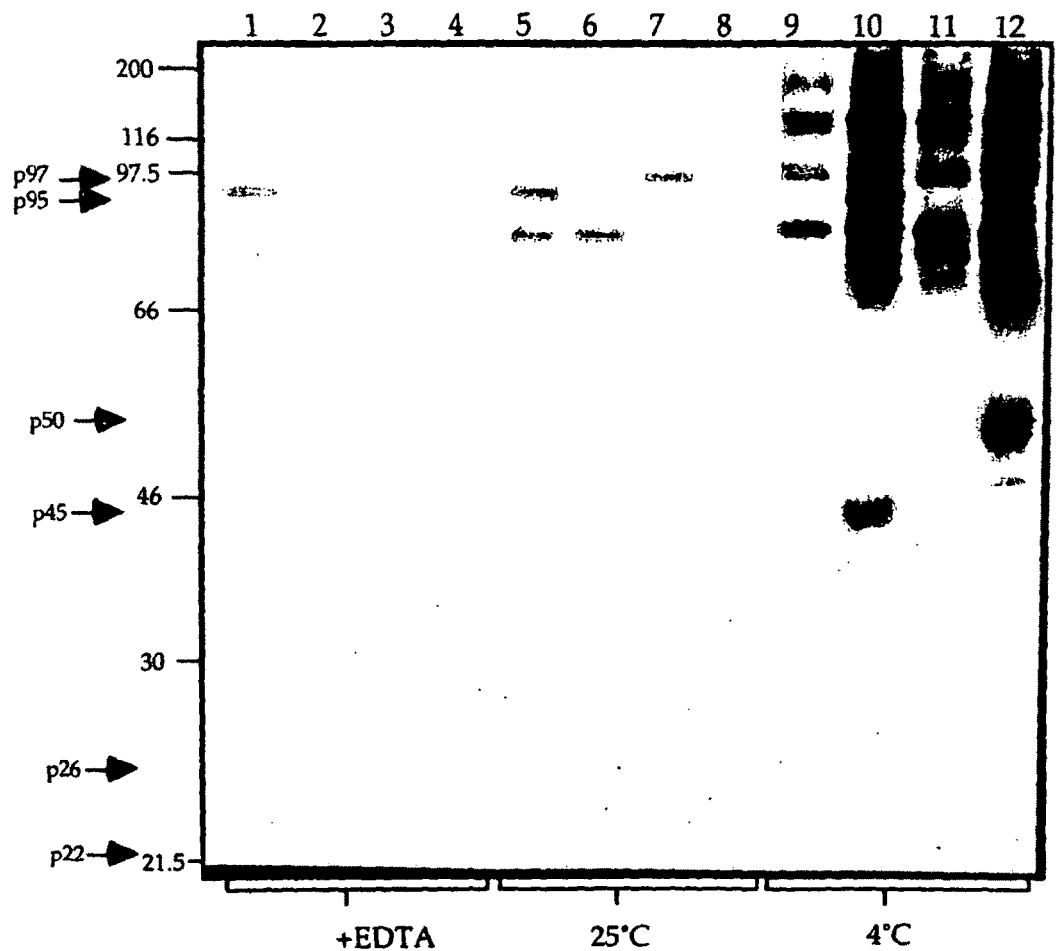
FIG. 22: Anti-Apo-4 P1 polyclonal antibodies precipitate prominent bands at 45 Kd and 95 Kd and anti-apo-4 P2 antibodies precipitate major bands at 50 Kd and 97 Kd from surface biotinylated transfectants. Apo-4 transfectants were first EDTA lifted (Lanes 1-4) or surface labelled in situ at 25° C. (Lanes 5-8) or 4° C. (Lanes 9-12). Crude anti-apo-4 P1c pre-bleed sera—Lanes 2, 6 and 9; anti-P1c antisera—Lanes 1, 5 and 10; Anti-apo-4 P2c pre-bleed sera—Lanes 4, 8 and 11; anti-P2c antisera—Lanes 3, 7 and 12. Only p95 and p100 bind independently of divalent cations while the rest require labelling at 4° C. in the absence of EDTA to achieve efficient labelling. On a longer exposure, anti-P1 showed a minor band at 22 Kd and anti-P2 showed minor bands at 26 Kd and 22 Kd.

Intact COS cells transfected with the apo-4 gene were then surface biotinylated either 1) following EDTA lifting 2) in situ for 20 min at 25° C. followed by labelling at 4° C. or 3) in situ at 4° C. without EDTA lifting. Cells were then lysed in 1% NP-40 and immunoprecipitated with the P1 or P2 antisera to examine protein product size. Labelling in situ at 4° C. was found to produce the largest number of unique immunoprecipitated proteins. Apo-4 P1 polyclonal antibodies precipitate prominent bands at p45 and p95, and a minor band at p22 (FIG. 22, Lane 10). P2 antibodies precipitate major bands at p50 and p97, and minor bands at p26 and p22 (Lane 12). On a longer exposure, p45 (Lane 5) and p97 (Lane 7) appear from cells labelled at 25° C. while p95 (Lane 5) and p97 (Lane 7) appear to be temperature-independent. Only p95 (Lanes 1) and p97 (Lane 3) bind independently of divalent cations while the others require labelling at 4° C. in the absence of EDTA to achieve efficient labelling.

The sizes of the protein products obtained in IVT&T were then compared with those precipitated with the P1 and P2 polyclonal antibodies using COS transfectants metabolically labelled with $^{35}$S and surface labelled with biotin (Table 4). Only proteins distinct from the control are listed. $^{35}$S labelled proteins were shown to run about 5 Kd higher than biotinylated transfectants, possibly due to the interaction of label with the protein or a difference between types of gel used.

Apo-4 Antibody and Fc-CD33 Precipitate a 50 Kd Band

Figure 23:
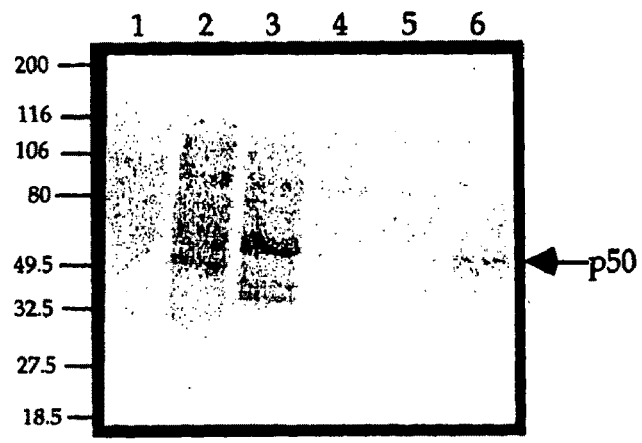
FIG. 23: Purified P1 is able to precipitate proteins in the same region as Fc-CD33 from K562. $^{35}$S labelled K562 were immunoprecipitated with purified apo-4 antisera and Fc-CD33 using stringent washing conditions. Mouse Ig (Lane 1) and purified anti-CD22 antisera (Lane 2) do not show the 50/55 Kd doublet precipitated by anti-apo-4 P1 (Lane 3). A 50 Kd band is faintly shown by anti-apo4 P2 (Lane 4) and anti-apo-4 P3 (Lane 5) and more strongly by Fc-CD33 (Lane 6) as shown at the arrow. Proteins were run on a 5-20% gradient gel for SDS-PAGE.

Crude anti-P1 (P1c), P2 (P2c) and P3 (P3c) antisera were purified against affinity columns coupled to the appropriate peptide and subjected to immunoprecipitation and immunohistochemistry to compare reactivity. In an initial assay with purified P1 (P1p), P2 (P2p), P3 (P3p) and Fc-CD33 on K562, a differential reactivity was shown (FIG. 23).

Following immunoprecipitation using stringent "high-salt/low-salt" washing conditions, purified P1 (P1p) demonstrated four distinct bands at about 38 Kd, 39 Kd, 50 Kd and 55 Kd in K562 (FIG. 23, Lane 2). p50 co-migrated with Fc-CD33 alone (Lane 6) and was absent from the controls (Lanes 1 and 2) and P2p and P3p (Lanes 4 and 5), demonstrating that P1p and Fc-CD33 appeared to precipitate a band of the same weight.

Fc-CD33 Precipitates a 50 Kd Band from K562 and TFs

Figure 24:
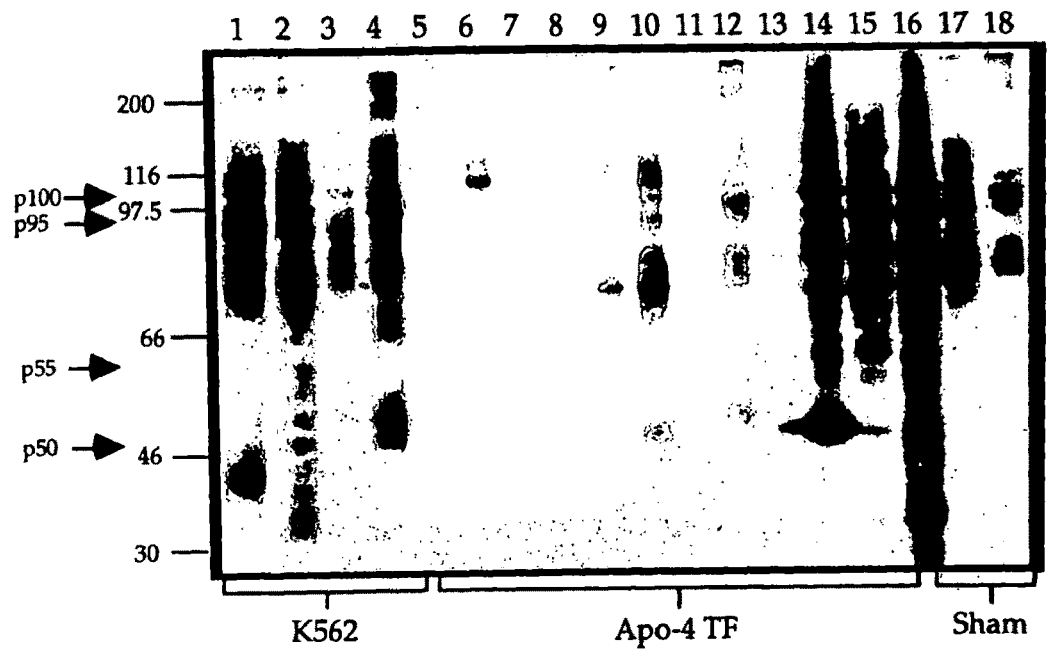
FIG. 24. Fc-CD33 precipitates a band at 50 Kd from K562 and apo-4 transfectants. The band at 50 Kd is compared with anti-P1, P2, and P3 crude and purified antisera in NHS-biotin labelled K562 (Lane 1-5), and apo-4 (Lane 6-16) and sham transfectants (Lane 17-18). In K562, a band at 48/50 was weakly precipitated by P1p (Lane 2), more strongly by Fc-CD33 (Lane 4) and was partially blocked by the addition of P1 peptide as were bands at 95 and 105 Kd (Lane 3). Denatured p48/50 from K562 Plc immunoprecipitates was not recognized by Fc-CD33 (Lane 5) p48/50 was not precipitated by purified anti-CD22 antisera (22p) (Lane 1). In apo-4 transfectants, P1c precipitated a pronounced band at an average weight of 50 Kd (Lane 14), faintly seen in P2c which precipitated a higher band at 55 Kd (Lane 15) which comigrates with the 55 Kd band seen with Plc (Lane 14). P3c only precipitated a distinct band at 32 Kd (Lane 16). Fc-CD33 also precipitated a band at 50 Kd (Lane 12) which was not seen in sham transfectants (Lane 18). P1p was unable to precipitate a protein at 50 Kd in either apo-4 transfectants (Lane 6) or sham transfectants (Lane 17); P1p peptide blocked the band at 100 Kd (Lane 7). P2p (Lane 9) showed a weak band at 50 Kd which was blocked by peptide (Lane 8). P3p precipitated a faint band at 50 Kd (Lane 10). All P3p bands were blocked by peptide (Lane 11). Fc-CD33 does not reprecipitate proteins from P1p precipitates (Lane 13). This assay shows that purified antibodies do not precipitate the predominant 50 Kd apo-4 transcript as well as the crude antisera, that Fc-CD33 cannot recognize denatured proteins precipitated with P1 and that Fc-CD33 can recognize p50 in COS transfectants.

Fc-CD33 and purified apo-4 antisera were coupled to beads in an attempt to increase their avidity in immunoprecipitations. In this assay, the ability of crude anti-apo-4 P1 (P1c) and purified anti-apo-4 P1 (P1p) antisera to precipitate specific proteins was compared using stringent washing conditions (FIG. 24). In apo-4 transfectants (TF) P1c was shown to precipitate a pronounced band at 50 Kd (Lane 14) not seen with P1p (Lane 6) or with P1c in sham TF (Lane 17) demonstrating its specificity. Fc-CD33 also weakly precipitated a band at 50 Kd in apo-4 TF (Lane 12) and a stronger signal in K562 (Lane 4) weakly shown with P1p (Lane 2) that was partially blocked with P1 peptide (Lane 3) and not shown with anti-CD22 antisera (Lane 1). P3p showed a faint band at 50 Kd and a stronger one at 68 Kd (Lane 10) that were blocked by peptide (Lane 11), reinforcing the readthrough hypothesis by demonstrating that P3p could detect the 50 Kd band, likely in the same frame as P1 (Lane 14). P2p showed faint bands at 55 Kd and 68 Kd that were mostly blocked by peptide (Lane 8). This gel shows that anti-apo-4 P1c antisera can precipitate a protein at 50 Kd in COS transfectants, which is in the same region as one precipitated by Fc-CD33, distinct from SHAM transfectants. P1p is less efficient than P1c in precipitating this protein and P1c was thus used to detect p50 in future immunoprecipitation experiments. It was suspected that protein purification may have decreased the stability of purified P1c.

p50 can be Specifically Blocked by Peptide

To test whether p50 could be specifically immunoprecipitated and blocked by peptide, apo-4 and CD22 transfectants (TF) and K562 cells were surface-labelled with NHS-biotin and immunoprecipitated with anti-apo-4 P1c to reveal bands at p50 and 95-100 Kd in apo-4 TFs (FIG. 25B, Lane 8) that could be blocked by P1 peptide (Lane 6). CD22 TFs were unable to precipitate this band (Lane 9). A band at p50 was precipitated in K562 with P1c (Lane 5) and Fc-CD33 (Lane 3) and partially blocked by peptide (Lane 4), which may be due to the polyclonal nature of the antisera. P1p was only able to specifically precipitate a band at 68 Kd in K562 (Lane 2) that was completely blocked by P1 peptide (Lane 1).

This gel reinforces the finding that p50 is specific to apo-4 transfectants, that it can be blocked by peptide and that a surface-labelled band of the same size can be precipitated by P1c and Fc-CD33 in K562, although it is only partially blocked by peptide.

Apo-4 Appears to Exist as a Cell Surface Heterodimer

Figure 25A:
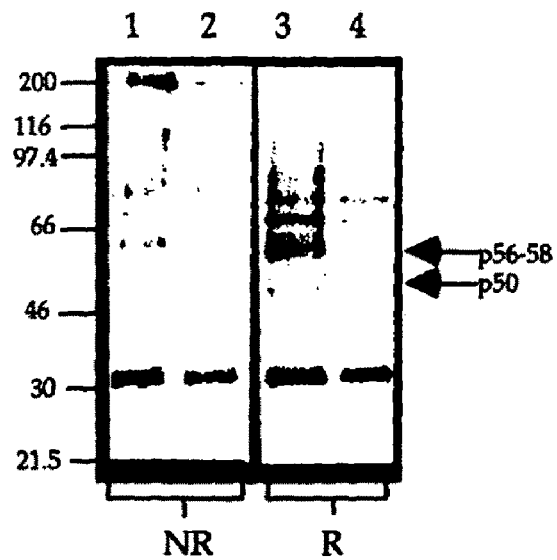
FIG. 25A: Anti-P1 antisera specifically precipitates a band at p50 in apo-4 transfectants which can be blocked by peptide. NHS-biotin labelled K562 and apo-4 and CD22 transfectants were immunoprecipitated with crude P1 (P1c) or purified (P1p) antisera in the presence and absence of P1 peptide and washed using stringent conditions and ECL detection. p50 was immunoprecipitated with Plc in apo-4 transfectants (Lane 8) and blocked with P1 peptide (Lane 6) but was not precipitated by CD22 without P1 peptide (Lane 9) or with peptide (Lane 7). Plc also precipitated a band at 50 Kd in K562 (Lane 5) which was partially blocked by peptide (Lane 4), which also appeared in Fc-CD33 immunoprecipitates (Lane 3). P1p precipitated a band at about 58 Kd which was completely blocked by peptide. P1p precipitated a doublet at 62/64 Kd (Lane 2) which was completely blocked by peptide (Lane 1).

To determine whether apo-4 was disulfide linked to itself or to another protein, a peptide blocking experiment was performed under reducing and non-reducing conditions on surface biotinylated apo-4 transfectants (FIG. 25A). Under non-reducing conditions, p50 was shown exist as a single band at about 62 Kd (Lane 1). Under reducing conditions, bands of 50 Kd and 56-58 Kd (Lane 3) were blocked by peptide (Lane 4) indicating that apo-4 may exist as a heterodimer on the cell surface.

Predicted STADEN and GeneID Splice Sites

The presence of stop codons in the P1 ORF identified in apo-4 prompted a search for potential splice sites in the cDNA. Potential donor and acceptor sites appeared throughout the apo-dystrophin-4 cDNA. The GeneID program predicted 32 donor and 8 acceptor sites (above 72% probability with known acceptor sites) (Guigo, R. et al., *J. Mol. Biol.*, 226: 141-157, 1992). The Staden program predicted 28 splice donor and 28 acceptor sites within the default range and 39 more outside the default range (Staden, R., *Methods in Enzymology*, 183: 193-211, 1990). The equation $2^{(donors+acceptors)-2}$ with the maximum number of both is $2^{(31+67)-2}$ or $2^{96}$ or $7.9^{28}$ possible combinations of splice donors and acceptors in the apo-dystrophin-4 cDNA. This increases the probability that the regions, upstream and downstream of exon 79, previously thought to be only intronic or untranslated could contain exons expressed under certain circumstances, such as when the apo-4 cDNA is placed downstream of a strong promoter or when an inversion or other enhancing element is present downstream. The exons and introns predicted here, according to given splice sites, are named in relation to known introns and exons, specifically, exon 79. An attempt was made to predict reasonably spliced mature cDNAs while conserving the proposed upstream exon, 78.3, and using the splice donor and acceptor sites generated from GeneID and Staden to achieve the longest ORF possible.

Figure 26D:
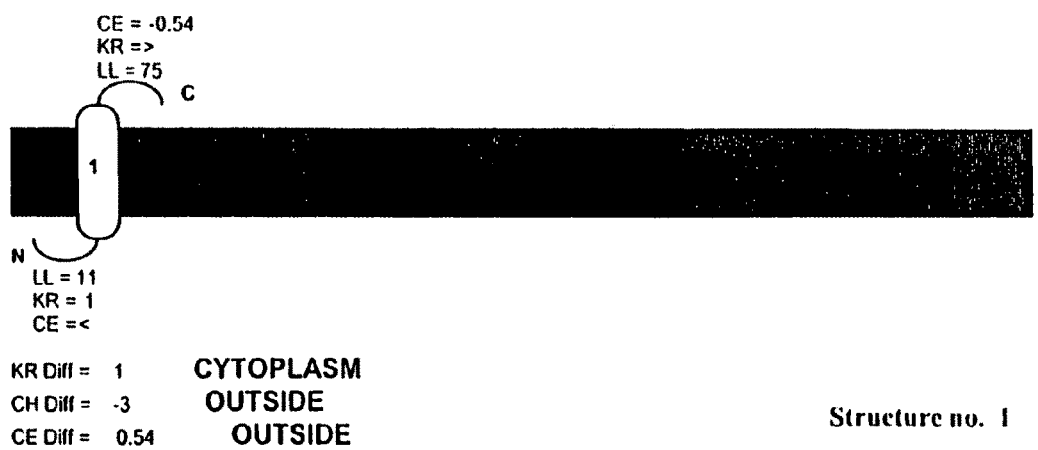
Figure 35D:
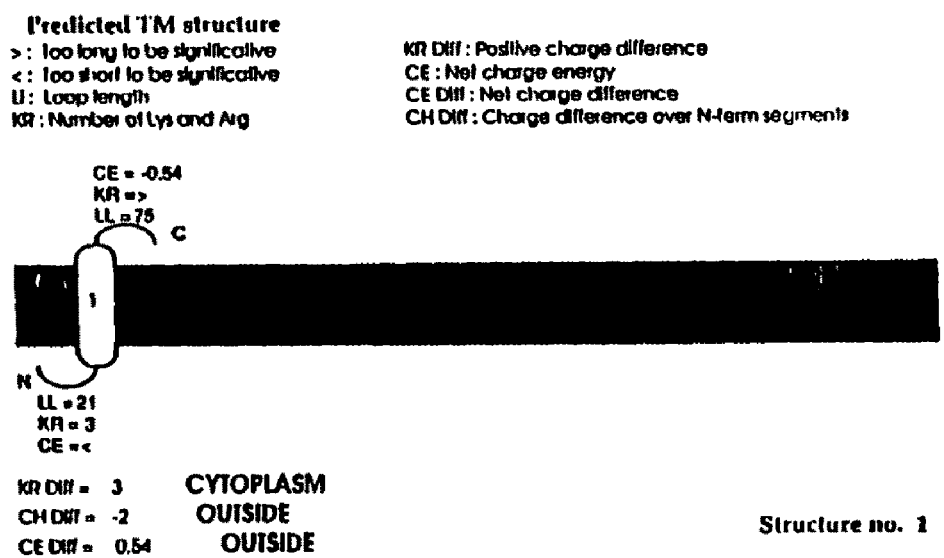

A proposed splice product "H2" is shown (FIG. 26) that includes the proposed N-terminal exon 78.3. An additional proposed splice product appears in FIG. 35. Based on the amino acid sequence of the spliced product, all potential splice products predict a Type II transmembrane (TM) protein using the TopPred 1.2 program (Claros, M. G. and G. von Heijne, *CABIOS*, 10: 685-686, 1994). With Type II proteins, the transmembrane domain acts as the signal peptide and the N-terminal region usually remains in the cytoplasm, except in the case of some cell-surface molecules with multiple TM domains. If apo-dystrophin-4 coded for a Type 1 protein using the first available methionine, a signal peptide could be cleaved off to leave a 14 aa extracellular domain, assuming the suppression of the first stop codon. TopPred has predicted that the same 20 amino acid region in the putative exon 78.3 is a "certain" transmembrane domain in all proposed splice products. This finding lends weight to the suggestion that exon 78.3 could act as a functional exon to produce a transmembrane protein either through readthrough of stop codons or splicing in the COS cell system and potentially in vivo. The proposed splice products are listed with their proposed donor and acceptor sites. Predicted proteins are presented with the transmembrane domain(s) underlined.

H2 represents the longest splice product yet obtainable. These findings argue that, if any, only the 22 Kd band produced from in vitro transcription and translation could have been the product of splicing or premature truncation of the translated product due to the presence of internal stop codons. It is highly unlikely that the 45-50 Kd bands could have been produced from a spliced apo-4 cDNA.

Predicted Structure of Full-Length Apo-4 Protein

The full-length apo-4 gene was able to produce non-glycosylated proteins in vitro at average weights of 50, 40 and 25 Kd from a 997 bp apo-4 gene plus 45 bp to the Pst I site (FIG. 20A). If all 1042 base pairs were utilized, a maximum 52 Kd product should have been produced. 50 Kd was near this, thus raising the possibility that the stop codons in the sequence were not being recognized, possibly from a suppression element in the inversion or in the sequence immediately upstream, considering that no protein was produced in the absence of the inversion. The UTR 3' of the dystrophin full-length cDNA comprises 2.677 Kb. Based on the precedents indicating that elements within the 3' UTR are capable of suppressing stop codons (Honigman et al. 1991), Type I and Type II proteins were predicted from a proposed gene in which all of the thymidines in stop codons were changed to adenines to allow for readthrough, which happens when RNA is "edited" by adenosine deaminase (Bass, B. L. and H. Weintraub, *Cell,* 48: 607-613, 1987). In addition, the AATTAA site at 989 bp may have been utilized as a cryptic polyadenylation site, as recognition of this sequence has been reported at least 2% of the time in those cases studied (Hames, B. D. and D. M. Glover. Transcription and Splicing. In Frontiers in Molecular Biology, Oxford: IRL Press, 97-129, 1988). The "RNA edited" 997 bp of the apo-4 gene was translated and demonstrated a continuous open reading frame. The peptide sequence was then subjected to a MacVector search for putative start, signal peptide cleavage and glycosylation sites that appear below along with predicted protein sizes. Assuming readthrough, nine potential initiating methionines are identified in apo-4 (Table 3). Staden-predicted probability based on Kozak sequence are listed in parentheses, with 93% at the M at +34 (+100 nt) being the highest. Type I potential protein sizes (methionines with cleaved signal peptides between 17-27 amino acids were included; 20-23 amino acids is the average length, but known signal peptides range from 14-45 amino acids (Barclay, A. N. et al., The Leucocyte Antigen Facts Book. 424. Academic Press Limited, 1993). Type II proteins do not cleave off the signal peptide thus allowing for a longer predicted protein product. The largest potential apo-4 protein product is a Type II 97 Kd protein, which would require the 660 bp of the CDM8 vector sequence to its internal polyadenylation site and utilization of the first available methionine (Table 3B).

In theory, many proteins could be produced from an apo-4 gene in which the stop codons are suppressed. With the predicted N-glycosylation sites along this region, the protein predicted from this gene would be 97 Kd (Table 3B); without the CDM8 sequence it would be about 50.85 Kd with a 31 aa N-terminus and will be termed apo-4F, the predicted structure of which appears in FIGS. 37A and 37B. As previously shown, a 97 Kd protein could be precipitated from COS transfectants with an anti-apo-4 P1 polyclonal antisera in the presence and absence of EDTA (FIG. 22). Alternatively, if the AATAAA sequence at position 632 in apo-4 were utilized, starting at M@34, a 210aa Type II protein is predicted with two N-glycosylation sites and a weight of 32.5 Kd. In addition, two histone methylation sites have been identified in the inversion as shown below.

RK^NYKGKRK          (SEQ ID NO: 14)

These sites could provide an additional explanation for the ability of the cDNA to produce protein in the absence of a conventional Poly A site. In histones, these sites are utilized instead of polyadenylation to give stability to the RNA message prior to producing a protein. This analysis demonstrates that the N-terminus of apo-4 could appear on the surface of a transfectant as calculated from the amino acid sequence.

TopPred Analysis Predicts Five TM Domains

Figure 27C:
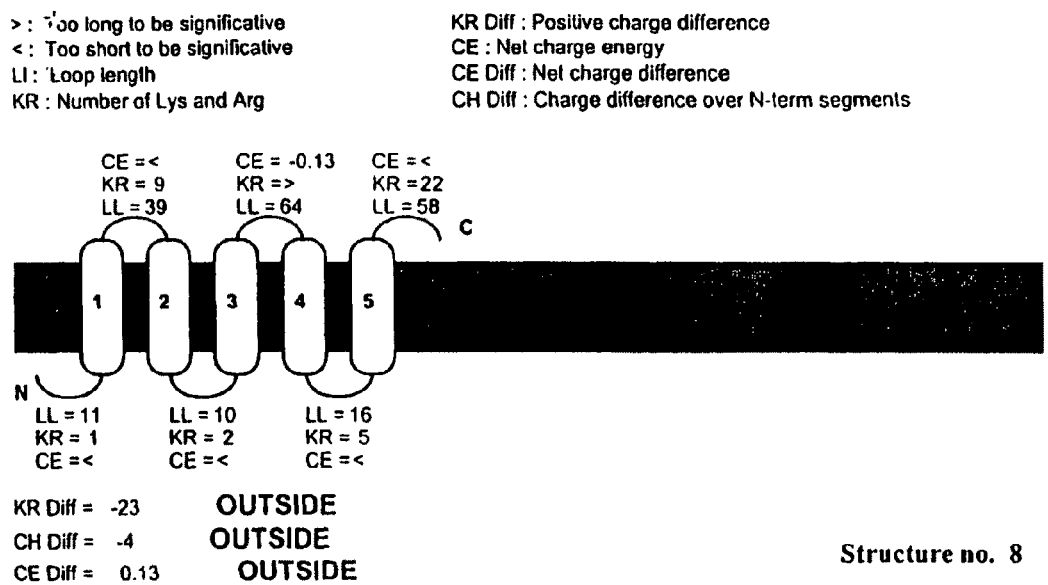

The apo-4 readthrough product beginning at the second available methionine (apo-4S) was then subjected to TopPred to identify putative transmembrane (TM) domains using Kyte-Doolittle analysis. Apo-4S predicts an 11 aa N-terminus and five putative transmembrane domains (FIGS. 27A, 27B and 27C). Domains 1 and 3 are certain and 2, 4 and 5 are putative. The sequence obtained when stop codons are suppressed shows a 303 amino acid structure with an N-glycosylation site at +12 (NQS), which could be utilized if the N-terminus were extracellular. Although the structure predicted using all five TM domains calculates an N-terminus on the outside of the cell (FIG. 27B), the predicted transmembrane domain structure to which the program defaulted shows a cytoplasmic N-terminus but predicts that it is probably on the outside of the cell (FIG. 27C). An extracellular N-terminus with multiple TM domains would share a similar channel-like structure with the C5aR, f-Met-Leu-Phe-R, and IL-8 receptors (Barclay 1993).

Figure 37C:
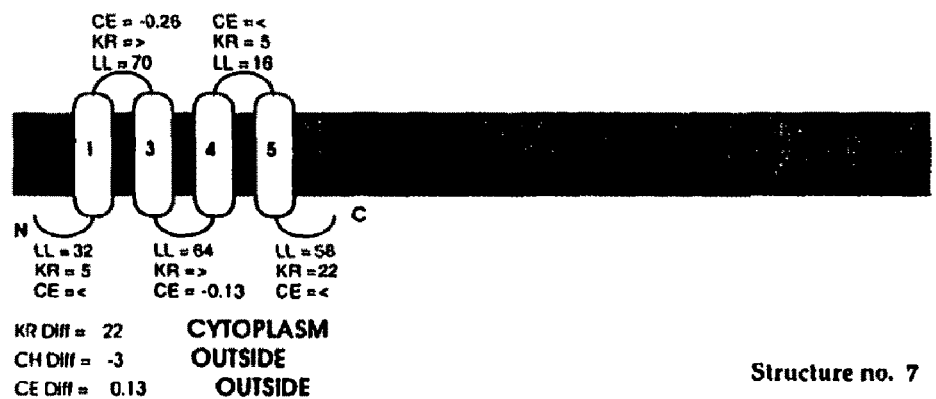

A TopPred product beginning at the first available M at +9 aa, apo-4F (full-length) appears in FIGS. 37A and 37B and also predicts two certain and four possible TM domains, although the 31 aa N-terminus is predicted to be cytoplasmic in a putative four-domain structure. An apo-4 product beginning at the M at +34 shares an equivalent predicted structure with apo-4F with an extracellular N-terminus. Whether the N-terminus is extra or intracellular, extracellular recognition could occur via the extracellular portions of the apo-4 protein and/or the N-terminus (FIGS. 37A and 37B). Two other N-glycosylation sites were identified in the full-length apo-4 readthrough product at 93 (NQT), 203 (NKS). In a five TM domain structure, the final two could only be utilized on Apo-4S or F if the N-terminus were intracellular and the first two could only be utilized on Apo-4F if the N-terminus were extracellular. If only the two certain TM domains were utilized and the N-terminus were on the outside, the first two and the last site could be used. N-glycosylation would account for a size discrepancy between an in vitro synthesized protein and one immunoprecipitated from transfectants and cell lines. Peptide sequencing of both major products from transfectants would be the only way to confirm the protein sequence.

Apo-4 P1 Antibodies Suggest Specific Staining in Tissues

Staining was performed in collaboration with Helen Turley, Department of Cellular Science, John Radcliffe Hospital on frozen sections from cerebellum, cerebral cortex, muscle, tonsil, and spleen and cytospins of K562. Sections and cells were probed with crude and purified anti-P1, P2 and, in some cases, P3 antibodies using the biotin-avidin system to attempt to detect apo-4 transcripts in these tissues. To assess their binding capability in situ, anti-apo-4 antibodies and Fc-CD33 were used to probe apo-4 and control transfectants at 4° C. and the signal was detected with fluorescent antibodies.

Figure 28:
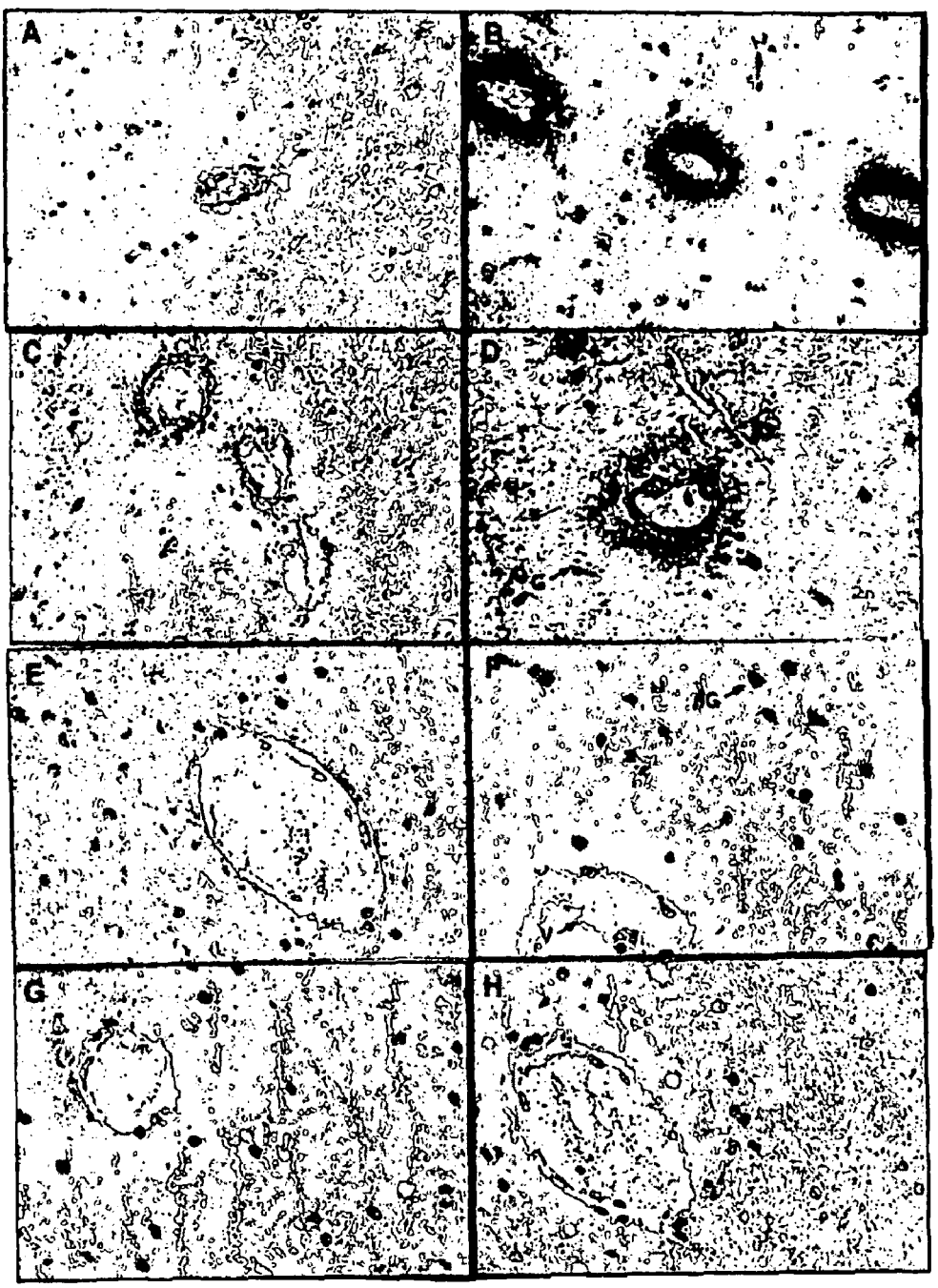
FIG. 28: Anti-apo-4 P1 and anti-apo-4 P2 antibodies show staining on vessels and glial cells in brain. Frozen sections from cerebral cortex (A-H) and cerebellum (1-L) were probed with crude and purified P1p and P2p antisera. P1c (B) and P2c (D) showed pronounced staining of vessels and glial cells over P1-pb (A) and P2-pb (C). Purified P1p (F-G) retained staining of glial cells but showed reduced staining of vessels, as did P2p (H) as compared with no antibody (E). In cerebellum, P1p (J) and P2p (K) showed staining of Purkinje cells more pronounced in P1p than in P3p (L) or no antibody (I); all three anti-apo-4 antisera showed staining of the granule cell layer "G". Images are a 40× magnification.
Figure 28:
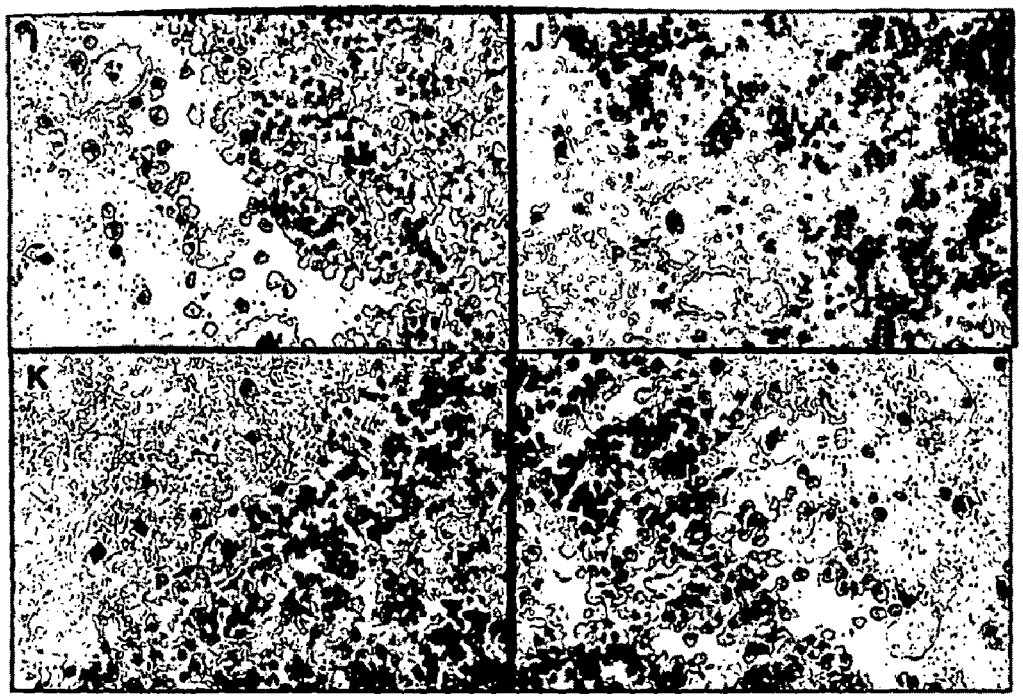

In cerebral cortex (FIG. 28, A-D) anti-P1c (28C) and anti-P2c (28D) showed positive staining on microglial cells and vessels compared with pre-bleed controls (P1c—28A, P2c—28D). Purified antisera was then tested on cerebral cortex (FIG. 28, E-H) and cerebellum (FIG. 28L). Cerebral cortex retained microglial staining but lost most vessel staining with P1p (28F) seen more clearly with a 40× magnification (28G), while P2p showed some microglial and no vessel staining (28H). In response to tissue damage, microglia transform into large amoeboid phagocytic cells and are thus considered to be members of the macrophage-monocyte defense system (Wheater, P. R. et al., Functional Histology. 24-37, 64-75, 87-101. Churchill Livingstone, 1987), suggesting a potential connection between the brain and lymphocytes. In cerebellum, a marked contrast was shown between the absence of staining with no antibody (28I), and some Purkinje cell and granular staining with P1p (28J) less so with P2p (28K) and much less with P3p (28L), similar to the control. In cerebellum, each granule synapses with several hundred Purkinje cells to coordinate movement (Wheater et al. 1987).

Figure 29:
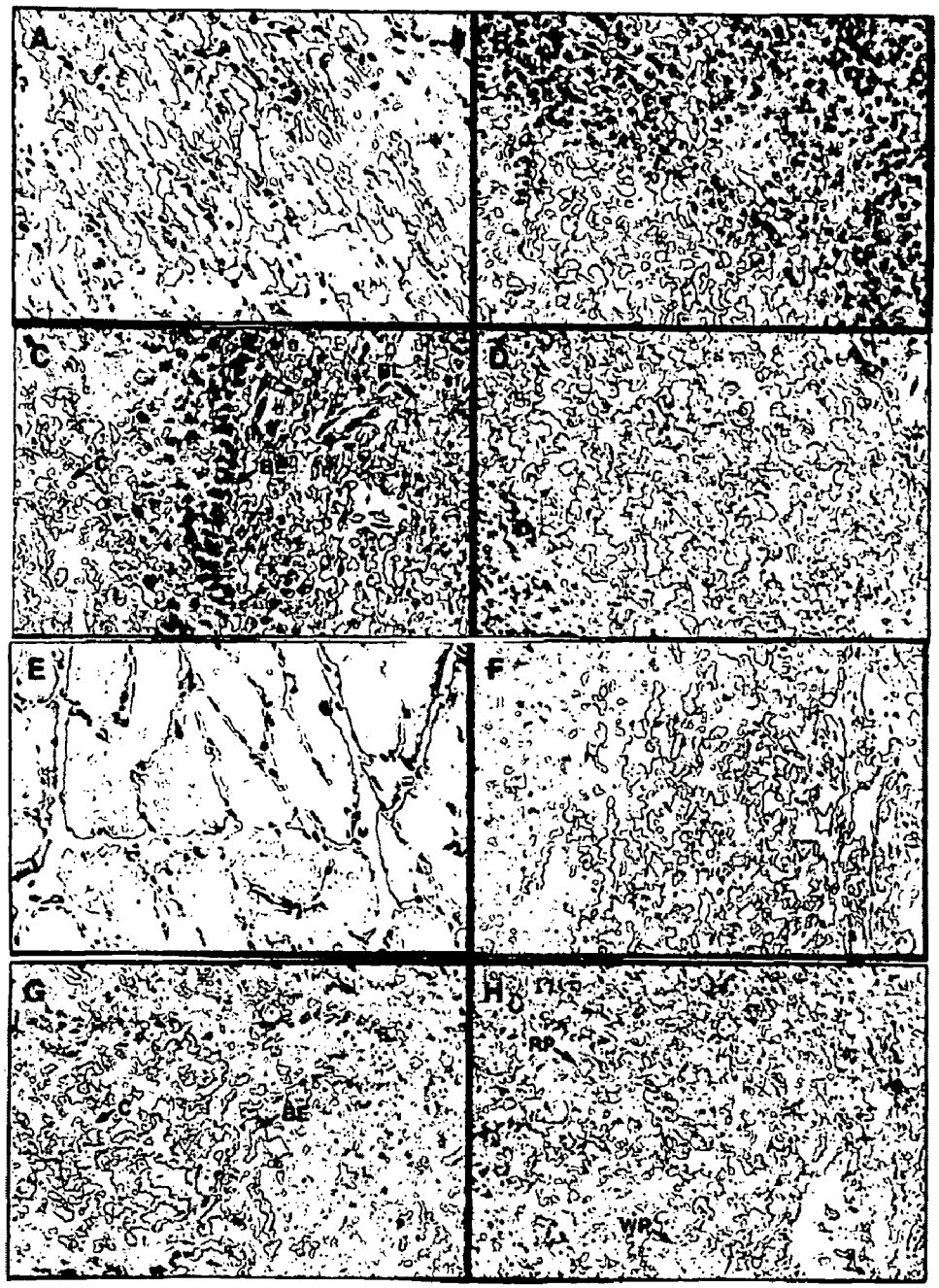
FIG. 29: Purified anti-apo-4 antisera show staining in muscle, tonsil and spleen. In muscle, P1p (E) shows some muscle cell staining as compared with P2p (I) or no antibody (A). Crude and purified antisera were tested in tonsil in which P1c (J) showed some lymphocyte staining in the basal layer "BL" and crypt epithelial "C" staining compared with no antibody (B) and the P1c pre-bleed (F). P1p showed similar but fainter staining (C) while P2p (G) and P3p (K) also showed weaker staining on basal epithelium "BE" and BL. In spleen, no staining was shown without antibody (D) while P1p (H) and P2p(L) showed some red pulp "RP" but no white pulp "WP" staining. Images are a 40× magnification.
Figure 29:
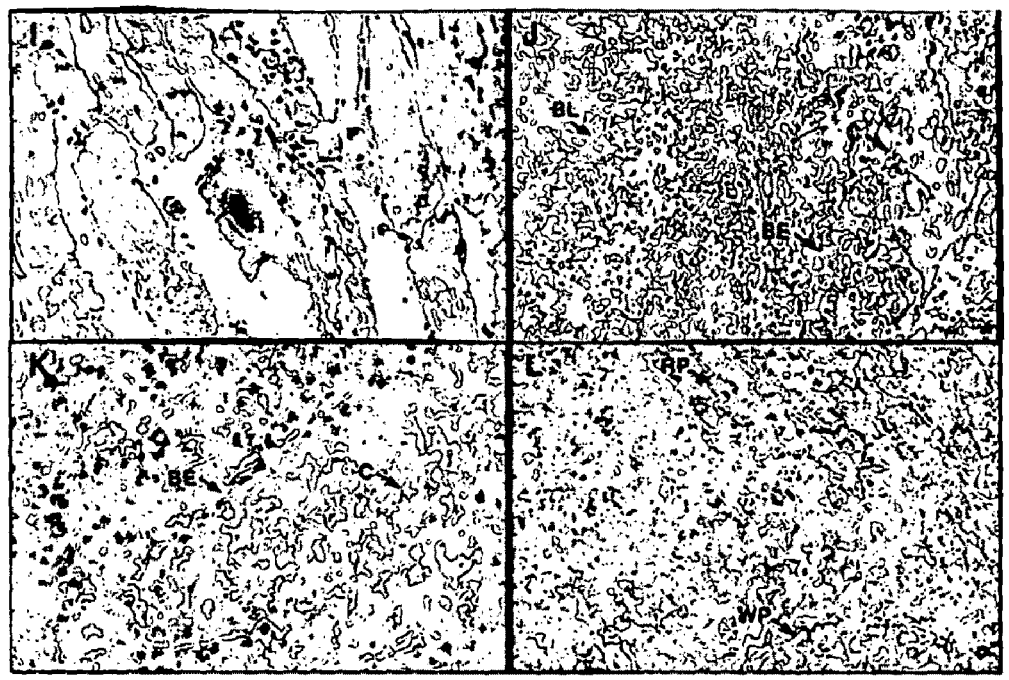

Purified P1, P2 and P3 antibodies were then tested on Muscle (FIG. 29, A-C), Tonsil (FIG. 29, D-I) and Spleen (FIG. 29, J-L) on which P2p and P3p were also tested. In muscle, P1p (29B) gave stronger staining than P2p (29C), which appeared to give no staining. Crude and purified antisera were tested in tonsil in which P1c (29F) showed some basal layer lymphocyte and pronounced basal epithelial staining compared with no antibody (29D) and the P1c pre-bleed (29E). P1p showed a similar but less intense pattern of staining (29G) while P2p (29H) and P3p (29I) showed fainter staining on vessels and epithelium. In spleen, no staining was shown without antibody (29J) while P1p (29K) and P2p (29L) showed some red pulp but no white pulp staining of lymphocytes.

In K562 cytospins (FIG. 30, A-H) P1c (30B) and P2c (30D) showed apparent intracellular staining, although P1c stained throughout the cytoplasm and nucleus, excepting the nucleolus, and P2c stained only around the nucleus. The staining could have been extracellular, as the cell surface covers the nucleus and could give what appears to be nuclear and cytoplasmic staining. P1c gave the most pronounced staining, but both gave intense staining relative to their respective pre-bleeds, P1c (30A) and P2c (30C). Purified antisera gave less intense staining, although again it appeared to be intracellular and faintly extracellular for P1p (30F), P2p (30G) and less so for P3p (30H), although all three were more pronounced than the negative control (30E). In a FACS analysis comparing the ability of anti-apo-4 P1c to stain cell lines, K562 showed 5.64% positive staining followed by 4.31% on the leukemic T cell line CEM and 1.84% on the leukemic T cell line HSB2 (data not shown). Protein searches of the peptide sequence used to generate the antisera revealed no matches and some distant homologues with an identity of 30% indicating that the antisera does not recognize any known proteins. The ability of anti-apo-4 P1 to stain cortical glial and cerebellar granule and Purkinje cells is very similar to the staining pattern shown for brain and Purkinje dystrophin and apo-dystrophins 1 and 2 (Ahn and Kunkel 1993; Blake, D. J. et al., 1994) indicating that apo-4 may be involved in movement.

An Extracellular N-Terminus is Stained

Figure 31:
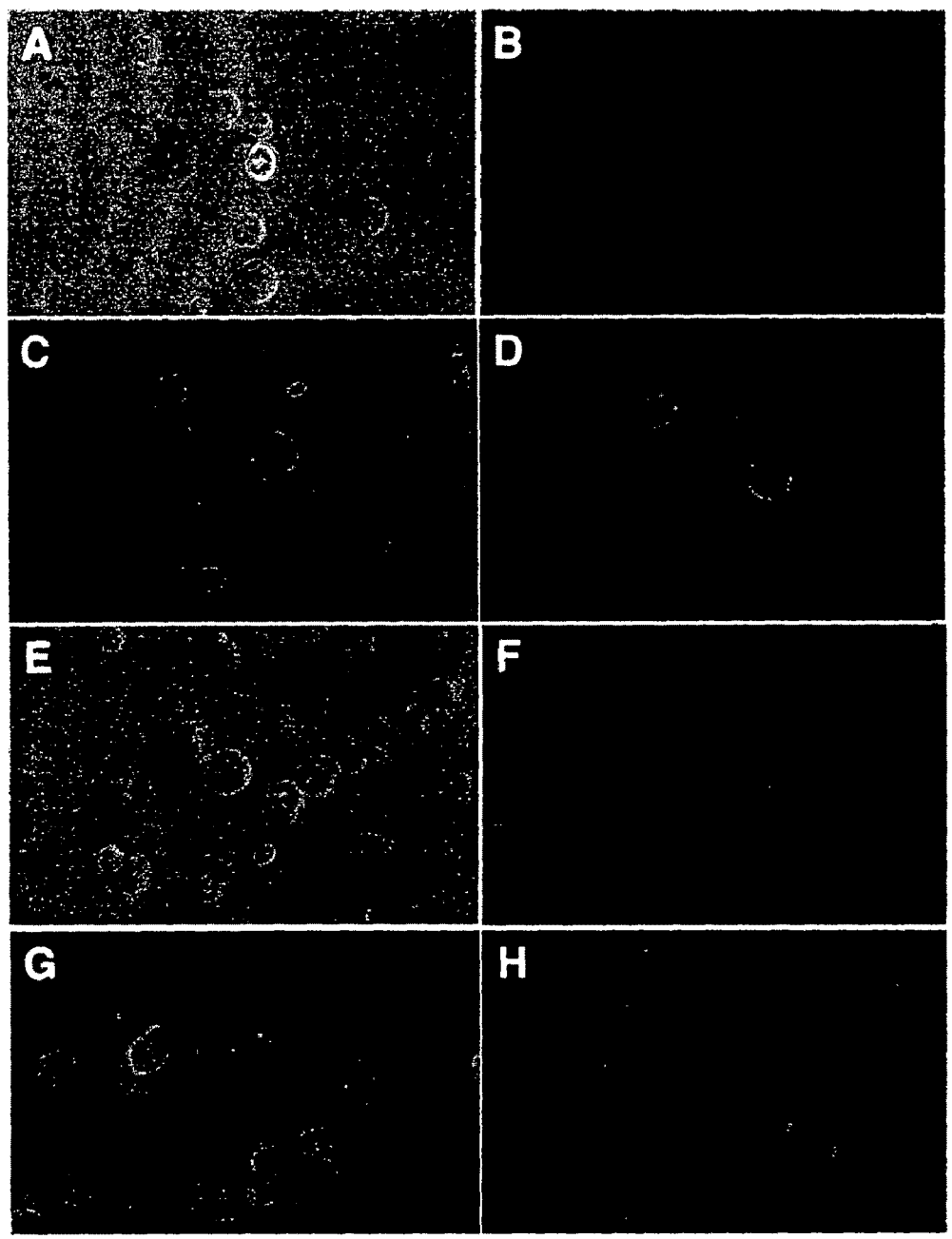
FIG. 31: Anti-apo-4 P1 antibodies specifically stain transfectants. Crude and purified anti-CD22 and anti-apo-4 antisera were compared in Apo-4 and CD22 transfectants and signal detected by FITC-labelled secondary antibodies. Samples are shown with phase-contrast images to assess transfection and staining efficiency. Apo-4 transfectants show superior staining with anti-P1c antisera (A-B) compared with anti-P1p (E-F) and negligible staining with anti-CD22p (I-J). CD22 transfectants show strong but inferior staining with anti-CD22c (C-D) compared with strong staining using anti-CD22p (G-H) and negligible staining using anti-P1p (K-L). All fluorescent images represent eight second exposures.
Figure 31:
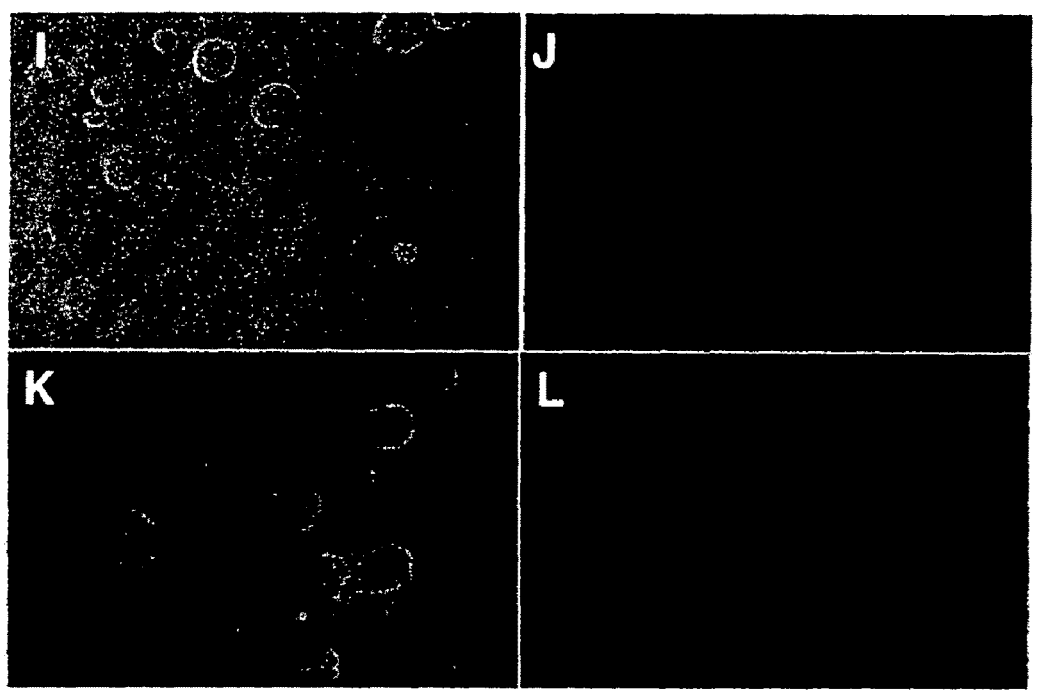

Crude and purified Anti-apo-4 and anti-CD22 antisera were compared in Apo-4 and CD22 transfectants stained in situ with signal detected by FITC-labelled secondary antibodies (FIG. 31). A comparison with phase-contrast images allowed an assessment of transfection and staining efficiency. Apo-4 transfectants show superior staining with anti-P1c antisera (A-B) compared with anti-P1p (E-F) and negligible staining with anti-CD22p (1-J). CD22 transfectants show strong but inferior staining with anti-CD22c (C-D) compared with strong staining with anti-CD22p (G-H) and negligible staining with anti-P1p (K-L).

Figure 32:
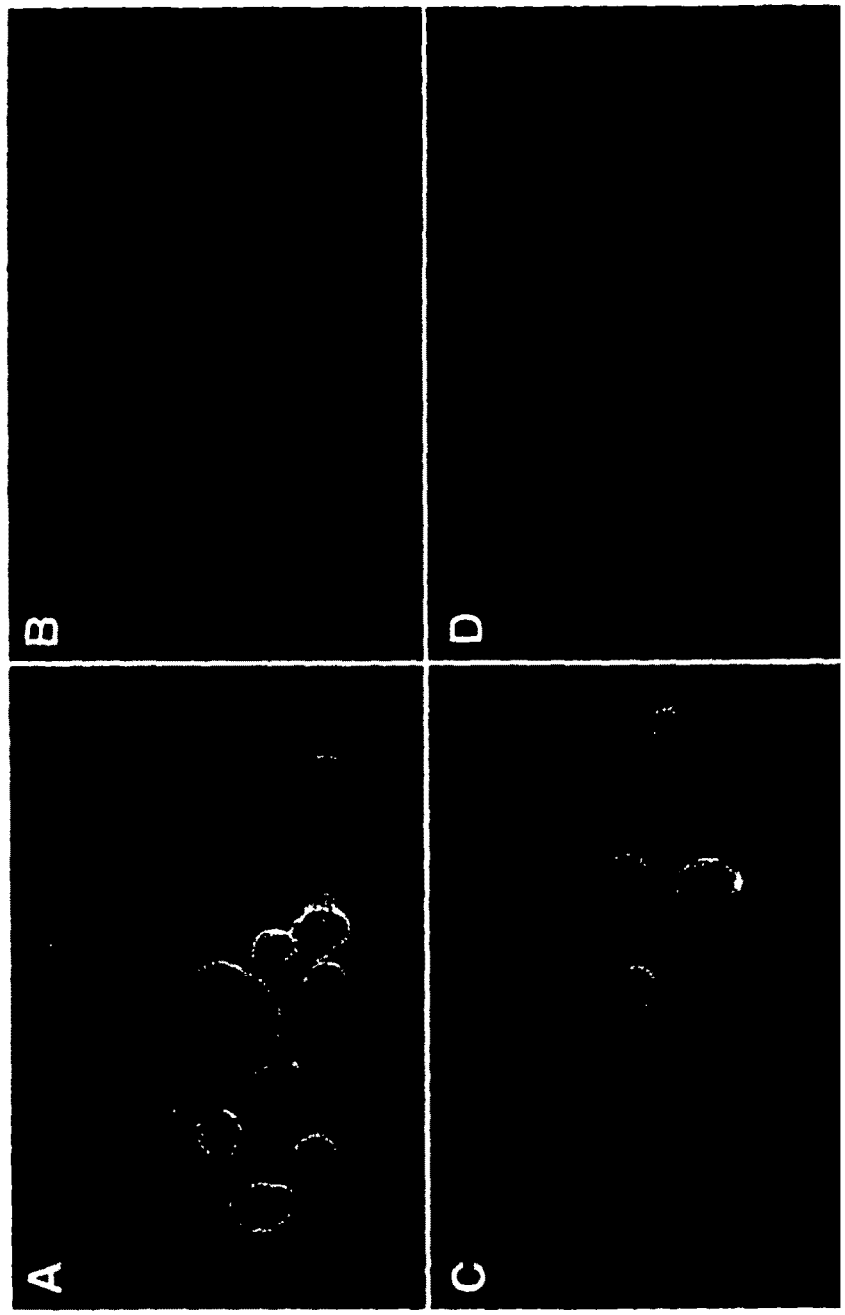
FIG. 32: Anti-apo-4 P1 antisera show pronounced staining on apo-4 transfectants compared with sham transfectants. Phase contrast microscopy and immunofluorescent microscopy was used to compare anti-apo-4 staining in transfectants. Anti-apo-4 P1c gave no staining on sham transfectants (A-B) but showed highly specific staining on apo-4 transfectants (E-F) compared with anti-CD22p antisera which gave no staining (C-D) and anti-apo-4 P1p which gave slightly less staining (G-H).
Figure 32:
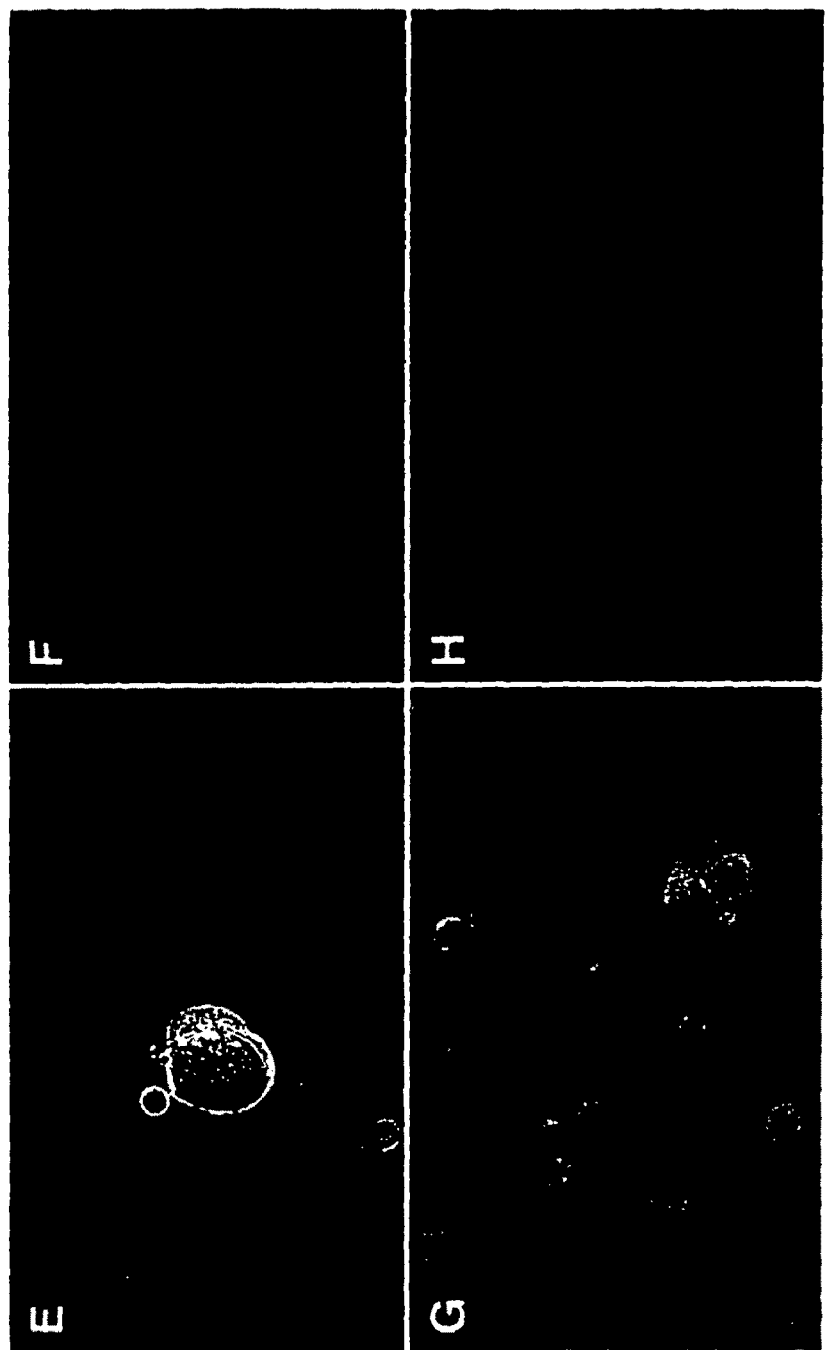

Phase contrast microscopy and immunofluorescent microscopy were again used to compare anti-apo-4 staining in transfectants (FIG. 32). Anti-apo-4 P1c gave no staining on sham transfectants (A-B) but showed highly specific staining on apo-4 transfectants (E-F) compared with anti-CD22p antisera, which gave no staining (E-F), and anti-apo-4 P1p, which gave slightly less staining (G-H). The apo-4 staining in FIGS. 31B and 32F demonstrate that apo-4 staining clearly occurs at the cell surface indicating that the sequence recognized by anti-apo-4 P1c is extracellular and arguing that either the apo-4S and/or apo-4F models predict an extracellular N-terminus in COS cell transfectants.

Fc-CD33 Shows Low-Level Apo-4 Staining

Figure 33:
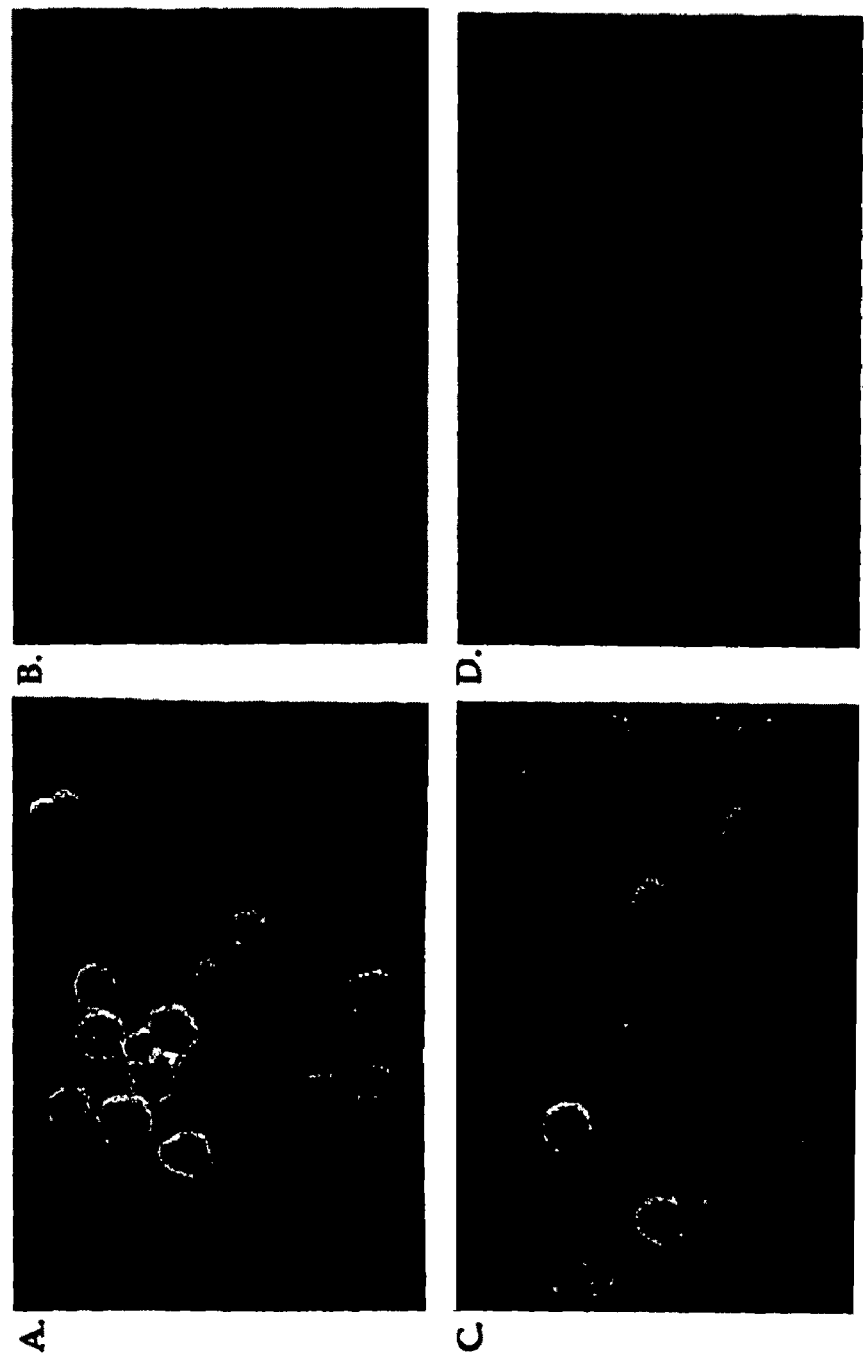
FIG. 33: Fc-CD33 shows some staining on apo-4 transfectants. Fc-CD33 shows no staining on sham transfectants (A-B) and some staining on apo-4 transfectants (C-D).

Apo-4 transfectants were examined for Fc-CD33 staining (FIG. 33). Fc-CD33 showed no staining on sham transfectants (A-B) and faint, although visible, staining on apo-4 transfectants confirming that Fc-CD33 was capable of binding apo-4 in a COS cell transfectant (C-D). CD33 polyclonal antibody staining is shown on CD33 transfectants (E-F).

Characterization of Apo-4

Binding studies with Fc-CD33 on iodinated cells revealed that it was capable of binding several ligands, at, on average 46 Kd, 54 Kd, and 61 Kd on K562, and an additional ligand from 97.4-110 Kd on U937 and possibly HL-60. Transfected candidate cDNAs isolated from panning bound between 2-10%, on average in FACS analyses and sequencing of three of these candidates revealed that they were ICAM-1 (p95-110 Kd) and a novel transcript with homology to the 3' end of dystrophin, termed here as apo-dystrophin-4, which demonstrated low-affinity binding to Fc-CD33 in iodination data with proteins precipitated at 50/66 Kd and 97-100 Kd, with a slight variation in protein product weight between assays. Attempts to repeat the ICAM-1 binding with metabolic labelling were unsuccessful however antibody blocking studies on various cell lines are necessary to assess its ability to bind Fc-CD33 in vivo. Isolating multiple ligands that require coexpression to achieve binding could not be achieved from a number of attempts with the low-avidity and low-affinity binding properties of at least five Fc-adhesins tested. Apo-4 was thus characterized as a low-affinity ligand.

Apo-4 Expression and Fc-CD33 Binding

Apo-dystrophin-4 cDNA was isolated in the second round of panning from a placental cDNA library with Fc-CD33. Protein expression studies and in situ staining on apo-4 transfectants suggest that it can bind CD33 with low-affinity, but only under optimal transfection conditions with freshly isolated Fc-protein. A full-length readthrough product from apo-4 with a 7, 9 or 31 amino acid N-terminus predicts two to four N-glycosylation sites available for intercellular binding. CD33 has been shown to bind N-linked sugars exclusively (Sgroi, D. et al., *J. Biol. Chem.*, 271: 18803-18809, 1996) and the proposed structure of a full-length product of apo-4 displays two potential N-glycosylation sites, while ICAM-1 possesses five N-glycosylation sites compatible with CD33 binding.

The Inversion could Result from Several Factors

The structure of the 1 Kb apo-4 clone showed a 137 bp inversion at the 3' end, which could result from the insertion of a downstream direct repeat into a compatible upstream location during recombination in genomic DNA (FIG. 18C). The 3' 274 bp including the inversion was reproduced in RT-PCR products obtained from placental DNA (Sigma) and in first-round cDNA from the cell lines K562, HL-60, U937, CEM, THP1, KG-1, brain and a small amount from HepG2. The partial conservation of recombination signal sequences (RSS's) or repeats near the inversion in genomic DNA may contribute to an explanation for the reproducibility of the results in leukemic cell lines. In dystrophin, the 3 Kb of 3' untranslated regions (UTRs) is conserved to 95% homology in chicken but has no known function. A novel regulatory role for 3' UTRs in growth and differentiation has recently been demonstrated in differentiated skeletal muscle cells (Rastinejad, F. and H. M. Blau, *Cell,* 72: 903-917, 1993). It was suggested that the 3' UTRs of certain differentiation-specific RNAs can function as trans-acting regulators in a feedback loop that inhibits cell division and promotes differentiation. Transcripts from the 3' UTR of alpha tropomysin have also been shown to act as tumor suppressors (Rastinejad, F. et al., *Cell,* 75: 1107-1117 1993). Apo-4 appears to be the product of a functional illegitimate recombination event in the 3' UTR of dystrophin and may carry out a related function.

A Potential Role for RAG-1 and RAG-2 in the Inversion

The recombinase activating genes (RAG-1 and RAG-2) have been shown to be essential to produce rearrangement as recently reviewed (Gellert, M., *Annu. Rev. Genet.,* 26: 425-446, 1992). The inversion products obtained in T cell lines may suggest a role for RAG-1 and RAG-2. Although only RAG-1 is present in murine brain and both are normally found only in lymphocytes, it is possible that myeloid cells contain low levels of RAG-1 and RAG-2 in association with other factors important in rearrangement. Other known factors include the TdT enzyme that generates non-templated insertions, some endonucleases that cut at or near signals, two heptamer-binding proteins, a nonamer-binding protein, and a protein (RBP-Jk) that binds to 23-spacer signals have been found in murine lymphoid extracts. The inversion was originally isolated from placental DNA, which may suggest a role for a factor with a broader distribution than lymphoid cells. A suggested pathway of rearrangement, diagrammed below, may have resulted from a multifactorial contribution from RSS's, and/or indirect and direct repeats aiding the action of the inversion as a small transposon-like element.

Transcription of Apo-4 does not Require a TATA Box

A transcription initiation site was mapped at −70 bp upstream of the first met in apo-4. Although the longest ORF and potential splice product only predicted a protein of 21.5 Kd, in vitro translation produced products at 22 Kd, 40 Kd and 50 Kd, which depended on the presence of the inversion to be produced. This suggests that the inversion controls the 5' end of the protein, possibly as a downstream enhancer, consistent with previous reports that the 3' UTR can regulate the 5' end of the gene (Jackson 1993). Anti-apo-4-P1c antisera were able to precipitate a major product at p48-50 Kd and one at p95 and P2c precipitated products at p50 and p97 from COS cell transfectants (FIG. 22) suggesting that stop codons in the sequence were not recognized. Known mechanisms of "readthrough" include RNA editing (T to A or A to G) by adenosine deaminase (dsRAD), which usually only occurs at a few RNA sites, or suppression of stop codons by signaling motifs in the sequence or by modification of the tRNAs reading the sequence. It is also possible that the hydrophobic regions identified in the apo-4 gene could act to bind DNA and potentially regulate transcription as occurs in the DNA binding regions found in c-myc to which the DNA binding protein MAX binds (Blackwood, E. M. and R. N. Eisenman, *Science,* 251: 1211-1217, 1991).

Proposed Explanations for Stop-Codon "Readthrough"

This is the first known case of a dystrophin transcript being expressed on the surface of leukemic and potentially other cells. How can protein(s) be obtained using this system if stop codons appear in the sequence between the beginning of the cDNA and the start of the ORF of interest? Anthony Monaco originally described the "reading-frame hypothesis," which stated that DMD would result from a mutation that shifted the reading frame in dystrophin, thus prematurely truncating the protein (Monaco, A. P. et al., *Genomics,* 2: 90-95, 1988). This hypothesis has been shown to be accurate in 92% of DMD cases (Koenig, M. et al., *Cell,* 50: 509-517, 1987). However, recent work on DMD patients shows that despite nonsense mutations that should result in the complete absence of dystrophin, a small proportion of "revertant" dystrophin is present in muscle fibers. "Exon skipping" has been proposed to account for this, as the exons flanking the mutation are skipped in the revertant mRNA (Nicholson, L. V. et al., *J. Med. Genet.* 29: 892-896, 1992; Sherratt, T. G. et al., *Am. J. Hum. Genet.* 53: 1007-1015, 1993). Exon skipping resulting in frame restoration has also been observed in illegitimate (ectopic) dystrophin transcripts isolated from lymphocytes and fibroblasts (Chelly, J. et al., *Cell,* 63: 1239-1248, 1990; Roberts, R. G. et al., *Am. J. Hum. Genet.,* 49: 298-310, 1991). Frameshift mutations that should delete dystrophin also demonstrate 12-15% dystrophin levels and ribosomal frameshifting and reinitiation are two mechanisms proposed to account for the correction (Gangopadhyay, S. B. et al., *Am. J. Hum. Genet.* 51: 562-570, 1992). The dystrophin gene appears to use a variety of mechanisms to correct mutations to preserve some form of this life-saving protein.

Four additional mechanisms are also suggested: 1) splicing of the RNA following transcription to eliminate stop codons 2) "readthrough" of the stop codons by the translational apparatus or by the transcriptional apparatus that allows the stop codons to be bypassed, 3) RNA editing, and 4) a combination of events that accounts for transcripts of varying lengths, such as readthrough of transcripts initiated at different methionines. Even one splicing event would require the excision of intronic sequence of at least 20-100 bp, which would reduce the weight of the longest possible product from 1-5 Kd. Assuming a 100 bp intron per splice, each splice would represent a loss of 5 Kd in weight from the longest potential product. The longest product that could be produced from the available potential splice sites in apo-4 was 19.5 Kd making splicing an unlikely event. Using the first available methionine at 9 aa in the given sequence, if all stop codons were eliminated, would produce an ORF of 323 amino acids if polyadenylation occurred at the 3' end of apo-4. That the in vitro products are 40 Kd and 50 Kd implies that they occurred through either readthrough of stop codons, RNA editing, or some combination of the two. Readthrough is the most likely since levels of adenosine deaminase are unlikely to be high enough in an in vitro system to produce RNA editing. RNA editing cannot be completely ruled out without further experimentation, however, and has been shown to account for differentially polyadenylated forms of apolipoprotein, which enable it to be directed to different tissues (Davidson, N. O., *Ann. Med.*, 25: 539-543, 1993) and has been used therapeutically to correct an upstream nonsense mutation (Woolf, T. M. et al., *Proc. Natl. Acad. Sci. USA*, 92: 8298-8302, 1995).

Several theories have been advanced to explain the mechanism of "readthrough" mainly based on the "wobble hypothesis," which allows for flexibility in reading the third base by tRNA (Atkins, J. F. et al., *Annu. Rev. Genet.*, 25: 201-228, 1991; Tuohy, T. M. et al., *J. Mol. Biol.*, 228: 1042-1054, 1992). Indeed, a codon ending in A does not necessarily code for any specific amino acids given the potential wobble of tRNA and/or the modification of the tRNA reading it. Readthrough could also result from the strong T7 promoter or some other element interacting with the RNA polymerase to allow transcription to continue. This is more common in phage and may be related to the homology apo-4 shares with viruses found in protein homology searches of the 5' end of the gene. In mice, a 60 bp sequence at the extreme 3' end of the sequence can control protein production (Braun, R. E., *Enzyme*, 44: 120-128, 1990). In apo-4 all or part of the 137 bp sequence at the 3' end could control protein production so that all stop codons are suppressed by one or more of the proposed mechanisms suggested above. The AATTAA sequence at the extreme 3' end of apo-4 appears to serve as a cryptic polyadenylation site, as it is in the right place to produce p50 from the "strong" met at +34 aa. In addition to the novel proteins characterized in this study, the inversion itself likely contains powerful clues about 3' motifs capable of regulating protein production that are worthy of further study, principally by placing the inversion sequence downstream of other DNA with stop codons that terminate translation. The products of apo-4 appear to be regulated despite readthrough and it is important to study further the effects of apo-4 in vivo.

The observations reported hereinabove have been provoking in that the explanation for the production of both the apo-4 transcript and its translation products demand the involvement of rare or novel mechanisms. It is also appreciated that the techniques employed are working at the limits of sensitivity and resolution in some cases. Validation of the entire genomic rearrangement predicted to underlie the production of the apo-4 transcript has yet to be obtained. Wide acceptance for the model presented may await complete sequencing of the genomic region containing the rearrangement and of the corresponding protein products of apo-4. Until then, the results obtained can be taken to represent an intriguing combination of findings suggesting the existence of a potentially highly significant phenomenon.

Relationship of Apo-Dystrophin to Known Inversions and Translocations

Figure 38A:
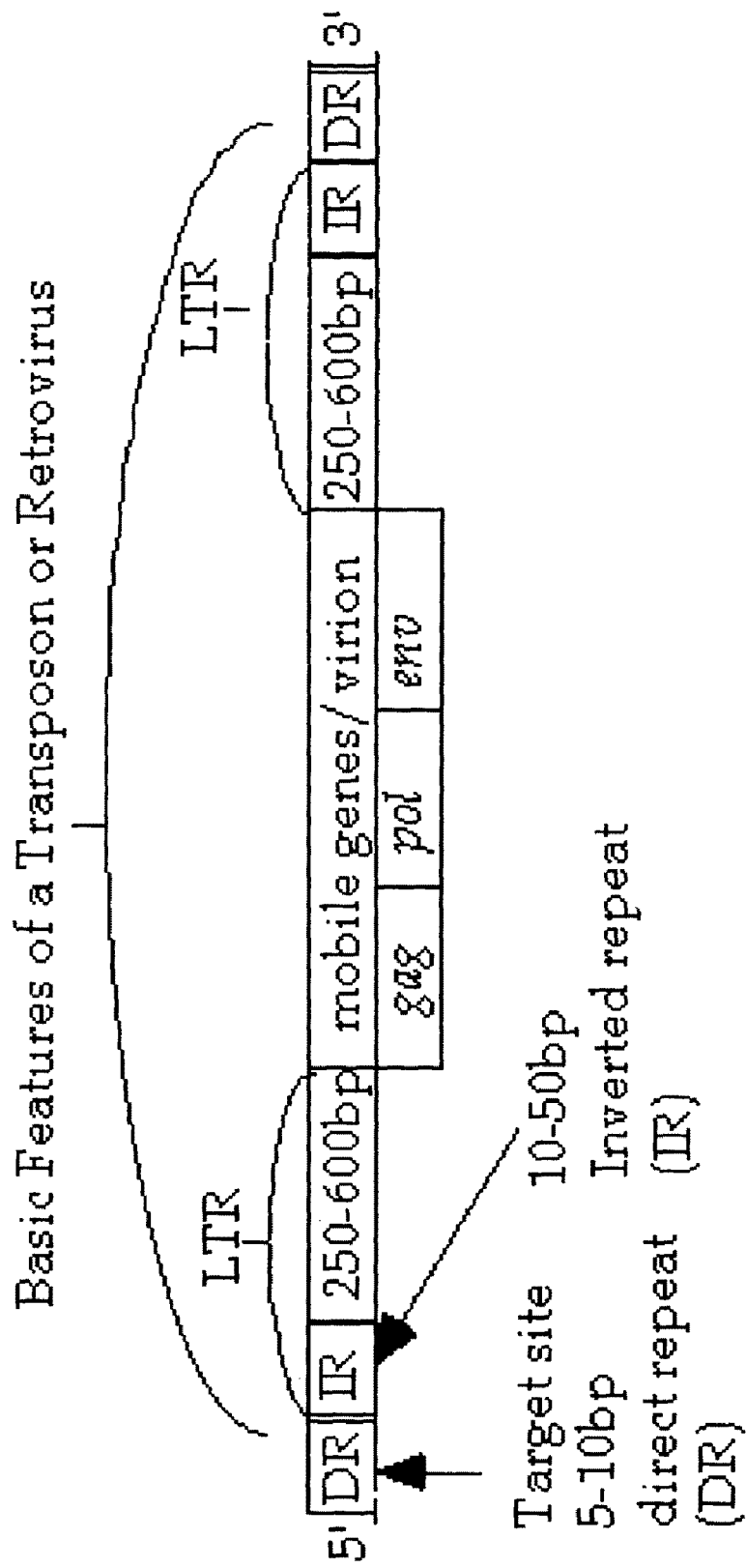
FIGS. 38A and 38B: The apo-4 inversion shares several features with transposable elements.
Figure 38B:
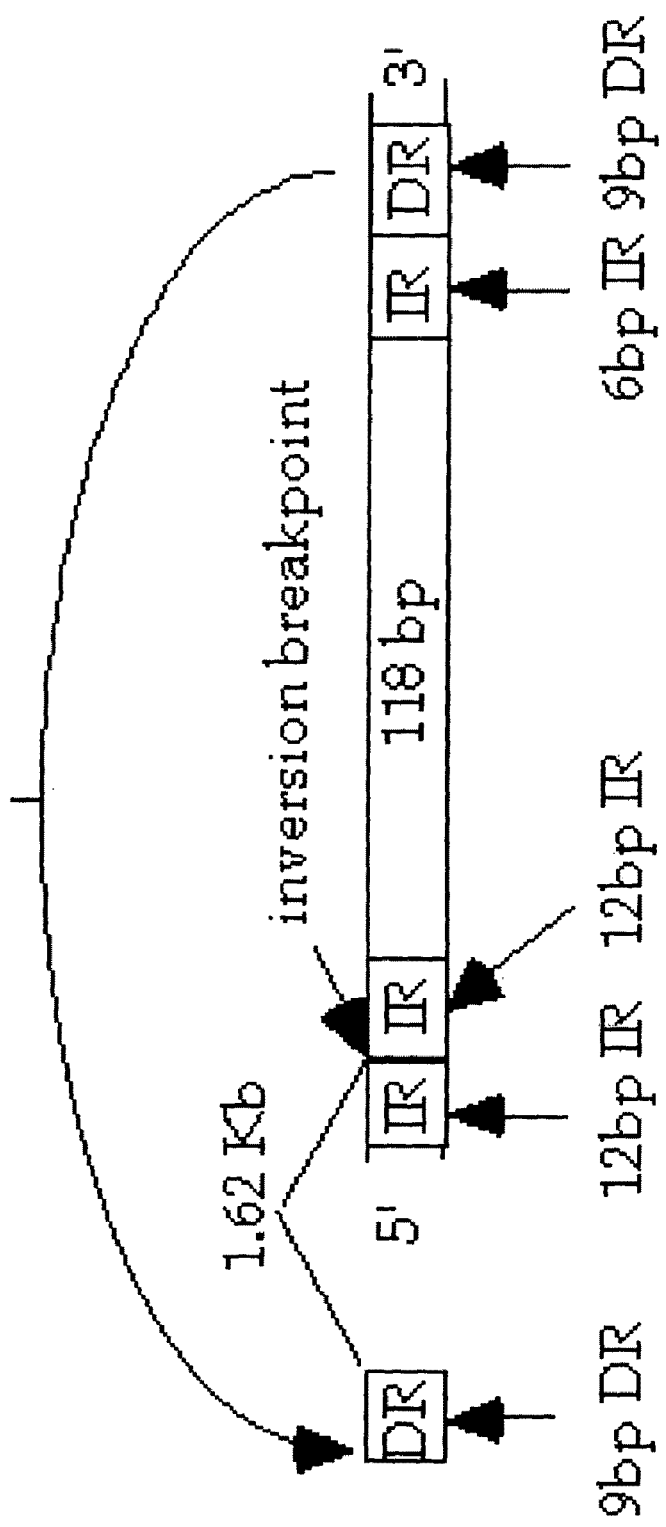

Through the panning process, a putative low-affinity ligand for CD33 was isolated and termed apo-dystrophin-4. The apo-4 cDNA contains an inversion at its 3' end which appears necessary for the production of its two major protein products. In chronic and acute leukemic cells, and less commonly in lymphoma, both chromosomal and genomic DNA translocations and inversions often give rise to unique "fusion proteins" (Rabbitts, T. H., *Cell*, 67: 641-644, 1991). The chromosomal rearrangement of 11q23 leads to the production of an active myeloid-lymphoid leukemia (MLL) gene at the point of fusion of the translocation consisting of the 5' segment of MLL and a 3' segment of the other gene (Rowley, J. D., *Nature*, 354: 233-235, 1995). A similar fusion product, bcr-abl, is produced with the fusion of the bcr element with the abelson leukemia virus element in the chromosome 9:22 translocation often found in Chronic Myelogenous Leukemia (CML) cells (reviewed in Varmus, H. E., *Annu. Rev. Genet.*, 18: 553-612, 1984). The triggers for an aberrant rearrangement of these unstable genetic elements are not known but repetitive elements in the DNA, such as Alu repeats or aberrant rearrangements of the type found in immunoglobulin are thought to be among them (reviewed in Bishop, J. M., *Annu. Rev. Biochem.*, 52: 301-354, 1983). Retroviral insertion is another common mechanism of gene activation of protooncogenes as described for v-src and c-src. Insertion of the Rous sarcoma virus next to normal genes brings about acute transformation due to high transcription of the activated oncogene. Similarly, retroviral elements already present in the DNA can rearrange themselves next to protooncogenes elsewhere and transform them into oncogenes. The DNA intermediates which occur during the replication of retroviruses are structurally and, as has been proposed, perhaps functionally related to transposable elements (Majors, J. E. et al., *Cold Spring Harb. Symp. Quant. Biol*, 2: 731-738, 1981) which were first described in maize (McClintock, B., *Cold Spring Harbor Symposium*, 21: 197-216, 1956) (FIG. 38A). A similar mechanism of activation is proposed for apo-dystrophin-4 gene which appears to insert an inverted sequence containing the basic hallmarks of a retrovirus or transposable element (FIG. 38B), into a specific target site in the dystrophin gene prior to splicing and most likely during gene rearrangement.

Figure 39A:
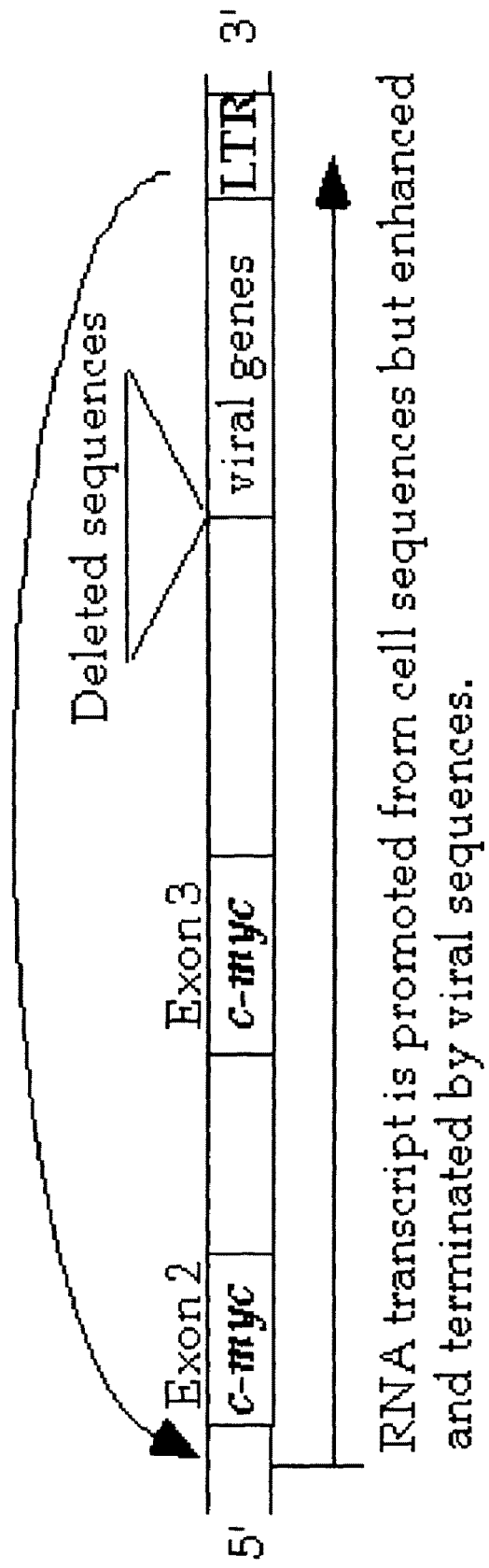
FIGS. 39A and 39B: A proposed mechanism of activation of the apo-4 gene based on the retroviral insertion model of c-myc. The apo-4 inversion in vitro appears to act as an enhancer closely resembling a model previously outlined for the action of the c-myc oncogene with a retroviral enhancer insertion. This is illustrated by the removal of the inversion in apo-4 which produces a complete loss of translation in the gene. The upper diagram is adapted from Darnell, J. et al., (Molecular Cell Biology. 1062. Scientific American Books, 1986) based on retroviral insertion behavior previously described (Payne et al., Multiple arrangements of viral DNA and an activated host oncogene in bursal lymphomas. *Nature*, 295: 209-214, 1982).

A well studied example of retroviral transposition occurs with the insertion of the avian leukemia virus next to c-myc by virtue of the two LTRs which allow insertion upstream or downstream of the myc gene (Payne, G. S. et al., *Nature*, 295: 209-214, 1982) (FIG. 39A). c-myc is also implicated in Burkitt's Lymphoma (Croce, C. M. et al., *Proc. Natl. Acad. Sci. USA*, 81: 3170-3174, 1984), BL-Acute T-cell Leukemia (reviewed in Rabbitts 1991). Insertion of the retrovirus upstream in the correct 5'-3' orientation is referred to as "promoter insertion" while insertion upstream in the 3'-5' orientation upstream or the 5'-3' direction downstream results in "enhancer insertion" by virtue of the ability of the 3' LTR to act as an enhancer in either orientation (Payne et al. 1982) (FIG. 39A). Of primary importance to this study is the third model in which the 5' LTR is deleted and the 3' LTR acts as a transcription enhancer of the 5' end of independent genes which are not transcribed in its absence, as illustrated (FIG. 39A). Retroviruses have the ability to ignore the stop codons present in their own genomes as is shown by the production of the readthrough protein gag-pol rather than the individual proteins gag and pol by the action of a glutamyl-tRNA which allows the stop codon to be bypassed and a single protein to be generated. It is possible that the same process could function to suppress the stop codons in apo-4 to allow translation to proceed.

Figure 39B:
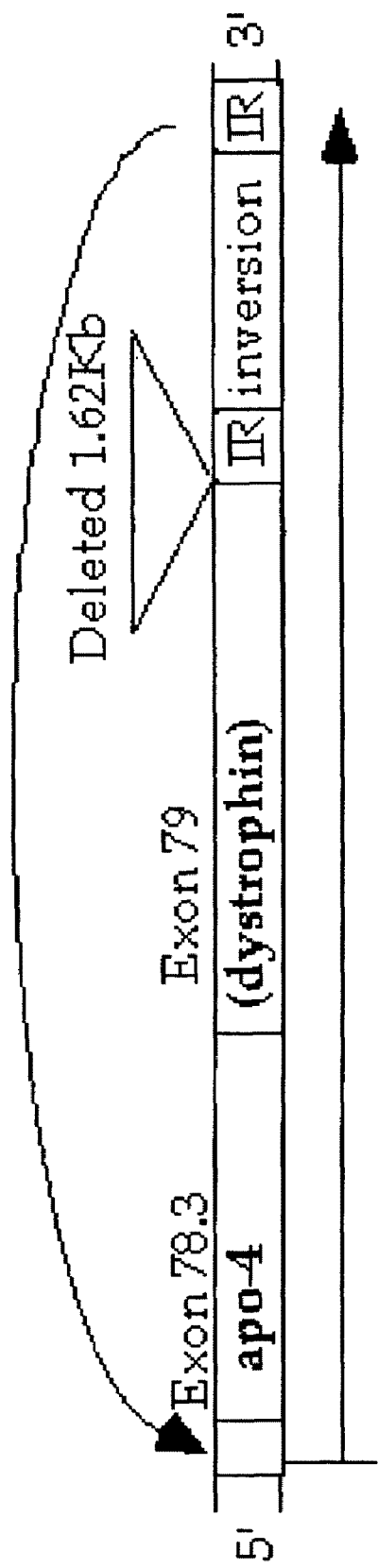

Following rearrangement of the dystrophin 3' sequence as shown above, it is proposed that the inversion could act as a downstream myc-like transcriptional enhancer (FIG. 39B). In a similar fashion, the 72 bp SV40 enhancer can increase transcription in either orientation at distances of up to several Kb upstream or downstream of the start site (Banerji, J. et al., *Cell*, 27: 299-308, 1981) (FIG. 39A). The inversion may not only direct upstream transcription by acting as an enhancer to recruit transcriptional activators, but may recruit some of these DNA binding proteins to its hydrophobic regions to direct the production of translation products.

If this mechanism is indeed active, the 5' 453 bp of the apo-4 gene may represent an activated oncogene which is normally dormant and/or spliced out of the dystrophin gene. This may explain why the inversion was readily reproducible in several leukemic cell lines. It may have an independent function in normal cells, however, and such a possibility cannot be ruled out. The apparent retroviral or transposable behavior of the inversion may have larger implications. It may help explain why nucleotide and protein sequence searches of the 5' 453 bp of the apo-4 gene often yielded significant homology only to viruses. It is possible that part or all of the 3' end of dystrophin represents an ancient form of viral material which has integrated itself into the genome to become a permanent part of the gene, as suggested by identifying the inversion in genomic DNA. Indeed, the Alu repeat found downstream of the inversion and spliced out in apo-4 may form part of an enhancer suppressor as was recently shown with the probable in vivo formation of an Alu cruciform, thought to silence the activity of a 3' CD8 enhancer (Hanke, J. H. et al., *J. Mol. Biol.*, 246: 63-73, 1995). Alu repeats are thought to be over 30 million years old (Britten, R. J., *Proc. Natl. Acad. Sci.* 91: 6148-6150, 1994) and originally retrotransposons (Weiner, A. M. et al., *Ann. Rev. Biochem.* 55: 631-661, 1986). Although apo-4 appears to have the unusual property that all of its internal stop codons are not recognized, only two major and a possible third minor transcript are produced from the gene indicating that there is some element of active transcriptional and translational control. In bacteriophage λ transcription can continue by virtue of changed secondary structure under conditions of low tryptophan; if a 2-3 stem-loop forms rather than a 3-4 stem-loop transcription will continue (Yanofsky, C., *Nature,* 289: 751-758, 1981). Secondary structure may also contribute to the readthrough of apo-4 stop codons. All of these activities may be controlled by the inversion which could enhance the production of normal and mutated dystrophin. If the inversion does act as a bi-directional enhancer it may help explain the exon-skipping observed with other dystrophin mutations (Nicholson et al. 1992; Sherratt et al. 1993). To test this, it will be important to put the inversion sequence and as much relevant upstream DNA as necessary to 707 bp next to other genes and examine its ability to control transcription and/or translation.

Figure 25B:
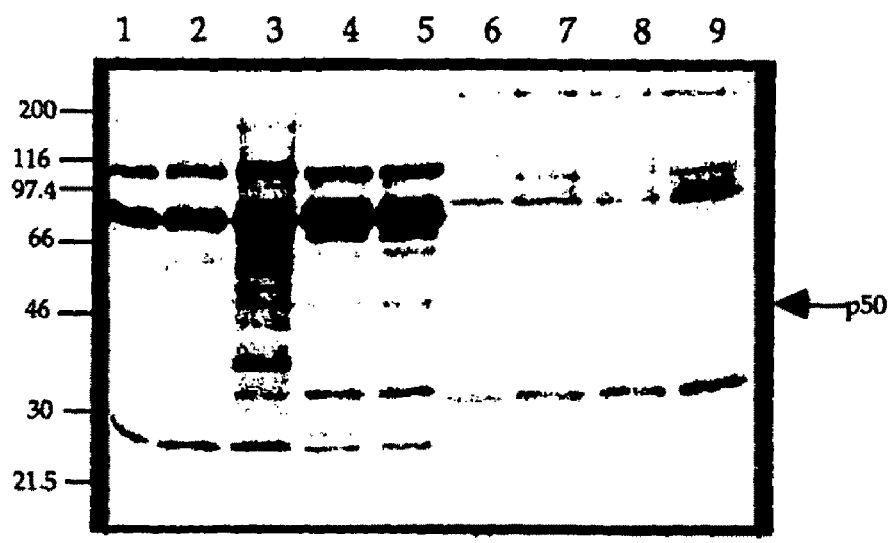
FIG. 25B: Immunoprecipitation of apo-4 under nonreduced and reduced conditions shows possible linkage with a separate subunit. Apo-4 transfectants were labelled with NHS-biotin and immunoprecipitated with the anti-apo 4 P1 antisera (Lanes 1 and 3) and the antisera blocked with peptide (Lanes 2 and 4) and subjected to SDS-PAGE under nonreducing (Lanes 1 and 2) and reducing (Lanes 3 and 4) conditions. Under non-reducing conditions, apo-4 runs at about 62 Kd and a high molecular weight species is blocked at 106-108 Kd (Lane 1). Under reducing conditions, two bands are blocked by peptide at 50 Kd and 56-58 Kd indicating that apo-4 may exist as a heterodimer on the cell surface.
Figure 30:
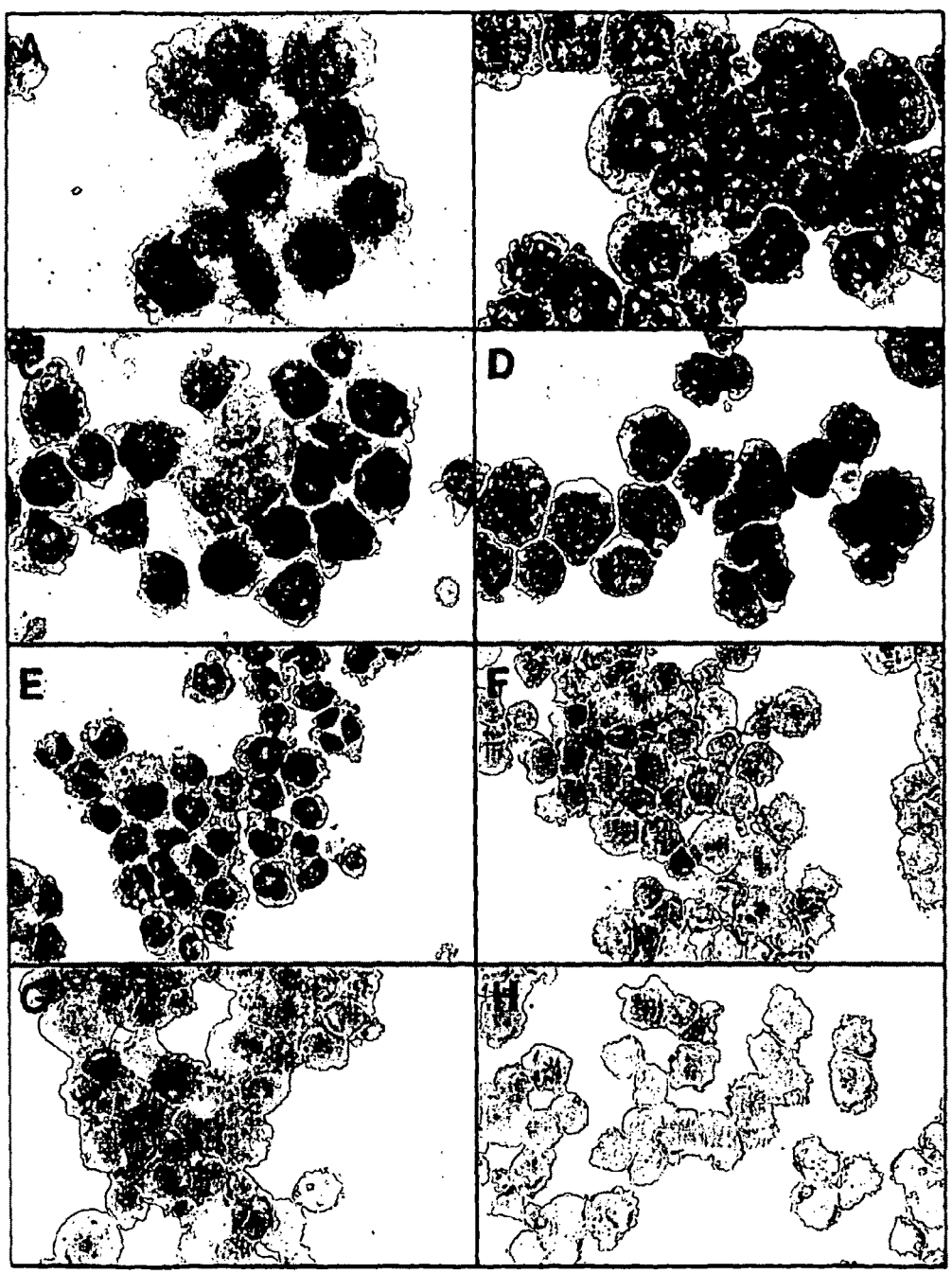
FIG. 30A through FIG. 30H: Crude and purified anti-apo-4 antisera show intracellular staining in K562. In K562 cytospins anti-apo-4 P1c (B) showed apparent nuclear but not nucleolar staining as shown by the white regions within the nucleus; the unstained nucleus may be mitotic. Staining of the cell surface could give the appearance of intracellular staining, suggested by the staining throughout the cytoplasm. Anti-apo-4 P2c (D) shows no nuclear and some apparent cytoplasmic staining concentrated around the nucleus. Both gave stronger staining than their respective pre-bleeds, P1c-pb (A) and P2c-pb (C). Purified antisera gave less intense staining than crude antisera. As in B, the staining with P1p (F) appeared to be across the cell surface and/or within the cytoplasm and possibly in the nucleus. P2p (G) gave only apparent cytoplasmic staining as did P3p (H) more weakly, although all three were more pronounced than a control with no antibody (E). Images are a 40× magnification.

To summarize the findings on apo-4 it is important to look at the evidence for its expression in COS cells and in cell lines, most of which is known from K562. This study suggests that in a COS cell, apo-4 produces major bands at 55 Kd and 50 Kd which can be blocked by peptide (FIGS. 24-25). p50 has an extracellular N-terminus as shown by fluorescent staining and it is likely that p55 does as well, although fluorescent staining would need to be done to prove this. It is also possible for Fc-CD33 to bind p50 in vitro, given optimal transfection conditions. In two separate immunoprecipitation experiments on labelled K562, Fc-CD33 appeared to bind a 50 Kd doublet in the same region as purified anti-apo-4 P1p antisera, which was almost completely blocked in one experiment (FIG. 24) and partially blocked in another (FIG. 25B). In the first experiment, P1p failed to precipitate the 50 Kd band in transfectants although it could precipitate the bands in K562. Crude anti-apo-4 could precipitate a band in both transfectants and K562, but it was more difficult to block the crude antisera (FIG. 25B). Immunohistochemistry showed that crude antisera (P1c) also gave pronounced staining on K562 which was distinct from that shown with P2c, which is not unexpected considering that P2c recognizes sequence in the putative transmembrane domain (FIG. 30). In addition, FACS analysis on K562 using anti-apo-4 P1c as a probe produced a significant shift of the curve above the pre-bleed control (data not shown). Although the possibility of cross-reactivity cannot be excluded with a polyclonal antisera on the cell lines and tissues, the evidence suggests that apo-4 is specifically expressed there, particularly the staining pattern in brain which is in the same areas as other apo-dystrophin proteins. Peptide sequencing of the large amounts of protein products obtainable from transfectants would allow a definitive answer to the peptide sequence obtained from the transfected apo-4 gene, particularly which amino-acids were produced from "wobble" or readthrough. Making monoclonal antibodies against these products would also allow for greater specificity in both the immunoprecipitation and staining work to confirm the results presented here. It could be useful to ligate the 5' end of apo-4 into the pIG1 vector and raise monoclonal antibodies against the soluble protein although if the N-terminus were only 7-9 amino acids it may restrict this avenue.

Whether or not the full-length apo-4 product can be detected in RNA from tissues has not been completely confirmed in these studies. The first 876 bp of the gene were reproducible as was the inversion in a number of RT-PCR experiments attempted, but these "overlapping clones" were not reproduced as a full-length transcript with the primers designed near the extreme ends of the gene. The finding that the inversion appears to exist in genomic DNA lends weight to the evidence that the transcript is in some copies of normal genomic DNA. Parts of other rare transcripts have been amplified by using a "nested PCR" technique in which primers at the putative ends of a clone were used on the first PCR, and the product was reamplified using another set of primers immediately inside the original ones. In this way, two overlapping clones were produced after 60 rounds of PCR (Lejeune, S. et al., *Clin. Cancer Res.*, 1: 215-222, 1994). On examining the primers used, however, it may be that the F1 primer was unstable with 1st round cDNA when used with R1 due to the stretch of eight As at its 5' end. That the 1st 876 bp and the inversion could be produced from RNA suggests that the entire gene could be produced. A reasonable next step would be to try to reproduce the entire gene by "walking" back to the R1 primer with existing antisense oligonucleotides 3' of the inversion in combination with primers immediately 5' of the putative starting methionines.

The primer extension data produced two compelling pieces of evidence. First, a putative transcription start site was identified which is in the standard location predicted for use by the second or third available methionines. Second, the start site coincided with the start of an upstream exon identified by the GRAIL search. This exon is in the same frame as apo-4 and shares the same hydrophobic character seen in the 5' hydrophobic promoter element GCN4 in yeast which acts as a DNA binding protein to stimulate enhancer activity and is dependent on its hydrophobic residues to do so (Drysdale, C. M. et al., *Mol. Cell. Biol.,* 15: 1220-1233, 1995) as is the DNA binding protein tax which binds the basic portion of the HTLV-1 genome (Baranger, A. M. et al., *Nature,* 376: 606-608, 1995) and the MAX protein in its binding to c-myc (Blackwood and Eisenman 1991). The existence of this sequence as a continuous transcript from the apo-4 gene suggests that apo-4 may have resulted from a truncated transcript which actually possesses a hydrophobic 5' UTR which could also act as a DNA binding protein to regulate transcription. It may work in concert with the other hydrophobic regions seen in apo-4 to regulate transcription and/or translation. The apo-4 gene will provide many exciting avenues for future work and it is suggested that it may be useful as a new marker for leukemia therapy.

In future work it would be informative to cotransfect the ICAM-1 and apo-4 transcripts to determine whether enhanced CD33 ligand binding could be produced. Binding could be confirmed by blocking studies with anti-ICAM-1 antibodies. Although several attempts failed to reproduce Fc-CD33 binding to ICAM-1 in immunoprecipation studies, in vivo studies using blocking antibodies against both Fc-CD33 and anti-ICAM-1 antibodies on cell lines were not attempted and these could provide some evidence of binding. It is hoped that the results presented in this study will offer useful insights both into basic biological processes and potential therapeutic advances in leukemia.

While the invention has been described herein with reference to the preferred embodiments, it is to be understood that it is not intended to limit the invention to the specific forms disclosed. On the contrary, it is intended that the invention cover all modifications and alternative forms falling within the scope of the appended claims.

TABLE 1

RT-PCR provides evidence of potential splice products

| RT-PCR sample origin (order follows blots 6.15A-D) | Approximate Hybridised Fragment Size (Kb) | Oligo Probe F2.2R @188 cDNA position 3.0 | F2 @713 series. order probed 2.1 | RSP2 @849 1.2 |
|---|---|---|---|---|
| Placental DNA F2 + R1 | 0.3 | not tested (NT) | ++ | + |
| | 0.2 (r) | | ++ | + |
| | 0.1 (r) | | ++ | + |
| Placental DNA F1 + R1 | 1.0 | NT | – | – |
| | 0.6 | | – | – |
| | 0.3 (r) | | ++ | – |
| | 0.2 (r) | | + | – |
| | 0.1 | | – | – |
| Placental DNA F1 + R2 | 0.7 | NT | – | – |
| | 0.5 | | – | – |
| | 0.4 | | – | – |
| | 0.2 | | – | – |
| | 0.1 | | – | – |
| Patient LB ** RNA F1 + R2 | 0.5 | NT | – | – |
| | 0.4 | | – | – |
| | 0.1 | | – | – |
| Patient NJ ** RNA F1 + R2 | 0.5 | NT | – | – |
| | 0.4 | | – | – |
| | 0.3 | | – | – |
| | 0.1 | | – | – |
| Placental cDNA F1 + R1 (+control) | 1.2 | NT | (+) | – |
| | 1.0 | | + | + |
| | 0.6 (s) | | + | (+) |
| HepG2 RNA F2 + R1 | 0.3 | NT | (+) | – |
| | 0.1 (s) | | ++ | ++ |
| HepG2 RNA F1 + R1 | 1.0 | NT | – | – |
| | 0.1 (s) | | (+) | – |
| HepG2 RNA F1 + R2 | 0.5 | NT | – | – |
| | 0.1 (s) | | – | – |
| K562 RNA F2 + R1 | 0.3 | NT | ++ | + |
| | 0.2 (s) | | ++ | – |
| | 0.1 (s) | | ++ | ++ |
| K562 RNA F1 + R1 | 1.0 | – | – | – |
| | 0.7 (s) | (+) | – | – |
| | 0.4 (s) | (+) | – | – |
| | 0.2 (s) | – | + | – |
| | 0.1 (s) | – | ++ | – |
| K562 RNA F1 + R2 | 0.5 | NT | – | – |
| | 0.1 (s) | | – | – |
| K562 RNA F1 + R2o | 0.9 | + | NT | NT |
| | 0.7 (s) | ++ | | |

TABLE 1-continued

RT-PCR provides evidence of potential splice products

| | 0.4 (s) | ++ | | |
|---|---|---|---|---|
| | 0.2 (s) | ++ | | |
| | 0.1 (s) | + | | |
| K562 + PMA RNA F1 + R2o | 0.9 | (+) | NT | NT |
| | 0.7 (s) | + | | |
| | 0.4 (s) | + | | |
| | 0.2 (s) | + | | |
| | 0.1 (s) | – | | |
| HL-60 RNA F2 + R1 | 0.3 | NT | ++ | + |
| | 0.1 (s) | | ++ | (+) |
| HL-60 RNA F1 + R1 | 1.2 | – | + | – |
| | 0.29 (s) | (+) | – | – |
| | 0.1 (s) | – | ++ | – |
| Oligo Probe | Fragment Size | F2.2R | F2 | RSP2 |
| HL-60 RNA F1 + R2 | 0.5 | NT | – | – |
| | 0.3 (s) | | – | (+) |
| HL-60 RNA F1 + R2o | 1.2 | (+) | NT | NT |
| | 0.9 | (+) | | |
| | 0.7 (s) | ++ | | |
| | 0.4 (s) | + | | |
| | 0.2 (s) | + | | |
| | 0.1 (s) | (+) | | |
| HL-60 + PMA RNA, F1 + R1 | 1.0 | – | NT | NT |
| | 0.2 (s) | (+) | | |
| HL-60 + PMA RNA F1 + R2o | 1.2 | (+) | NT | NT |
| | 0.9 | (+) | | |
| | 0.7 (s) | ++ | | |
| | 0.4 (s) | + | | |
| | 0.2 (s) | + | | |
| | 0.1 (s) | (+) | | |
| CEM RNA F2 + R1 | 0.3 | NT | ++ | – |
| | 0.1 (s) | | ++ | (–) |
| CEM RNA F1 + R1 | 1.0 | – | – | – |
| | 0.1 (s) | | (+) | – |
| CEM RNA F1 + R2 | 0.5 | NT | – | – |
| | 0.1 (s) | | – | – |
| CEM RNA F1 + R2o | 0.9 | – | NT | NT |
| | 0.7 (s) | + | | |
| | 0.4 (s) | + | | |
| | 0.2 (s) | + | | |
| | 0.1 (s) | – | | |
| Placental RNA F1 + R1 | 1.0 | – | NT | NT |
| Placental RNA F1 + R2o | 0.9 | – | NT | NT |
| | 0.7 (s) | + | | |
| | 0.4 (s) | + | | |
| | 0.2 (s) | + | | |
| | 0.1 (s) | – | | |
| U937 RNA F1 + R1 | 1.0 | – | – | – |
| | 0.1 (s) | – | (+) | – |
| U937 RNA F1 + R2 | 0.5 | NT | – | – |
| | 0.1 (s) | | – | – |
| U937 RNA F1 + R2o | 0.9 | – | NT | NT |
| | 0.7 (s) | + | | |
| | 0.4 (s) | + | | |
| | 0.2 (s) | + | | |
| | 0.1 (s) | – | | |
| Brain RNA ** F2 + R1 | 0.3 | NT | NT | + |
| | 0.1 (s) | | | (+) |
| TH1 RNA ** F2 + R1 | 0.3 | NT | NT | + |
| | 0.1 (s) | | | (+) |
| KG-1 RNA ** F2 + R1 | 0.3 | NT | NT | + |
| | 0.1 (s) | | | (+) |
| HPB-ALL cDNA, F1 + R1 | 1.0 | NT | NT | + |
| Primers Alone (–control) | <1.2 | – | NT | NT |

* Expected RT-PCR fragment sizes, which correspond to the apo-dystrophin-4 cDNA sizes, are: F2 + R1 - 274 bp (~0.3 Kb); F1 + R1 - 979 bp (~1.0 Kb); F1 + R2 - 468 bp (~0.5 Kb); F1 + R2o - 868 bp (0.9 Kb) bp. All cDNA was made directly from RNA before subjecting it to PCR unless otherwise indicated ("cDNA" means that the sample was taken from a cDNA library and DNA means that the sample was genomic DNA); ++ = strong signal; + = medium signal; (+) = weak signal; – = no signal, (r) = potential rearrangements; (s) = potential splice product; productsless than 0.1 Kb are typically considered "primer dimers".
** Primers alone were used in these RT-PCR reactions, and gave a negative result, but were not reloaded on the Southern due to lack of room on the gel. In the same reaction, Patients LB and NJ gave negative results for F1 + R1, F1 + R2 and F2 + R1.

TABLE 2

Subcloned RT-PCR products in pBluescript SK+

| Tissue | Primers | Predicted Product Size | Product size | Product Sequenced* | Alignment with apo cDNA | Splicing? |
|---|---|---|---|---|---|---|
| Human Brain (a) | F2 + R1 | 274 bp | ~274 bp | 274 bp | 96.9% | no |
| Human Brain (c) | F2 + R1 | " | ~274 bp | 195 bp | 95.8% | no |
| U937 cDNA | F1 + R2 | 468 bp | ~450 bp | 238 bp | 97.9% | no |
| HPB-ALL cDNA | F1 + R1 | 979 bp | ~950 bp | 139 bp | 67.2% (50% at peptide) | unlikely |

*Several potential splice products were obtained, with those sequenced shown above. In brain, two products were obtained sharing close but not exact homology with the original apo-4 cDNA, as well as one 5' product (8-11) and one cDNA full-length product that was not an exact duplication of the apo-4 cDNA from an HPB-ALL cDNA library.

TABLES 3A-3B

Type I (A) And Type II (B) Apo-4 Proteins Predicted With Nonsense Suppression

3A. Type I Proteins Predicted From The 997 bp Apo-4 Gene

| Methionine start site*** | Signal Peptidase Cleavage Site (+length of Signal Peptide) | Cleaved Peptide length (aas) (+N-terminus length) | Position & Length of 1st TM domain | Predicted protein Weight (no. aa × 150) |
|---|---|---|---|---|
| @9 (.76)+ | @25 (17 aas) | 307 (15) | @40-60 | 46.0 Kd (+2N = 52 Kd) |
| @9 (.76) (+) | @39 (31 aas) | 293 (1) | @40-60 | 43.9 Kd (+2N = 49.9 Kd) |
| @30 (.77) | @48 (19 aas) | 284 (5) | @40-60 | 42.6 Kd (+2N = 48.6 Kd) |
| @34 (.93) | @48 (15 aas) | 284 (5) | @40-60 | 42.6 Kd (+2N = 48.6 Kd) |
| @67 (.74) | @93 (27 aas) | 239 (27) | @101-121 | 35.8 Kd (+2N = 41.8 Kd) |
| @120 (.77) | @142 (23 aas) | 188 (74) | @217-237 | 28.2 Kd (+1N = 31.2 Kd) |

3B. Type II Proteins Predicted From The Apo-4 Gene

| Methionine start site position (+GeneID probability) | amino acids to 1st predicted TMD = N-terminus | Position & Length of 1st TM domain | Pred. Pep. length (aas) | Predicted protein Weight (no. aa × 150) | +Extra Weight from vector to *Pst I (IVT&T) (+15 aas = 2.25 Kd) or **AATAAA/CDM8 |
|---|---|---|---|---|---|
| @9 (.76)(+CDM8)+ | 31 | @40-60 | 547 | 82.1 Kd (+5N = 97 Kd) | **97.00 Kd |
| @9 (.76)+ | 31 | @40-60 | 324 | 48.6 Kd (+2N = 54.6 Kd) | *50.85 Kd (56.85K) |
| @30 (.77)+ | 10 | @40-60 | 302 | 45.3 Kd (+2N = 51.3 Kd) | *47.55 Kd (53.55K) |
| @34 (.93)+ | 6 | @40-60 | 298 | 44.7 Kd (+2N = 50.7 Kd) | *46.95 Kd (52.95K) |
| @67 (.74) | 34 | @101-121 | 265 | 39.7 Kd (+2N = 45.7 Kd) | *41.95 Kd (47.95k) |
| @110 (.77) | 0 | @110-120 | 222 | 33.3 Kd (+1N = 36.3 Kd) | *35.55 Kd (41.55K) |
| @120 (.77) | 12 | @132-152 | 212 | 31.8 Kd (+1N = 34.8 Kd) | *34.05 Kd (40.05K) |
| @160 (.84) | 57 | @217-237 | 172 | 25.8 Kd (+1N = 28.8 Kd) | *28.05 Kd (34.05K) |
| @168 (.83) | 49 | @217-237 | 164 | 24.6 Kd (+1N = 27.6 Kd) | *26.85 Kd (32.85K) |
| @175 (.77) | 42 | @217-237 | 157 | 23.5 Kd (+1N = 26.5 Kd) | *25.75 Kd (31.75K) |
| @184 (<.67) | 33 | @217-237 | 148 | 22.2 Kd (+1N = 25.2 Kd) | *24.45 Kd (30.45K) |

***All T's in stop codons were changed to A's in the existing apo-4 gene, as happens with RNA characterization of an apo-dystrophin cDNA editing with adenosine deaminase. Predicted amino acid sequence was analyzed using Mac Vector for starting methionines, N-glycosylationsites and predicted weight. The Staden predicted probability of M being utilized based on Kozak sequences appears in parentheses after each M. Product weights, with N-glycosylation added, which are close to products obtained from in vivo labelling are highlighted. All weights are based on the assumption that the AATTAA site at 989 in apo-4 is used for polyadenylation unless otherwise indicated, as the original transcripts produced in vitro could not have used polyadenylation sites in the vector. "+" indicates the only products that would allow full or (+) partial recognition by the anti-apo-4 P1 antisera.

TABLE 4

Size Comparison Of Proteins Obtained From In Vitro Translation And Immunoprecipitation

| *IVT&T-RRL-R | IVT&T RRL-NR | IVT&T WGE-R | IVT&T WGE-NR | P1-R COS 35$_S$ | P2-R COS 35$_S$ | Fc-CD33-R COS 35$_S$ | P1-R biotin | P2-R biotin | Fc-CD33 $^{125}$I COS |
|---|---|---|---|---|---|---|---|---|---|
| Pst I | Pst I | Pst I | Pst I | 50 Kd | 55 Kd | 50/55 Kd | 95 Kd | 97 Kd | 100 |
| 50 Kd | 52 Kd | 44 Kd-f | 45 Kd-f | | | | 45 Kd | 50 Kd | 66-f |
| 40 Kd | 42 Kd | 32 Kd | 34 Kd | 30 Kd | 30 Kd | 30 Kd? | | 26 Kd-f | 50-f |
| 25 Kd | 27 Kd | 22 Kd-f | 24 Kd | | | | 22 Kd-f | 22 Kd-f | 45-f |
| Hpa-1 44 | Hpa-1 | Hpa-1 | Hpa-1 | | | | | | |

TABLE 4-continued

Size Comparison Of Proteins Obtained From In Vitro Translation And Immunoprecipitation

| *IVT&T-RRL-R | IVT&T RRL-NR | IVT&T WGE-R | IVT&T WGE-NR | P1-R COS 35$_S$ | P2-R COS 35$_S$ | Fc-CD33-R COS 35$_S$ | P1-R biotin | P2-R biotin | Fc-CD33 $^{125}$I COS |
|---|---|---|---|---|---|---|---|---|---|
| Kd-f | 45 Kd-f | 45 Kd-f 32 Kd | 45 Kd-f 37 Kd | | | | | | |

*The table shows that proteins obtained with different labelling systems are similar in weight. IVT&T = in vitro transcription & translation; RRL = rabbit reticulocyte lysates; WGE = wheat germ extracts; R = reduced; NR = nonreduced; f = faintly labelled band; P1 = protein immunoprecipitated from COS cell transfectants with purified polyclonal antisera P1, P2 and P3; biotin = COS cells surface labelled with biotin.

---

I claim:

1. A method of screening leukemic cells, comprising analyzing DNA of cells to detect the presence of SEQ ID NO: 2 or a fragment of SEQ ID NO: 2 comprising nucleotides 710-996 of SEQ ID NO: 2, SEQ ID NO: 67 or SEQ ID NO: 70, or the complements thereof; wherein said presence indicates the presence of a sub-population of leukemic cells having an Apo-4 mutation.

2. A method of screening cells for an Apo-4 mutation, the method comprising analyzing DNA of cells to detect the presence of SEQ ID NO: 2 or a fragment of SEQ ID NO: 2 comprising nucleotides 710-996 of SEQ ID NO: 2, SEQ ID NO: 67 or SEQ ID NO: 70, or the complements thereof, wherein said presence indicates the presence of the Apo-4 mutation in DNA of the cells.

* * * * *

SEQUENCE LISTING

<160> NUMBER OF SEQ ID NOS: 87

<210> SEQ ID NO 1
<211> LENGTH: 137
<212> TYPE: DNA
<213> ORGANISM: Homo sapiens

<400> SEQUENCE: 1

```
attataaagg aaaaagaaaa taacgcaatg gacaagtggt gaagctgtga actcaggtgt      60
gcacaattat caggaacacc ccaaaaccaa agtgaggtag aaatagcatg agaagccgtg     120
tttgatgtta attaatt                                                    137
```

<210> SEQ ID NO 2
<211> LENGTH: 996
<212> TYPE: DNA
<213> ORGANISM: Homo sapiens

<400> SEQUENCE: 2

```
gtggtttgat tgatagtaaa aaaaatgttc gttaatacaa gtagagagta agtaatcaat      60
caatcactca tagccaaggt ggaaaagatg tatcccatca tggaatattc ctgttctgat     120
agaaatcttg tgcttatcta tggaattctt ttgatatata tttacattgg gaacctgaat     180
gtagcttgac attttttccat gtaaacacca gtagcctgat ccaacattaa gctgatacta     240
acaaacaacg tgtaatggct tcattaataa ggctttgctt cttcctggaa actggtgaaa     300
aatcaaacct tgttgtgtac accctcgatg cagcttctgt gttgtcttca cccagaaatg     360
gggaatgatt tcccaaatgg caagaaaaca gagtgatgct atctatctgc acctttttgta     420
aagtctgtct ttctttctct ttgttttcca ggacacaatg taggaagtct tttccacatg     480
gcagatgatt tgggcagagc gatggagtcc ttagtatcag tcatgacaga tgaagaagga     540
gcagaataaa tgttttacaa ctcctgattc ccgcatggtt tttataatat tcatacaaca     600
aagaggatta gacagtaaga gtttacaaga aataaatcta tatttttgtg aagggtagtg     660
gtattatact gtagatttca gtagtttcta agtctgttat tgttttgtta acaatggcag     720
gttttacacg tctatgcaat tgtacaaaaa agttataaga aaactacatg taaaatcttg     780
atagctaaat aacttgccat ttcttttatat ggaacgcatt ttgggttgtt taaaaattta     840
taacagttat aaagaaagaa ttataaagga aaaagaaaat aacgcaatgg acaagtggtg     900
aagctgtgaa ctcaggtgtg cacaattatc aggaacaccc caaaaccaaa gtgaggtaga     960
aatagcatga gaagccgtgt ttgatgttaa ttaatt                              996
```

<210> SEQ ID NO 3

-continued

```
<211> LENGTH: 13
<212> TYPE: PRT
<213> ORGANISM: Homo sapiens

<400> SEQUENCE: 3

Met Tyr Pro Ile Met Glu Tyr Ser Cys Ser Asp Arg Asn
1               5                   10

<210> SEQ ID NO 4
<211> LENGTH: 13
<212> TYPE: PRT
<213> ORGANISM: Homo sapiens

<400> SEQUENCE: 4

Tyr Ile Tyr Ile Gly Asn Leu Asn Val Ala Asp Thr Met
1               5                   10

<210> SEQ ID NO 5
<211> LENGTH: 18
<212> TYPE: PRT
<213> ORGANISM: Homo sapiens

<400> SEQUENCE: 5

Asp Asp Leu Gly Arg Ala Met Glu Ser Leu Val Ser Val Met Thr Asp
1               5                   10                  15

Glu Glu

<210> SEQ ID NO 6
<211> LENGTH: 10
<212> TYPE: DNA
<213> ORGANISM: Homo spaiens

<400> SEQUENCE: 6
acttacctgt                                                          10

<210> SEQ ID NO 7
<211> LENGTH: 22
<212> TYPE: DNA
<213> ORGANISM: Homo sapiens

<400> SEQUENCE: 7
ttataaagaa agaattataa ag                                            22

<210> SEQ ID NO 8
<211> LENGTH: 42
<212> TYPE: DNA
<213> ORGANISM: Homo sapiens

<400> SEQUENCE: 8
ccttggctat gagtgattga ttgattactt actctctact tg                      42

<210> SEQ ID NO 9
<211> LENGTH: 20
<212> TYPE: DNA
<213> ORGANISM: Homo sapiens

<400> SEQUENCE: 9
gattgatagt aaaaaaaatg                                               20

<210> SEQ ID NO 10
<211> LENGTH: 21
<212> TYPE: DNA
<213> ORGANISM: Homno sapiens

<400> SEQUENCE: 10
```

```
caatggcagg ttttacacgt c                                              21
```

<210> SEQ ID NO 11
<211> LENGTH: 20
<212> TYPE: DNA
<213> ORGANISM: Homo sapiens

<400> SEQUENCE: 11

```
ggaaaagact tccacattgt                                                20
```

<210> SEQ ID NO 12
<211> LENGTH: 22
<212> TYPE: DNA
<213> ORGANISM: Homo sapiens

<400> SEQUENCE: 12

```
cttttttcctt tataattctt tc                                            22
```

<210> SEQ ID NO 13
<211> LENGTH: 22
<212> TYPE: DNA
<213> ORGANISM: Homo sapiens

<400> SEQUENCE: 13

```
catcaaacac ggcttctcat gc                                             22
```

<210> SEQ ID NO 14
<211> LENGTH: 9
<212> TYPE: PRT
<213> ORGANISM: Homo sapiens

<400> SEQUENCE: 14

```
Arg Lys Asn Tyr Lys Gly Lys Arg Lys
1               5
```

<210> SEQ ID NO 15
<211> LENGTH: 18
<212> TYPE: DNA
<213> ORGANISM: Homo sapiens

<400> SEQUENCE: 15

```
gttcgttaat acaagtag                                                  18
```

<210> SEQ ID NO 16
<211> LENGTH: 18
<212> TYPE: DNA
<213> ORGANISM: Homo sapiens

<400> SEQUENCE: 16

```
gccaaggtgg aaaagatg                                                  18
```

<210> SEQ ID NO 17
<211> LENGTH: 18
<212> TYPE: DNA
<213> ORGANISM: Homo sapiens

<400> SEQUENCE: 17

```
ccagtagcct gatccaac                                                  18
```

<210> SEQ ID NO 18
<211> LENGTH: 15
<212> TYPE: DNA
<213> ORGANISM: Homo sapiens

```
<400> SEQUENCE: 18
ggcttcatta ataag                                              15

<210> SEQ ID NO 19
<211> LENGTH: 17
<212> TYPE: DNA
<213> ORGANISM: Homo sapiens

<400> SEQUENCE: 19
ggcaaagaaa cagagtg                                            17

<210> SEQ ID NO 20
<211> LENGTH: 17
<212> TYPE: DNA
<213> ORGANISM: Homo sapiens

<400> SEQUENCE: 20
caggacacaa tgtagga                                            17

<210> SEQ ID NO 21
<211> LENGTH: 23
<212> TYPE: DNA
<213> ORGANISM: Homo sapiens

<400> SEQUENCE: 21
gttataaaga aagaattata aag                                     23

<210> SEQ ID NO 22
<211> LENGTH: 18
<212> TYPE: DNA
<213> ORGANISM: Homo sapiens

<400> SEQUENCE: 22
gaaaataacg caatggac                                           18

<210> SEQ ID NO 23
<211> LENGTH: 19
<212> TYPE: DNA
<213> ORGANISM: Homo sapiens

<400> SEQUENCE: 23
gatgggatac atcttttcc                                          19

<210> SEQ ID NO 24
<211> LENGTH: 20
<212> TYPE: DNA
<213> ORGANISM: Homo sapiens

<400> SEQUENCE: 24
caagctacat tcaggttccc                                         20

<210> SEQ ID NO 25
<211> LENGTH: 18
<212> TYPE: DNA
<213> ORGANISM: Homo sapiens

<400> SEQUENCE: 25
ggactccatc gctctgcc                                           18

<210> SEQ ID NO 26
<211> LENGTH: 16
<212> TYPE: DNA
<213> ORGANISM: Homo sapiens
```

<400> SEQUENCE: 26
gacttagaaa ctactg                                                                                                                     16

<210> SEQ ID NO 27
<211> LENGTH: 19
<212> TYPE: DNA
<213> ORGANISM: Homo sapiens

<400> SEQUENCE: 27
atagacgtgt aaaacctgc                                                                                                                  19

<210> SEQ ID NO 28
<211> LENGTH: 18
<212> TYPE: DNA
<213> ORGANISM: Homo sapiens

<400> SEQUENCE: 28
aactgttata aattttta                                                                                                                   18

<210> SEQ ID NO 29
<211> LENGTH: 22
<212> TYPE: DNA
<213> ORGANISM: Homo sapiens

<400> SEQUENCE: 29 cttttttcctt tataattctt tc                                                                                                             22

<210> SEQ ID NO 30
<211> LENGTH: 117
<212> TYPE: PRT
<213> ORGANISM: Homo sapiens

<400> SEQUENCE: 30

Met Phe Val Asn Thr Thr Lys Val Glu Lys Met Tyr Pro Ile Met Glu
1               5                   10                  15

Tyr Ser Cys Ser Asp Arg Asn Leu Val Leu Ile Tyr Gly Ile Leu Leu
            20                  25                  30

Ile Tyr Ile Tyr Ile Gly Asn Leu Asn Met Lys Lys Glu Gln Asn Lys
        35                  40                  45

Cys Phe Thr Thr Pro Asp Ser Arg Met Val Phe Ile Ile Phe Ile Gln
    50                  55                  60

Gln Arg Gly Leu Asp Ser Lys Ser Leu Gln Glu Ile Asn Leu Tyr Phe
65                  70                  75                  80

Cys Glu Gly Phe Tyr Thr Ser Met Gln Leu Tyr Lys Lys Val Ile Arg
                85                  90                  95

Lys Leu His Lys Ile Thr Gln Trp Thr Arg Thr Pro Gln Asn Gln Ser
            100                 105                 110

Glu Val Glu Ile Ala
        115

<210> SEQ ID NO 31
<211> LENGTH: 324
<212> TYPE: PRT
<213> ORGANISM: Homo sapiens

<400> SEQUENCE: 31

Met Phe Val Asn Thr Ser Arg Glu Lys Val Ile Asn Gln Ser Leu Ile
1               5                   10                  15

Ala Lys Val Glu Lys Met Tyr Pro Ile Met Glu Tyr Ser Cys Ser Asp
            20                  25                  30

Arg Asn Leu Val Leu Ile Tyr Gly Ile Leu Ile Tyr Ile Tyr Ile
            35                  40                  45

Gly Asn Leu Asn Val Ala Arg His Phe Ser Met Lys Thr Pro Val Ala
 50                  55                  60

Arg Ser Asn Ile Lys Leu Ile Leu Thr Asn Asn Val Lys Trp Leu His
 65                  70                  75                  80

Lys Lys Gly Phe Ala Ser Ser Trp Lys Leu Val Lys Asn Gln Thr Leu
                 85                  90                  95

Leu Cys Thr Pro Ser Met Gln Leu Leu Cys Cys Leu His Pro Glu Met
             100                 105                 110

Gly Asn Asp Phe Pro Asn Gly Lys Glu Thr Glu Arg Cys Tyr Leu Ser
             115                 120                 125

Ala Pro Phe Val Lys Ser Val Phe Leu Ser Leu Cys Phe Pro Gly His
             130                 135                 140

Asn Val Gly Ser Leu Phe His Met Ala Asp Asp Leu Gly Arg Ala Met
145                 150                 155                 160

Glu Ser Leu Val Ser Val Met Thr Asp Glu Glu Gly Ala Glu Lys Met
                 165                 170                 175

Phe Tyr Asn Ser Arg Phe Pro His Gly Phe Tyr Asn Ile His Thr Thr
             180                 185                 190

Lys Arg Ile Arg Gln Lys Glu Phe Thr Arg Asn Lys Ser Ile Phe Leu
             195                 200                 205

Arg Arg Val Val Val Leu Tyr Cys Arg Phe Gln Lys Phe Leu Ser Leu
             210                 215                 220

Leu Leu Phe Cys Lys Gln Trp Gln Val Leu His Val Tyr Ala Ile Val
225                 230                 235                 240

Gln Lys Ser Tyr Lys Lys Thr Thr Cys Lys Ile Leu Ile Ala Lys Lys
                 245                 250                 255

Leu Ala Ile Ser Leu Tyr Gly Thr His Phe Gly Leu Phe Lys Asn Leu
             260                 265                 270

Lys Gln Leu Lys Arg Lys Asn Tyr Lys Gly Lys Arg Lys Lys Arg Asn
             275                 280                 285

Gly Gln Val Val Lys Leu Arg Thr Gln Val Cys Thr Ile Ile Arg Asn
             290                 295                 300

Thr Pro Lys Pro Lys Arg Gly Arg Asn Ser Met Arg Ser Arg Val Arg
305                 310                 315                 320

Cys Lys Leu Ile

<210> SEQ ID NO 32
<211> LENGTH: 15
<212> TYPE: DNA
<213> ORGANISM: Homo sapiens

<400> SEQUENCE: 32
tggctgcaag cccaa                                                    15

<210> SEQ ID NO 33
<211> LENGTH: 77
<212> TYPE: PRT
<213> ORGANISM: Homo sapiens

<400> SEQUENCE: 33

Phe Pro Ile Gln Cys Ile Val His Gln Arg Ser Ile Gln Glu Phe Ile
 1               5                  10                  15

Ile Ile Ile Phe Asn Pro Ser Lys Ser Arg Glu Lys Ile Ala Thr Ser
                 20                  25                  30

```
Thr Ile Ala Ser Glu Ala Ser Gln Gln Pro Glu Thr Ala Leu Lys Lys
            35                  40                  45

Val Gly Val Ala Val Met Val Ala Val Ile Met Val Thr Asp Gly Trp
 50                  55                  60

Val Leu Val Met Val Val Val Val Lys Val Val Met
 65                  70                  75
```

<210> SEQ ID NO 34

<400> SEQUENCE: 34

000

<210> SEQ ID NO 35

<400> SEQUENCE: 35

000

<210> SEQ ID NO 36
<211> LENGTH: 6
<212> TYPE: PRT
<213> ORGANISM: Homo sapiens

<400> SEQUENCE: 36

```
Tyr Lys Gly Lys Arg Lys
1               5
```

<210> SEQ ID NO 37
<211> LENGTH: 8
<212> TYPE: PRT
<213> ORGANISM: Homo sapiens

<400> SEQUENCE: 37

```
Arg Asn Gly Gln Val Val Lys Leu
1               5
```

<210> SEQ ID NO 38
<211> LENGTH: 14
<212> TYPE: PRT
<213> ORGANISM: Homo sapiens

<400> SEQUENCE: 38

```
Thr Gln Val Cys Thr Ile Ile Arg Asn Thr Pro Lys Pro Lys
1               5                   10
```

<210> SEQ ID NO 39
<211> LENGTH: 9
<212> TYPE: PRT
<213> ORGANISM: Homo sapiens

<400> SEQUENCE: 39

```
Gly Arg Asn Ser Met Arg Ser Arg Val
1               5
```

<210> SEQ ID NO 40
<211> LENGTH: 13
<212> TYPE: PRT
<213> ORGANISM: Homo sapiens

<400> SEQUENCE: 40

```
Leu Ile Val Lys Lys Met Phe Val Asn Thr Ser Arg Glu
1               5                   10
```

<210> SEQ ID NO 41
<211> LENGTH: 45
<212> TYPE: PRT
<213> ORGANISM: Homo sapiens

<400> SEQUENCE: 41

Val Ile Asn Gln Ser Leu Ile Ala Lys Val Glu Lys Met Tyr Pro Ile
1               5                   10                  15

Met Glu Tyr Ser Cys Ser Asp Arg Asn Leu Val Leu Ile Tyr Gly Ile
            20                  25                  30

Leu Leu Ile Tyr Ile Tyr Ile Gly Asn Leu Asn Val Ala
        35                  40                  45

<210> SEQ ID NO 42
<211> LENGTH: 11
<212> TYPE: PRT
<213> ORGANISM: Homo sapiens

<400> SEQUENCE: 42

Ser Asn Ile Lys Leu Ile Leu Thr Asn Val
1               5                   10

<210> SEQ ID NO 43
<211> LENGTH: 41
<212> TYPE: PRT
<213> ORGANISM: Homo sapiens

<400> SEQUENCE: 43

Gly Phe Ala Ser Ser Trp Lys Leu Val Lys Asn Gln Thr Leu Leu Cys
1               5                   10                  15

Thr Pro Ser Met Gln Leu Leu Cys Cys Leu His Pro Glu Met Gly Asn
            20                  25                  30

Asp Phe Pro Asn Gly Lys Glu Thr Glu
        35                  40

<210> SEQ ID NO 44
<211> LENGTH: 50
<212> TYPE: PRT
<213> ORGANISM: Homo sapiens

<400> SEQUENCE: 44

Cys Tyr Leu Ser Ala Pro Phe Val Lys Ser Val Phe Leu Ser Leu Cys
1               5                   10                  15

Phe Pro Gly His Asn Val Gly Ser Leu Phe His Met Ala Asp Asp Leu
            20                  25                  30

Gly Arg Ala Met Glu Ser Leu Val Ser Val Met Thr Asp Glu Glu Gly
        35                  40                  45

Ala Glu
    50

<210> SEQ ID NO 45
<211> LENGTH: 5
<212> TYPE: PRT
<213> ORGANISM: homo sapiens

<400> SEQUENCE: 45

Met Phe Tyr Asn Ser
1               5

<210> SEQ ID NO 46
<211> LENGTH: 16

```
<212> TYPE: PRT
<213> ORGANISM: Homo sapiens

<400> SEQUENCE: 46

Phe Pro His Gly Phe Tyr Asn Ile His Thr Thr Lys Arg Ile Arg Gln
1               5                   10                  15

<210> SEQ ID NO 47
<211> LENGTH: 10
<212> TYPE: PRT
<213> ORGANISM: Homo sapiens

<400> SEQUENCE: 47

Glu Phe Thr Arg Asn Lys Ser Ile Phe Leu
1               5                   10

<210> SEQ ID NO 48
<211> LENGTH: 10
<212> TYPE: PRT
<213> ORGANISM: Homo sapiens

<400> SEQUENCE: 48

Arg Val Val Val Leu Tyr Cys Arg Phe Gln
1               5                   10

<210> SEQ ID NO 49
<211> LENGTH: 8
<212> TYPE: PRT
<213> ORGANISM: Homo sapiens

<400> SEQUENCE: 49

Phe Leu Ser Leu Leu Leu Phe Cys
1               5

<210> SEQ ID NO 50
<211> LENGTH: 26
<212> TYPE: PRT
<213> ORGANISM: Homo sapiens

<400> SEQUENCE: 50

Gln Trp Gln Val Leu His Val Tyr Ala Ile Val Gln Lys Ser Tyr Lys
1               5                   10                  15

Lys Thr Thr Cys Lys Ile Leu Ile Ala Lys
            20                  25

<210> SEQ ID NO 51
<211> LENGTH: 16
<212> TYPE: PRT
<213> ORGANISM: Homo sapiens

<400> SEQUENCE: 51

Leu Ala Ile Ser Leu Tyr Gly Thr His Phe Gly Leu Phe Lys Asn Leu
1               5                   10                  15

<210> SEQ ID NO 52
<211> LENGTH: 9
<212> TYPE: PRT
<213> ORGANISM: Homo sapiens

<400> SEQUENCE: 52

Arg Lys Asn Tyr Lys Gly Lys Arg Lys
1               5

<210> SEQ ID NO 53
<211> LENGTH: 1233
```

```
<212> TYPE: DNA
<213> ORGANISM: Homo sapiens

<400> SEQUENCE: 53
tagtttccta ttcaatgtat agtgcaccaa aggtcaattc aagagtttat tattattatt       60
ttcaacccaa gtaaaagcag agagaaaata gccacctcca ccatagcctc agaagcaagc      120
caacagcctg aaacagcttt gaaatgaaaa gttggtgtgg cggtgatggt ggcagtgata      180
atggtgacct gggtgctggt gatggtagtg gtagttgtga aggtggtgat ggatggtgtg      240
gtttgattga tagtaaaaaa aatgttcgtt aatacaagta gagagtaagt aatcaatcaa      300
tcactcatag ccaaggtgga aaagatgtat cccatcatgg aatattcctg ttctgataga      360
aatcttgtgc ttatctatgg aattcttttg atatatattt acattgggaa cctgaatgta      420
gcttgacatt tttccatgta aacaccagta gcctgatcca acattaagct gatactaaca      480
aacaacgtgt aatggcttca ttaataaggc tttgcttctt cctggaaact ggtgaaaaat      540
caaaccttgt tgtgtacacc ctcgatgcag cttctgtgtt gtcttcaccc agaaatgggg      600
aatgatttcc caaatggcaa agaaacagag tgatgctatc tatctgcacc ttttgtaaag      660
tctgtctttc tttctctttg ttttccagga cacaatgtag gaagtctttt ccacatggca      720
gatgatttgg gcagagcgat ggagtcctta gtatcagtca tgacagatga agaaggagca      780
gaataaatgt tttacaactc ctgattcccg catggttttt ataatattca tacaacaaag      840
aggattagac agtaagagtt tacaagaaat aaatctatat ttttgtgaag ggtagtggta      900
ttatactgta gatttcagta gtttctaagt ctgttattgt tttgttaaca atggcaggtt      960
ttacacgtct atgcaattgt acaaaaaagt tataagaaaa ctacatgtaa aatcttgata     1020
gctaaataac ttgccatttc tttatatgga acgcattttg ggttgtttaa aaattataa      1080 cagttataaa gaaagaatta taaggaaaa agaaaataac gcaatggaca agtggtgaag     1140
ctgtgaactc aggtgtgcac aattatcagg aacaccccaa aaccaaagtg aggtagaaat     1200
agcatgagaa gccgtgtttg atgttaatta att                                  1233

<210> SEQ ID NO 54
<211> LENGTH: 386
<212> TYPE: PRT
<213> ORGANISM: Homo sapiens

<400> SEQUENCE: 54

Phe Pro Ile Gln Cys Ile Val His Gln Arg Ser Ile Gln Glu Phe Ile
1               5                   10                  15

Ile Ile Ile Phe Asn Pro Ser Lys Ser Arg Glu Lys Ile Ala Thr Ser
            20                  25                  30

Thr Ile Ala Ser Glu Ala Ser Gln Gln Pro Glu Thr Ala Leu Lys Lys
        35                  40                  45

Val Gly Val Ala Val Met Val Ala Val Ile Met Val Thr Trp Val Leu
    50                  55                  60

Val Met Val Val Val Val Lys Val Met Asp Gly Val Leu
65                  70                  75                  80

Ile Val Lys Lys Met Phe Val Asn Thr Ser Arg Glu Val Ile Asn Gln
                85                  90                  95

Ser Leu Ile Ala Lys Val Glu Lys Met Tyr Pro Ile Met Glu Tyr Ser
            100                 105                 110

Cys Ser Asp Arg Asn Leu Val Leu Ile Tyr Gly Ile Leu Leu Ile Tyr
        115                 120                 125

Ile Tyr Ile Gly Asn Leu Asn Val Ala His Phe Ser Met Thr Pro Val
```

```
                130                 135                 140
Ala Ser Asn Ile Lys Leu Ile Leu Thr Asn Asn Val Trp Leu His Gly
145                 150                 155                 160

Phe Ala Ser Ser Trp Lys Leu Val Lys Asn Gln Thr Leu Leu Cys Thr
                165                 170                 175

Pro Ser Met Gln Leu Leu Cys Cys Leu His Pro Glu Met Gly Asn Asp
            180                 185                 190

Phe Pro Asn Gly Lys Glu Thr Glu Cys Tyr Leu Ser Ala Pro Phe Val
                195                 200                 205

Lys Ser Val Phe Leu Ser Leu Cys Phe Pro Gly His Asn Val Gly Ser
210                 215                 220

Leu Phe His Met Ala Asp Asp Leu Gly Arg Ala Met Glu Ser Leu Val
225                 230                 235                 240

Ser Val Met Thr Asp Glu Gly Ala Glu Met Phe Tyr Asn Ser Phe
                245                 250                 255        Phe

Pro His Gly Phe Tyr Asn Ile His Thr Thr Lys Arg Ile Arg Gln Glu
            260                 265                 270

Phe Thr Arg Asn Lys Ser Ile Phe Leu Arg Val Val Leu Tyr Cys
                275                 280                 285

Arg Phe Gln Phe Leu Ser Leu Leu Phe Cys Gln Trp Gln Val Leu
290                 295                 300

His Val Tyr Ala Ile Val Gln Lys Ser Tyr Lys Thr Thr Cys Lys
305                 310                 315                 320

Ile Leu Ile Ala Lys Leu Ala Ile Ser Leu Tyr Gly Thr His Phe Gly
                325                 330                 335

Leu Phe Lys Asn Leu Gln Leu Arg Lys Asn Tyr Lys Gly Lys Arg Lys
                340                 345                 350

Arg Asn Gly Gln Val Val Lys Leu Thr Gln Val Cys Thr Ile Ile Arg
                355                 360                 365

Asn Thr Pro Lys Pro Lys Gly Arg Asn Ser Met Arg Ser Arg Val Cys
            370                 375                 380

Leu Ile
385

<210> SEQ ID NO 55
<211> LENGTH: 47
<212> TYPE: PRT
<213> ORGANISM: Homo sapiens

<400> SEQUENCE: 55

Phe Pro Ile Gln Cys Ile Val His Gln Arg Ser Ile Gln Glu Phe Ile
1               5                   10                  15

Ile Ile Ile Phe Asn Pro Ser Lys Ser Arg Glu Lys Ile Ala Thr Ser
                20                  25                  30

Thr Ile Ala Ser Glu Ala Ser Gln Gln Pro Glu Thr Ala Leu Lys
        35                  40                  45

<210> SEQ ID NO 56
<211> LENGTH: 32
<212> TYPE: PRT
<213> ORGANISM: Homo sapiens

<400> SEQUENCE: 56

Lys Val Gly Val Ala Val Met Val Ala Val Ile Met Val Thr Asp Gly
1               5                   10                  15

Trp Val Leu Val Met Val Val Val Val Lys Val Val Met Val Val
                20                  25                  30
```

<210> SEQ ID NO 57
<211> LENGTH: 1044
<212> TYPE: DNA
<213> ORGANISM: Homo sapiens

<400> SEQUENCE: 57

```
ttcacaggct taagcagcca gtaaatgaca atttatgtgg tagtcaggtc actgtgctgg      60
taatggtgat cttagcaggc agagaaggtg gtagtgattt gatagtaaaa gtgtagacta    120
tacaacagaa taaatacaag tatagtaaat ccaacaaagt gtgaaaggtg tgtgccatta    180
cacatctttc tcggtgataa gagccttgtc tatgaagttc tgagatgtgt taggaagatg    240
aatcatcaat ttacatttct ccccatcaaa tgacaccatg ctgatccagt attaagctaa    300
tactaacacc atgcaatgct tcattaacaa ggatttgctt cttgctagaa atgggtaaaa    360
acggactgtg gtctgtatac cttcaatgca gcttatgtgt tgtcttttcc tgaaatggta    420
atgactccca atagtggcaa ccaggggtac aatacttgca cactttgtaa actctttctt    480
tctctttgtt ttccaggaca caatgtagga agccttttcc acatggcaga tgatttgggc    540
agagcgatgg agtccttagt ttcagtcatg acagatgaag aaggagcaga ataaatgttt    600
tacaactcct gattcccgca tggtttttat aatattcgta caacaaagag gattagacag    660
taagagttta caagaaataa aatctatatt tttgtgaagg gtagtggtac tatactgtag    720
atttcagtag tttctaagtc tgttattgtt ttgttaacaa tggcaggttt tacacgtcta    780
tgcaattgta caaaaaagtt aaaagaaaac atgtaaaatc ttgatagcta aataacttgc    840
catttcttta tatggaacgc attttgggtt gtttaaaaat ttataacagt tataaagaaa    900
gattgtaaac taaagtgtgc tttataaaaa aagttgttta taaaaacccc taaacaaaca    960
cacacgcaca cacacacaca cacacacaca cacacacaca ctgaggcagc acattgtttt   1020
gcattacttt agcgtgtatc atat                                          1044
```

<210> SEQ ID NO 58
<211> LENGTH: 1234
<212> TYPE: DNA
<213> ORGANISM: Homo sapiens

<400> SEQUENCE: 58

```
ctagttttcct attcaatgta tagtgcacca aggtcaatt caagagttta ttattattat       60
tttcaaccca gtaaaagca gagagaaaat agccacctcc accatagcct cagaagcaag      120
ccaacagcct gaaacagctt tgaaatgaaa agttggtgtg gcggtgatgg tggcagtgat      180
aatggtgacc gatggttggg tgctggtgat ggtagtggta gttgtgaagg tggtgatggt      240
ggtttgattg atagtaaaaa aaatgttcgt taatacaagt agagagtaag taatcaatca      300
atcactcata gccaaggtgg aaaagatgta tcccatcatg gaatattcct gttctgatag      360
aaatcttgtg cttatctatg gaattctttt gatatatatt tacattggga acctgaatgt      420
agcttgacat ttttccatgt aaacaccagt agcctgatcc aacattaagc tgatactaac      480
aaacaacgtg taatggcttc attaataagg ctttgcttct tcctggaaac tggtgaaaaa      540
tcaaaccttg ttgtgtacac cctcgatgca gcttctgtgt tgtcttcacc cagaaatggg      600
gaatgatttc ccaaatggca agaaacaga gtgatgctat ctatctgcac cttttgtaaa      660
gtctgtcttt ctttctcttt gttttccagg acacaatgta ggaagtcttt tccacatggc      720
agatgatttg ggcagagcga tggagtcctt agtatcagtc atgacagatg aagaaggagc      780
agaataaatg ttttacaact cctgattccc gcatggtttt tataatattc atacaacaaa      840
```

```
gaggattaga cagtaagagt ttacaagaaa taaatctata tttttgtgaa gggtagtggt    900
attatactgt agatttcagt agtttctaag tctgttattg ttttgttaac aatggcaggt    960
tttacacgtc tatgcaattg tacaaaaaag ttataagaaa actacatgta aaatcttgat   1020
agctaaataa cttgccattt ctttatatgg aacgcatttt gggttgttta aaaatttata   1080
acagttataa agaaagaatt ataaaggaaa agaaaataa cgcaatggac aagtggtgaa    1140
gctgtgaact caggtgtgca caattatcag gaacacccca aaaccaaagt gaggtagaaa   1200
tagcatgaga agccgtgttt gatgttaatt aatt                               1234
```

<210> SEQ ID NO 59
<211> LENGTH: 302
<212> TYPE: PRT
<213> ORGANISM: Homo sapiens

<400> SEQUENCE: 59

```
Met Tyr Pro Ile Met Glu Tyr Ser Cys Ser Asp Arg Asn Leu Val Leu
 1               5                  10                  15

Ile Tyr Gly Ile Leu Leu Ile Tyr Ile Tyr Ile Gly Asn Leu Asn Val
            20                  25                  30

Ala Arg His Phe Ser Met Lys Thr Pro Val Ala Arg Ser Asn Ile Lys
        35                  40                  45

Leu Ile Leu Thr Asn Asn Val Lys Trp Leu His Lys Lys Gly Phe Ala
    50                  55                  60

Ser Ser Trp Lys Leu Val Lys Asn Gln Thr Leu Leu Cys Thr Pro Ser
65                  70                  75                  80

Met Gln Leu Leu Cys Cys Leu His Pro Glu Met Gly Asn Asp Phe Pro
                85                  90                  95

Asn Gly Lys Glu Thr Glu Arg Cys Tyr Leu Ser Ala Pro Phe Val Lys
            100                 105                 110

Ser Val Phe Leu Ser Leu Cys Phe Pro Gly His Asn Val Gly Ser Leu
        115                 120                 125

Phe His Met Ala Asp Asp Leu Gly Arg Ala Met Glu Ser Leu Val Ser
    130                 135                 140

Val Met Thr Asp Glu Glu Gly Ala Glu Lys Met Phe Tyr Asn Ser Arg
145                 150                 155                 160

Phe Pro His Gly Phe Tyr Asn Ile His Thr Thr Lys Arg Ile Arg Gln
                165                 170                 175

Lys Glu Phe Thr Arg Asn Lys Ser Ile Phe Leu Arg Arg Val Val Val
            180                 185                 190

Leu Tyr Cys Arg Phe Gln Lys Phe Leu Ser Leu Leu Phe Cys Lys
    195                 200                 205

Gln Trp Gln Val Leu His Val Tyr Ala Ile Val Gln Lys Ser Tyr Lys
    210                 215                 220

Lys Thr Thr Cys Lys Ile Leu Ile Ala Lys Lys Leu Ala Ile Ser Leu
225                 230                 235                 240

Tyr Gly Thr His Phe Gly Leu Phe Lys Asn Leu Lys Gln Leu Lys Arg
                245                 250                 255

Lys Asn Tyr Lys Gly Lys Arg Lys Arg Asn Gly Gln Val Val Lys
            260                 265                 270

Leu Arg Thr Gln Val Cys Thr Ile Ile Arg Asn Thr Pro Lys Pro Lys
        275                 280                 285

Arg Gly Asn Ser Met Arg Ser Arg Val Arg Cys Lys Leu Ile
    290                 295                 300
```

<210> SEQ ID NO 60
<211> LENGTH: 111
<212> TYPE: DNA
<213> ORGANISM: Homo sapiens

<400> SEQUENCE: 60
tttataacag ttataaagaa agattgtaaa ctaaagtgtg ctttataaaa aaagttgtt    60 tataaaaacc cctaaaaaca aaacaaacac acacacacac acatacacac a            111

<210> SEQ ID NO 61
<211> LENGTH: 260
<212> TYPE: DNA
<213> ORGANISM: Homo sapiens

<400> SEQUENCE: 61
aattagcttt tggagagtgg gttttgtcca ttattaataa ttaattaatt aacatcaaac    60
acggcttctc atgctatttc tacctcactt tggttttggg gtgttcctga taattgtgca   120
cacctgagtt cacagcttca ccacttgtcc attgcgttat tttctttttc ctttataatt   180
ctttcttttt ccttcataat taacagttat aagaaagaa ttataaagga aaagaaaat    240 aacgcaatgg acaagtggtg                                                260

<210> SEQ ID NO 62
<211> LENGTH: 17
<212> TYPE: DNA
<213> ORGANISM: Homo sapiens

<400> SEQUENCE: 62
gccctcattc tggagac                                                   17

<210> SEQ ID NO 63
<211> LENGTH: 17
<212> TYPE: DNA
<213> ORGANISM: Homo sapiens

<400> SEQUENCE: 63
gcggtgatgg tggcagt                                                   17

<210> SEQ ID NO 64
<211> LENGTH: 107
<212> TYPE: PRT
<213> ORGANISM: Homo sapiens

<400> SEQUENCE: 64

Met Tyr Pro Ile Met Glu Tyr Ser Cys Ser Asp Arg Asn Leu Val Leu
1               5                   10                  15

Ile Tyr Gly Ile Leu Leu Ile Tyr Ile Tyr Ile Gly Asn Leu Asn Met
            20                  25                  30

Lys Lys Glu Gln Asn Lys Cys Phe Thr Thr Pro Asp Ser Arg Met Val
        35                  40                  45

Phe Ile Ile Phe Ile Gln Gln Arg Gly Leu Asp Ser Lys Ser Leu Gln
    50                  55                  60

Glu Ile Asn Leu Tyr Phe Cys Glu Gly Phe Tyr Thr Ser Met Gln Leu
65                  70                  75                  80

Tyr Lys Lys Val Ile Arg Lys Leu His Lys Ile Thr Gln Trp Thr Arg
                85                  90                  95

Thr Pro Gln Asn Gln Ser Glu Val Glu Ile Ala
            100                 105

<210> SEQ ID NO 65
<211> LENGTH: 137
<212> TYPE: DNA
<213> ORGANISM: Homo sapiens

<400> SEQUENCE: 65
taatatttcc tttttctttt attgcgttac ctgttcacca cttcgacact tgagtccaca    60
cgtgttaata gtccttgtgg ggttttggtt tcactccatc tttatcgtac tcttcggcac   120
aaactacaat taattaa                                                  137

<210> SEQ ID NO 66
<211> LENGTH: 40
<212> TYPE: PRT
<213> ORGANISM: Homo sapiens

<400> SEQUENCE: 66

Tyr Lys Gly Lys Arg Lys Arg Asn Gly Gln Val Val Lys Leu Thr Gln
1               5                   10                  15

Val Cys Thr Ile Ile Arg Asn Thr Pro Lys Pro Lys Gly Arg Asn Ser
            20                  25                  30

Met Arg Ser Arg Val Cys Leu Ile
        35                  40

<210> SEQ ID NO 67
<211> LENGTH: 147
<212> TYPE: DNA
<213> ORGANISM: Homo sapiens

<400> SEQUENCE: 67
taaagaaaga attataaagg aaaaagaaaa taacgcaatg gacaagtggt gaagctgtga    60
actcaggtgt gcacaattat caggaacacc ccaaaaccaa agtgaggtag aaatagcatg   120
agaagccgtg tttgatgtta attaatt                                       147

<210> SEQ ID NO 68
<211> LENGTH: 147
<212> TYPE: DNA
<213> ORGANISM: Homo sapiens

<400> SEQUENCE: 68
atttctttct taatatttcc tttttctttt attgcgttac ctgttcacca cttcgacact    60
tgagtccaca cgtgttaata gtccttgtgg ggttttggtt tcactccatc tttatcgtac   120
tcttcggcac aaactacaat taattaa                                       147

<210> SEQ ID NO 69
<211> LENGTH: 43
<212> TYPE: PRT
<213> ORGANISM: Homo sapiens

<400> SEQUENCE: 69

Arg Lys Asn Tyr Lys Gly Lys Arg Lys Arg Asn Gly Gln Val Val Lys
1               5                   10                  15

Leu Thr Gln Val Cys Thr Ile Ile Arg Asn Thr Pro Lys Pro Lys Gly
            20                  25                  30

Arg Asn Ser Met Arg Ser Arg Val Cys Leu Ile
        35                  40

<210> SEQ ID NO 70
<211> LENGTH: 287

```
<212> TYPE: DNA
<213> ORGANISM: Homo sapiens

<400> SEQUENCE: 70
aacaatggca ggttttacac gtctatgcaa ttgtacaaaa aagttataag aaaactacat    60
gtaaaatctt gatagctaaa taacttgcca tttctttata tggaacgcat tttgggttgt   120
ttaaaaattt ataacagtta taagaaaga attataaagg aaaaagaaaa taacgcaatg    180
gacaagtggt gaagctgtga actcaggtgt gcacaattat caggaacacc ccaaaaccaa   240
agtgaggtag aaatagcatg agaagccgtg tttgatgtta attaatt                 287

<210> SEQ ID NO 71
<211> LENGTH: 287
<212> TYPE: DNA
<213> ORGANISM: Homo sapiens

<400> SEQUENCE: 71
ttgttaccgt ccaaaatgtg cagatacgtt aacatgtttt ttcaatattc ttttgatgta    60
cattttagaa ctatcgattt attgaacggt aaagaaatat accttgcgta aacccaaca    120 aatttttaaa tattgtcaat atttctttct taatatttcc ttttcttt attgcgttac     180 ctgttcacca cttcgacact tgagtccaca cgtgttaata gtccttgtgg ggttttggtt   240
tcactccatc tttatcgtac tcttcggcac aaactacaat taattaa                 287

<210> SEQ ID NO 72
<211> LENGTH: 84
<212> TYPE: PRT
<213> ORGANISM: Homo sapiens

<400> SEQUENCE: 72

Val Leu His Val Tyr Ala Ile Val Gln Lys Ser Tyr Lys Lys Thr Thr
  1               5                  10                  15

Cys Lys Ile Leu Ile Ala Lys Leu Ala Ile Ser Leu Tyr Gly Thr His
             20                  25                  30

Phe Gly Leu Phe Lys Asn Leu Gln Leu Arg Lys Asn Tyr Lys Gly Lys
         35                  40                  45

Arg Lys Arg Asn Gly Gln Val Val Lys Leu Thr Gln Val Cys Thr Ile
     50                  55                  60

Ile Arg Asn Thr Pro Lys Pro Lys Gly Arg Asn Ser Met Arg Ser Arg
 65                  70                  75                  80

Val Cys Leu Ile

<210> SEQ ID NO 73
<211> LENGTH: 996
<212> TYPE: DNA
<213> ORGANISM: Homo sapiens

<400> SEQUENCE: 73
caccaaacta actatcattt ttttacaag caattatgtt catctctcat tcattagtta    60
gttagtgagt atcggttcca ccttttctac atagggtagt accttataag gacaagacta   120
tctttagaac acgaatagat accttaagaa aactatatat aaatgtaacc cttggactta   180
catcgaactg taaaaggta catttgtggt catcggacta ggttgtaatt cgactatgat    240
tgtttgttgc acattaccga agtaattatt ccgaaacgaa aaggacctt tgaccacttt    300 ttagtttgga acaacacatg tgggagctac gtcgaagaca caacagaagt gggtcttac    360 cccttactaa agggtttacc gtttctttgt ctcactacga tagatagacg tggaaaacat   420
```

-continued

```
ttcagacaga aagaaagaga aacaaaaggt cctgtgttac atccttcaga aaaggtgtac    480
cgtctactaa acccgtctcg ctacctcagg aatcatagtc agtactgtct acttcttcct    540
cgtcttattt acaaaatgtt gaggactaag ggcgtaccaa aaatattata agtatgttgt    600
ttctcctaat ctgtcattct caaatgttct ttatttagat ataaaaacac ttcccatcac    660
cataatatga catctaaagt catcaaagat tcagacaata acaaaacaat tgttaccgtc    720
caaaatgtgc agatacgtta acatgttttt tcaatattct tttgatgtac attttagaac    780
tatcgattta ttgaacggta aagaaatata ccttgcgtaa aacccaacaa attttttaaat   840
attgtcaata tttctttctt aatatttcct ttttctttta ttgcgttacc tgttcaccac    900
ttcgacactt gagtccacac gtgttaatag tccttgtggg gttttggttt cactccatct    960
ttatcgtact cttcggcaca aactacaatt aattaa                              996
```

<210> SEQ ID NO 74
<211> LENGTH: 309
<212> TYPE: PRT
<213> ORGANISM: Homo sapiens

<400> SEQUENCE: 74

```
Val Val Leu Ile Val Lys Lys Met Phe Val Asn Thr Ser Arg Glu Val
1               5                   10                  15

Ile Asn Gln Ser Leu Ile Ala Lys Val Glu Lys Met Tyr Pro Ile Met
            20                  25                  30

Glu Tyr Ser Cys Ser Asp Arg Asn Leu Val Leu Ile Tyr Gly Ile Leu
        35                  40                  45

Leu Ile Tyr Ile Tyr Ile Gly Asn Leu Asn Val Ala His Phe Ser Met
    50                  55                  60

Thr Pro Val Ala Ser Asn Ile Lys Leu Ile Leu Thr Asn Asn Val Trp
65                  70                  75                  80

Leu His Gly Phe Ala Ser Ser Trp Lys Leu Val Lys Asn Gln Thr Leu
                85                  90                  95

Leu Cys Thr Pro Ser Met Gln Leu Leu Cys Cys Leu His Pro Glu Met
            100                 105                 110

Gly Asn Asp Phe Pro Asn Gly Lys Glu Thr Glu Cys Tyr Leu Ser Ala
        115                 120                 125

Pro Phe Val Lys Ser Val Phe Leu Ser Leu Cys Phe Pro Gly His Asn
    130                 135                 140

Val Gly Ser Leu Phe His Met Ala Asp Asp Leu Gly Arg Ala Met Glu
145                 150                 155                 160

Ser Leu Val Ser Val Met Thr Asp Glu Glu Gly Ala Glu Met Phe Tyr
                165                 170                 175

Asn Ser Phe Pro His Gly Phe Tyr Asn Ile His Thr Thr Lys Arg Ile
            180                 185                 190

Arg Gln Glu Phe Thr Arg Asn Lys Ser Ile Phe Leu Arg Val Val Val
        195                 200                 205

Leu Tyr Cys Arg Phe Gln Phe Leu Ser Leu Leu Phe Cys Gln Trp
    210                 215                 220

Gln Val Leu His Val Tyr Ala Ile Val Gln Lys Ser Tyr Lys Lys Thr
225                 230                 235                 240

Thr Cys Lys Ile Leu Ile Ala Lys Leu Ala Ile Ser Leu Tyr Gly Thr
                245                 250                 255

His Phe Gly Leu Phe Lys Asn Leu Gln Leu Arg Lys Asn Tyr Lys Gly
            260                 265                 270
```

Lys Arg Lys Arg Asn Gly Gln Val Val Lys Leu Thr Gln Val Cys Thr
        275                 280                 285

Ile Ile Arg Asn Thr Pro Lys Pro Lys Gly Arg Asn Ser Met Arg Ser
    290                 295                 300

Arg Val Cys Leu Ile
305

<210> SEQ ID NO 75
<211> LENGTH: 761
<212> TYPE: DNA
<213> ORGANISM: Artificial Sequence
<220> FEATURE:
<223> OTHER INFORMATION: Consensus sequence

<400> SEQUENCE: 75

```
acagctaaag caaatgaaat tagaaggtgc tggtatggtt taggaagggt gtgtgtttga      60
tgaaattcaa aataaagtaa caagtgaaag tgttccataa ttcggatctt tctatgattc     120
tgaattttag aacatctttt ccaaacaact gatccaatta agctatacta acacagcttc     180
attaaaaggt ttgcttcttc tgaaaggtaa aacactgttg taacctcatg cagctttgtg     240
ttgtcttcca aggaatgatc caagaaagat cttgcacttt gtaaatcttt ctttctcttt     300
gttttccagg acacaatgta ggaagctttt ccacatggca gatgatttgg gcagagcgat     360
ggagtcctta gttcagtcat gacagatgaa gaaggagcag aataaatgtt ttacaactcc     420
tgattcccgc atggttttta taatattcta caacaaagag gattagacag taagagttta     480
caagaaataa atctatattt ttgtgaaggg tagtggtata tactgtagat ttcagtagtt     540
tctaagtctg ttattgtttt gttaacaatg gcaggtttta cacgtctatg caattgtaca     600
aaaaagttaa agaaaacatg taaatcttg atagctaaat aacttgccat ttctttatat      660
ggaacgcatt ttgggttgtt taaaaattta taacagttat aaagaaagat aaaaaaaaaa     720
ataaaaccag cacaaaccaa caatgaggag atgatttgtt a                        761
```

<210> SEQ ID NO 76
<211> LENGTH: 16
<212> TYPE: DNA
<213> ORGANISM: Artificial Sequence
<220> FEATURE:
<223> OTHER INFORMATION: Synthetic

<400> SEQUENCE: 76

```
cacagtgaca aaaacc                                                     16
```

<210> SEQ ID NO 77
<211> LENGTH: 111
<212> TYPE: DNA
<213> ORGANISM: Artificial Sequence
<220> FEATURE:
<223> OTHER INFORMATION: Synthetic

<400> SEQUENCE: 77

```
tttataacag ttataaagaa agattgtaaa ctaaagtgtg ctttataaaa aaaagttgtt      60
tataaaaacc cctaaaaaca aaacaaacac acacacacac acatacacac a              111
```

<210> SEQ ID NO 78
<211> LENGTH: 111
<212> TYPE: DNA
<213> ORGANISM: Artificial Sequence
<220> FEATURE:
<223> OTHER INFORMATION: Synthetic

<400> SEQUENCE: 78
aaatattgtc aatatttctt tctaacattt gatttcacac gaaatatttt ttttcaacaa    60
atatttttgg ggattttgt tttgtttgtg tgtgtgtgtg tgtatgtgtg t              111

<210> SEQ ID NO 79
<211> LENGTH: 108
<212> TYPE: DNA
<213> ORGANISM: Artificial Sequence
<220> FEATURE:
<223> OTHER INFORMATION: Synthetic

<400> SEQUENCE: 79
tttataacag ttataaagaa agattataaa ggaaaaagaa aataaaatgg acaagtggtg    60
aatgtgaact caggtgtgca caattatcag gaacacccca aaaccaaa                108

<210> SEQ ID NO 80
<211> LENGTH: 200
<212> TYPE: DNA
<213> ORGANISM: Artificial Sequence
<220> FEATURE:
<223> OTHER INFORMATION: Synthetic

<400> SEQUENCE: 80
aattagcttt tggagagtgg gttttgtcca ttattaataa ttaattaatt aacatcaaac    60
acggcttctc atgctatttc tacctcactt tggttttggg gtgttcctga taattgtgca   120
cacctgagtt cacagcttca ccacttgtcc attgcgttat tttcttttc ctttataatt   180 cttctttttt ccttcataat                                              200

<210> SEQ ID NO 81
<211> LENGTH: 200
<212> TYPE: DNA
<213> ORGANISM: Artificial Sequence
<220> FEATURE:
<223> OTHER INFORMATION: Synthetic

<400> SEQUENCE: 81
ttaatcgaaa acctctcacc caaaacaggt aataattatt aattaattaa ttgtagtttg    60
tgccgaagag tacgataaag atggagtgaa accaaaaccc cacaaggact attaacacgt   120
gtggactcaa gtgtcgaagt ggtgaacagg taacgcaata aaagaaaaag gaaatattaa   180
gaaagaaaaa ggaagtatta                                              200

<210> SEQ ID NO 82
<211> LENGTH: 158
<212> TYPE: DNA
<213> ORGANISM: Artificial Sequence
<220> FEATURE:
<223> OTHER INFORMATION: Synthetic

<400> SEQUENCE: 82
aattaattaa catcaaacac ggcttctcat gctatttcta cctcactttg gttttggggt    60
gttcctgata attgtgcaca cctgagttca cagcttcacc acttgtccat tgcgttattt   120 tcttttcct ttataattct ttctttataa ctgttata                           158

<210> SEQ ID NO 83
<211> LENGTH: 10
<212> TYPE: DNA
<213> ORGANISM: Artificial Sequence
<220> FEATURE:
<223> OTHER INFORMATION: Synthetic

```
<400> SEQUENCE: 83
aaagaaagat                                                            10

<210> SEQ ID NO 84
<211> LENGTH: 10
<212> TYPE: DNA
<213> ORGANISM: Artificial Sequence
<220> FEATURE:
<223> OTHER INFORMATION: Synthetic

<400> SEQUENCE: 84
ttctttcttt                                                            10

<210> SEQ ID NO 85
<211> LENGTH: 60
<212> TYPE: DNA
<213> ORGANISM: Homo sapiens

<400> SEQUENCE: 85
taacagttat aaagaaagaa ttataaagga aaaagaaaat aacgcaatgg acaagtggtg     60

<210> SEQ ID NO 86
<211> LENGTH: 60
<212> TYPE: DNA
<213> ORGANISM: Homo sapiens

<400> SEQUENCE: 86
attgtcaata tttctttctt aatatttcct ttttcttta ttgcgttacc tgttcaccac     60

<210> SEQ ID NO 87
<211> LENGTH: 15
<212> TYPE: DNA
<213> ORGANISM: Artificial Sequence
<220> FEATURE:
<223> OTHER INFORMATION: Synthetic

<400> SEQUENCE: 87
tggctgcaag cccaa                                                      15
```